(12) United States Patent
Gersbach et al.

(10) Patent No.: US 11,976,307 B2
(45) Date of Patent: May 7, 2024

(54) GENETIC CORRECTION OF MUTATED GENES

(71) Applicant: Duke University, Durham, NC (US)

(72) Inventors: Charles Gersbach, Durham, NC (US); David Ousterout, Durham, NC (US)

(73) Assignee: Duke University, Durham, NC (US)

( * ) Notice: Subject to any disclaimer, the term of this patent is extended or adjusted under 35 U.S.C. 154(b) by 173 days.

(21) Appl. No.: 16/890,232

(22) Filed: Jun. 2, 2020

(65) Prior Publication Data

US 2021/0040460 A1 Feb. 11, 2021

Related U.S. Application Data

(62) Division of application No. 15/634,425, filed on Jun. 27, 2017, now Pat. No. 10,711,256, which is a division of application No. 14/397,420, filed as application No. PCT/US2013/038536 on Apr. 26, 2013, now Pat. No. 9,738,879.

(60) Provisional application No. 61/639,227, filed on Apr. 27, 2012.

(51) Int. Cl.
| | |
|---|---|
| *C12N 9/22* | (2006.01) |
| *A61K 48/00* | (2006.01) |
| *C07K 14/47* | (2006.01) |
| *C12N 15/11* | (2006.01) |
| *C12N 15/90* | (2006.01) |

(52) U.S. Cl.
CPC .............. *C12N 9/22* (2013.01); *A61K 48/005* (2013.01); *C07K 14/4708* (2013.01); *C12N 15/111* (2013.01); *C12N 15/907* (2013.01); *C12N 2310/20* (2017.05); *C12N 2320/30* (2013.01)

(58) Field of Classification Search
CPC ........... C12N 9/22; C12N 15/11; C07K 14/47
See application file for complete search history.

(56) References Cited

U.S. PATENT DOCUMENTS

| | | | |
|---|---|---|---|
| 3,687,808 A | 8/1972 | Merigan, Jr. | |
| 4,469,863 A | 9/1984 | Ts'o et al. | |
| 4,476,301 A | 10/1984 | Imbach et al. | |
| 4,501,729 A | 2/1985 | Boucher et al. | |
| 4,554,101 A | 11/1985 | Hopp | |
| 4,587,044 A | 5/1986 | Miller et al. | |
| 4,605,735 A | 8/1986 | Miyoshi et al. | |
| 4,667,025 A | 5/1987 | Miyoshi et al. | |
| 4,737,323 A | 4/1988 | Martin et al. | |
| 4,762,779 A | 8/1988 | Snitman | |
| 4,789,737 A | 12/1988 | Miyoshi et al. | |
| 4,824,941 A | 4/1989 | Gordon et al. | |
| 4,828,979 A | 5/1989 | Klevan et al. | |
| 4,835,263 A | 5/1989 | Nguyen et al. | |
| 4,845,205 A | 7/1989 | Huynh et al. | |
| 4,876,335 A | 10/1989 | Yamane et al. | |
| 4,904,582 A | 2/1990 | Tullis | |
| 4,948,882 A | 8/1990 | Ruth | |
| 4,958,013 A | 9/1990 | Letsinger | |
| 5,013,830 A | 5/1991 | Ohsuka et al. | |
| 5,023,243 A | 6/1991 | Tullis | |
| 5,034,506 A | 7/1991 | Summerton et al. | |
| 5,082,830 A | 1/1992 | Brakel et al. | |
| 5,109,124 A | 4/1992 | Ramachandran et al. | |
| 5,112,963 A | 5/1992 | Pieles et al. | |
| 5,118,802 A | 6/1992 | Smith et al. | |
| 5,130,302 A | 7/1992 | Spielvogel et al. | |
| 5,134,066 A | 7/1992 | Rogers et al. | |
| 5,138,045 A | 8/1992 | Cook et al. | |
| 5,149,797 A | 9/1992 | Pederson et al. | |
| 5,166,315 A | 11/1992 | Summerton et al. | |
| 5,175,273 A | 12/1992 | Bischofberger et al. | |
| 5,177,196 A | 1/1993 | Meyer et al. | |
| 5,185,444 A | 2/1993 | Summerton et al. | |
| 5,188,897 A | 2/1993 | Suhadolnik et al. | |
| 5,214,134 A | 5/1993 | Weis et al. | |
| 5,214,136 A | 5/1993 | Lin et al. | |
| 5,216,141 A | 6/1993 | Benner | |
| 5,218,105 A | 6/1993 | Cook et al. | |
| 5,219,740 A | 6/1993 | Miller et al. | |
| 5,220,007 A | 6/1993 | Pederson et al. | |
| 5,235,033 A | 8/1993 | Summerton et al. | |
| 5,245,022 A | 9/1993 | Weis et al. | |
| 5,254,469 A | 10/1993 | Warren, III | |
| 5,256,775 A | 10/1993 | Froehler | |
| 5,258,506 A | 11/1993 | Urdea et al. | |
| 5,262,536 A | 11/1993 | Hobbs, Jr. | |
| 5,264,423 A | 11/1993 | Cohen et al. | |
| 5,264,562 A | 11/1993 | Matteucci | |
| 5,264,564 A | 11/1993 | Matteucci | |
| 5,272,250 A | 12/1993 | Spielvogel et al. | |

(Continued)

FOREIGN PATENT DOCUMENTS

| | | |
|---|---|---|
| CA | 2749305 A1 | 7/2010 |
| EP | 3009511 A2 | 4/2016 |

(Continued)

OTHER PUBLICATIONS

U.S. Appl. No. 17/636,750, filed Feb. 18, 2022.
U.S. Appl. No. 17/636,754, filed Feb. 18, 2022.
U.S. Appl. No. 17/766,003, filed Apr. 1, 2022.
U.S. Appl. No. 63/314,183, filed Feb. 25, 2022.
U.S. Appl. No. 63/314,256, filed Feb. 25, 2022.
U.S. Appl. No. 63/317,847, filed Mar. 8, 2022.
U.S. Appl. No. 63/325,037, filed Mar. 29, 2022.
U.S. Appl. No. 63/325,039, filed Mar. 29, 2022.

(Continued)

*Primary Examiner* — Karen Cochrane Carlson
(74) *Attorney, Agent, or Firm* — Michael Best & Friedrich LLP

(57) ABSTRACT

Disclosed herein are transcription activator-like effector nuclease (TALEN)-related compositions and methods of using said TALENs for correcting mutant genes.

15 Claims, 17 Drawing Sheets

Specification includes a Sequence Listing.

(56) References Cited

U.S. PATENT DOCUMENTS

| | | |
|---|---|---|
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,473 A | 4/1996 | Camerini-Otero et al. |
| 5,510,475 A | 4/1996 | Agrawal et al. |
| 5,512,439 A | 4/1996 | Horner et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,593,972 A | 1/1997 | Weiner et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,633,360 A | 5/1997 | Bischofberger et al. |
| 5,652,355 A | 7/1997 | Metelev et al. |
| 5,652,356 A | 7/1997 | Agrawal |
| 5,663,312 A | 9/1997 | Chaturvedula et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,922 A | 12/1997 | Cook et al. |
| 5,714,331 A | 2/1998 | Buchardt et al. |
| 5,719,262 A | 2/1998 | Buchardt et al. |
| 5,750,692 A | 5/1998 | Cook et al. |
| 5,773,700 A | 6/1998 | Van Grinsven et al. |
| 5,962,428 A | 10/1999 | Carrano et al. |
| 6,140,081 A | 10/2000 | Barbas |
| 6,207,453 B1 | 3/2001 | Maass et al. |
| 6,268,490 B1 | 7/2001 | Imanishi et al. |
| 6,287,860 B1 | 9/2001 | Monia et al. |
| 6,453,242 B1 | 9/2002 | Eisenberg et al. |
| 6,462,254 B1 | 10/2002 | Vernachio et al. |
| 6,534,261 B1 | 3/2003 | Cox, III et al. |
| 6,734,291 B2 | 5/2004 | Kochkine et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,060,809 B2 | 6/2006 | Wengel et al. |
| 7,074,596 B2 | 7/2006 | Darzynkiewicz et al. |
| 7,084,125 B2 | 8/2006 | Wengel |
| 7,449,561 B1 | 11/2008 | Sommer et al. |
| 7,572,582 B2 | 8/2009 | Wengel et al. |
| 7,728,118 B2 | 6/2010 | Wood et al. |
| 7,745,651 B2 | 6/2010 | Heyes et al. |
| 7,799,565 B2 | 9/2010 | MacLachlan et al. |
| 8,278,036 B2 | 10/2012 | Kariko et al. |
| 8,450,107 B1 | 5/2013 | Zhang et al. |
| 8,586,526 B2 | 11/2013 | Gregory et al. |
| 8,697,359 B1 | 4/2014 | Zhang et al. |
| 8,889,356 B2 | 11/2014 | Zhang |
| 8,993,233 B2 | 3/2015 | Zhang et al. |
| 9,139,554 B2 | 9/2015 | Hope et al. |
| 9,458,205 B2 | 10/2016 | Gregory et al. |
| 9,738,879 B2 * | 8/2017 | Gersbach ............... C12N 15/111 |
| 9,828,582 B2 | 11/2017 | Perez-Pinera et al. |
| 9,834,791 B2 | 12/2017 | Zhang et al. |
| 9,890,364 B2 | 2/2018 | Joung et al. |
| 10,190,106 B2 | 1/2019 | Wolfe et al. |
| 10,266,850 B2 | 4/2019 | Doudna et al. |
| 10,676,735 B2 | 6/2020 | Gersbach et al. |
| 10,704,060 B2 | 7/2020 | Gersbach et al. |
| 10,711,256 B2 * | 7/2020 | Gersbach ............ C07K 14/4708 |
| 10,745,714 B2 | 8/2020 | Gersbach et al. |
| 11,155,796 B2 | 10/2021 | Gersbach et al. |
| 11,421,251 B2 | 8/2022 | Gersbach et al. |
| 11,427,817 B2 | 8/2022 | Josephs et al. |
| 2002/0160940 A1 | 10/2002 | Case et al. |
| 2004/0142025 A1 | 7/2004 | MacLachlan et al. |
| 2004/0175727 A1 | 9/2004 | Draghia-Akli et al. |
| 2004/0192593 A1 | 9/2004 | Draghia-Akli et al. |
| 2004/0204345 A1 | 10/2004 | Case et al. |
| 2006/0068395 A1 | 3/2006 | Wood et al. |
| 2006/0211647 A1 | 9/2006 | Khan |
| 2007/0042031 A1 | 2/2007 | MacLachlan et al. |
| 2007/0042462 A1 | 2/2007 | Hildinger |
| 2007/0059795 A1 | 3/2007 | Moore et al. |
| 2007/0185042 A1 | 8/2007 | Tsai et al. |
| 2007/0192880 A1 | 8/2007 | Muyan et al. |
| 2008/0070299 A1 | 3/2008 | Wood et al. |
| 2008/0090291 A1 | 4/2008 | Wood et al. |
| 2008/0200409 A1 | 8/2008 | Wilson et al. |
| 2009/0018031 A1 | 1/2009 | Trinklein et al. |
| 2010/0035968 A1 | 2/2010 | Rasmussen et al. |
| 2010/0076057 A1 | 3/2010 | Sontheimer et al. |
| 2010/0261175 A1 | 10/2010 | Rasmussen et al. |
| 2010/0267018 A1 | 10/2010 | Wengel et al. |
| 2011/0145940 A1 | 6/2011 | Voytas et al. |
| 2011/0197290 A1 | 8/2011 | Fahrenkrug et al. |

(56) References Cited

U.S. PATENT DOCUMENTS

| | | | |
|---|---|---|---|
| 2011/0263682 A1 | 10/2011 | De Kimpe et al. |
| 2011/0301073 A1 | 12/2011 | Gregory et al. |
| 2011/0301218 A1 | 12/2011 | Bozzoni et al. |
| 2012/0207744 A1 | 8/2012 | Mendlein et al. |
| 2013/0274129 A1 | 10/2013 | Katzen et al. |
| 2014/0140969 A1 | 5/2014 | Beausejour et al. |
| 2014/0170753 A1 | 6/2014 | Zhang |
| 2014/0179006 A1 | 6/2014 | Zhang |
| 2014/0186958 A1 | 7/2014 | Zhang et al. |
| 2014/0234975 A1 | 8/2014 | Silva et al. |
| 2014/0295557 A1 | 10/2014 | Joung et al. |
| 2014/0309177 A1 | 10/2014 | Perez-Pinera et al. |
| 2014/0315862 A1 | 10/2014 | Kaye |
| 2014/0356956 A1 | 12/2014 | Church et al. |
| 2014/0357530 A1 | 12/2014 | Zhang et al. |
| 2015/0024499 A1 | 1/2015 | Brouns et al. |
| 2015/0044772 A1 | 2/2015 | Zhao |
| 2015/0045413 A1 | 2/2015 | De Visser et al. |
| 2015/0056705 A1 | 2/2015 | Conway et al. |
| 2015/0079064 A1 | 3/2015 | Gersbach et al. |
| 2015/0159178 A1 | 6/2015 | Green et al. |
| 2016/0002634 A1 | 1/2016 | Sazani et al. |
| 2016/0040189 A1 | 2/2016 | Kennedy et al. |
| 2016/0058889 A1 | 3/2016 | Olson et al. |
| 2016/0281166 A1 | 9/2016 | Bhattacharjee et al. |
| 2017/0198308 A1 | 7/2017 | Qi et al. |
| 2017/0204407 A1 | 7/2017 | Gilbert et al. |
| 2017/0283831 A1 | 10/2017 | Zhang et al. |
| 2017/0298331 A1 | 10/2017 | Gersbach et al. |
| 2017/0327806 A1 | 11/2017 | Joung et al. |
| 2018/0023064 A1 | 1/2018 | Gersbach et al. |
| 2018/0073012 A1 | 3/2018 | Liu et al. |
| 2018/0094238 A1 | 4/2018 | Perez-Pinera et al. |
| 2018/0135109 A1 | 5/2018 | Jayaram et al. |
| 2018/0201951 A1 | 7/2018 | Guilak et al. |
| 2018/0251735 A1 | 9/2018 | Ko |
| 2018/0291370 A1 | 10/2018 | Gersbach et al. |
| 2018/0305719 A1 | 10/2018 | Perez-Pinera et al. |
| 2018/0320197 A1 | 11/2018 | Gersbach et al. |
| 2018/0327740 A1 | 11/2018 | Gifford et al. |
| 2018/0334688 A1 | 11/2018 | Gersbach et al. |
| 2018/0353615 A1 | 12/2018 | Gersbach et al. |
| 2019/0032049 A1 | 1/2019 | Naldini et al. |
| 2019/0038776 A1 | 2/2019 | Pyle et al. |
| 2019/0048337 A1 | 2/2019 | Hsu et al. |
| 2019/0062790 A1 | 2/2019 | Doudna et al. |
| 2019/0078119 A1 | 3/2019 | Wilson et al. |
| 2019/0106710 A1 | 4/2019 | Zhang et al. |
| 2019/0127713 A1 | 5/2019 | Gersbach et al. |
| 2019/0134221 A1 | 5/2019 | Bumcrot et al. |
| 2019/0136229 A1 | 5/2019 | Josephs et al. |
| 2019/0151476 A1 | 5/2019 | Gersbach et al. |
| 2019/0183932 A1 | 6/2019 | Mackall et al. |
| 2019/0194633 A1 | 6/2019 | Gersbach et al. |
| 2019/0201402 A1 | 7/2019 | Jiang et al. |
| 2019/0248854 A1 | 8/2019 | Tremblay et al. |
| 2019/0264232 A1 | 8/2019 | Hou et al. |
| 2019/0351074 A1 | 11/2019 | Ahituv et al. |
| 2019/0359959 A1 | 11/2019 | Jaenisch et al. |
| 2019/0374655 A1 | 12/2019 | Kabadi et al. |
| 2020/0002731 A1 | 1/2020 | Frendewey et al. |
| 2020/0056206 A1 | 2/2020 | Tremblay et al. |
| 2020/0080108 A1 | 3/2020 | Jaskula-Ranga et al. |
| 2020/0109406 A1 | 4/2020 | Miller et al. |
| 2020/0123533 A1 | 4/2020 | Wang et al. |
| 2020/0216549 A1 | 7/2020 | Fukumura et al. |
| 2020/0216810 A1 | 7/2020 | Metelitsa et al. |
| 2020/0260698 A1 | 8/2020 | Kyrychenko et al. |
| 2020/0318139 A1 | 10/2020 | Gersbach et al. |
| 2020/0332307 A1 | 10/2020 | Hummel et al. |
| 2020/0347105 A1 | 11/2020 | Gersbach et al. |
| 2021/0002665 A1 | 1/2021 | Gersbach et al. |
| 2021/0032654 A1 | 2/2021 | Gersbach et al. |
| 2021/0322577 A1 | 10/2021 | Lande et al. |
| 2022/0098561 A1 | 3/2022 | Gersbach et al. |
| 2022/0177879 A1 | 6/2022 | Gersbach et al. |
| 2022/0184229 A1 | 6/2022 | Gersbach et al. |
| 2022/0195406 A1 | 6/2022 | Gersbach et al. |
| 2022/0305141 A1 | 9/2022 | Gersbach et al. |
| 2022/0307015 A1 | 9/2022 | Gersbach et al. |
| 2022/0364124 A1 | 11/2022 | Gersbach et al. |
| 2022/0396790 A1 | 12/2022 | Gersbach et al. |
| 2023/0032846 A1 | 2/2023 | Gersbach et al. |
| 2023/0047669 A1 | 2/2023 | Josephs et al. |
| 2023/0383270 A1 | 11/2023 | Gersbach et al. |
| 2023/0383297 A1 | 11/2023 | Gersbach et al. |
| 2023/0392132 A1 | 12/2023 | Gersbach et al. |
| 2024/0026352 A1 | 1/2024 | Gersbach et al. |

FOREIGN PATENT DOCUMENTS

| | | |
|---|---|---|
| EP | 3209783 B1 | 11/2021 |
| EP | 3995584 A1 | 5/2022 |
| JP | 2015-534817 A | 12/2015 |
| JP | 2016-521452 A | 7/2016 |
| JP | 2016-521452 A2 | 7/2016 |
| JP | 2016-521975 A | 7/2016 |
| JP | 2016-523082 A | 8/2016 |
| KR | 20190134673 A | 12/2019 |
| WO | WO 1991/18114 A1 | 11/1991 |
| WO | WO 1992/000387 A1 | 1/1992 |
| WO | WO 1993/007883 A1 | 4/1993 |
| WO | WO 1993/024640 A2 | 12/1993 |
| WO | WO 1994/016737 A1 | 8/1994 |
| WO | WO 1998/053058 A1 | 11/1998 |
| WO | WO 1998/053059 A1 | 11/1998 |
| WO | WO 1998/053060 A1 | 11/1998 |
| WO | 2001/083793 A2 | 11/2001 |
| WO | WO 2001/083783 A2 | 11/2001 |
| WO | WO 2002/016536 A1 | 2/2002 |
| WO | WO 2003/016496 A2 | 2/2003 |
| WO | WO2003/072788 A1 | 9/2003 |
| WO | WO 2007/019301 A2 | 2/2007 |
| WO | WO 2008/006028 A2 | 1/2008 |
| WO | WO 2008/070859 A2 | 6/2008 |
| WO | WO 2010/075424 A2 | 7/2010 |
| WO | WO2010/144740 A1 | 12/2010 |
| WO | WO 2011/036640 A2 | 3/2011 |
| WO | 2011/141820 A1 | 11/2011 |
| WO | WO 2011/154427 A1 | 12/2011 |
| WO | WO 2012/136476 A1 | 10/2012 |
| WO | WO 2013/098244 A1 | 7/2013 |
| WO | WO 2013/163628 A2 | 10/2013 |
| WO | WO 2013/176772 A1 | 11/2013 |
| WO | WO 2014/018423 A2 | 1/2014 |
| WO | WO 2014/059255 A1 | 4/2014 |
| WO | WO 2014/065596 A1 | 5/2014 |
| WO | WO 2014/081855 A1 | 5/2014 |
| WO | 2014/093622 A2 | 6/2014 |
| WO | 2014/093712 A1 | 6/2014 |
| WO | WO 2014/089290 A1 | 6/2014 |
| WO | WO 2014/093479 A1 | 6/2014 |
| WO | WO 2014/093595 A1 | 6/2014 |
| WO | WO 2014/093655 A2 | 6/2014 |
| WO | WO 2014/093661 A2 | 6/2014 |
| WO | WO 2014/093709 A1 | 6/2014 |
| WO | WO 2014/144288 A1 | 9/2014 |
| WO | WO 2014/144592 A2 | 9/2014 |
| WO | WO 2014/186585 A2 | 11/2014 |
| WO | WO 2014/204726 A1 | 12/2014 |
| WO | WO 2015/006747 A2 | 1/2015 |
| WO | WO2015/035136 A2 | 3/2015 |
| WO | WO 2015/048690 A1 | 4/2015 |
| WO | WO 2015/070083 A1 | 5/2015 |
| WO | WO2015/089427 A1 | 6/2015 |
| WO | WO 2015/155686 A2 | 10/2015 |
| WO | WO2015/161276 A2 | 10/2015 |
| WO | 2016/011080 A2 | 1/2016 |
| WO | WO2016/011070 A2 | 1/2016 |
| WO | WO2016/049258 A2 | 3/2016 |
| WO | WO 2016/063264 A1 | 4/2016 |
| WO | WO 2016/070070 A1 | 5/2016 |
| WO | WO 2016/081924 A1 | 5/2016 |
| WO | WO2016/114972 A1 | 7/2016 |

(56) References Cited

FOREIGN PATENT DOCUMENTS

| | | |
|---|---|---|
| WO | WO2016/123578 A1 | 8/2016 |
| WO | WO 2016/161380 A1 | 10/2016 |
| WO | WO 2016/187717 A1 | 12/2016 |
| WO | WO 2017/015637 A1 | 1/2017 |
| WO | WO 2017/035416 A2 | 3/2017 |
| WO | WO 2017/049266 A2 | 3/2017 |
| WO | WO2017/049407 A1 | 3/2017 |
| WO | WO 2017/066497 A2 | 4/2017 |
| WO | WO 2017/070632 A2 | 4/2017 |
| WO | WO 2017/072590 A1 | 5/2017 |
| WO | WO 2017/075478 A2 | 5/2017 |
| WO | WO 2017/095967 A2 | 6/2017 |
| WO | WO 2017/139505 A2 | 8/2017 |
| WO | WO 2017/165859 A1 | 9/2017 |
| WO | 2017/180976 A1 | 10/2017 |
| WO | WO 2017/180915 A2 | 10/2017 |
| WO | WO 2017/193029 A2 | 11/2017 |
| WO | 2018/002812 A1 | 1/2018 |
| WO | WO 2018/017751 A1 | 1/2018 |
| WO | WO 2018/017754 A1 | 1/2018 |
| WO | WO 2018/031762 A1 | 2/2018 |
| WO | WO 2018/035388 A1 | 2/2018 |
| WO | WO 2018/035495 A1 | 2/2018 |
| WO | WO 2018/081504 A1 | 5/2018 |
| WO | WO 2018/098480 A1 | 5/2018 |
| WO | WO 2018/129296 A1 | 7/2018 |
| WO | 2018/162702 A1 | 9/2018 |
| WO | 2018/179578 A1 | 10/2018 |
| WO | WO 2018/191388 A1 | 10/2018 |
| WO | 2019/023291 A2 | 1/2019 |
| WO | WO 2019/002590 A1 | 1/2019 |
| WO | WO 2019/067786 A1 | 4/2019 |
| WO | WO 2019/077001 A1 | 4/2019 |
| WO | WO 2019/079514 A1 | 4/2019 |
| WO | 2019/084050 A1 | 5/2019 |
| WO | WO 2019/092505 A1 | 5/2019 |
| WO | 2019/113472 A1 | 6/2019 |
| WO | 2019/123014 A1 | 6/2019 |
| WO | WO 2019/144061 A1 | 7/2019 |
| WO | 2019/204750 A1 | 10/2019 |
| WO | WO 2019/232069 A1 | 12/2019 |
| WO | WO 2020/124257 A1 | 6/2020 |
| WO | WO 2020/163396 A1 | 8/2020 |
| WO | WO 2020/210776 A1 | 10/2020 |
| WO | WO 2020/214609 A1 | 10/2020 |
| WO | WO 2020/214613 A1 | 10/2020 |
| WO | WO 2020/257665 A1 | 12/2020 |
| WO | WO 2021/026516 A1 | 2/2021 |
| WO | WO 2021/034984 A2 | 2/2021 |
| WO | WO 2021/034987 A1 | 2/2021 |
| WO | WO 2021/055956 A1 | 3/2021 |
| WO | WO 2021/067878 A1 | 4/2021 |
| WO | WO 2021/113536 A1 | 6/2021 |
| WO | WO 2021/222268 A1 | 11/2021 |
| WO | WO 20217222314 A1 | 11/2021 |
| WO | WO 20217222327 A1 | 11/2021 |
| WO | WO 20217222328 A1 | 11/2021 |
| WO | WO 20217226555 A2 | 11/2021 |
| WO | 2022/038264 A1 | 2/2022 |
| WO | 2022/087321 A1 | 4/2022 |
| WO | 2022/104159 A1 | 5/2022 |
| WO | 2022/133062 A1 | 6/2022 |
| WO | WO 2022/187288 A2 | 9/2022 |
| WO | WO2023/200998 A2 | 10/2023 |

OTHER PUBLICATIONS

U.S. Appl. No. 63/330,679, filed Apr. 13, 2022.
U.S. Appl. No. 63/372,373, filed Mar. 8, 2022.
PCT/US2022/018400, Mar. 1, 2022.
U.S. Appl. No. 63/330,691, filed Apr. 13, 2022.
U.S. Appl. No. 17/471,935, filed Sep. 10, 2021.
U.S. Appl. No. 17/633,467, filed Feb. 7, 2022.
U.S. Appl. No. 63/335,122, filed Apr. 26, 2022.
U.S. Appl. No. 63/342,027, filed May 13, 2022.
Aartsma-Rus et al., "Antisense-mediated exon skipping: a versatile tool with therapeutic and research applications," RNA 13, 2007, 1609-1624.
Aartsma-Rus et al., "Exploring the frontiers of therapeutic exon skipping for Duchenne muscular dystrophy by double targeting within one or multiple exons," Mol Ther, 2006, 14:401-407.
Aartsma-Rus et al., "Theoretic applicability of antisense-mediated exon skipping for Duchenne muscular dystrophy mutations," Hum Mutat, 2009, 30:293-299.
Adler et al., "Nonviral direct conversion of primary mouse embryonic fibroblasts to neuronal cells," Molecular therapy, 2012 Nucleic acids 1, e32.
Aiuti et al., "Lentiviral hematopoietic stem cell gene therapy in patients with Wiskott-Aldrich syndrome," Science, 2013, 341(6148): p. 1233151.
Anders et al., "Differential expression analysis for sequence count data," Genome biology 11, 2010, R106.
Anguela et al., "Robust ZFN-mediated genome editing in adult hemophilic mice," Blood, 2013, 122:3283-3287.
Aoki et al., "Bodywide skipping of exons 45-55 in dystrophic mdx52 mice by systemic antisense delivery," Proc Natl Acad Sci USA, 2012, 109:13763-13768.
Bartsevich et al., "Engineered zinc finger proteins for controlling stem cell fate," Stem Cells 21, 2003, 632-637.
Beerli et al., "Chemically regulated zinc finger transcription factors," J Biol Chem, 2000, 275(42):32617-27.
Beerli et al., "Engineering polydactyl zinc-finger transcription factors," Nat Biotechnol 20, 2002, 135-141.
Beerli et al., "Positive and negative regulation of endogenous genes by designed transcription factors," Proc Natl Acad Sci U S A 97, 2000, 1495-1500.
Beerli et al., "Toward controlling gene expression at will: specific regulation of the erbB-2/HER-2 promoter by using polydactyl zinc finger proteins constructed from modular building blocks," Proc Natl Acad Sci U S A 95, 1998, 14628-14633.
Beltran et al., "Re-activation of a dormant tumor suppressor gene maspin by designed transcription factors," Oncogene 26, 2007, 2791-2798.
Benedetti et al., "Repair or Replace? Exploiting Novel Gene and Cell Therapy Strategies for Muscular Dystrophies," FEBS Journal, 2013, 280:4263-4280.
Berghella et al., "Reversible immortalization of human myogenic cells by site-specific excision of a retrovirally transferred oncogene," Human gene therapy 10, 1999, 1607-1617.
Bhakta et al., "Highly active zinc-finger nucleases by extended modular assembly," Genome Res, 2013, 530-538.
Bidou et al., "Sense from nonsense: therapies for premature stop codon diseases," Trends in Molecular Medicine 18, 2012, 679-688.
Blancafort et al., "Scanning the human genome with combinatorial transcription factor libraries," Nat Biotechnol 21, 2003, 269-274.
Boch et al., "Breaking the code of DNA binding specificity of TAL-type III effectors," Science 326, 2009, 1509.
Bowles et al., "Phase 1 Gene Therapy for Duchenne Muscular Dystrophy Using a Translation Optimized AAV Vector," Molecular Therapy 20, 2012, 443-455.
Brunet et al., "Chromosomal translocations induced at specific loci in human stem cells," Proc Natl Acad Sci USA, 2009, 106:10620-10625.
Buler et al., "Energy-sensing factors coactivator peroxisome proliferator-activated receptor gamma coactivator 1-alpha (PGC-1 alpha) and AMP-activated protein kinase control expression of inflammatory mediators in liver," The Journal of Biological Chemistry, Jan. 13, 2012, vol. 287, No. 3, pp. 1847-1860.
Bultmann et al., "Targeted transcriptional activation of silent oct4 pluripotency gene by combining designer TALEs and inhibition of epigenetic modifiers," Nucleic Acids Res 40, 2012, 5368-5377.
Cerletti et al., "Highly efficient, functional engraftment of skeletal muscle stem cells in dystrophic muscles," Cell 134, 2008, 37-47.
Cermak et al., "Efficient design and assembly of custom TALEN and other TAL effector-based constructs for DNA targeting," Nucleic Acids Res 30, 2011, pp. 1-11.

(56) References Cited

OTHER PUBLICATIONS

Chapdelaine et al., "Meganucleases can restore the reading frame of a mutual dystrophin," Gene therapy 17, 2010, 846-858.
Cheng et al., "Multiplexed activation of endogenous genes by CRISPR-on, an RNA-guided transcriptional activator system," Cell Res, 2013, 23(10):1163-1171.
Cho et al., "Analysis of off-target effects of CRISPR/Cas-derived RNA-guided endonucleases and nickases," Genome Res, 2014, 24:132-141.
Cho et al., "Targeted genome engineering in human cells with the Cas9 RNA-guided endonuclease," Nat Biotechnol 31, 2013, 230-232.
Christian et al., "Targeting DNA double-strand breaks with TAL effector nucleases," Genetics 186, 2010, 757-761.
Cirak et al., "Exon skipping and dystrophin restoration in patients with Duchenne muscular dystrophy after systemic phosphorodiamidate morpholino oligomer treatment: an open-label, phase 2, dose-escalation study," Lancet 378, 2011, 595-605.
Cong et al., "Multiplex Genome Engineering Using CRISPR/Cas Systems," Science 339, 2013, 819-823.
Cornu et al., "DNA-binding specificity is a major determinant of the activity and toxicity of zinc-finger nucleases," Mol Ther, 2008, 16:352-358.
Cornu et al., "Quantification of zinc finger nuclease-associated toxicity," Meth Mol Biol, 2010, 649:237-245.
Cradick et al., "CRISPR/Cas9 systems targeting beta-globin and CCR5 genes have substantial off-target activity," Nucleic Acids Res, 2013, 41(20):9584-92.
Darabi et al., "Human ES-and iPS-derived myogenic progenitors restore dystrophin and improve contractility upon transplantation in dystrophic mice," Cell Stem Cell 10, 2012, 610-619.
Dezawa et al., "Bone marrow stromal cells generate muscle cells and repair muscle degeneration," Science Signaling 309, 2005, 314-317.
Ding et al., "A TALEN Genome-Editing System for Generating Human Stem Cell-Based Disease Models," 2013, Cell Stem Cell 12, 238-251.
Ding et al., "Enhanced efficiency of human pluripotent stem cell genome editing through replacing TALENs with CRISPRs," Cell Stem Cell, 2013, 12:393-394.
Doyle et al., "TAL Effector-Nucleotide Targeter (TALE-NT) 2.0: tools for TAL effector design and target prediction," Nucleic Acids Res 40, 2012, W117-122.
Doyon et al., "Enhancing zinc-finger-nuclease activity with improved obligate heterodimeric architectures," Nat Methods 8, 2010, 74-79.
Edelstein et al., "Gene therapy clinical trials worldwide 1989-2004—an overview," J. Gene Med., 2004, vol. 6, pp. 597-602.
Esvelt et al., "Orthogonal Cas9 proteins for RNA-guided gene regulation and editing," Nature Methods 2013, 10(11):1116-21.
Farinelli et al., "Lentiviral vectors for the treatment of primary immunodeficiencies," J Inherit Metab Dis, 2014, 37:525-533.
Farzadfard et al., "Tunable and Multifunctional Eukaryotic Transcription Factors Based on CRISPR/Cas," ACS Synth Biol, 2013, 604-613.
Flanigan et al., "Mutational spectrum of DMD mutations in dystrophinopathy patients: application of modern diagnostic techniques to a large cohort," Human mutation 30, 2009, 1657-1666.
Fonfara et al., "Phylogeny of Cas9 determines functional exchangeability of dual-RNA and Cas9 among orthologous type II CRISPR-Cas systems," Nucleic Acids Res, 2013, 42(4):2577-2590.
Fu et al., "High-frequency off-target mutagenesis induced by CRISPR-Cas nucleases in human cells," Nat Biotechnol, 2013, 31(9):822-6.
Fu et al., "Improving CRISPR-Cas nuclease specificity using truncated guide RNAs," Nat Biotechnol 32, 2014, 279-284.
Gaj et al., "Targeted gene knockout by direct delivery of zinc-finger nuclease proteins," Nature Methods, 2012, 9(8):805-807.
Gaj et al., "ZFN, TALEN, and CRISPR/Cas-based methods for genome engineering," Trends Biotechnol, 2013, 31:397-405.
Garg et al., "Engineering synthetic TAL effectors with orthogonal target sites," Nucleic Acids Res 40, 2012, 7584-7595.
Gertz et al., "Transposase mediated construction of RNA-seq libraries," Genome Res 22, 2012, 134-141.
Goemans et al., "Systemic administration of PRO051 in Duchenne's muscular dystrophy," The New England journal of medicine 364, 2011, 1513-1522.
Gou et al., "A novel approach for the construction of multiple shRNA expression vectors," J Gene Med, 2007, 9(9):751-63.
Graslund et al., "Exploring strategies for the design of artificial transcription factors: targeting sites proximal to known regulatory regions for the induction of gamma-globin expression and the treatment of sickle cell disease," J Biol Chem 280, 2005, 3707-3714.
Gregorevic et al., "Systemic delivery of genes to striated muscles using adeno-associated viral vectors," Nat Med, 2004, 10:828-834.
Guo et al., "Directed evolution of an enhanced and highly efficient FokI cleavage domain for zinc finger nucleases," J Mol Biol, 2010, 400:96-107.
Guschin et al., "A rapid and general assay for monitoring endogenous gene modification," Methods Mol Biol 649, 2010, 247-256.
Hockemeyer et al., "Efficient targeting of expressed and silent genes in human ESCs and iPSCs using zinc-finger nucleases," Nat Biotechnol, 2009, 27(9):851-7.
Hockemeyer et al., "Genetic engineering of human pluripotent cells using TALE nucleases," Nat Biotechnol 29, 2011, 731-734.
Hoffman et al., "Dystrophin: the protein product of the Duchenne muscular dystrophy locus," Cell, 1987, 51:919.
Hou et al., "Efficient genome engineering in human pluripotent stem cells using Cas9 from Neisseria meningitidis," Proc Natl Acad Sci USA, 2013, 110:15644-15649.
Hsu et al., "Dissecting Neural Function Using Targeted Genome Engineering Technologies," ACS Chem. Neurosci., 2012, pp. 603-610.
Hsu et al., "DNA targeting specificity of RNA-guided Cas9 nucleases," Nature Biotechnology 31, 2013, 827-832.
Humbert et al., "Targeted gene therapies: tools, applications, optimization", Critical Reviews in Biochemistry and Molecular Biology, CRC Press, vol. 47, No. 3, Apr. 2012, pp. 264-281.
Hwang et al., "Efficient genome editing in zebrafish using CRISPR-Cas system," Nat Biotechnol, 2013, 31(3):227-9.
Jinek et al., "A programmable dual-RNA-guided DNA endonuclease in adaptive bacterial immunity," Science 337, 2012, 816-821.
Jinek et al., "RNA-programmed genome editing in human cells," eLife 2, 2013, e00471.
Jinek et al., "Structures of Cas9 endonucleases reveal RNA-mediated conformational activation," Science, 2014, 343(6176):1247997.
Joung et al., "TALENs: a widely applicable technology for targeted genome editing," Nature Reviews Molecular Cell Biology 14, 2013, 49-55.
Kayali et al., "Site-directed gene repair of the dystrophin gene mediated by PNA-ssODNs," Human Molecular Genetics, vol. 19, No. 16, Aug. 15, 2010, pp. 3266-3281.
Kearns et al., "Cas9 effector-mediated regulation of transcription and differentiation in human pluripotent stem cells," Development, 2014, 141(1):219-23.
Kim et al., "Surrogate reporters for enrichment of cells with nuclease-induced mutations," Nat Methods, 2011, 8:941-943.
Kim et al., "TALENs and ZFNs are associated with different mutation signatures," Nat Methods, 2013, 10(3):185.
Kimura et al., "Cell-lineage regulated myogenesis for dystrophin replacement: a novel therapeutic approach for treatment of muscular dystrophy," Hum Mol Genet 17, 2008, 2507-2517.
Konermann et al., "Optical control of mammalian endogenous transcription and epigenetic states," Nature, 2013, 500(7463): 472-6.
Konieczny et al., "Gene and cell-mediated therapies for muscular dystrophy," Muscle Nerve, 2013, 47:649-663.
Kubokawa et al., "Molecular characterization of the 5'-UTR of retinal dystrophin reveals a cryptic intron that regulates translational activity," Molecular Vision, 2010, vol. 16, pp. 2590-2597.
Kwa et al., "Chromatin modifying agents—the cutting edge of anticancer therapy," Drug Discovery Today, 2011, 16(13/14):543-547.

(56) References Cited

OTHER PUBLICATIONS

Kyte et al., "A Simple Method for Displaying the Hydropathic Character of a Protein," J. Mol. Biol., 1982, 157:105-132.
Langmead et al., "Ultrafast and memory-efficient alignment of short DNA sequences to the human genome," Genome biology 10, 2009, R25.
Larson et al., "CRISPR interference (CRISPRi) for sequence-editing control of gene expression," Nat Protoc, 2013, 8(11): 2180-96.
Latta-Mahieu et al., "Gene transfer of a chimeric trans-activator is immunogenic and results in short-lived transgene expression," Human Gene Therapy, Sep. 2002, vol. 13, No. 13, pp. 1611-1620.
Lattanzi et al., "High efficiency myogenic conversion of human fibroblasts by adenoviral vector-mediated MyoD gene transfer. An alternative strategy for ex vivo gene therapy of primary myopathies," The Journal of clinical investigation 101, 1998, 2119-2128.
Lee et al., "Targeted chromosomal deletions in human cells using zinc finger nucleases," Genome research 20, 2010, 81-89.
Li et al., "In vivo genome editing restores haemostasis in a mouse model of haemophilia," Nature 475, 2011, 217-221.
Li et al., "Marginal level dystrophin expression improves clinical outcome in a strain of dystrophin/utrophin double knockout mice," PLoS One, 2010, 5:e15286.
Li et al., "Modularly assembled designer TAL effector nucleases for targeted gene knockout and gene replacement in eukaryotes," Nucleic Acids Research, 2011, vol. 39, No. 14, pp. 6315-6325.
Li et al., "Transcription activator-like effector hybrids for conditional control and rewiring of chromosomal transgene expression," Scientific reports 2, 2012, 897.
Liang et al., "Engineering biological systems with synthetic RNA molecules," Mol Cell 43, 2011, 915-926.
Lohmueller et al., "A tunable zinc finger-based framework for Boolean logic computation in mammalian cells," Nucleic Acids Res 40, 2012, 5180-5187.
Lovric et al., "Terminal Differentiation of Cardiac and Skeletal Myocytes Induces Permissivity to AAV Transduction by Relieving Inhibition Imposed by DNA Damage Response Proteins," Molecular Therapy, 2012, 2087-2097.
Lu et al., "The status of exon skipping as a therapeutic approach to duchenne muscular dystrophy," Molecular Therapy 19, 2011, 9-15.
Lund et al., "Promoter-targeted phage display selections with preassembled synthetic zinc finger libraries for endogenous gene regulation," Journal of Molecular Biology, 2004, vol. 340, pp. 599-613.
Luo et al., "Synthetic DNA delivery systems," Nature Biotechnology, 2000, vol. 18, pp. 33-37.
Maeder et al., "Robust, synergistic regulation of human gene expression using TALE activators," Nature Methods, vol. 10, No. 3, pp. 243-246, Feb. 10, 2013, including pp. 1/14-14/14 of Supplementary Material.
Maeder, "Targeted DNA demethylation and activation of endogenous genes using programmable TALE-TET1 fusion proteins," Nat Biotechnol, 2013, 31(12): 1137-42.
Mali et al., "Cas9 as a versatile tool for engineering biology," Nat Methods, 2013, 10(10): 957-63.
Mali et al., "CAS9 transcriptional activators for target specificity screening and paired nickases for cooperative genome engineering," Nat Biotechnol, 2013, 31(9): 833-8.
Mali et al., "RNA-Guided Human Genome Engineering via Cas9," Science 339, 2013, 823-826.
Mamchaoui et al., "Immortalized pathological human myoblasts: towards a universal tool for the study of neuromuscular disorders," Skelet Muscle 1, 2011, 1-11.
Mendell et al., "Dystrophin immunity in Duchenne's muscular dystrophy," New England Journal of Medicine 363, 2010, 1429-1437.
Mendenhall et al., "Locus-specific editing of histone modification at endogenous enhancers," Nat Biotechnol, 2013, 31(12): 1133-6.
Mercer et al., "Regulation of Endogenous Human Gene Expression by Ligand-Inducible TALE Transcription Factors," ACS Synth Biol, 2013.
Miller et al., "A TALE nuclease architecture for efficient genome editing," Nat Biotechnol 29, 2011, 143-148.
Moscou et al., "A simple cipher governs DNA recognition by TAL effectors," Science 326, 2009, 1501.
Murphy et al., "The in vitro transcription of the 7SK RNA gene by RNA polymerase III is dependable only on the presence of an upstream promoter," Cell, 1987, 51:81-87.
Mussolino et al., "A novel TALE nuclease scaffold enables high genome editing activity in combination with low toxicity," Nucleic Acids Res 39, 2011, 9283-9293.
Myslinski et al., "An unusually compact external promoter for RNA polymerase III transcription of the human H1RNA gene," Nucleic Acids Res, 2001, 29:2502-2509.
Negroni et al., "In Vivo Myogenic Potential of Human CD133+ Muscle-derived Stem Cells: A Quantitative Study," Molecular Therapy 17, 2009, 1771-1778.
Nishimasu et al., "Crystal structure of cas9 in complex with guide RNA and target DNA Cell," 2014, 156(5): 935-49.
Ohshima et al., "Nucleotide sequence of mouse genomic loci including a gene or pseudogene for U6 (4.85) nuclear RNA," Nucleic Acids Res, 1981, 9:5145-5158.
Ousterout et al., "Reading frame correction by targeted genome editing restores dystrophin expression in cells from Duchenne muscular dystrophy patients," Mol Ther, 2013, 21:1718-1726.
Palu et al., "In pursuit of new developments for gene therapy of human diseases," J. Biotechnol, 1999, vol. 68, pp. 1-13.
Papayannakos et al., "Understanding lentiviral vector chromatin targeting: working to reduce insertional mutagenic potential for gene therapy," Gene Ther, 2013, 20(6): 581-8.
Park et al., "Phenotypic alteration of eukaryotic cells using randomized libraries of artificial transcription factors," Nat Biotechnol 21, 2003, 1208-1214.
Pattanayak et al., "High-throughput profiling of off-target DNA cleavage reveals RNA-programmed Cas9 nuclease specificity," Nat Biotechnol, 2013, 31(9): 839-43.
Peault et al., "Stem and progenitor cells in skeletal muscle development, maintenance, and therapy," Molecular Therapy 15, 2007, 867-877.
Perez et al., "Establishment of HIV-1 resistance in CD4+ T cells by genome editing using zinc-finger nucleases," Nature biotechnology 26, 2008, 808-816.
Perez-Pinera et al., "Advances in targeted genome editing," Current Opinion in Chemical Biology 16, 2012, 268-277.
Perez-Pinera et al., "Gene targeting to the ROSA26 locus directed by engineered zinc finger nucleases," Nucleic Acids Research, 2012, 40:3741-3752.
Perez-Pinera et al., "RNA-guided gene activation by CRISPR-Cas9-based transcription factors," Nat Methods, 2013, 10:973-976.
Perez-Pinera et al., "Synergistic and tunable human gene activation by combinations of synthetic transcription factors," Nature Methods, vol. 10, No. 3, pp. 239-244, Feb. 3, 2013, including pp. 1/12-12-12 of Supplementary Material.
Perez-Pinera et al., "Synergistic Transcriptional Activation by Combinations of Engineered TALEs" was publicly presented at the American Society of Gene & Cell Therapy's 15th Annual Meeting in Philadelphia, Pennsylvania during the Late Abstracts Poster Session III: Saturday, May 19, 2012. Abstract 855.
Persons, "Lentiviral vector gene therapy: effective and safe?" Mol Ther, 2010, 18(5): 861-2.
Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23:635-646.
Pichavant et al., "Current status of pharmaceutical and genetic therapeutic approaches to treat DMD," Molecular Therapy 19, 2011, 830-840.
Polstein et al., "Light-inducible spatiotemporal control of gene activation by customizable zinc finger transcription factors," J Am Chem Soc, 2012, 134(40): 16480-3.
Popplewell et al., "Gene correction of a duchenne muscular dystrophy mutation by meganuclease-enhanced exon knock-in," Hum Gene Ther, 2013, 24:692-701.

(56) References Cited

OTHER PUBLICATIONS

Qi et al., "Repurposing CRISPR as an RNA-guided platform for sequence-specific control of gene expression," Cell 152, 2013, 1173-1183.
Ran et al., "Double nicking by RNA-guided CRISPR Cas9 for enhanced genome editing specificity," Cell, 2013, 154(6): 1380-9.
Rebar et al., "Induction of angiogenesis in a mouse model using engineered transcription factors," Nat Med 8, 2002, 1427-1432.
Reyon et al., "FLASH assembly of TALENs for high-throughput genome editing," Nat Biotechnol 30, 2012, 460-465.
Rousseau et al., "Endonucleases: tools to correct the dystrophin gene" The Journal of Gene Medicine, 2011, vol. 13, pp. 522-537.
Saito et al., "Specific activation of microRNA-127 with downregulation of the proto-oncogene BCL6 by chromatin-modifying drugs in human cancer cells," Cancer Cell, 2006, vol. 9, pp. 435-443.
Salmon et al., "Production and titration of lentiviral vectors," Curr Protoc Neurosci, 2006, Chapter 4: Unit 4 21.
Sambrook et al., Molecular Cloning and Laboratory manual, Second Ed., Cold Spring Harbor, 1989, pp. 16.7-16.8.
Schmid-Burgk et al., "A ligation-independent cloning technique for high-throughput of transcription activator-like effector genes," Nat Biotechnol 31, 2012, 76-81.
Scholze et al., "TAL effectors are remote controls for gene activation," Current Opinion in Microbiology, Jan. 2011, vol. 14, pp. 47-53.
Schultz et al., "Recombinant adeno-associated virus transduction and integration," Molecular Therapy 16, 2008, 1189-1199.
Sebastiano et al., "In Situ Genetic Correction of the Sickle Cell Anemia Mutation in Human Induced Pluripotent Stem Cells Using Engineered Zinc Finger Nucleases," Stem Cells 29, 2011, 1717-1726.
Seidel et al., "Chromatin-modifygin agents in anti-cancer therapy," Biochimie, 2012, vol. 94, pp. 2264-2279.
Seto et al., "Gene Replacement Therapies for Duchenne Muscular Dystrophy Using Adeno-Associated Viral Vectors," Current Gene Therapy, 2012, 12:139-151.
Sharma et al., "Efficiency of nonhomologous DNA and joining varies among somatic tissues, despite similarity in mechanism," Cellular and Molecular Life Science 68, 2011, 661-676.
Silva et al., "Meganucleases and other tools for targeted genome engineering: perspective and challenges for gene therapy," Current gene therapy, 2011, 11:11-27.
Şöllü et al., "Autonomous zinc-finger nuclease pairs for targeted chromosomal deletion," Nucleic acids research 38, 2010, 8269-8276.
Song et al., "Dnase-seq: a high-resolution technique for mapping active gene regulatory elements across the genome from mammalian cells," Cold Spring Harbor protocols 2010, 2010(2):11.
Song et al., "Open chromatin defined by DNaseI and FAIRE identifies regulatory elements that shape cell-type identify," Genome Res 21, 2011, 1757-1767.
Sun et al., "Optimized TAL effector nucleases (TALENs) for use in treatment of sickle cell disease," Molecular bioSystems 8, 2012, 1255-1263.
Szyf, "Epigenetics, DNA methylation, and chromatin modifying drugs," Annual Review of Pharmacology and Toxicology, 2009, vol. 49, pp. 243-263.
Takeshima et al., "Mutation spectrum of the dystrophin gene in 442 Duchene/Becker muscular dystrophy cases from one Japanese referral center," Journal of Human Genetics, 2010, 55:379-388.
Taniguchi-Ikeda et al., "Pathogenic exon-trapping by SVA retrotransposon and rescue in Fukuyama muscular dystrophy," Nature 478, 2011, 127-131.
Tebas et al., "Gene editing of CCR5 in autologous CD4 T cells of persons infected with HIV," N Engl J Med, 2014, 370:901-910.
Tedesco et al., "Repairing skeletal muscle: regenerative potential of skeletal muscle stem cells," J Clin Invest, 2010, 120:11-19.
Tedesco et al., "Stem Cell-Mediated Transfer of a Human Artificial Chromosome Ameliorates Musculat Dystrophy," Science Translational Medicine 3, 2011, 96ra78-96ra78.
Tedesco et al., "Transplantation of Genetically Corrected Human iPSC-Derived Progenitors in Mice with Limb-Girdle Muscular Dystrophy," Science Translational Medicine 4, 2012, 140ra189.
Urnov et al., "Highly efficient endogenous human gene correction using designed zinc-finger nucleases," Nature 435, 2005, 646-651.
Van Putten et al., "Low dystrophin levels in heart can delay heart failure in mdx mice," J Mol Cell Cardiol, 2014, 69C:17-23.
Van Putten et al., "Low dystrophin levels increase survival and improve muscle pathology and function in dystrophin/utrophin double-knockout mice," FASEB J, 2013, 27:2484-2495.
Verma et al., "Gene Therapy: Twenty-first century medicine," Annual Review of Biochemistry, 2005, vol. 74, pp. 711-738.
Verma et al., "Gene therapy—promises, problems and prospects," Nature, 1997, vol. 389, pp. 239-242.
Vierbuchen et al., "Direct conversion of fibroblasts to functional neurons by defined factors," Nature 463, 2010, 1035-1041.
Wang et al., "Adeno-associated virus vector carrying human minidystrophin genes effectively ameliorates muscular dystrophy in mdx mouse model," Proc Natl Acad Sci US A., 2000, 97(25):13714-13719.
Wang et al., "One-Step Generation of Mice Carrying Mutations in Multiple Genes by CRISPR-Cas-Mediated Genome Engineering," Cell, 2013, 153(4): 910-8.
Wein et al., "Efficient bypass of mutations in dysferlin deficient patient cells by antisense-induced exon skipping," Hum Mutat 31, 2010, 136-142.
Welch et al., "PTC124 targets genetic disorders caused by nonsense mutations," Nature 447, 2007, 87-91.
Yan et al., "Drugging the undruggable: Transcription therapy for cancer," Biochimica et Biophysica Acta (BBA)—Reviews on Cancer, Jan. 2013, vol. 1835, No. 1, pp. 76-85.
Yang, "Optimization of scarless human stem cell genome editing," Nucleic Acids Res, 2013, 41:9049-9061.
Yusa et al., "Targeted gene correction of α1-antitrypsin deficiency in induced pluripotent stem cells," Nature 478, 2011, 391-394.
Zhang et al. "Efficient construction of sequence-specific TAL effectors for modulating mammalian transcription," Nat Biotechnol 29, 2011, 149-153.
Zhu et al., "Cellular senescence in human telomerase reverse transcriptase and cyclin-dependent kinase 4: consequences in aging muscle and therapeutic strategies for muscular dystrophies," Aging cell 6, 2007, 515-523.
Zou et al., "Site-specific gene correction of a point mutation in human iPS cells derived from an adult patient with sickle cell disease," Blood 118, 2011, 4599-4608.
International Search Report and Written Opinion for Application No. PCT/US14/41190 dated Dec. 17, 2014 (14 pages).
International Search Report and Written Opinion for Application No. PCT/US13/38536 dated Nov. 29, 2013 (27 pages).
European Extended Search Report for Application No. 13781472.9 dated Feb. 3, 2016 (11 pages).
European Examination Report for Application No. 13781472.9 dated Mar. 2, 2017 (5 pages).
European Patent Office Action for Application No. 13781472.9 dated Jan. 4, 2018 (4 pages).
European Patent Office Extended Search Report for Application No. 19179921.2 dated Oct. 17, 2019 (10 pages).
European Patent Office Action for Application No. 19179921.2 dated Jan. 29, 2021 (5 pages).
United States Patent Office Action for U.S. Appl. No. 14/220,116 dated Jul. 22, 2015 (26 pages).
United States Patent Office Final Action for U.S. Appl. No. 14/220,116 dated May 4, 2016 (29 pages).
United States Patent Office Action for U.S. Appl. No. 14/220,116 dated Dec. 2, 2016 (16 pages).
United States Patent Office Action for U.S. Appl. No. 14/220,116 dated Jul. 19, 2017 (15 pages).
United States Patent Office Notice of Allowance for U.S. Appl. No. 14/220,116 dated Sep. 19, 2017 (8 pages).
United States Patent Office Action for U.S. Appl. No. 14/397,420 dated Jun. 2, 2016 (8 pages).
United States Patent Office Action for U.S. Appl. No. 14/397,420 dated Oct. 5, 2016 (10 pages).

(56) References Cited

OTHER PUBLICATIONS

United States Patent Office Action for U.S. Appl. No. 14/895,316 dated Dec. 15, 2016 (13 pages).
United States Patent Office Action for U.S. Appl. No. 14/895,316 dated Mar. 21, 2018 (8 pages).
United States Patent Office Action for U.S. Appl. No. 14/895,316 dated Oct. 22, 2018 (11 pages).
United States Patent Office Action for U.S. Appl. No. 14/895,316 dated Apr. 19, 2019 (11 pages).
United States Patent Office Notice of Allowance for U.S. Appl. No. 14/895,316 dated Sep. 30, 2019 (9 pages).
United States Patent Office Notice of Allowance for U.S. Appl. No. 14/895,316 dated Jan. 27, 2020 (7 pages).
United States Patent Office Action for U.S. Appl. No. 15/634,425 dated Aug. 8, 2019 (10 pages).
United States Patent Office Notice of Allowance for U.S. Appl. No. 15/634,425 dated Mar. 9, 2020 (8 pages).
United States Patent Office Action for U.S. Appl. No. 15/789,348 dated Feb. 22, 2018 (14 pages).
United States Patent Office Action for U.S. Appl. No. 15/789,348 dated Aug. 13, 2018 (15 pages).
United States Patent Office Action for U.S. Appl. No. 15/789,348 dated May 22, 2019 (13 pages).
United States Patent Office Action for U.S. Appl. No. 15/789,348 dated Dec. 10, 2019 (18 pages).
United States Patent Office Action for U.S. Appl. No. 15/789,348 dated Jun. 26, 2020 (25 pages).
United States Patent Office Action for U.S. Appl. No. 15/991,333 dated Apr. 19, 2019 (12 pages).
United States Patent Office Action for U.S. Appl. No. 15/991,333 dated Oct. 4, 2019 (6 pages).
United State Patent Office Notice of Allowance for U.S. Appl. No. 15/991,333 dated Apr. 13, 2020 (8 pages).
United States Patent Office Action for U.S. Appl. No. 15/789,348 dated Jan. 27, 2021 (16 pages).
Wang et al., "Efficient delivery of genome-editing proteins using bioreducible lipid nanoparticles," Proc Natl Acad USA, 2016, 113(11): 2868-2873.
Yang et al., "Gene Reactivation by 5-Aza-2'-Deoxycytidine-Induced Demethylation Requires SRCAP-Mediated HZA.Z Insertion to Establish Nucleosome Depleted Regions", PLoS Genetics, 2012, vol. 8, Issue 3, e1002604, 12 pages.
Zenser et al., "A new TAP system for isolation of plant protein complexes and subsequent mass-spec analysis," <https://www.sigmaaldrich.com/deepweb/assets/sigmaaldrich/product/documents/388/028/flag_ha_tap_poster.pdf> published 2008, printed as pp. 1/4-4/4.
United States Patent Office Action for U.S. Appl. No. 15/789,348 dated Sep. 21, 2021 (20 pages).
United States Patent Office Action for U.S. Appl. No. 16/858,689 dated Nov. 16, 2021 (14 pages).
U.S. Appl. No. 17/603,243, filed Oct. 12, 2021.
U.S. Appl. No. 17/603,329, filed Oct. 12, 2021.
U.S. Appl. No. 17/603,330, filed Oct. 12, 2021.
PCT/US2021/056122, Oct. 21, 2021.
PCT/US2021/054292, Oct. 8, 2021.
PCT/US2021/054636, Oct. 12, 2021.
PCT/US2021/059270, Nov. 12, 2021.
United States Patent Office Action for U.S. Appl. No. 16/927,679 dated Jun. 14, 2022 (11 pages).
Ousterout et al., "Genetic Correction of Duchenne Muscular Dystrophy Using Zinc Finger Nucleases," Mol. Ther., 2013, vol. 21, Supplement 1, 292, p. S111-S112.
Rousseau et al., "New TALENs To Correct the Reading Frame of Exon 54 of the Dystrophin Gene," Mol. Ther., 2013, vol. 21, Supplement 1, 293, p. S112.
United States Patent Office Action for U.S. Appl. No. 16/858,689 dated Mar. 4, 2022 (8 pages).
United States Patent Office Action for U.S. Appl. No. 15/789,348 dated Mar. 21, 2022 (23 pages).
'T Hoen et al., "Generation and characterization of transgenic mice with the full-length human DMD gene," J. Biol. Chem., 2008, 283: 5899-5907.
Acosta et al., "Use of two gRNAs for CRISPR/Cas9 improves bi-allelic homologous recombination efficiency in mouse embryonic stem cells," Genesis, 2018, 56(5): 1-8.
Adamson et al., "A Multiplexed Single-Cell CRISPR Screening Platform Enables Systematic Dissection of the Unfolded Protein Response," Cell, 2016, 167: 1867-1882 e1821.
Adamson et al., "A Multiplexed Single-Cell CRISPR Screening Platform Enables Systematic Dissection of the Unfolded Protein Response," Cell, 2016, 167: 1867-1882.e21.
Aguilar et al., "Transcriptional and Chromatin Dynamics of Muscle Regeneration after Severe Trauma," Stem Cell Rep, 2016, 7: 983-997.
Ahlenius et al., "FoxO3 regulates neuronal reprogramming of cells from postnatal and aging mice," Proc Natl Acad Sci U S A, 2016, 113: 8514-8519.
Albuquerque et al., "Mammalian nicotinic acetylcholine receptors: from structure to function," Physiol Rev, 2009, 89: 73-120.
Aloia, "Epigenetic Regulation of Cell-Fate Changes That Determine Adult Liver Regeneration After Injury," Front. Cell Dev. Biol., 2021, 9: 643055.
Amabile et al., "Inheritable Silencing of Endogenous Genes by Hit-and-Run Targeted Epigenetic Editing," Cell, 2016, 167(1): 219-232.e14.
Amabile et al., "Permanent Epigenetic Silencing of Human Genes With Artificial Transcriptional Repressors,", Molecular Therapy, 2015, 23(Suppl. 1): S275.
Amoasii et al., "Gene editing restores dystrophin expression in a canine model of Duchenne muscular dystrophy," Science, 2018, 362: 86-91.
Amoasii et al., "Single-cut genome editing restores dystrophin expression in a new mouse model of muscular dystrophy," Sci Transl Med, Nov. 2017, 9(418): eaan8081.
Andersen et al., "Dual role of delta-like 1 homolog (DLK1) in skeletal muscle development and adult muscle regeneration," Development, 2013, 140: 3743-3753.
Arechavala-Gomeza et al., "Comparative analysis of antisense oligonucleotide sequences for targeted skipping of exon 51 during dystrophin pre-mRNA splicing in human muscle," Human Gene Therapy, 2007, 18: 798-810.
Arnett et al., "Adeno-associated viral vectors do not efficiently target muscle satellite cells," Molecular Therapy Methods & Clinical Development, 2014, 1: 14038.
Asokan et al., "Reengineering a receptor footprint of adeno-associated virus enables selective and systemic gene transfer to muscle," Nat Biotechnol, 2010, 28: 79-82.
Asrani et al., "Burden of liver diseases in the world," J Hepatol, 2019, 70(1): 151-171.
Bae et al., "Cas-OFFinder: a fast and versatile algorithm that searches for potential off-target sites of Cas9 RNA-guided endonucleases," Bioinformatics, 2014, 30: 1473-1475.
Balboa et al., "Conditionally Stabilized dCas9 Activator for Controlling Gene Expression in Human Cell Reprogramming and Differentiation," Stem Cell Rep, 2015, 5: 448-459.
Baratta et al., "Cellular organization of normal mouse liver: a histological, quantitative immunocytochemical, and fine structural analysis," Histochem Cell Biol, 2009, 131(6): 713-726.
Barberi et al., "Derivation of engraftable skeletal myoblasts from human embryonic stem cells," Nat Med, 2007, 13: 642-648.
Barr et al., "Predominant Expression of Alternative PAX3 and PAX7 Forms in Myogenic and Neural Tumor Cell Lines," Cancer Res, 1999, 59: 5443-5448.
Barrangou et al., "CRISPR provides acquired resistance against viruses in prokaryotes," Science, 2007, 315(5819): 1709-1712.
Bartel et al., "Isolation of new ribozymes from a large pool of random sequences," Science, 1993, 261(5127): 1411-1418.
Bauer et al., "An erythroid enhancer of BCL11A subject to genetic variation determines fetal hemoglobin level," Science 342, 2013, 253-257.
Beaudry et al., "Directed evolution of an RNA enzyme," Science, 1992, 257(5070): 635-641.

(56) References Cited

OTHER PUBLICATIONS

Bengtsson et al., "Muscle-specific CRISPR/Cas9 dystrophin gene editing ameliorates pathophysiology in a mouse model for Duchenne muscular dystrophy," Nat Commun, 2017, 8: 1-10.
Bernstein et al., "An integrated encyclopedia of DNA elements in the human genome," Nature, 2012, 489: 57-74.
Bieth et al., "Highly restricted deletion of the SNORD116 region is implicated in Prader-Willi Syndrome," Eur J Hum Genet, 2015, 23: 252-255.
Bittel et al., "Prader-Willi syndrome: clinical genetics, cytogenetics and molecular biology," Expert Rev Mol Med, 2005, 7(14): 1-20.
Black et al., "Targeted Epigenetic Remodeling of Endogenous Loci by CRISPR/Cas9-Based Transcriptional Activators Directly Converts Fibroblasts to Neuronal Cells," Cell Stem Cell, 2016, 19: 406-414.
Bladen et al., "The TREAT-NMD DMD Global Database: analysis of more than 7,000 Duchenne muscular dystrophy mutations," Human Mutation, 2015, 36(4):395-402.
Blakemore et al., "Editing of Human Genes May Begin by Year's End in the U.S." Smithsonian.com, <https://www.smithsonianmag.com/smart-news/editing-human-genes-may-begin-years-end-us-180959532/?no-ist> 2016.
Blancafort et al., "Writing and rewriting the epigenetic code of cancer cells: from engineered proteins to small molecules," Mol. Pharmacol., 2013, 83(3): 563-576.
Boldrin et al., "Donor satellite cell engraftment is significantly augmented when the host niche is preserved and endogenous satellite cells are incapacitated," Stem Cells, 2012, 30: 1971-1984.
Bolger et al., "Trimmomatic: a flexible trimmer for Illumina sequence data," Bioinformatics, 2014, 30: 2114-2120.
Braasch et al., "Novel Antisense and Peptide Nucleic Acid Strategies for Controlling Gene Expression," Biochemistry, 2002, 41: 4503-4510.
Breaker et al., "Inventing and improving ribozyme function rational design versus iterative selection methods," TIBTECH, 1994, 12: 268-274.
Breaker, "Are engineered proteins getting competition from RNA?," Curr. Op. Biotech., 1996, 7(4): 442-448.
Briguet et al., "Histological parameters for the quantitative assessment of muscular dystrophy in the mdx-mouse," Neuromuscul. Disord., 2004, 14: 675-682.
Briner et al., "Guide RNA Functional Modules Direct Cas9 Activity and Orthogonality," Molecular Cell, 2014, 56(2): 333-339.
Briner et al., "Lactobacillus buchneri genotyping on the basis of clustered regularly interspaced short palindromic repeat (CRISPR) locus diversity," Appl. Environ. Microbiol., 2014, 80: 994-1001.
Brummelkamp et al., "A system for stable expression of short interfering RNAs in mammalian cells," Science, 2002, 296(5567): 550-553.
Brunger et al., "CRISPR/Cas9 Editing of Murine Induced Pluripotent Stem Cells for Engineering Inflammation-Resistant Tissues," Arthritis Rheumatol, 2017, 69: 1111-1121.
Brunger et al., "Genome Engineering of Stem Cells for Autonomously Regulated, Closed-Loop Delivery of Biologic Drugs," Stem Cell Reports, 2017, 8: 1202-1213.
Buenrostro et al., "Transposition of native chromatin for fast and sensitive epigenomic profiling of open chromatin, DNA-binding proteins and nucleosome position," Nat Methods, 2013, 10: 1213-1218.
Buiting, "Prader-Willi syndrome and Angelman syndrome," Am J Med Genet C Semin Med Genet, 2010, 154C(3): 365-376.
Burnett et al., "Deficiency in prohormone convertase PC1 impairs prohormone processing in Prader-Willi syndrome," J Clin Invest, 2017, 127: 293-305.
Busskamp et al., "Rapid neurogenesis through transcriptional activation in human stem cells," Mol Syst Biol, 2014, 10: 760.
Cano-Rodriguez et al., "Writing of H3K4Me3 overcomes epigenetic silencing in a sustained but context-dependent manner," Nat Commun, 2016, 7: 12284.
Canver et al., "BCL11A enhancer dissection by Cas9-mediated in situ saturating mutagenesis," Nature, 2015, 527: 192-197.
Carroll, "A CRISPR approach to gene targeting," Molecular Therapy, 2012, 20: 1658-1660.
Cassidy et al., "Prader-Willi syndrome," Eur J Hum Genet, 2009, 17(1): 3-13.
Cassidy et al., "Prader-Willi syndrome," Genet Med, 2012, 14: 10-26.
Cencic et al., "Protospacer adjacent motif (PAM)-distal sequences engage CRISPR Cas9 DNA target cleavage," PLoS one, 2014, 9, e109213, 13 pages.
Chal et al., "Differentiation of pluripotent stem cells to muscle fiber to model Duchenne muscular dystrophy," Nat Biotechnol, 2015, 33: 962-969.
Chamberlain et al., "Progress toward Gene Therapy for Duchenne Muscular Dystrophy, " Mol. Ther., 2017, 25: 1125-1131.
Chanda et al., "Generation of induced neuronal cells by the single reprogramming factor ASCL1," Stem Cell Reports, 2014, 3: 282-296.
Chang et al., "Integrating Combinatorial Lipid Nanoparticle and Chemically Modified Protein for Intracellular Delivery and Genome Editing," Acc. Chem. Res., 2019, 52: 665-675.
Cheloufi et al., "The histone chaperone CAF-1 safeguards somatic cell identity," Nature, 2015, 528: 218-224.
Chen et al., "Acetylation of RelA at discrete sites regulates distinct nuclear functions of NF-KB," The EMBO Journal, 2002, 21(23): 6539-6548.
Chen et al., "Dynamic imaging of genomic loci in living human cells by an optimized CRISPR/Cas systemm," Cell, 2013, 155: 1479-1491.
Chen et al., "Enrichr: interactive and collaborative HTML5 gene list enrichment analysis tool," BMC Bioinformatics, 2013, 14: 128.
Chen et al., "Genome-wide CRISPR screen in a mouse model of tumor growth and metastasis," Cell, 2015, 160: 1246-1260.
Chen et al., "microRNA-1 and microRNA-206 regulate skeletal muscle satellite cell proliferation and differentiation by repressing Pax7," J Cell Biol, 2010, 190: 867-879.
Chen et al., "Targeted activation of diverse CRISPR-Cas systems for mammalian genome editing via proximal CRISPR targeting," Nature Communications, 2017, 8: 14958.
Chen et al., "Vitamin D receptor suppresses proliferation and metastasis in renal cell carcinoma cell lines via regulating the expression of the epithelial Ca2+ channel TRPV5," PLoS One, 2018, 13: e0195844.
Childers et al., "Gene therapy prolongs survival and restores function in murine and canine models of myotubular myopathy," Sci Transl Med, 2014, 6: 220ra210.
Christoffersen et al., "Ribozymes as human therapeutic agents," J. Med. Chem., 1995, 38(12): 2023-2037.
Chronis et al., "Cooperative Binding of Transcription Factors Orchestrates Reprogramming," Cell, 2017, 168: 442-459 e420.
Concise Encyclopedia of Polymer Science And Engineering, 1990, pp. 858-859.
Cooper et al., "Improved induction of immune tolerance to factor IX by hepatic AAV-8 gene transfer," Hum Gene Ther, 2009, 20: 767-776.
Corces et al., "The chromatin accessibility landscape of primary human cancers," Science, 2018, 362(6413): eaav1898.
Cordier et al., "Muscle-specific promoters may be necessary for adeno-associated virus- mediated gene transfer in the treatment of muscular dystrophies," Hum. Gene Ther., 2001, 12: 205-215.
Crooke et al., "Pharmacokinetic properties of several novel oligonucleotide analogs in mice," J. Pharmacol. Exp. Ther., 1996, 277(2): 923-937.
Cruvinel et al., "Reactivation of maternal SNORD116 cluster via SETDB1 knockdown in Prader- Willi syndrome iPSCs," Hum Mol Genet, 2014, 23: 4674-4685.
Dahlman et al., "Orthogonal gene knockout and activation with a catalytically active Cas9 nuclease," Nat Biotechnol, 2015, 33(11): 1159-1161, correction in Nat Biotechnol, Apr. 2016, 34(4): 441.
D'Alessio et al., "A Systematic Approach to Identify Candidate Transcription Factors that Control Cell Identity," Stem Cell Reports, 2015, 5: 763-775.

(56) References Cited

OTHER PUBLICATIONS

Daley et al., "CRISPhieRmix: a hierarchical mixture model for CRISPR pooled screens," Genome Biol, 2018, 19: 159.
Darabi et al., "Functional skeletal muscle regeneration from differentiating embryonic stem cells," Nat Med, 2008, 14: 134-143.
Darmanis et al., "A survey of human brain transcriptome diversity at the single cell level," Proc Natl Acad Sci U S A, 2015, 112: 7285-7290.
Datlinger et al., "Pooled CRISPR screening with single-cell transcriptome readout," Nat. Methods, 2017, 14: 297-301.
De Mesmaeker et al., "Antisense Oligonucleotides," Acc. Chem. Res., 1995, 28: 366-374.
De Smith et al., "A deletion of the HBII-85 class of small nucleolar RNAs (snoRNAs) is associated with hyperphagia, obesity and hypogonadism," Hum Mol Genet, 2009, 18: 3257- 3265.
Deconinck et al., "Utrophin-Dystrophin-Deficient Mice as a Model for Duchenne Muscular Dystrophy," Cell, 1997, 90(4): 717-727.
Dempster et al., "Extracting Biological Insights from the Project Achilles Genome-Scale CRISPR Screens in Cancer Cell Lines," Cold Spring Harbor Laboratory, 2019, 35 pages.
Diao et al., "A new class of temporarily phenotypic enhancers identified by CRISPR/Cas9- mediated genetic screening," Genome Res, 2016, 26: 397-405.
Dirks et al., "Triggered amplification by hybridization chain reaction," Proceedings of the National Academy of Sciences of the United States of America, 2004, 101(43): 15275-15278.
Dixit et al., "Perturb-Seq: Dissecting Molecular Circuits with Scalable Single-Cell RNA Profiling of Pooled Genetic Screens," Cell, 2016, 167: 1853-1866.e17.
Dobin et al., "STAR: ultrafast universal RNA-seq aligner," Bioinformatics, 2013, 29: 15-21.
Du et al., "Genetic interaction mapping in mammalian cells using CRISPR interference," Nat Methods, 2017, 14: 577-580.
Duan et al., "Expanding AAV packaging capacity with transsplicing or overlapping vectors: a quantitative comparison, " Molecular Therapy, 2001, 4: 383-391.
Duan et al., "Genome-wide identification of CRISPR/Cas9 off-targets in human genome," Cell research, 2014, 24(8): 1009-12.
Duan, "Systemic AAV Micro-dystrophin Gene Therapy for Duchenne Muscular Dystrophy," Molecular Therapy, 2018, 26(10): 2337-2356.
Duker et al., "Paternally inherited microdeletion at 15q11.2 confirms a significant role for the SNORD116 C/D box snoRNA cluster in Prader-Willi syndrome," Eur J Hum Genet, 2010, 18: 1196-1201.
Dumont et al., "Dystrophin expression in muscle stem cells regulates their polarity and asymmetric division," Nat Med, 2015, 21: 1455-1463.
Dumont et al., "Intrinsic and extrinsic mechanisms regulating satellite cell function," Development, 2015, 142: 1572-1581.
Dunbar et al., "Gene therapy comes of age," Science, 2018, 359: eaan4672.
Dykeman, "An implementation of the Gillespie algorithm for RNA kinetics with logarithmic time update," Nucleic Acids Research, 2015, 45(12): 5708-5715.
Eguchi et al., "Reprogramming cell fate with a genome-scale library of artificial transcription factors," Proc Natl Acad Sci U S A, 2016, 113: E8257-E8266.
Encode Project Consortium, "Expanded encyclopaedias of DNA elements in the human and mouse genomes," Nature, 2020, 583: 699-710.
Englisch et al., Chemically Modified Oligonucleotides as Probes and Inhibitors, Angewandle Chemie, International Edition, 1991, 30(6): 613-629.
Eraslan et al., "Deep learning: new computational modelling techniques for genomics," Nat. Rev. Genet., 2019, 20: 389-403.
Ernsberger, "Role of neurotrophin signalling in the differentiation of neurons from dorsal root ganglia and sympathetic ganglia," Cell Tissue Res, 2009, 336: 349-384.
Ernst et al., "ChromHMM: automating chromatin-state discovery and characterization," Nat. Methods, 2012, 9: 215-216.

Erwin et al., "Synthetic transcription elongation factors license transcription across repressive chromatin," Science, 2017, 358: 1617-1622.
Fagerlund et al., "The Cpf1 CRISPR-Cas protein expands genome-editing tools," Genome Biology, 2015, 16:251.
Fairclough et al., "Therapy for Duchenne muscular dystrophy: renewed optimism from genetic approaches," Nat. Rev. Genet., 2013, 14: 373-378.
Farasat et al., "A Biophysical Model of CRISPR/Cas9 Activity for Rational Design of Genome Editing and Gene Regulation," PLOS Computational Biology, 2016, 12(1): e1004724.
Farasat, "Sequence-to-Function Models for Efficient Optimization of Metabolic Pathways and Genetic Circuits," Ph. D. Thesis, 2015, 254 pages.
FDA approval brings first gene therapy to the United States, <https://www.fda.gov/newsevents/newsroom/pressannouncements/ucm574058.htm> (Aug. 30, 2017).
FDA approves first drug for spinal muscular atrophy, <https://www.fda.gov/newsevents/newsroom/pressannouncements/ucm534611.htm> (Dec. 23, 2016).
FDA approves first-of-its kind targeted RNA-based therapy to treat a rare disease, <https://www.fda.gov/newsevents/newsroom/pressannouncements/ucm616518.htm> (Aug. 10, 2018).
FDA approves novel gene therapy to treat patients with a rare form of inherited vision loss, <https://www.fda.gov/newsevents/newsroom/pressannouncements/ucm589467.htm> (Dec. 18, 2017).
FDA grants accelerated approval to first drug for Duchenne muscular dystrophy, <https://www.fda.gov/newsevents/newsroom/pressannouncements/ucm521263.htm> (Sep. 19, 2016).
Flamm et al., "RNA folding at elementary step resolution," RNA, 2000, 6: 325-338.
Flandin et al., "Lhx6 and Lhx8 coordinately induce neuronal expression of Shh that controls the generation of interneuron progenitors," Neuron, 2011, 70: 939-950.
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol. Biosyst., 2009, 5: 838-843.
Forget, "Molecular basis of hereditary persistence of fetal hemoglobin," Ann N Y Acad Sci, 1998, 850, 38-44.
Frank et al., "HDAC inhibitors cause site-specific chromatin remodeling at PU. 1-bound enhancers in K562 cells," Epigenetics Chromatin, 2016, 9: 15.
Friedland et al., "Characterization of Staphylococcus aureus Cas9: a smaller Cas9 for all-in-one adeno-associated virus delivery and paired nickase applications," Genome Biology, 2015, 16(16):257, 10 pages.
Friedland et al., "*Staphyloccocus aureus* Cas9: An Alternative Cas9 for Genome Editing Applications," Molecular Therapy, 2015, 23(Suppl. 1): S224.
Friedland et al., "*Staphyloccocus aureus* Cas9: An Alternative Cas9 for Genome Editing Applications, " Retrieved from the Internet: <http://www.editasmedicine.com/data/documents/ASGCT%20poster 2015 Ari.pdf> Retrieved on Feb. 28, 2018.
Fu et al., "Landscape of target: guide homology effects on Cas9-mediated cleavage," Nucleic Acids Research, 2014, 42(22): 13778-13787.
Fulco et al., "Activity-by-contact model of enhancer-promoter regulation from thousands of CRISPR perturbations," Nature Genetics, 2019, 51: 1664-1669.
Fulco et al., "Systematic mapping of functional enhancer-promoter connections with CRISPR interference," Science, 2016, 354: 769-773.
Fulmer-Smentek et al., "Association of acetylated histones with paternally expressed genes in the Prader-Willi deletion region," Hum Mol Genet, 2001, 10: 645-652.
Gait, "Oligoribonucleotides," Antisense Research and Applications, 1993, Chapter 16, pp. 290-299.
Gaj et al., "Structure-Guided Reprogramming of Serine Recombinase DNA Sequence Specificity," Proc Natl Acad Sci U S A, 2011, 108(2): 498-503.

(56) References Cited

OTHER PUBLICATIONS

Gao et al., "Complex transcriptional modulation with orthogonal and inducible dCas9 regulators," Nat Methods, 2016, 13: 1043-1049.
Gascon et al., "Direct Neuronal Reprogramming: Achievements, Hurdles, and New Roads to Success," Cell Stem Cell, 2017, 21: 18-34.
Gasiunas et al., "Cas9-crRNA ribonucleoprotein complex mediates specific DNA cleavage for adaptive immunity in bacteria," Proc. Natl. Acad. Sci., 2012, 109: E2579-E2586.
Gasperini et al., "A Genome-wide Framework for Mapping Gene Regulation via Cellular Genetic Screens," Cell, 2018, 176(1-2); 377-390.e19.
Gaudelli et al., "Directed evolution of adenine base editors with increased activity and therapeutic application," Nat Biotechnol, Jul. 2020, 38(7): 892-900.
Gaudelli et al., "Programmable base editing of A•T to G•C in genomic DNA without DNA cleavage," Nature, Nov. 2017, 551(7681): 464-471.
Gebeyehu et al., "Novel biotinylated nucleotide—analogs for labeling and colorimetric detection of DNA," Nucl. Acids Res., 1987, 15(11): 4513-4534.
Gee et al., "Cellular Reprogramming Genome Editing, and Alternative CRISPR Cas9 Technologies for Precise Gene Therapy of Duchenne Muscular Dystrophy," Stem Cells International, 2017, pp. 1-11.
Gemberling et al., "Transgenic mice for in vivo epigenome editing with CRISPR-based systems," Nat Methods, 2021, 18(8): 965-974.
Genbank Accenssion AP006627.1 (2016).
Genbank Accenssion BA000004.3 (2016).
Genbank Accenssion BAB04055.1 (2016).
GenBank Accession AF214528.1 (2000).
GenBank Accession No. AAC75803.1 (2018).
GenBank Accession No. AIN33136.1 (2014).
GenBank Accession No. BAB04055.1 (2017).
GenBank Accession No. EOT14076.1 (2013).
GenBank Accession No. AK019325 (2010).
GenBank Accession No. BB730912 (2001).
GenBank Accession No. BC010291 (2006).
GenBank Accession No. BC026642.1 (2007).
GenBank Accession No. BI143915 (2011).
GenBank Accession No. NM_020562.1 (2004).
GenBank Accession X51934.1 (1997).
GenBank P38036.2 (2013).
Gersbach et al., "Targeted plasmid integration into the human genome by an engineered zinc-finger recombinase," Nucleic Acids Res, 2011, 39: 7868-7878.
Ghisletti et al., "Identification and characterization of enhancers controlling the inflammatory gene expression program in macrophages," Immunity, 2010, 32: 317-328.
Gibson et al., "Enzymatic assembly of DNA molecules up to several hundred kilobases," Nature Methods, 2009, 6(5): 343-345.
Gilbert et al., "CRISPR-mediated modular RNA-guided regulation of transcription in eukaryotes," Cell, 2013, 154: 442-451.
Gillespie, "A general method for numerically simulating the stochastic time evolution of coupled chemical reactions," Journal of computational physics, 1976, 22: 403-434.
Gilman et al., "Distal CCAAT box deletion in the A gamma globin gene of two black adolescents with elevated fetal A gamma globin," Nucleic Acids Res 16, 1988, 10635-10642.
Goldstein et al., "In Situ Modification of Tissue Stem and Progenitor Cell Genomes," Cell Reports, 2019, 27: 1254-1264.e7.
Gomaa et al., "Programmable Removal of Bacterial Strains by Use of Genome-Targeting CRISPR-Cas Systems," 2014, mBio 5(1): e00928-13.
Gonda "Aerosols for delivery of therapeutic and diagnostic agents to the respiratory tract," Critical Reviews in Therapeutic Drug Carrier Systems, 1990 6:273-313.

Gong et al., "Molecular insights into DNA interference by CRISPR-associated nuclease-helicase Cas3," Proc Natl Acad Sci U S A, 2014, 111(46): 16359-64.
Gray et al., "G quadruplexes are genomewide targets of transcriptional helicases XPB and XPD," Nat. Chem. Biol, 2014, 10: 313-318.
Gregorevic et al., "Systemic microdystrophin gene delivery improves skeletal muscle structure and function in old dystrophic mdx mice," Mol Ther, 2008, 16: 657-664.
Grissa et al., "CRISPRFinder: a web tool to identify clustered regularly interspaced short palindromic repeats," Nucleic Acids Res., 2007, 35(Web Server issue): W52-57.
Guo et al., "Harnessing accurate non-homologous end joining for efficient prease deletion in CRISPR/Cas9-mediated genome editing, " Genome Biology, 2018, 19: 170, 20 pages.
Guo, J. et al., "Directed evolution of an enhanced and highly efficient FokI cleavage domain for zinc finger nucleases," J Mol Biol, 2010.
Hacein-Bey-Abina et al., "LMO2-associated clonal T cell proliferation in two patients after gene therapy for SCID-X1," Science, 2003, 302: 415-419.
Hakim et al., "Evaluation of Muscle Function of the Extensor Digitorum Longus Muscle Ex vivo and Tibialis Anterior Muscle In situ in Mice," J. Vis. Exp., 2013, 1-8.
Hakim et al., "Systemic gene transfer reveals distinctive muscle transduction profile of tyrosine mutant AAV-1, -6, and -9 in neonatal dogs," Mol. Ther. Methods Clin. Dev., 2014, 1:14002.
Hall et al., "Prevention of Muscle Aging by Myofiber-Associated Satellite Cell Transplantation," Sci Transl Med, 2010, 2: 57ra83.
Hardy et al., "Comparative Study of Injury Models for Studying Muscle Regeneration in Mice," PloS ONE, 2016, 11: e0147198.
Harper et al., "Modular flexibility of dystrophin: implications for gene therapy of Duchenne muscular dystrophy," Nat. Med., 2002, 8: 253-261.
Harrow et al., "GENCODE: The reference human genome annotation for The ENCODE Project," Genome Res, 2012, 22: 1760-1774.
Hart et al., "High-Resolution CRISPR Screens Reveal Fitness Genes and Genotype-Specific Cancer Liabilities," Cell, 2015, 163: 1515-1526.
Hayward et al., "Whole-genome landscapes of major melanoma subtypes," Nature, 2017, 545: 175-180.
He et al., "Molecular Genetic Mechanisms of Hereditary Spherocytosis: Current Perspectives," Acta Haematol., 2018, 139: 60-66.
Heagerty et al., "Time-dependent ROC curves for censored survival data and a diagnostic marker," Biometrics, 2000, 56(2): 337-344.
Heasman, "Morpholino oligos: making sense of antisense?," Dev. Biol., 2002, 243(2): 209-214.
Henikoff et al., "Amino acid substitution matrices from protein blocks, " Proc. Natl. Acad. Sci. USA, 1992, 89: 10915-9.
Henning et al., "Epigenetic control of CD8 + T cell differentiation," Nat Rev Immunol, 2018, 18(5): 340-356.
Hilton et al., "Enabling functional genomics with genome engineering," Genome Research, 2015, 25(10):1442-1455.
Himeda et al., "Design and Testing of Regulatory Cassettes for Optimal Activity in Skeletal and Cardiac Muscles," Methods Mol Biol, 2011, 709: 3-19 (Published Online Dec. 2010).
Hori et al., "Simple and reproducible hepatectomy in the mouse using the clip technique," World J Gastroenterol, 2012, 18(22): 2767-2774.
Horlbeck et al., "Compact and highly active next-generation libraries for CRISPR-mediated gene repression and activation," eLife, 2016, 5: e19760.
Howarth et al., "A monovalent streptavidin with a single femtomolar biotin binding site," Nature methods, 2006, 3(4): 267-273.
Hsu et al., "Development and applications of CRISPR-Cas9 for genome engineering," Cell, 2014, 157: 1262-1278.
Huang et al., "Generation and comparison of CRISPR-Cas9 and Cre-mediated genetically engineered mouse models of sarcoma," Nature Communications, 2017, 8(15999): 1-11.
Huang et al., "Impaired respiratory function in mdx and mdx/utrn+/− mice," Muscle & Nerve, 2011, 43(2): 263-267.
Huntriss et al., "Imprinted expression of SNRPN in human preimplantation embryos," Am J Hum Genet, 1998, 63: 1009-1014.

(56) References Cited

OTHER PUBLICATIONS

Inoue et al., "Runx transcription factors in neuronal development," Neural Dev, 2008, 3: 20.

Isaac et al., "Dystrophin and utrophin "double knockout" dystrophic mice exhibit a spectrum of degenerative musculoskeletal abnormalities," Journal of Orthopaedic Research, 2013, 31(3): 343-349.

Lyombe-Engembe et al., "Efficient Restoration of the Dystrophin Gene Reading Frame and Protein Structure in DMD Myoblasts Using the CinDel Method," Molecular Therapy—Nucleic Acids, 2016, 5:e283.

Jansen et al., "Identification of genes that are associated with DNA repeats in prokaryotes, " Mol Microbiol, 2002, 43(6): 1565-1575.

Jeltsch et al., "Application of DNA methyltransferases in targeted DNA methylation," Appl. Microbiol. Biotechnol., 2007, 75(6): 1233-1240.

Jepsen et al., "Locked nucleic acid: a potent nucleic acid analog in therapeutics and biotechnology," Oligonucleotides, 2004, 14(2): 130-146.

Jiang et al., "A Cas9-guide RNA complex preorganized for target DNA recognition," Science, 2015, 348, 1477-1481.

Jiang et al., "Notch signaling deficiency underlies age-dependent depletion of satellite cells in muscular dystrophy," Disease Models & Mechanisms, 2014, 7: 997-1004.

Jiang et al., "RNA-guided editing of bacterial genomes using CRISPR-Cas systems," Nat. Biotechnol., 2013, 31:233-239.

Jimenez et al., "Activation of the beta-globin locus control region precedes commitment to the erythroid lineage," Proceedings of the National Academy of Sciences, 1992, 89: 10618-10622.

Jiwlawat et al., "Current Progress and Challenges for Skeletal Muscle Differentiation from Human Pluripotent Stem Cells Using Transgene-Free Approaches," Stem Cells Int, Apr. 2018, Article ID 6241681, 18 pages.

Jobling et al., "Chitayat-Hall and Schaaf-Yang syndromes:a common aetiology: expanding the phenotype of MAGEL2-related disorders," J Med Genet, 2018, 55: 316-321.

Jooss et al., "Transduction of dendritic cells by DNA viral vectors directs the immune response to transgene products in muscle fibers," J. Virol., 1998, 72: 4212-4223.

Josephs et al., "Structure and specificity of the RNA-guided endonuclease Cas9 during DNA interrogation, target binding and cleavage," Nucleic Acids Research, 2015, 43(18): 8924-8941.

Joyce, "Amplification, mutation and selection of catalytic RNA," Gene, 1989, 82(1): 83-87.

Joyce, "Directed molecular evolution," Scientific American, 1992, 267(6): 90-97.

Jurkowska and Jeltsch, "Silencing of Gene Expression by Targeted DNA Methylation: Concepts and Approaches," Methods Mol. Biol. 649, 2010, Chapter 9: 149-161.

Kabadi et al., "Engineering Synthetic TALE and CRISPR/Cas9 Transcription Factors for Regulating Gene Expression," Methods, 2014, 69(2): 188-197.

Kabanov et al., "A new class of antivirals: antisense oligonucleotides combined with a hydrophobic substituent effectively inhibit influenza virus reproduction and synthesis of virus- specific proteins in MDCK cells," FEBS Lett., 1990, 259: 327-330.

Karlin et al., "Applications and statistics for multiple high-scoring segments in molecular sequences," Proc. Natl. Acad. Sci. USA, 1993, 90: 5873-77.

Kauppinen et al., "Locked nucleic acid (LNA): High affinity targeting of RNA for diagnostics and therapeutics," Drug Discov Today Technol, 2005, 2(3): 287-290.

Keefe et al., "Muscle stem cells contribute to myofibers in sedentary adult mice," Nat Commun, 2015, 6: 7087.

Keil et al., "Brain transcriptome databases: a user's guide," J Neurosci, 2018, 38(10): 2399- 2412.

Kempfer et al., "Methods for mapping 3D chromosome architecture," Nat. Rev. Genet., 2020, 21: 207-226.

Keys et al., "A genome-wide screen in the mouse liver reveals sex-specific and cell non- autonomous regulation of cell fitness," bioRxiv preprint doi: https://doi.org/10.1101/2021.01.30.428976, posted Feb. 1, 2021.

Khambata-Ford et al., "Identification of Promoter Regions in the Human Genome by Using a Retroviral Plasmid Library-Based Functional Reporter Gene Assay," Genome Research, 2003, 13: 1765-1774.

Khodakov et al., "Protected DNA strand displacement for enhanced single nucleotide discrimination in double-stranded DNA," Scientific reports, 2015, 5: 8721.

Khurana et al., "Role of non-coding sequence variants in cancer," Nat. Rev. Genet., 2016, 17: 93-108.

Kim et al., "A Histone acetylation contributes to chromatin looping between the locus control region and globin gene by influencing hypersensitive site formation," Biochim Biophys Acta, 2013, 1829: 963-969.

Kim et al., "Epigenetic therapy of Prader-Willi Syndrome," Transl Res, 2019, 208: 105-118.

Kim et al., "Expansion and Purification Are Critical for the Therapeutic Application of Pluripotent Stem Cell-Derived Myogenic Progenitors," Stem Cell Rep, 2017, 9: 12-22.

Kim et al., "Targeting the histone methyltransferase G9a activates imprinted genes and improves survival of a mouse model of Prader-Willi syndrome," Nat Med, 2017, 23: 213-222.

Kim et al., "Engineering and Application of Zinc Finger Proteins and TALEs for Biomedical Research," Mol Cells, 2017, 40(8): 533-541.

Klann et al., "CRISPR-based methods for high-throughput annotation of regulatory DNA," Curr Opin Biotechnol, 2018, 52: 32-41.

Klann et al., "CRISPR-Cas9 epigenome editing enables high-throughput screening for functional regulatory elements in the human genome," Nat Biotechnol, 2017, 35: 561-568.

Klann et al., "Genome-wide annotation of gene regulatory elements linked to cell fitness," bioRxiv doi: 10.1101/2021.03.08.434470. Preprint posted Mar. 9, 2021, 42 pages.

Kleinstiver et al., "Broadening the targeting range of Staphylococcus aureus CRISPR-Cas9 by modifying PAM recognition, " Nature Biotechnology, 2015, 33(12): 1293-1298.

Kleinstiver et al., "Engineered CRISPR-Cas9 nucleases with altered PAM specificities," Nature, 2015, 523(7561): 481-485.

Kleinstiver et al., "Genome-wide specificities of CRISPR-Cas Cpf1 nucleases in human cells," Nature Biotechnology, 2016, 34(8): 869-874.

Koblan et al., "Improving cytidine and adenine base editors by expression optimization and ancestral reconstruction," Oct. 2018, 36(9): 843-846.

Kocak, "Synthetic Transcription Factors and their Effects on Endogenous DNA Methylation in Human Cells," Thesis submitted in partial fulfillment of the requirements for the degree of Master of Science in the Department of Biomedical Engineering in the Graduate School of Duke University, 2013, p. 1-29.

Kocher et al., "Phylogenetic Analysis of the SNORD116 Locus," Genes, 2017, 8(12): 358.

Kodaka et al., "Skeletal Muscle Cell Induction from Pluripotent Stem Cells," Stem Cells Int, Apr. 2017, Article ID 1376151, 16 pages.

Koerber et al., "DNA shuffling of adeno-associated virus yields functionally diverse viral progeny," Mol Ther, 2008, 16: 1703-1709.

Komor et al., "Programmable editing of a target base in genomic DNA without double-stranded DNA cleavage," Nature, 2016, 533(7603): 420-424.

Koo et al., "Functional Rescue of Dystrophin Deficiency in Mice Caused by Frameshift Mutations Using Campylobacter jejuni Cas9," Molecular Therapy, 2018 26(6): 1529-1538.

Koopmans et al., "SynGO: An Evidence-Based, Expert-Curated Knowledge Base for the Synapse," Neuron, 2019, 103: 217-234 e214.

Koppanati et al., "Improvement of the mdx mouse dystrophic phenotype by systemic in utero AAV8 delivery of a minidystrophin gene," Gene Ther, 2010, 17: 1355-1362.

(56) References Cited

OTHER PUBLICATIONS

Korkmaz et al., "Functional genetic screens for enhancer elements in the human genome using CRISPR-Cas9," Nat Biotechnol, 2016, 34: 192-198.
Kornberg et al., "DNA Replication," 1980, pp. 75-77.
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, 1998, 54(14): 3607-3630.
Kreis et al., "The Multifaceted p21 (Cip1/Waf1/CDKN1A) in Cell Differentiation, Migration and Cancer Therapy," Cancers (Basel), 2019, 11(9): 1220.
Kuhnel et al., "Tumor-specific adenoviral gene therapy: Transcriptional repression of gene expression by utilizing p53- signal transduction pathways," Cancer Gene Ther., 2004, 11: 28-40.
Kumar et al., "Artificial evolution and natural ribozymes," FASEB Journal, 1995, 9: 1183-1195.
Kurreck, "Antisense technologies. Improvement through novel chemical modifications," European Journal of Biochemistry, 2003, 270(8): 1628-1644.
Kwon et al., "Myogenic Progenitor Cell Lineage Specification by CRISPR/Cas9-Based Transcriptional Activators," Stem cell reports, 2020, 14: 755-769.
Lacerra et al., "Restoration of hemoglobin A synthesis in erythroid cells from peripheral blood of thalassemic patients," Proc. Natl. Acad. Sci., 2000, 97(17): 9591-9596.
Lai et al., "Partial restoration of cardiac function with ΔPDZ nNOS in aged mdx model of Duchenne cardiomyopathy," Hum Mol Genet., 2014, 23(12): 3189-3199.
Lake et al., "Integrative single-cell analysis of transcriptional and epigenetic states in the human adult brain," Nat Biotechnol, 2018, 36: 70-80.
Lam et al., "Rapid and Efficient Differentiation of Human Pluripotent Stem Cells into Intermediate Mesoderm That Forms Tubules Expressing Kidney Proximal Tubular Markers," J Am Soc Nephrol JASN, 2014, 25: 1211-1225.
Lambert et al., "The Human Transcription Factors," Cell, 2018, 172: 650-665.
Lamey et al., "Pax genes in myogenesis: alternate transcripts add complexity," Histol Histopathol, 2004, 19: 1289-1300.
Landry et al., "Expression of the leukemia oncogene Lmo2 is controlled by an array of tissue- specific elements dispersed over 100 kb and bound by Tal1/Lmo2, Ets, and Gata factors," Blood, 2009, 113: 5783-5792.
Langouet et al., "Zinc finger protein 274 regulates imprinted expression of transcripts in Prader- Willi syndrome neurons," Hum Mol Genet, 2018, 27: 505-515.
Laumont et al., "Noncoding regions are the main source of targetable tumor-specific antigens," Sci. Transl. Med., 2018, 10(470): eaau5516, 11 pages.
Lawrence et al., "Discovery and saturation analysis of cancer genes across 21 tumour types," Nature, 2014, 505: 495-501.
Lee et al., "Activation of innate immunity is required for efficient nuclear reprogramming," Cell, 2012, 151: 547-558.
Lee et al., "Expression of small interfering RNAs targeted against HIV-1 rev transcripts in human cells," Nature Biotechnol, 2002, 20(5): 500-505.
Lee et al., "Nanoparticle delivery of Cas9 ribonucleoprotein and donor DNA in vivo induces homology-directed DNA repair," Nat Biomed Eng, 2017, 1: 889-901.
Lenoir et al., "PICKLES: the database of pooled in-vitro CRISPR knockout library essentiality screens," Nucleic Acids Res, 2018, 46: D776-D780.
Lesnik et al., "Relative thermodynamic stability of DNA, RNA, and DNA: RNA hybrid duplexes: relationship with base composition and structure," Biochemistry, 1995, 34(34): 10807-10815.
Letsinger et al., "Cholesteryl-conjugated oligonucleotides: synthesis, properties, and activity as inhibitors of replication of human immunodeficiency virus in cell culture," Proc. Natl. Acad. Sci. USA, 1989, 86(17): 6553-6556.
Levin et al., "Position-dependent effects of locked nucleic acid (LNA) on DNA sequencing and PCR primers," Nuc. Acids. Res., 2006, 34: e142.
Levskaya et al., "Synthetic biology: engineering *Escherichia coli* to see light," Nature, 2005, 438:441-442.
Li et al., "Chimeric DNA methyltransferases target DNA methylation to specific DNA sequences and repress expression of target genes, " Nucleic Acids Res., 2007, 35(1): 100-112.
Li et al., "Engineering and selection of shuffled AAV genomes: a new strategy for producing targeted biological nanoparticles," Mol Ther, 2008, 16: 1252-1260.
Li et al., "Ex vivo cell-based CRISPR/Cas9 genome editing for therapeutic applications," Biomaterials, 2020, 234: 119711.
Li et al., "Precise correction of the dystrophin gene in duchenne muscular dystrophy patient induced pluripotent stem cells by TALEN and CRISPR-Cas9," Stem Cell Reports, 2015, 4: 143- 154.
Li et al., "Preservation of muscle force in Mdx3cv mice correlates with low-level expression of a near full-length dystrophin protein," Am. J. Pathol., 2008, 172: 1332-1341.
Li et al., "RSEM: accurate transcript quantification from RNA-Seq data with or without a reference genome," BMC Bioinformatics, 2011, 12: 323.
Li et al., "Synthetic muscle promoters: activities exceeding naturally occurring regulatory sequences," Nature Biotechnology, 1999, 17: 241-245.
Li et al., "The autism-related gene SNRPN regulates cortical and spine development via controlling nuclear receptor Nr4a1," Sci Rep, 2016, 6: 29878.
Lian et al., "Robust cardiomyocyte differentiation from human pluripotent stem cells via temporal modulation of canonical Wnt signaling," Proc Natl Acad Sci, 2012, 109: E1848-E1857.
Liao et al., "In Vivo Target Gene Activation via CRISPR/Cas9-Mediated Trans-epigenetic Modulation," Cell, 2017, 171: 1495-1507.
Liao et al., "The Subread aligner: fast, accurate and scalable read mapping by seed-and-vote," Nucleic Acids Res, 2013, 41: e108.
Lim et al., "Application of CRISPR/Cas9 for the Treatment of Duchenne Muscular Dystrophy," Journal of Personalized Medicine, 2018, 8(4): 1-20.
Limberis et al., "Transduction efficiencies of novel AAV vectors in mouse airway epithelium in vivo and human ciliated airway epithelium in vitro," Molecular therapy: the journal of the American Society of Gene Therapy, 2009, 17: 294-301.
Lin et al., "Essential Role of the 58-kDa Microspherule Protein in the Modulation of Daxx-dependent Transcriptional Repression as Revealed by Nucleolar Sequestration," J Biol Chem, 2002, 277: 25446-25456.
Liu et al., "Adeno-associated virus-mediated microdystrophin expression protects young mdx muscle from contraction-induced injury," Mol. Ther., 2005, 11: 245-256.
Liu et al., "CRISPR Activation Screens Systematically Identify Factors that Drive Neuronal Fate and Reprogramming," Cell Stem Cell, 2018, 23: 758-771 e758.
Liu et al., "CRISPR-Based Chromatin Remodeling of the Endogenous Oct4 or Sox2 Locus Enables Reprogramming to Pluripotency," Cell Stem Cell, 2018, 22: 252-261 e254.
Liu et al., "Editing DNA Methylation in the Mammalian Genome," Cell, Sep. 2016, 167(1): 233-247.
Liu et al., "Monte Carlo simulation for single RNA unfolding by force," Biophysical journal, 2005, 88(1): 76-84.
Long et al., "Postnatal genome editing partially restores dystrophin expression in a mouse model of muscular dystrophy," Science, 2016, 351(6271): 400-403.
Luo et al., "Repurposing endogenous type I CRISPR-Cas systems for programmable gene repression," Nucleic Acids Research, 2014, 43(1): 674-681.
Ma et al., "Targeted gene suppression by inducing de novo DNA methylation in the gene promoter," Epigenetics Chromatin, 2014, 7: 20.
Machinek et al., "Programmable energy landscapes for kinetic control of DNA strand displacement," Nature communications, 2014, 5: 5324, 9 pages.

(56) References Cited

OTHER PUBLICATIONS

MacPherson et al., "Flexible guide-RNA design for CRISPR applications using Protospacer Workbench," Nature biotechnology, 2015, 33(8).
Mader et al., "CRISPR RNA-guided activation of endogenous human genes," Nature Methods, 2013, 10(10): 977-979.
Madigan et al., "Engineering AAV receptor footprints for gene therapy," Curr Opin Virol, 2016, 18: 89-96.
Madisen et al., "A robust and high-throughput Cre reporting and characterization system for the whole mouse brain," Nat Neurosci, 2010, 13: 133-140.
Maeder et al., "Robust, synergistic regulation of human gene expression using TALE activators," Nat Methods, 2013, 10(3): 243-245.
Magli et al., "PAX7 Targets, CD54, Integrin α9β1, and SDC2, Allow Isolation of Human ESC/iPSC-Derived Myogenic Progenitors," Cell Rep, 2017, 19: 2867-2877.
Maheshri et al., "Directed evolution of adeno-associated virus yields enhanced gene delivery vectors," Nat Biotechnol, 2006, 24: 198-204.
Majzner et al., "Clinical lessons learned from the first leg of the CAR T cell journey," Nature Medicine, 2019, 25(9): 1341-1355.
Makarova et al., "An updated evolutionary classification of CRISPR-Cas systems, " Nature Reviews Microbiology, 2015, 13:722-736.
Makarova et al., "Evolution and classification of the CRISPR-Cas systems," Nature Reviews Microbiology, 2011, pp. 467-477.
Mann et al., "Improved antisense oligonucleotide induced exon skipping in the mdx mouse model of muscular dystrophy," J. Gene Med., 2002, 4: 644-654.
Manning et al., "What has the mdx mouse model of duchenne muscular dystrophy contributed to our understanding of this disease?," Journal of Muscle Research and Cell Motility, 2015, 36: 155-167.
Manoharan et al., "Chemical Modifications to Improve Uptake and Bioavailability of Antisense Oligonucleotides," Ann. N. Y. Acad. Sci., 1992, 660: 306-309.
Manoharan et al., "Cholic acid-oligonucleotide conjugates for antisense applications," Bioorg. Med. Chem. Let., 1994, 4(8): 1053-1060.
Manoharan et al., "Introduction of a lipophilic thioether tether in the minor groove of nucleic acids for antisense applications," Bioorg. Med. Chem. Let., 1993, 3(12): 2765-2770.
Manoharan et al., "Lipidic Nucleic Acids," Tetrahedron Lett, 1995, 36: 3651-3654.
Manoharan et al., "Oligonucleotide Conjugates: Alteration of the Pharmacokinetic Properties of Antisense Agents," Nucleosides & Nucleotides, 1995, 14: 969-973.
Martin et al., "A New Access to 2'-O-Alkylated Ribonucleosides and Properties of 2'-O-Alkylated Oligoribonucleotides," Helv. Chim. Acta, 1995, 78: 486-504.
Maruyama et al., "Epigenetic Regulation of Cell Type-Specific Expression Patterns in the Human Mammary Epithelium," PLoS Genetics, 2011, 7(4): e1001369, 15 pages.
Mastellos et al., "Inducing and characterizing liver regeneration in mice: Reliable models, essential "readouts" and critical perspectives," Curr Protoc Mouse Biol., 2013, 3(3): 141-170.
Mathews et al., "Expanded sequence dependence of thermodynamic parameters improves prediction of RNA secondary structure," Journal of Molecular Biology, 1999, 288(5): 911-940.
Maurano et al., "Systematic localization of common disease-associated variation in regulatory DNA," Science, 2012, 337: 1190-1195.
Maxwell et al., "A detailed cell-free transcription-translation-based assay to decipher CRISPR protospacer-adjacent motifs," Methods, 2018, 143: 48-57.
McCarthy et al., "Schaaf-Yang syndrome overview: Report of 78 individuals," Am J Med Genet A, 2018, 176(12): 2564-2574.
McFadden et al., "The Hand1 and Hand2 transcription factors regulate expansion of the embryonic cardiac ventricles in a gene dosage-dependent manner," Development, 2005, 132: 189-201.

McGreevy et al., "Animal models of Duchenne muscular dystrophy: from basic mechanisms to gene therapy," Disease Models Mechanisms, 2015, 8(3): 195-213.
McTigue et al., "Sequence-dependent thermodynamic parameters for locked nucleic acid (LNA)-DNA duplex formation," Biochemistry, 2004, 43(18): 5388-5405.
Mertens et al., "Evaluating cell reprogramming, differentiation and conversion technologies in neuroscience," Nat Rev Neurosci, 2016, 17: 424-437.
Mevissen et al., "Molecular basis of Lys11-polyubiquitin specificity in the deubiquitinase Cezanne," Nature, 2016, 538(7625): 402-405.
Meyers et al., "Computational correction of copy No. effect improves specificity of CRISPR-Cas9 essentiality screens in cancer cells," Nat. Genet., 2017, 49: 1779-1784.
Miller et al., "Transcriptional landscape of the prenatal human brain," Nature, 2014, 508: 199-206.
Min et al., "CRISPR Correction of Duchene Muscular Dystrophy," Annual Review of Medicine, Epub Oct. 2018, 70: 239-255.
Mishra et al., "Improved leishmanicidal effect of phosphorotioate antisense oligonucleotides by LDL-mediated delivery," Biochim. Biophys. Acta, 1995, 1264(2): 229-237.
Miyagishi et al., "U6 promoter-driven siRNAs with four uridine 3' overhangs efficiently suppress targeted gene expression in mammalian cells," Nature Biotechnol, 2002, 20(5): 497-500.
Mojica et al., "Intervening sequences of regularly spaced prokaryotic repeats derive from foreign genetic elements," J Molec Evolution, 2005, 60(2): 174-182.
Mojica et al., "Short motif sequences determine the targets of the prokaryotic CRISPR defence system," Microbiology, 2009, 155: 733-740.
Montalbano et al., "High-Throughput Approaches to Pinpoint Function within the Noncoding Genome," Mol. Cell, 2017, 68: 44-59.
Montarras, "Direct Isolation of Satellite Cells for Skeletal Muscle Regeneration," Science, 2005, 309: 2064-2067.
Moore et al., "Transcription Activator-like Effectors: A Toolkit for Synthetic Biology," ACS Synth Biol, 2014, 3(10): 708-716.
Morris et al., "Dissecting engineered cell types and enhancing cell fate conversion via CellNet," Cell, 2014, 158: 889-902.
Muir et al., "Engraftment potential of dermal fibroblasts following in vivo myogenic conversion in immunocompetent dystrophic skeletal muscle," Mol. Ther. Methods Clin. Dev., 2014, 1:14025.
Murray et al., "Codon usage in plant genes," Nucl. Acids Res., 1989, 17:477-498.
Naguibneva et al., "An LNA-based loss-of-function assay for micro-RNAs," Biomed Pharmacother, 2006, 60: 633-638.
Najm et al., "Orthologous CRISPR-Cas9 enzymes for combinatorial genetic screens," Nat Biotechnol, 2018, 36: 179-189.
Naldini, "Gene therapy returns to centre stage," Nature, 2015, 526: 351-360.
Nam et al., "Cas5d protein processes pre-crRNA and assembles into a Cascade-like interference complex in Subtype I-C/Dvulg CRISPR-Cas system," Structure, 2012, 20:1574- 1584.
Nance et al., "AAV9 Edits Muscle Stem Cells in Normal and Dystrophic Adult Mice," Molecular Therapy, 2019, 27: 1568-1585.
Nasevicius et al., "Effective targeted gene 'knockdown' in zebrafish," Nat. Genet., 2000, 26(2): 216-220.
Nelson et al., "Engineering Delivery Vehicles for Genome Editing," Annual review of chemical and biomolecular engineering, 2016, 7: 637-662.
Nelson et al., "Genome engineering: a new approach to gene therapy for neuromuscular disorders," Nat Rev Neurol, 2017, 13: 647-661.
Nelson et al., "Local and Systemic Gene Editing in a Mouse Model of Duchenne Muscular Dystrophy," Molecular Therapy, 2016, 24(Supp 1):S191.
Nelson et al., "Long-term evaluation of AAV-CRISPR genome editing for Duchenne muscular dystrophy," Nature Medicine, 2019, 25(3): 427-432.
Nguyen et al., "Transcriptional Enhancers in the Regulation of T Cell Differentiation," Front. Immunol., 2015, 6: 462.
Nielsen et al., "Sequence-selective recognition of DNA by strand displacement with a thymine-substituted polyamide," Science, 1991, 254: 1497-1500.

(56) References Cited

OTHER PUBLICATIONS

Nikfarjam et al., "A Model of Partial Hepatectomy in Mice," Journal of Investigative Surgery, 2004, 17(5): 291-294.
Nowotny et al., "Crystal structures of RNase H bound to an RNA/DNA hybrid: substrate specificity and metal-dependent catalysis," Cell, 2005, 121(7): 1005-1016.
Nuñez et al., "Genome-wide programmable transcriptional memory by CRISPR-based epigenome editing," Cell, 2021, 184(9): P2503-2519.
O'Brien et al., "GT-Scan: identifying unique genomic targets," Bioinformatics, 2014, 30: 2673- 2675.
Oberhauser et al., "Effective incorporation of 2'-O-methyl-oligoribonucleotides into liposomes and enhanced cell association through modification with thiocholesterol," Nucl. Acids Res., 1992, 20(3): 533-538.
Obika et al., "Stability and structural features of the duplexes containing nucleoside analogues with a fixed N-type conformation, 2'-0,4'-C-methyleneribonucleosides," Tetrahedron Lett. 1998, 39(30): 5401-5404.
O'Connell et al., "Programmable RNA recognition and cleavage by CRISPR/Cas9," Nature, 2014, 516: 263-266.
Odom et al., "Microutrophin Delivery Through rAAV6 Increases Lifespan and Improves Muscle Function in Dystrophic Dystrophin/Utrophin-deficient Mice," Molecular Therapy, 2008, 16(9): 1539-1545.
O'Geen et al., "dCas9-based epigenome editing suggests acquisition of histone methylation is not sufficient for target gene repression," Nucleic Acids Res, 2017, 45: 9901-9916.
O'Geen et al., "Ezh2-dCas9 and KRAB-dCas9 enable engineering of epigenetic memory in a context-dependent manner," Epigenetics Chromatin, 2019, 12: 26.
Olguin et al., "Pax-7 up-regulation inhibits myogenesis and cell cycle progression in satellite cells: a potential mechanism for self-renewal," Dev Biol, 2004, 275: 375-388.
Orgel, "Selection in vitro," Proc. R. Soc. B, 1979, 205: 435-442.
Orlando et al., "Promoter capture Hi-C-based identification of recurrent noncoding mutations in colorectal cancer," Nat. Genet., 2018, 50: 1375-1380.
Orom et al., "LNA-modified oligonucleotides mediate specific inhibition of microRNA function," Gene, 2006, 372: 137-141.
Ousterout et al., "Correction of dystrophin expression in cells from duchenne muscular dystrophy patients through genomic excision of exon 51 by zinc finger nucleases," Molecular Therapy 23, 2015, 523-532.
Ousterout et al., "Multiplex CRISPR/Cas9-based genome editing for correction of dystrophin mutations that cause Duchenne muscular dystrophy," Nature Communications, 2015, 6:6244.
Ousterout, "Genetic Correction of Duchenne Muscular Dystrophy using Engineered Nucleases," Dept. of Biomedical Engineering Duke University (Dissertation), 2014, pp. 1-204.
Paddison et al., "Short hairpin RNAs (shRNAs) induce sequence-specific silencing in mammalian cells," Genes & Dev, 2002, 16(8): 948-958.
Paez-Espino et al., "CRISPR immunity drives rapid phage genome evolution in Streptococcus thermophilus," mBio, 2015, 6(2): e00262-15.
Pang et al., "Induction of human neuronal cells by defined transcription factors," Nature, 2011, 476: 220-223.
Papapetrou, "Induced pluripotent stem cells, past and future," Science, 2016, 353: 991-992.
Parekh et al., "Mapping Cellular Reprogramming via Pooled Overexpression Screens with Paired Fitness and Single-Cell RNA-Sequencing Readout," Cell Systems, 2018, 7: 548- 555.e548.
Park et al., "Multi-Parametric MRI at 14T for Muscular Dystrophy Mice Treated with AAV Vector- Mediated Gene Therapy," PloS One, 2015, 10(4): e0124914.
Paul et al., "Effective expression of small interfering RNA in human cells," Nature Biotechnol, 2002, 20(5): 505-508.
Pawlikowski et al., "Regulation of skeletal muscle stem cells by fibroblast growth factors," Dev Dyn, 2017, 246: 359-367.

Penczek et al., "Three-dimensional reconstruction of single particles embedded in ice," Ultramicroscopy, 1992, 40, 33-53.
Perez-Pinera et al., "Synergistic and tunable human gene activation by combinations of synthetic transcription factors," Nat Methods, 2013, 10: 239-242.
Pigozzo et al., "Revertant Fibers in the mdx Murine Model of Duchenne Muscular Dystrophy: An Age- and Muscle-Related Reappraisal," PLoS One, 2013, 8(8): e72147.
Pinello et al., "Analyzing CRISPR genome-editing experiments with CRISPResso," Nat Biotechnol, 2016, 34(7):695-697.
Polstein et al., "A light-inducible CRISPR-Cas9 system for control of endogenous gene activation," Nature Chemical Biology, 2015, 11: 198-200.
Ponting et al., "Evolution and functions of long noncoding RNAs," Cell, 2009, 136(4): 629-641.
Povero et al., "Lipid-induced toxicity stimulates hepatocytes to release angiogenic microparticles that require Vanin-1 for uptake by endothelial cells," Sci Signal, 2013, 6(296): ra88.
Powell et al., "A Prader-Willi locus lncRNA cloud modulates diurnal genes and energy expenditure," Hum Molec Genet, 2013, 22: 4318-4328.
Prykhozhij et al., "CRISPR MultiTargeter: A Web Tool to Find Common and Unique CRISPR Single Guide RNA Targets in a Set of Similar Sequences," PLoS One, 2015, 10(3): e0119372.
Puccini et al., "Colorectal cancer: epigenetic alterations and their clinical implications", Biochim Biophys Acta, 2017, vol. 1868, No. 2, pp. 439-448.
Rackham et al., "A predictive computational framework for direct reprogramming between human cell types," Nature Genetics, 2016, 48: 331-335.
Raeburn et al., "Techniques for drug delivery to the airways, and the assessment of lung function in animal models," J. Pharmacol. Toxicol. Meth., 1992, 27:143-159.
Rajagopal et al., "High-throughput mapping of regulatory DNA," Nat. Biotechnol, 2016, 34: 167- 174.
Ramachandran et al., "Nitric Oxide Signaling Pathway in Duchenne Muscular Dystrophy Mice: Upregulation of L-arginine Transport," Biochem. J., 2012, 449: 133-142.
Ran et al., "Genome engineering using the CRISPR-Cas9 system," Nature Protocols, 2013, 8(11): 2281-2308.
Rao et al., "Engineering human pluripotent stem cells into a functional skeletal muscle tissue," Nat Commun, 2018, 9: 126.
Ratcliff et al., "A novel single-molecule study to determine protein-protein association constants," Journal of the American Chemical Society, 2001, 123(24): 5632-5635.
Rauscher et al., "GenomeCRISPR—a database for high-throughput CRISPR/Cas9 screens," Nucleic Acids Res, 2017, 45: D679-D686.
Rheinbay et al., "Analyses of non-coding somatic drivers in 2,658 cancer whole genomes," Nature, 2020, 578: 102-111.
Rhodes et al., "G-quadruplexes and their regulatory roles in biology," Nucleic Acids Res, 2015, 43: 8627-8637.
Richter et al., "Phage-assisted evolution of an adenine base editor with improved Cas domain compatibility and activity," Nat Biotechnol, Jul. 2020, 38(7): 883-891.
Riordan et al., "Application of CRISPR/Cas9 for biomedical discoveries," Cell & Bioscience, 2015, 5(1):11 pages.
Rmilah et al., "Understanding the marvels behind liver regeneration," Wiley Interdiscip Rev Dev Biol., 2019, 8(3): e340.
Roadmap Epigenomics Consortium, "Integrative analysis of 111 reference human epigenomes," Nature, 2015, 518: 317-330.
Rodriguez et al., "Clustering by fast search and find of density peaks," Science, 2014, 344(6191): 1492-1496.
Roudaut et al., "Restriction of calpain3 expression to the skeletal muscle prevents cardiac toxicity and corrects pathology in a murine model of limb-girdle muscular dystrophy," Circulation, 2013, 128: 1094-1104.
Russa et al. "The New State of the Art: Cas9 for Gene Activation and Repression, " Molecular and Cellular Biology, 2015, 35(22):3800-3809.
Rutkauskas et al., "Directional R-loop formation by the CRISPR-Cas surveillance complex cascade provides efficient off-target site rejection," Cell reports, 2015, 10, 1534-1543.

(56) References Cited

OTHER PUBLICATIONS

Sacco et al., "Short Telomeres and Stem Cell Exhaustion Model Duchenne Muscular Dystrophy in mdx/mTR Mice," Cell, 2010, 143: 1059-1071.
Sagal et al., "Proneural transcription factor Atoh1 drives highly efficient differentiation of human pluripotent stem cells into dopaminergic neurons," Stem Cells Transl Med, 2014, 3: 888-898.
Sahoo et al., "Prader-Willi phenotype caused by paternal deficiency for the HBII-85 C/D box small nucleolar RNA cluster," Nat Genet, 2008, 40: 719-721.
Saitoh et al., "Parent-of-Origin Histone Acetylation and Reactivation of a Key Imprinted Gene Locus in Prader-Willi Syndrome," Am J Hum Genet, 2000, 66: 1958-1962.
Salmon et al., "Production and titration of lentiviral vectors," Curr Protoc Hum Genet, 2007, Chapter 12, Unit 12.10, Supplement 54, 24 pages.
Salva et al., "Design of tissue-specific regulatory cassettes for high-level rAAV-mediated expression in skeletal and cardiac muscle," Mol. Ther., 2007, 15:320-329.
Sambasivan et al., "Embryonic founders of adult muscle stem cells are primed by the determination gene Mrf4," Developmental Biology, 2013, 381: 241-255.
Sanghvi et al., "Heterocyclic Base Modifications in Nucleic Acids and their Applications in Antisense Oligonucleotides," 1993, Antisense Research and Applications, Chapter 15, pp. 274-285.
Sanjana et al., "High-resolution interrogation of functional elements in the noncoding genome," Science, 2016, 353: 1545-1549.
Sanson et al., "Optimized libraries for CRISPR-Cas9 genetic screens with multiple modalities," Nat Commun, 2018, 9: 5416.
SantaLucia et al., "Improved nearest-neighbor parameters for predicting DNA duplex stability," Biochemistry, 1996, 35(11): 3555-3562.
Schaaf et al., "Truncating mutations of MAGEL2 cause Prader-Willi phenotypes and autism," Nat Genet, 2013, 45(11): 1405-1408.
Schifrut et al., "Genome-wide CRISPR Screens in Primary Human T Cells Reveal Key Regulators of Immune Function," Cell, 2018, 175(7): 1958-1971.e15.
Schmidt et al., "GenomeRNAi: a database for cell-based and in vivo RNAi phenotypes, 2013 update," Nucleic Acids Res, 2013, 41: D1021-6.
Schmittgen et al., "Analyzing real-time PCR data by the comparative CT method," Nature Protocols, 2008, 3(6): 1101-1108.
Schreck et al., "DNA hairpins destabilize duplexes primarily by promoting melting rather than by inhibiting hybridization," Nucleic Acids Research, 2015, 43(13): 6181-6190.
Schreck et al., "DNA hairpins primarily promote duplex melting rather than inhibiting hybridization," 2014, arXiv preprint arXiv: 1408.4401.
Schultz et al., "SETDB1: a novel KAP-I-associated histone H3, lysine 9-specific methyltransferase that contributes to HP1-mediated silencing of euchromatic genes by KRAB zinc-finger proteins," Genes & Development, 2002, 16: 919-932.
Segal and Meckler, "Genome Engineering at the Dawn of the Golden Age," Annu. Rev. Genomics Hum. Genet., 2013, 14: 135-158.
Semenova et al., "The Cas6e ribonuclease is not required for interference and adaptation by the E. coli type I-E CRISPR-Cas system," Nucleic Acids Res, 2015, 43(12):6049-61.
Sengupta et al., "Super-Enhancer-Driven Transcriptional Dependencies in Cancer," Trends Cancer Res, 2017, 3: 269-281.
Sentmanat et al., "A Survey of Validation Strategies for CRISPR-Cas9 Editing," Scientific Reports, 2018, 8: 888.
Sequence alignment: SEQ ID No. 102920 (2019).
Sequence alignment: SEQ ID No. 102921 (2019).
Sequence alignment: SEQ ID No. 103735 (2019).
Sequence alignment: SEQ ID No. 103736 (2019).
Serra et al., "Predicting thermodynamic properties of RNA," Methods in Enzymology, 1995, 259: 242-261.
Shalem et al., "Genome-scale CRISPR-Cas9 knockout screening in human cells, " Science, 2014, 343: 84-87.
Sharma et al., "In vivo genome editing of the albumin locus as a platform for protein replacement therapy," Blood, 2015, 126: 1777-1784.
Shea et al., "Synthesis, hybridization properties and antiviral activity of lipid- oligodeoxynucleotide conjugates," Nucl. Acids Res, 1990, 18: 3777-3783.
Shelton et al., "Derivation and Expansion of PAX7-Positive Muscle Progenitors from Human and Mouse Embryonic Stem Cells," Stem Cell Rep, 2014, 3: 516-529.
Shen et al., "Combinatorial CRISPR-Cas9 screens for de novo mapping of genetic interactions," Nat Methods, 2017, 14: 573-576.
Shen et al., "Engraftment of a galactose receptor footprint onto adeno-associated viral capsids improves transduction efficiency," J Biol Chem, 2013, 288(40): 28814-28823.
Shin et al., "Microdystrophin Ameliorates Muscular Dystrophy in the Canine Model of Duchenne Muscular Dystrophy," Mol. Ther., 2013, 21: 750-757.
Shlyakhtenko et al., "Silatrane-based surface chemistry for immobilization of DNA, protein-DNA complexes and other biological materials, " Ultramicroscopy, 2003, 97: 279-287.
Siddique et al., "Targeted methylation and gene silencing of VEGF-A in human cells by using a designed Dnmt3a-Dnmt3L single-chain fusion protein with increased DNA methylation activity," J. Mol. Biol., 2013, 425(3): 479-491.
Simpson, "Contacts between Escherichia coli RNA polymerase and thymines in the lac UV5 promoter," Proc. Natl. Acad. Sci. USA, 1979, 76: 3233-3237.
Singh et al. "Protein Engineering Approaches in the Post-Genomic Era," Current Protein and Peptide Science, 2017, 18: 1-11.
Skene et al., "Genetic identification of brain cell types underlying schizophrenia," Nat Genet, 2018, 50: 825-833.
Soejima et al., "Imprinting centers, chromatin structure, and disease," J Cell Biochem, 2005, 95(2): 226-233.
Song et al., "Non-immunogenic utrophin gene therapy for the treatment of muscular dystrophy animal models," Nature Medicine, 2019, 25(10): 1505-1511.
Stanton et al., "Chemical modification study of antisense gapmers," Nucleic Acid Ther., 2012, 22(5): 344-359.
Stemmer et al., "CCTop: An Intuitive, Flexible and Reliable CRISPR/Cas9 Target Prediction Tool," PLoS One, 2015, 10(4): e0124633.
Stephens, "False discovery rates: a new deal," Biostatistics, 2017, 18: 275-294.
Stepper et al., "Efficient targeted DNA methylation with chimeric dCas9-Dnmt3a-Dnmt3L methyltransferase," Nucleic Acids Res., 2017, 45(4): 1703-1713.
Stolzenburg et al., "Targeted silencing of the oncogenic transcription factor SOX2 in breast cancer," Nucleic Acids Res., 2012, 40(14): 6725-6740.
Stuelsatz et al., "A Contemporary Atlas of the Mouse Diaphragm: Myogenicity, Vascularity, and the Pax3 Connection" J Histochem Cytochem, 2012, 60(9): 638-657.
Sugimoto et al., "Thermodynamic parameters to predict stability of RNA/DNA hybrid duplexes," Biochemistry, 1995, 34: 11211-11216.
Sugimoto et al., "Thermodynamics-structure relationship of single mismatches in RNA/DNA duplexes," Biochemistry, 2000, 39: 11270-11281.
Sui et al., "A DNA vector-based RNAi technology to suppress gene expression in mammalian cells," PNAS, 2002, 99(8): 5515-5520.
Sun et al., "Phage mutations in response to CRISPR diversification in a bacterial population," Environmental microbiology, 2013, 15(2): 463-470.
Sur et al., "The role of enhancers in cancer," Nat. Rev. Cancer, 2016, 16: 483-493.
Sutcliffe et al., "Deletions of a differentially methylated CpG island at the SNRPN gene define a putative imprinting control region," Nature Genetics, 1994, 8: 52-58.
Suzuki et al., "In vivo genome editing via CRISPR/Cas9 mediated homology-independent targeted integration," Nature, 2016, 540: 144-149.
Svinarchuk et al., "Inhibition of HIV proliferation in MT-4 cells by antisense oligonucleotide conjugated to lipophilic groups," Biochimie, 1993, 75: 49-54.

(56) References Cited

OTHER PUBLICATIONS

Szczelkun et al., "Direct observation of R-loop formation by single RNA-guided Cas9 and Cascade effector complexes," Proceedings of the National Academy of Sciences, 2014, 6 pages.
Szostak, "in Vitro Genes," TIBS, 1993, 17: 89-93.
Szymczak et al., "Correction of multi-gene deficiency in vivo using a single 'self-cleaving' 2A peptide-based retroviral vector," Nature Biotechnology, 2004, 22(5): 589-594.
Takahashi et al., "A decade of transcription factor-mediated reprograming to pluripotency," Nature Reviews, 2016, 17: 183-193.
Takahashi et al., "Induction of pluripotent stem cells from mouse embryonic and adult fibroblast cultures by defined factors," Cell, 2006, 126: 663-676.
Takami et al., "Complete Genome Sequence of the Alkaliphilic Bacterium Bacillus halodurans and Genomic Sequence Comparison with Bacillus subtilis," Nucleic Acids Research, 2000, 28(21): 4317-4331.
Tam et al., "Benefits and limitations of genome-wide association studies," Nat. Rev. Genet., 2019, 20: 467-484.
Tan et al., "Efficient derivation of lateral plate and paraxial mesoderm subtypes from human embryonic stem cells through GSKi-mediated differentiation," Stem Cells Dev, 2013, 22: 1893-1906.
Tan et al., "Rationally engineered Staphylococcus aureus Cas9 nucleases with high genome- wide specificity," Proc. Nat. Acad. Sci. USA, 2019, 116(46): 20969-20976.
Teratani-Ota et al., "Induction of specific neuron types by overexpression of single transcription factors," In Vitro Cell Dev Biol Anim, 2016, 52(9): 961-973.
Theodorou et al., "A high throughput embryonic stem cell screen identifies Oct-2 as a bifunctional regulator of neuronal differentiation," Genes Dev, 2009, 23: 575-588.
Thorgeirsson et al., "A variant associated with nicotine dependence, lung cancer and peripheral arterial disease," Nature, 2008, 452: 638-642.
Tian et al., "CRISPR Interference-Based Platform for Multimodal Genetic Screens in Human iPSC-Derived Neurons," Neuron, 2019, 104: 239-255 e212.
Tinsley et al., "Amelioration of the dystrophic phenotype of mdx mice using a truncated utrophin transgene," Nature, 1996, 384(6607): 349-353.
Tracy, "Human DNA sequence from clone RP11-34D15 on chromosome 10, complete sequence," Genbank entry, National Center for Biotechnology Information, <https://www.ncbi.nlm.nih.gov/nucleotide/AL139819.8> 2012.
Tsai et al., "GUIDE-seq enables genome-wide profiling of off-target cleavage by CRISPR-Cas nucleases," Nature biotechnology, 2015, 33(2): 187-197.
Tsuchiya et al., "The "Spanning Protocol": A new DNA extraction method for efficient single-cell genetic diagnosis," Journal of Assisted Reproduction Genetics, 2005, 22(11-12):407-14.
Tsunemoto et al., "Diverse reprogramming codes for neuronal identity," Nature, 2018, 557: 375-380.
Tycko et al., "Screening S. aureus CRISPR-Cas9 Paired Guide RNAs for Efficient Targeted Deletion in Duchenne Muscular Dystrophy," Editas, Poster presented on May 5, 2016.
Tyle, "Iontophoretic Devices for Drug Delivery," Pharm. Res., 1986, 3: 318-326.
U.S. Appl. No. 17/471,935, filed Sep. 10, 2021, by Gersbach et al. (Copy not submitted herewith pursuant to the waiver of 37 C.F.R. § 1.98(a)(2)(iii) issued by the Office on Sep. 21, 2004).
U.S. Appl. No. 17/636,750, filed Feb. 18, 2022, by Gersbach et al. (Copy not submitted herewith pursuant to the waiver of 37 C.F.R. § 1.98(a)(2)(iii) issued by the Office on Sep. 21, 2004).
U.S. Appl. No. 17/636,754, filed Feb. 18, 2022, by Gersbach et al. (Copy not submitted herewith pursuant to the waiver of 37 C.F.R. § 1.98(a)(2)(iii) issued by the Office on Sep. 21, 2004).
Urrutia, "KRAB-containing zinc-finger repressor proteins," Genome Biol., 2003, 4(10): 231.
Usman et al., "Catalytic RNA (Ribozymes) as Drugs," Ann. Rep. Med. Chem., 1995, Chapter 30, pp. 285-294.

van Arensbergen et al., "Genome-wide mapping autonomous promoter activity in human cells," Nature Biotechnology, 2017, 35(2): 145-153.
van der Oost et al., "Unravelling the structural and mechanistic basis of CRISPR-Cas systems," Nature Reviews Microbiology, 2014, 12: 479-492.
van Deutekom et al., "Advances in Duchenne muscular dystrophy gene therapy," Nat. Rev. Genet., 2003, 4: 774-783.
Vaquerizas et al., "A census of human transcription factors: function, expression and evolution," Nat Rev Genet, 2009, 10: 252-263.
Veltrop et al., "A dystrophic Duchenne mouse model for testing human antisense oligonucleotides," PLOS One, 2018, 13(2): e0193289, 18 pages.
Verkhusha et al., "GFP-like flourescent proteins and chromoproteins of the class Anthozoa," Protein Structures: Kaleidoscope of Structural Properties and Functions, 2003, 405-439.
Vierbuchen et al., "Direct lineage conversions: unnatural but useful?," Nat Biotechnol, 2011, 29: 892-907.
Vierbuchen et al., "Molecular roadblocks for cellular reprogramming," Mol Cell, 2012, 47: 827- 838.
Vorobyov et al., "Expression of two protein isoforms of PAX7 is controlled by competing cleavage-polyadenylation and splicing, " Gene, 2004, 342: 107-112.
Wada et al., "Codon usage tabulated from the GenBank genetic sequence data," Nucl. Acids Res., 1990, 18: 2367-2411.
Waddell et al., "DIk1 Is Necessary for Proper Skeletal Muscle Development and Regeneration," Plos One, 2010, 5(11): e15055.
Waldrop et al., "Update in Duchenne and Becker muscular dystrophy," Current Opinion in Neurology, 2019, 32: 722-727.
Wang et al., "Adeno-associated virus serotype 8 efficiently delivers genes to muscle and heart," Nat. Biotechnol., 2005, 23: 321-328.
Wang et al., "Construction and analysis of compact muscle-specific promoters for AAV vectors," Gene Ther, 2008, 15: 1489-1499.
Wang et al., "Cyclohexene Nucleic Acids (CeNA): Serum Stable Oligonucleotides that Activate RNase H and Increase Duplex Stability with Complementary RNA," J. Am. Chem. Soc., 2000, 122: 8595-8602.
Wang et al., "Gene Essentiality Profiling Reveals Gene Networks and Synthetic Lethal Interactions with Oncogenic Ras," Cell, 2017, 168: 890-903.e15.
Wang et al., "Genetic screens in human cells using the CRISPR-Cas9 system," Science, 2014, 343: 80-84.
Wang et al., "Identification and characterization of essential genes in the human genome," Science, 2015, 350: 1096-1101.
Wang et al., "Potential of Epigenetic Therapy for Pader-Willi Syndrome," Trends in Pharmaceutical Sciences, 2019, 40(9): 605-608.
Wang et al., "Systemic human minidystrophin gene transfer improves functions and life span of dystrophin and dystrophin/utrophin-deficient mice," J. Orthop. Res., 2009, 27: 421-426.
Wang et al., "Unbiased detection of off-target cleavage by CRISPR-Cas9 and TALENs using integrase-defective lentiviral vectors," Nature biotechnology, 2015, 33(2): 175-8.
Wapinski et al., "Hierarchical mechanisms for direct reprogramming of fibroblasts to neurons," Cell, 2013, 155: 621-635.
Watkins et al., "Thermodynamic contributions of single internal rA.dA, rC.dC, rG.dG and rU.dT mismatches in RNA/DNA duplexes," Nucleic acids research, 2011, 39(5): 1894-1902.
Wei et al., "Targeting Regnase-1 programs long-lived effector T cells for cancer therapy," Nature, 2019, 576(7787): 471-476.
Weltner et al., "Human pluripotent reprogramming with CRISPR activators," Nat Commun Lond, 2018, 9: 1-12.
Westendorp et al., "E2F7 represses a network of oscillating cell cycle genes to control S-phase progression," Nucleic Acids Res, 2012, 40: 3511-3523.
Wherry, "T cell exhaustion," Nat. Immunology, 2011, 12: 492-499.
Wienert et al., "Editing the genome to introduce a beneficial naturally occurring mutation associated with increased fetal globin," Nat Commun 6, 2015, 7085.
Wiggins et al., "High flexibility of DNA on short length scales probed by atomic force microscopy," Nature nanotechnology, 2006, 1(2): 137-141.

(56) References Cited

OTHER PUBLICATIONS

Wilbie et al., "Delivery Aspects of CRISPR/Cas for in Vivo Genome Editing," Acc Chem Res, 2019, 52(6): 1555-1564.
Wiles et al., "CRISPR-Cas9_mediated genome editing and guide RNA design," Mammalian Genome, 2015, 26(9): 501-510.
Willmann et al., "Mammalian animal models for Duchenne muscular dystrophy," Neuromuscular Disorders, 2009, 19(4): 241-249.
Wood, "Neuromuscular disease: CRISPR/Cas9 gene-editing platform corrects mutations associated with Duchenne muscular dystrophy," Nature Reviews Neurology, 2015, 11(4):184.
Wu et al., "A Myogenic Double-Reporter Human Pluripotent Stem Cell Line Allows Prospective Isolation of Skeletal Muscle Progenitors," Cell Rep, 2018, 25: 1966-1981.e4.
Wu et al., "Induction of anion exchanger-1 translation and its opposite roles in the carcinogenesis of gastric cancer cells and differentiation of K562 cells," Oncogene, 2010, 29: 1987-1996.
Wu et al., "Unusual Processing Generates SPA LncRNAs that Sequester Multiple RNA Binding Proteins," Mol Cell, 2016, 64: 534-548.
Wu et al., "Genome-wide binding of the CRISPR endonuclease Cas9 in mammalian cells," Nat Biotechnol, 2014, 32: 670-676.
Wüst et al., "Metabolic Maturation during Muscle Stem Cell Differentiation Is Achieved by miR-1/133a-Mediated Inhibition of the Dlk1-Dio3 Mega Gene Cluster," Cell Metab, 2018, 27: 1026-1039.e6.
Wylie et al., "Distinct transcriptomes define rostral and caudal serotonin neurons," J Neurosci, 2010, 30: 670-684.
Xie et al., "Multiplexed Engineering and Analysis of Combinatorial Enhancer Activity in Single Cells," Mol. Cell, 2017, 66: 285-299.e5.
Xie et al., "sgRNAcas9: a software package for designing CRISPR sgRNA and evaluating potential off-target cleavage sites," PLoS One, 2014, 9(6): e100448.
Xu et al., "CRISPR-mediated Genome Editing Restores Dystrophin Expression and Function in mdx Mice," Molecular Therapy: The Journal of the American Society of Gene Therapy, 2016, 24(3):564-569.
Xu et al., "Direct lineage reprogramming: strategies, mechanisms, and applications," Cell Stem Cell, 2015, 16: 119-134.
Xu et al., "Human Satellite Cell Transplantation and Regeneration from Diverse Skeletal Muscles," Stem Cell Rep, 2015, 5: 419-434.
Xu et al., "Recent advances in neuroepigenetic editing," Curr Opin Neurobiol, 2019, 59: 26-33.
Xue et al., "Synthetic mRNAs Drive Highly Efficient iPS Cell Differentiation to Dopaminergic Neurons," Stem Cells Transl Med, 2019, 8: 112-123.
Yang et al., "Determination of protein-DNA binding constants and specificities from statistical analyses of single molecules: MutS-DNA interactions," Nucleic acids research, 2005, 33(13): 4322-4334.
Yang et al., "Generation of pure GABAergic neurons by transcription factor programming," Nat Methods, 2017, 14: 621-628.
Yin et al., "Long noncoding RNAs with snoRNA ends," Mol Cell, 2012, 48(2): 219-230.
Yin et al., "Programming biomolecular self-assembly pathways," Nature, 2008, 451(7176): 318-323.
You et al., "Design of LNA probes that improve mismatch discrimination," Nuc. Acids. Res., 2006, 34(8): e60.
Young et al., "A Single CRISPR-Cas9 Deletion Strategy that Targets the Majority of DMD Patients Restores Dystrophin Function in hiPSC-Derived Muscle Cells," Cell Stem Cell, 2016, 18: 533-540.
Young et al., "Creation of a Novel Humanized Dystrophic Mouse Model of Duchenne Muscular Dystrophy and Application of a CRISPR/Cas9 Gene Editing Therapy," Journal of Neuromuscular Diseases, 2017, 4(2): 139-145.
Younossi et al., "Epidemiology of chronic liver diseases in the USA in the past three decades," Gut, 2020, 69(3): 564-568.
Yu et al., "RNA interference by expression of short-interfering RNAs and hairpin RNAs in mammalian cells," PNAS, 2002, 99(9): 6047-6052.
Zetsche et al., "Cpf1 Is a Single RNA-Guided Endonuclease of a Class 2 CRISPR-Cas System," Cell, 2015, 163(3):759-71.
Zhang et al., "Comprehensive Structure-Function Study of Neurogenin3 Disease-Causing Alleles during Human Pancreas and Intestinal Organoid Development," Dev Cell, 2019, 50(3): 367-380.e7.
Zhang et al., "Efficient precise knockin with a double cute HDR donor after CRISPR/Cas9- mediated double-stranded DNA cleavage," Genome Biol, 2017 18(35): 18 pages.
Zhang et al., "Gene activation in human cells using CRISPR/Cpf1-p300 and CRISPR/Cpf1- SunTag systems," Protein Cell, 2018, 9: 380-383.
Zhang et al., "Myoediting: Toward Prevention of Muscular Dystrophy by Therapeutic Genome Editing," Physiological Reviews, 2018, 98(3): 1205-1240.
Zhang et al., "Propagated Perturbations from a Peripheral Mutation Show Interactions Supporting WW Domain Thermostability," Structure, 2018, 26: 1474-1485.
Zhang et al., "Rapid single-step induction of functional neurons from human pluripotent stem cells," Neuron, 2013, 78: 785-798.
Zhao et al., "High-efficiency transfection of primary human and mouse T lymphocytes using RNA electroporation," Mol. Ther., 2006, 13: 151-159.
Zhao et al., "Intracellular delivery of artificial transcription factors fused to the protein transduction domain of HIV-1 Tat," Protein Expr Purif, 2013, 90(1): 27-33.
Zhao et al., "The LIM-homeobox gene Lhx8 is required for the development of many cholinergic neurons in the mouse forebrain," Proc Natl Acad Sci U S A, 2003, 100: 9005-9010.
Zhou et al., "Haploinsufficiency of utrophin gene worsens skeletal muscle inflammation and fibrosis in mdx mice," Journal of the Neurological Sciences, 2008, 264(1): 106-111.
Zhu et al., "The role of histone deacetylase 7 (HDAC7) in cancer cell proliferation: regulation on c-Myc," J. Mol. Med, 2011, 89: 279-289.
United States Patent Office Action for U.S. Appl. No. 15/789,348 dated Sep. 15, 2022 (21 pages).
United States Patent Office Action for U.S. Appl. No. 16/858,689 dated Oct. 19, 2022 (11 pages).
NCBI Reference Sequence XM011532698.1 (2015).
NCBI Reference Sequence NM_004020.2 (2010).
NCBI Reference Sequence NG_028016.2 (2013).
United States Patent Office Action for U.S. Appl. No. 16/927,679 dated Nov. 22, 2022 (8 pages).
United States Patent Office Notice of Allowance for U.S. Appl. No. 15/789,348 dated Feb. 15, 2023 (11 Pages).
Yu et al., "Dystrophin-deficient large animal models: translational research and exon skipping," Am J Transl Res, 2015, 7(8): 1314-1331.
United States Patent Office Action for U.S. Appl. No. 16/927,679 dated Jun. 2, 2023 (12 pages).
PCT/US2023/063297, filed Feb. 24, 2023.
PCT/US2023/063296, filed Feb. 24, 2023.
U.S. Appl. No. 18/180,718, filed Mar. 8, 2023.
U.S. Appl. No. 18/030,745, filed Apr. 6, 2023.
U.S. Appl. No. 18/031,313, filed Apr. 11, 2023.
PCT/US2023/018559, filed Apr. 13, 2023.
U.S. Appl. No. 18/033,049, filed Apr. 20, 2023.
Ifuku et al., "Restoration of Dystrophin Protein Expression by Exon Skipping Utilizing CRISPR-Cas9 in Myoblasts Derived from DMD Patient iPS Cells," Methods Mol Biol, 2018, Chapter 12, pp. 191-217.
Min et al., "CRISPR Correction of Duchene Muscular Dystrophy Exon 44 Deletion Mutations in Mice and Human Cells," Science Advances, 2019, 5: eaav4324.
Robinson-Hamm et al., "Gene therapies that restore dystrophin expression for the treatment of Duchenne muscular dystrophy," Human Genetics, 2016, 135(9): 1029-1040.
United States Patent Office Action for U.S. Appl. No. 16/858,689 dated Mar. 23, 2023 (10 pages).
Adikusuma et al., "Versatile single-step-assembly CRISPR/Cas9 vectors for dual gRNA expression," 2017, 12(12): e0187236.

(56) References Cited

OTHER PUBLICATIONS

Carcagno et al., "Neurogenin3 Restricts Serotonergic Neuron Differentiation to the Hindbrain," The Journal of Neuroscience, 2014, 34(46): 15223-15233.
Kalsner et al., "Prader-Willi, Angelman, and 15q11-q13 Duplication Syndromes," Pediatric Clinics of North America United States, 2015, 62(3): 587-606.
Ohta et al., "Imprinting-Mutation Mechanisms in Prader-Willi Syndrome," The American Journal of Human Genetics, 1999,64(2): 397-413.
Yang et al., "A dual AAV system enables the Cas9-mediated correction of a metabolic liver disease in newborn mice," Nature Biotechnology, 2016, 34(3): 334-338.
United States Patent Office Action for U.S. Appl. No. 16/927,679 dated Sep. 21, 2023 (6 pages).
United States Patent Office Notice of Allowance for U.S. Appl. No. 15/789,348 dated Oct. 17, 2023 (7 pages).
United States Patent Office Notice of Allowance for U.S. Appl. No. 15/789,348 dated Jun. 15, 2023 (8 Pages).
Park et al., "Cas-Designer: a web-based tool for choice of CRISPR-Cas9 target sites," Bioinformatics, 2015, 31(24): 4014-4016.
Shen et al., "Massively parallel cis-regulatory analysis in the mammalian central nervous system," Genome Research, 2015, 26(2): 238-255.
Chhatwal et al., "Identification of cell-type-specific promoters within the brain using lentiviral vectors," Gene Therapy, 2007, 14(7): 575-583.
Trinklein et al., " Identification and functional analysis of human transcriptional promoters," Genome Research, 2003, 13(2): 308-312.
Abaandou et al., "Affecting HEK293 Cell Growth and Production Performance by Modifying the Expression of Specific Genes," Cells, 2021, 10: 1667, 21 pages.
Alerasool et al., "An efficient KRAB domain for CRISPRi applications in human cells," Nat Methods, 2020, 17: 1093-1096.
Alonso-Camino et al., "CARbodies: Human Antibodies Against Cell Surface Tumor Antigens Selected From Repertoires Displayed on T Cell Chimeric Antigen Receptors," Mol Ther Nucl Acids, 2013, 2: e93, 11 pages.
Azuma et al., "Robust expansion of human hepatocytes in Fah-/-/Rag2-/-/Il2rg-/- mice" Nat Biotechnol., 2007, 25(8): 903-910.
Bhakta et al., "The generation of zinc finger proteins by modular assembly," Methods Mol. Biol., 2010, 649: 3-30.
Bloomfield, "Quasi-Elastic Light Scattering Applications in Biochemistry and Biology," Ann. Rev. Biophys. Bioeng., 1981, 10: 421-450.
Boris-Lawrie et al., "Recent advances in retrovirus vector technology," Cur. Opin. Genet. Develop., 1993, 3: 102-109.
Bouhairie et al., "Familial hypercholesterolemia," Cardiol. Clin., 2015, 33(2): 169-179.
Braliou et al., "The v-ErbA oncoprotein quenches the activity of an erythroid-specific enhancer," Oncogene, 2001, 20(7): 775-87.
Brash et al., "Strontium phosphate transfection of human cells in primary culture: stable expression of the simian virus 40 large-T-antigen gene in primary human bronchial epithelial cells," Mol. Cell Biol., 1987, 7(5): 2031-2034.
Broude et al., "p21 (CDKN1A) is a negative regulator of p53 stability," Cell Cycle, 2007, 63(12): 1468-1471.
Buckingham, M. et al. "The role of Pax genes in the development oftissues and organs: Pax3 and Pax7 regulate muscle progenitor cell functions." Annu. Rev. Cell Dev. Biol. 23 (2007): 645-673.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA, 1993, 90: 8033-8037.
Cano-Rodriguez et al., "Epigenetic Editing: On the Verge of Reprogramming Gene Expression at Will," Curr Genet Med Rep, 2016, 4: 170-179.

Carlens et al., "Ex vivo T lymphocyte expansion for retroviral transduction: influence of serum-free media on variations in cell expansion rates and lymphocyte subset distribution," Exp Hematol, 2000, 28(10): 1137-46.
Cavalieri et al., "Human T lymphocytes transduced by lentiviral vectors in the absence of TCR activation maintain an intact immune competence," Blood, 2003, 102(2): 497-505.
Chakraborty et al. "553. AAV-fVlediated Delivery of HSV-Specific Homing Endonucleases To Neurons of the Trigeminal Ganglia for HSV-1 Inhibition." Molecular Therapy 22 (2014).
Chen et al., "Fusion protein linkers: property, design and functionality," Adv. Drug Deliv. Rev., 2013, 65(10): 1357-1369.
Chicaybam et al., "An efficient low cost method for gene transfer to T lymphocytes," PLoS ONE, 2013, 8(3): e60298, 11 pages.
Chylinski et al., "The trachNA and CasQ families of type II CRISPR-Cas immunity systems," RNA Biol., 2013, 10(5): 726-737.
Cooper et al., "T-cell clones can be rendered specific for CD19: toward the selective augmentation of the graft-versus-B-lineage leukemia effect," Blood, 2003, 101(4): 1637-1644.
Cortés-Mancera et al., "Gene-Targeted DNA Methylation: Towards Long-Lasting Reprogramming of Gene Expression?" Adv Exp Med Biol., 2022, 1389: 515-533.
Das et al., "Tet-On Systems For Doxycycline-inducible Gene Expression," Current Gene Therapy, 2016, 16: 156-167.
Defesche et al., "Familial hypercholesterolaemia," Nat. Rev. Dis. Primers, 2017, 3: 17093, 20 pages.
Deng et al., "Highly sensitive electrochemical methyltransferase activity assay," Anal Chem., 2014, 86: 2117-2123.
Fuks, "DNA methylation and histone modifications: teaming up to silence genes," Current Opinion in Genetics & Development, 2005, 15(5): 490-495.
Gersbach et al., "Synthetic zinc finger proteins: the advent oftargeted gene regulation and genome modification technologies," Acc. Chem. Res., 2014, 47(8): 2309-18.
Gowher et al., "Mechanism of stimulation of catalytic activity of Dnmt3A and Dnmt3B DNA-(cytosine-C5)-methyltransferases by Dnmt3L," J. Biol. Chem., 2005, 280(14): 13341-13348.
Gowher et al., "Molecular enzymology ofthe catalytic domains ofthe Dnmt3a and Dnmt3b DNA methyltransferases," J. Biol. Chem., 2002, 277(23): 20409-20414.
Hochstrasser et al., "CasA mediates Cas3-catalyzed target degradation during CRISPR RNA-guided interference," PNAS, 2014, 111(18): 6618-23.
Huang et al., "Ch 9: DNA transposons for modification of human primary T lymphocytes," Methods Mol Biol, 2009, 506: 115-126.
Jia et al., "Structure of Dnmt3a bound to Dnmt3L suggests a model for de novo DNA methylation," Nature, 2007, 449(7159): 248-251.
Johnston, "Biolistic transformation: microbes to mice," Nature, 1990, 346: 776-777.
Kao et al., "Ectopic DNMT3L triggers assembly of a repressive complex for retroviral silencing in somatic cells," J Virol., 2014, 88(18): 10680-95.
Kim et al., "Zinc-fingers and homeoboxes 1 (ZHX1) binds DNA methyltransferase (DNMT) 3B to enhance DNMT3B-mediated transcriptional repression," Biochemical and Biophysical Research Communications, 2007, 355(2): 318-323.
Koste et al., "T-cell receptortransfer into human T cells with ecotropic retroviral vectors," Gene Ther, 2014, 21(5): 533-538.
Lagace, "PCSK9 and LDLR degradation: regulatory mechanisms in circulation and in cells," Curr. Opin. Lipidol., 2014, 25(5): 387-393.
Lei et al., "Targeted DNA methylation in vivo using an engineered dCas9-MQ1 fusion protein," Nat. Commun, 2017, 8: 16026, 10 pages.
Li et al., "Development of fluorescent methods for DNA methyltransferase assay," Methods Appl. Fluoresc., 2017, 5: 012002, 8 pages.
Li et al., "The histone methyltransferase SETDB1 and the DNA methyltransferase DNMT3A interact directly and localize to promoters silenced in cancer cells," J. Biol. Chem., 2006, 281(28): 19489-19500.
Liu et al., "Design of polydactyl zinc-finger proteins for unique addressing within complex genomes," PNAS, 1997, 94(11): 5525-5530.

(56) References Cited

OTHER PUBLICATIONS

Ma et al., "Pol III Promoters to Express Small RNAs: Delineation of Transcription Initiation," Molecular Therapy—Nucleic Acids, 2014, 3: e161, 11 pages.
Makarova et al., "Annotation and Classification of CRISPR-Cas Systems," Methods Mol. Biol, 2015, 1311: 47-75.
Manuri et al., "piggyBac transposon/transposase system to generate CD19-specific T cells for the treatment of B-Iineage malignancies," Hum Gene Ther, 2010, 21(4): 427-437.
Mavrothalassitis et al., "Proteins ofthe ETS family with transcriptional repressor activity," Oncogene, 2000, 19: 6524-6532.
Miller et al., "Improved retroviral vectors for gene transfer and expression," BioTechniques, 1989, 7(9): 980-990.
Miller, "Retrovirus packaging cells," Human Gene Therapy, 1990, 1: 5-14.
Milone et al., "Clinical use of lentiviral vectors," Leukemia, 2018, 32(7): 1529-1541.
Mok et al., "Stabilized plasmid-lipid particles: factors influencing plasmid entrapment and transfection properties," Biochimica et Biophysica Acta, 1999, 1419(2): 137-150.
Moon et al., "Recent advances in the CRISPR genome editing tool set," Exp. Mol. Med., 2019, 51(11): 130,11 pages.
Moussa et al., "Here to stay: Writing lasting epigenetic memories," Cell, 2021, 184(9): 2281-2283.
Murphy et al., "The Transcriptional Repressive Activity of KRAB Zinc Finger Proteins Does Not Correlate with Their Ability to Recruit TRIM28," PLoS ONE, 2016, 11(9): e0163555, 19 pages.
O'Geen et al., "Determinants of heritable gene silencing for KRAB-dCas9 + DNMT3 and Ezh2-dCas9 + DNMT3 hit-and-run epigenome editing," Nucleic Acids Res, 2022, 50(6): 3239-3253.
Orth et al., "Structural basis of gene regulation by the tetracycline inducible Tet repressor-operator system," natural structural biology, 2000, 7(3): 215-219.
Park et al., "Treating cancer with genetically engineered T cells," Trends Biotechnol, 2011, 29(11): 550-557.
Peterson et al., "PCSK9 function and physiology," J. Lipid Res., 2008, 49(6): 1152-1156.
Pickar-Oliver et al., "The next generation of CRISPR-Cas technologies and applications," Nature Reviews Molecular Cell Biology, 2019, 20(8): 490-507.
Poh et al., "DNA Methyltransferase Activity Assays: Advances and Challenges," Theranostics, 2016, 6(3): 369-391.
Poirier et al., "The proprotein convertase PCSK9 induces the degradation of low density lipoprotein receptor (LDLR) and its closest family members VLDLR and ApoER2"J. Biol. Chem., 2008, 283: 2363-2372.
Policarpi et al., "Epigenetic editing: Dissecting chromatin function in context," Bioessays, 2021, 43(5): e2000316, 16 pages.
Saha et al., "The NIH Somatic Cell Genome Editing program," Nature, 2021, 592: 195-204.
Scarpa et al., "Characterization of recombinant helper retroviruses from moloney-based vectors in ecotropic and amphotropic packaging cell lines," Virology, 1991, 180: 849-852.
Schellenberger et al., "A recombinant polypeptide extends the in vivo half-life of peptides and proteins in a tunable manner," Nature Biotechnology, 2009, 27(12): 1186-1190.
Sharma et al., "Efficient Sleeping Beauty DNA Transposition From DNA Minicircles," Molec Ther Nucl Acids, 2013, 2(2): e74, 10 pages.
Stepper, "Dissertation: CRISPR-CasQ fusions for synthetic epigenetics," Von der Fakultat 4: Energie-, Verfahrens-und Biotechnik, Institut für Biochemie und Technische Biochemie der Università t Stuttgart, 2020, 148 pages.
Thakore et al., "385. Inhibiting the Myostatin Signaling Pathway using CRISPR/CasQ-Based Repressors." Molecular Therapy 2016, 24: S153.
Tycko et al., "High-Throughput Discovery and Characterization of Human Transcriptional Effectors," Cell, 2020, 183(7): 2020-2035.
Van Tedeloo et al., "High-level transgene expression in primary human T lymphocytes and adull bone marrow CD34+ cells via electroporation-mediated gene delivery," Gene Therapy, 2000, 7(16): 1431-1437.
Verhoeyen et al., "Ch 8: Lentiviral vector gene transfer into human T cells," Methods Mol Biol, 2009, 506: 97-114.
Wang et al., "Phenotypic and functional attributes of lentivirus modified CD19-specific human CD8+ central memory T cells manufactured at clinical scale," J. lmmunother, 2012, 35(9): 689-701.
Wright et al., "Rational design of a split-CasQ enzyme complex," PNAS, 2015, 112(10): 2984-2989.
Wright et al., "Standardized reagents and protocols for engineering zinc finger nucleases by modular assembly," Nat. Protoc., 2006, 1(3): 1637-1652.
Zetsche et al., "A split-CasQ architecture for inducible genome editing and transcription modulation," Nat. Biotechnol, 2015, 33(2): 139-142.
United States Patent Office Action for U.S. Appl. No. 16/858,689 dated Feb. 2, 2024 (16 pages).
Echevarria et al., "Exon-skipping advances for Duchenne muscular dystrophy," Human Molecular Genetics, 2018, 27 (R2): R163-R172.
Miller, "Non-viral CRISPR/Cas gene editing in vitro and in vivo enabled by synthetic nanoparticle co-delivery of 03159 mRNA and sgRNA," Angew Chem Int Engl, 2017, 56(4): 1059-1063.

\* cited by examiner

TN2 (Fok-ELDS) (SEQ ID NO:1):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNGGGKQALETVQRLLPVLCQDHGLTPDQVVAIAS
NGGGKQALETVQRLLPVLCQDHGLTPDQVVAIASNIGGKQALETVQRLLPVLCQDHGLTPDQVVAIASNGGGKQALETVQRLLPVLCQDHGLTPDQ
VVAIASNGGGKQALETVQRLLPVLCQDHGLTPDQVVAIASHDGGKQALETVQRLLPVLCQDHGLTPDQVVAIASNGGGKQALETVQRLLPVLCQDH
GLTPDQVVAIASHDGGKQALETVQRLLPVLCQDHGLTPDQVVAIASNIGGKQALETVQRLLPVLCQDHGLTPDQVVAIASNGGGKQALETVQRLLPVLC
QDHGLTPDQVVAIASNIGGKQALESIVAQLSRPDPALAALTNDHLVALACLGGRPAMDAVKKGLPHAPELIRRVNRRIGERTSHRVAQLVKSELEEKKS
ELRHKLKYVPHEYIELIEIARNPTQDRILEMKVMEFFMKVYGYRGEHLGGSRKPDGAIYTVGSPIDYGVIVDTKAYSGGYNLPIGQADEMERYVEENQT
RDKHLNPNEWWKVYPSSVTEFKFLFVSGHFKGNYKAQLTRLNHITNCNGAVLSVEELLIGGEMIKAGTLTLEEVRRKFNNGEINF

TN3 (Fok-ELDS) (SEQ ID NO:2):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNGGGKQALETVQRLLPVLCQDHGLTPDQVVAIAS
NNGGKQALETVQRLLPVLCQDHGLTPDQVVAIASNGGGKQALETVQRLLPVLCQDHGLTPDQVVAIASNGGGKQALETVQRLLPVLCQDHGLTPDQ
VVAIASNIGGKQALETVQRLLPVLCQDHGLTPDQVVAIASHDGGKQALETVQRLLPVLCQDHGLTPDQVVAIASNGGGKQALETVQRLLPVLCQDHGLT
PDQVVAIASNGGGKQALETVQRLLPVLCQDHGLTPDQVVAIASHDGGKQALETVQRLLPVLCQDHGLTPDQVVAIASNGGGKQALETVQRLLPVLCQDH
GLTPDQVVAIASNIGGKQALETVQRLLPVLCQDHGLTPDQVVAIASNGGGKQALETVQRLLPVLCQDHGLTPDQVVAIASNGGGKQALESIVAQLSRPD
PALAALTNDHLVALACLGGRPAMDAVKKGLPHAPELIRRVNRRIGERTSHRVAQLVKSELEEKKSELRHKLKYVPHEYIELIEIARNPTQDRILEMKVM
EFFMKVYGYRGEHLGGSRKPDGAIYTVGSPIDYGVIVDTKAYSGGYNLPIGQADEMERYVEENQTRDKHLNPNEWWKVYPSSVTEFKFLFVSGHFKGNY
KAQLTRLNHITNCNGAVLSVEELLIGGEMIKAGTLTLEEVRRKFNNGEINF

TN6 (Fok-KKRS) (SEQ ID NO:3):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNGGGKQALETVQRLLPVLCQDHGLTPDQVVAIAS
NNGGKQALETVQRLLPVLCQDHGLTPDQVVAIASNGGGKQALETVQRLLPVLCQDHGLTPDQVVAIASNGGGKQALETVQRLLPVLCQDHGLTPDQ
VVAIASNIGGKQALETVQRLLPVLCQDHGLTPDQVVAIASHDGGKQALETVQRLLPVLCQDHGLTPDQVVAIASNGGGKQALETVQRLLPVLCQDHGLT
PDQVVAIASNGGGKQALETVQRLLPVLCQDHGLTPDQVVAIASHDGGKQALETVQRLLPVLCQDHGLTPDQVVAIASNGGGKQALETVQRLLPVLCQDH
GLTPDQVVAIASNIGGKQALETVQRLLPVLCQDHGLTPDQVVAIASNGGGKQALETVQRLLPVLCQDHGLTPDQVVAIASNGGGKQALESIVAQLSRPD
PALAALTNDHLVALACLGGRPAMDAVKKGLPHAPELIRRVNRRIGERTSHRVAQLVKSELEEKKSELRHKLKYVPHEYIELIEIARNPTQDRILEMKVM
EFFMKVYGYRGEHLGGSRKPDGAIYTVGSPIDYGVIVDTKAYSGGYNLPIGQADEMQRYVKENQTRNKHINPNEWWKVYPSSVTEFKFLFVSGHFKGNY
KAQLTRLNRKTNCNGAVLSVEELLIGGEMIKAGTLTLEEVRRKFNNGEINF

Figure 2

TN8 (Fok-KKRS)(SEQ ID NO:4):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNGGGKQALETVQRLLPVLCQDHGLTPDQVVAIAS
HDGGKQALETVQRLLPVLCQDHGLTPDQVVAIASNGGGKQALETVQRLLPVLCQDHGLTPDQVVAIASNGGGKQALETVQRLLPVLCQDHGLTPDQVVA
IASNIGGKQALETVQRLLPVLCQDHGLTPDQVVAIASHDGGKQALETVQRLLPVLCQDHGLTPDQVVAIASNGGGKQALETVQRLLPVLCQDHGLT
PDQVVAIASHDGGKQALETVQRLLPVLCQDHGLTPDQVVAIASNIGGKQALETVQRLLPVLCQDHGLTPDQVVAIASNNGGKQALETVQRLLPVLC
QDHGLTPDQVVAIASNGGGKQALESIVAQLSRPDRILEMKVMEFFKVYGYRGEHLVALACLGGRPAMDAVKKGLPHAPELIRRVNRRIGERTSHRVAQLVKSELEEKKS
ELRHKLKYVPHEYIELIEIARNPTQDRILEMKVMEFFKVYGSPIDYGVIVDTKAYSGGYNLPIGQADEMQRYVKENQT
RNKHLNPNEWWKVYPSSVTEFKFLFVSGHFKGNYKAQLTRLNRKTNCNGAVLSVEELLIGGEMIKAGTLTLEEVRRKFNNGEINF

TN9 (Fok-ELDS)(SEQ ID NO:5):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNGGGKQALETVQRLLPVLCQDHGLTPDQVVAIAS
HDGGKQALETVQRLLPVLCQDHGLTPDQVVAIASNIGGKQALETVQRLLPVLCQDHGLTPDQVVAIASHDGGKQALETVQRLLPVLCQDHGLT
VVAIASNIGGKQALETVQRLLPVLCQDHGLTPDQVVAIASHDGGKQALETVQRLLPVLCQDHGLTPDQVVAIASNIGGKQALETVQRLLPVLCQDH
PDQVVAIASHDGGKQALETVQRLLPVLCQDHGLTPDQVVAIASNGGGKQALETVQRLLPVLCQDHGLTPDQVVAIASNIGGKQALETVQRLLPVLC
GLTPDQVVAIASNGGGKQALETVQRLLPVLCQDHGLTPDQVVAIASNGGGKQALETVQRLLPVLCQDHGLTPDQVVAIASNIGGKQALETVQRLLPVLCQDH
QDHGLTPDQVVAIASNGGGKQALESIVAQLSRPDPALAALTNDHLVALACLGGSRKPDGAIYTVGSPIDYGVIVDTKAYSGGYNLPIGQADEMERYVEENQT
ELRHKLKYVPHEYIELIEIARNPTQDRILEMKVMEFFMKVYGYRGEHLGGSRKPDGAIYTVGSPIDYGVIVDTKAYSGGYNLPIGQADEMERYVEENQT
RDKHLNPNEWWKVYPSSVTEFKFLFVSGHFKGNYKAQLTRLNHITNCNGAVLSVEELLIGGEMIKAGTLTLEEVRRKFNNGEINF

TN10 (Fok-ELDS)(SEQ ID NO:6):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNGGGKQALETVQRLLPVLCQDHGLTPDQVVAIAS
NGGGKQALETVQRLLPVLCQDHGLTPDQVVAIASNIGGKQALETVQRLLPVLCQDHGLTPDQVVAIASHDGGKQALETVQRLLPVLCQDHGLTPDQ
VVAIASNIGGKQALETVQRLLPVLCQDHGLTPDQVVAIASHDGGKQALETVQRLLPVLCQDHGLTPDQVVAIASNIGGKQALETVQRLLPVLCQDHGLT
PDQVVAIASHDGGKQALETVQRLLPVLCQDHGLTPDQVVAIASNGGGKQALETVQRLLPVLCQDHGLTPDQVVAIASNIGGKQALETVQRLLPVLC
GLTPDQVVAIASNGGGKQALETVQRLLPVLCQDHGLTPDQVVAIASNIGGKQALETVQRLLPVLCQDHGLTPDQVVAIASNIGGKQALETVQRLLPVLCQDH
QDHGLTPDQVVAIASNGGGKQALESIVAQLSRPDPALAALTNDHLVALACLGGSRKPDGAIYTVGSPIDYGVIVDTKAYSGGYNLPIGQADEMERYVEENQT
ELRHKLKYVPHEYIELIEIARNPTQDRILEMKVMEFFMKVYGYRGEHLGGSRKPDGAIYTVGSPIDYGVIVDTKAYSGGYNLPIGQADEMERYVEENQT
RDKHLNPNEWWKVYPSSVTEFKFLFVSGHFKGNYKAQLTRLNHITNCNGAVLSVEELLIGGEMIKAGTLTLEEVRRKFNNGEINF

Figure 2 (continued)

TN12 (Fok-ELDS)(SEQ ID NO:7):
MDYKDHDGDYKDHDIDYKDEDDKMAPKKKRKVGRGSVRSTVAQHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASHDGGKQALETVQRLLPVLCQDHGLTPDQVVAIAS
HDGGKQALETVQRLLPVLCQDHGLTPDQVVAIASNGGGKQALETVQRLLPVLCQDHGLTPDQVVAIASNIGGKQALETVQRLLPVLCQDHGLTPDQ
VVAIASNGGGKQALETVQRLLPVLCQDHGLTPDQVVAIASHDGGKQALETVQRLLPVLCQDHGLTPDQVVAIASNIGGKQALETVQRLLPVLCQDH
GLTPDQVVAIASNIGGKQALETVQRLLPVLCQDHGLTPDQVVAIASHDGGKQALETVQRLLPVLCQDHGLTPDQVVAIASHDGGKQALETVQRLLPVLC
QDHGLTPDQVVAIASHDGGKQALESIVAQLSRDPALAALTNDHLVALACLGGRPALELIYTVGSPIDYGVIVDTKAYSGGYNLPIGQADEMERYVEENQT
ELRHKLKYVPHEYIELIEIARNPTQDRILEMKVMEFFMKVYGYRGEHLGGSRKPDGAIYTVGSPIDYGVIVDTKAYSGGYNLPIGQADEMQRYVKENQT
RDKHLNPNEWWKVYPSSVTEFKFLFVSGHFKGNYKAQLTRLNHITNCNGAVLSVEELLIGGEMIKAGTLTLEEVRRKFNNGEINF

TN13 (Fok-KKRS)(SEQ ID NO:8):
MDYKDHDGDYKDHDIDYKDEDDDKMAPKKKRKVGRGSVRSTVAQHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASHDGGKQALETVQRLLPVLCQDHGLTPDQVVAIAS
NIGGKQALETVQRLLPVLCQDHGLTPDQVVAIASHDGGKQALETVQRLLPVLCQDHGLTPDQVVAIASNIGGKQALETVQRLLPVLCQDHGLTPDQVVA
IASNIGGKQALETVQRLLPVLCQDHGLTPDQVVAIASNGGGKQALETVQRLLPVLCQDHGLTPDQVVAIASNIGGKQALETVQRLLPVLCQDHGLTPDQ
VVAIASNIGGKQALETVQRLLPVLCQDHGLTPDQVVAIASNIGGKQALETVQRLLPVLCQDHGLTPDQVVAIASNIGGKQALETVQRLLPVLCQDH
GLTPDQVVAIASNIGGKQALETVQRLLPVLCQDHGLTPDQVVAIASHDGGKQALETVQRLLPVLCQDHGLTPDQVVAIASHDGGKQALETVQRLLPVLC
QDHGLTPDQVVAIASNGGGKQALES IVAQLSRDPALAALTNDHLVALACLGGSRKPDGAILRRVNRRIGERTSHRVAQLVKSELEEKKS
ELRHKLKYVPHEYIELIEIARNPTQDRILEMKVMEFFKFLFVSGHFKGNYKAQLTRLNRKTNCNGAVLSVEELLIGGEMIKAGTLTLEEVRRKENQT
RNKHINPNEWWKVYPSSVTEFKFLFVSGHFKGNYKAQLTRLNRKTNCNGAVLSVEELLIGGEMIKAGTLTLEEVRRKFNNGEINF

TN17 (Fok-KKRS)(SEQ ID NO:9):
MDYKDHDGDYKDHDIDYKDEDDKMAPKKKRKVGRGSVRSTVAQHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASHDGGKQALETVQRLLPVLCQDHGLTPDQVVAIAS
NGGGKQALETVQRLLPVLCQDHGLTPDQVVAIASNIGGKQALETVQRLLPVLCQDHGLTPDQVVAIASHDGGKQALETVQRLLPVLCQDHGLTPDQVVA
IASHDGGKQALETVQRLLPVLCQDHGLTPDQVVAIASNIGGKQALETVQRLLPVLCQDHGLTPDQVVAIASNGGGKQALETVQRLLPVLCQDHGLTPDQ
VVAIASNGGGKQALETVQRLLPVLCQDHGLTPDQVVAIASNIGGKQALETVQRLLPVLCQDHGLTPDQVVAIASNGGGKQALETVQRLLPVLCQDH
GLTPDQVVAIASHDGGKQALETVQRLLPVLCQDHGLTPDQVVAIASNIGGKQALETVQRLLPVLCQDHGLTPDQVVAIASHDGGKQALETVQRLLPVLC
QDHGLTPDQVVAIASHDGGKQALETVQRLLPVLCQDHGLTPDQVVAIASNGGGKQALESIVAQLS
RPDPALAALTNDHLVALACLGGRPAMDAVKKGLPHAPELIRRVNRRIGERTSHRVAQLVKSELRHKLKYVPHEYIELIEIARNPTQDRILEM
KVMEFFMKVYGYRGEHLGGSRKPDGAIYTVGSPIDYGVIVDTKAYSGGYNLPIGQADEMQRYVKENQTRNKHINPNEWWKVYPSSVTEFKFLFVSGHFK
GNYKAQLTRLNRKTNCNGAVLSVEELLIGGEMIKAGTLTLEEVRRKFNNGEINF

Figure 2 (continued)

TN26 (Fok-ELDS)(SEQ ID NO:10):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASHDGGKQALETVQRLLPVLCQDHGLTPDQVVAIAS
NGGGKQALETVQRLLPVLCQDHGLTPDQVVAIASHDGGKQALETVQRLLPVLCQDHGLTPDQVVAIASNGGGKQALETVQRLLPVLCQDHGLTPDQ
IASHDGGKQALETVQRLLPVLCQDHGLTPDQVVAIASNGGGKQALETVQRLLPVLCQDHGLTPDQVVAIASNIGGKQALETVQRLLPVLCQDHGLT
PDQVVAIASNNGGKQALETVQRLLPVLCQDHGLTPDQVVAIASNGGGKQALETVQRLLPVLCQDHGLTPDQVVAIASNGGGKQALETVQRLLPVLC
QDHGLTPDQVVAIASNNGGKQALETVQRLLPVLCQDHGLTPDQVVAIASNGGGKQALETVQRLLPVLCQDHGLTPDQVVAIASNGGGKQALESIVAQLS
RPDPALAALTNDHLVALACLGGRPAMDAVKKGLPHAPELIRRVNRRIGERTSHRVAQLVKSELEKKSELRHKLKYVPHEYIELIEIARNPTQDRILEM
KVMEFFMKVYGYRGEHLGGSRKPDGAIYTVGSPIDYGVIVDTKAYSGGYNLPIGQADEMERYVEENQTRDKHLNPNEWWKVYPSSVTEFKFLFVSGHFK
GNYKAQLTRLNHITNCNGAVLSVEELLIGGEMIKAGTLTLEEVRRKFNNGEINF

TN27 (Fok-KKRS)(SEQ ID NO:11):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASHDGGKQALETVQRLLPVLCQDHGLTPDQVVAIAS
HDGGKQALETVQRLLPVLCQDHGLTPDQVVAIASNGGGKQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASNGGGKQALETVQRLLPVLCQDHGLTPDQVVAIASNIGGKQALETVQRLLPVLCQDH
GLTPDQVVAIASNNGGKQALETVQRLLPVLCQDHGLTPDQVVAIASNGGGKQALETVQRLLPVLCQDHGLTPDQVVAIASHDGGKQALETVQRLLPVLC
QDHGLTPDQVVAIASNNGGKQALETVQRLLPVLCQDHGLTPDQVVAIASNGGGKQALETVQRLLPVLCQDHGLTPDQVVAIASNGGGKQALESIVAQLS
RPDPALAALTNDHLVALACLGGRPAMDAVKKGLPHAPELIRRVNRRIGERTSHRVAQLVKSELEKKSELRHKLKYVPHEYIELIEIARNPTQDRILEM
KVMEFFMKVYGYRGEHLGGSRKPDGAIYTVGSPIDYGVIVDTKAYSGGYNLPIGQADEMQRYVKENQTRNKHINPNEWWKVYPSSVTEFKFLFVSGHFK
GNYKAQLTRLNRKTNCNGAVLSVEELLIGGEMIKAGTLTLEEVRRKFNNGEINF

TN28 (Fok-ELDS)(SEQ ID NO:12):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASHDGGKQALETVQRLLPVLCQDHGLTPDQVVAIAS
NGGGKQALETVQRLLPVLCQDHGLTPDQVVAIASHDGGKQALETVQRLLPVLCQDHGLTPDQVVAIASNGGGKQALETVQRLLPVLCQDHGLTPDQVVA
IASNGGGKQALETVQRLLPVLCQDHGLTPDQVVAIASNGGGKQALETVQRLLPVLCQDHGLTPDQVVAIASNIGGKQALETVQRLLPVLCQDHGLT
PDQVVAIASNNGGKQALETVQRLLPVLCQDHGLTPDQVVAIASNGGGKQALETVQRLLPVLCQDHGLTPDQVVAIASHDGGKQALETVQRLLPVLC
QDHGLTPDQVVAIASNNGGKQALETVQRLLPVLCQDHGLTPDQVVAIASNGGGKQALETVQRLLPVLCQDHGLTPDQVVAIASNGGGKQALESIVAQLSRDPALAALTNDHLVALACLGGRPAMDAVKKGLP
HAPELIRRVNRRIGERTSHRVAQLVKSELEEKKSELRHKLKYVPHEYIELIEIARNPTQDRILEMKVMEFFMKVYGYRGEHLGGSRKPDGAIYTVGSPI
DYGVIVDTKAYSGGYNLPIGQADEMQRYVKENQTRNKHINPNEWWKVYPSSVTEFKFLFVSGHFKGNYKAQLTRLNHITNCNGAVLSVEELLGGEMIK
AGTLTLEEVRRKFNNGEINF

Figure 2 (continued)

TN29 (FoK-KKRS) (SEQ ID NO:13):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNIGGKQALETVQRLLPVLCQDHGLTPDQVVAIAS
NNGGKQALETVQRLLPVLCQDHGLTPDQVVAIASHDGGKQALETVQRLLPVLCQDHGLTPDQVVAIASNIGGKQALETVQRLLPVLCQDHGLTPDQVVA
IASNNGGKQALETVQRLLPVLCQDHGLTPDQVVAIASNGGGKQALETVQRLLPVLCQDHGLTPDQVVAIASNNGGKQALETVQRLLPVLCQDHGLT
PDQVVAIASHDGGKQALETVQRLLPVLCQDHGLTPDQVVAIASHDGGKQALETVQRLLPVLCQDHGLTPDQVVAIASNIGGKQALETVQRLLPVLCQDH
GLTPDQVVAIASNGGGKQALETVQRLLPVLCQDHGLTPDQVVAIASHDGGKQALETVQRLLPVLCQDHGLTPDQVVAIASHDGGKQALETVQRLLPVLC
QDHGLTPDQVVAIASHDGGKQALETVQRLLPVLCQDHGLTPDQVVAIASNGGGKQALESIVAQLSRPDPALAALTNDHLVALACLGGRPAMDAVKKGLP
HAPELIRRVNRRIGERTSHRVAQLIVKSELEEKKSELRHKLKYVPHEYIELIEIARNPTQDRILEMKVMEFFMKVYGYRGEHLGGSRKPDGAIYTVGSPI
DYGVIVDTKAYSGGYNLPIGQADEMQRYVKEMQTRNKHINPNEWWKVYPSSVTEFKFLFVSGHFKGNYKAQLTRLNRKTNCNGAVLSVEELLIGGEMIK
AGTLTLEEVRRKFNNGEINF

| | Target site (5'->3') | |
|---|---|---|
| TN45 (Right TALEN) | tTACTGATGCCAGGATT (- strand) | SEQ ID NO: 42 |
| TN50 (Left TALEN) | tGGAATTTGAAATATCC | SEQ ID NO: 43 |
| | | |
| Full target site | tGGAATTTGAAATATCCNNNNNNNNNNNNNNNAATCCTGGCATCAGTTa | SEQ ID NO: 44 |
| Human target site | tGGAATTTGAAATATCCGGGGGCCTCTACACGAATCCTGGCATCAGTTa | SEQ ID NO: 25 |
| Mouse target site | tGGAATTTGAAATATCCAGAGGGCTCTACAGAATCCTGGCATCAGTTa | SEQ ID NO: 45 |

B

RVDs

NI NI HD NG NN NI NG NN HD HD NI NN NN NI NG NG
NN NN NI NI NG NG NN NI NI NG MI NG HD HD

C

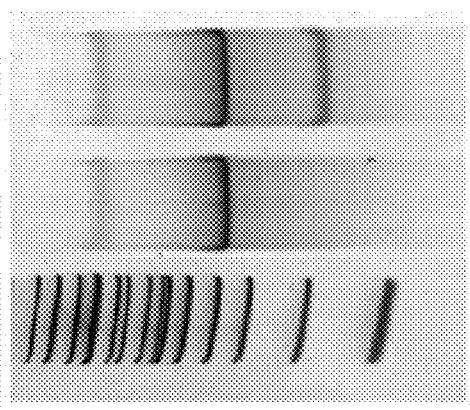

Figure 11

TN45 (Fok-KKRS) (SEQ ID NO:14):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNIGGKQALETVQRLLPVLCQDHGLTPDQVVAIAS
NIGGKQALETVQRLLPVLCQDHGLTPDQVVAIASHDGGKQALETVQRLLPVLCQDHGLTPDQVVAIASNGGKQALETVQRLLPVLCQDHGLTPDQVVA
IASNNGGKQALETVQRLLPVLCQDHGLTPDQVVAIASHDGGKQALETVQRLLPVLCQDHGLTPDQVVAIASNGGKQALETVQRLLPVLCQDHGLT
PDQVVAIASNIGGKQALETVQRLLPVLCQDHGLTPDQVVAIASNNGGKQALETVQRLLPVLCQDHGLTPDQVVAIASNGGKQALESIVAQLSRPD
GLTPDQVVAIASNIGGKQALETVQRLLPVLCQDHGLTPDQVVAIASNGGKQALETVQRLLPVLCQDHGLTPDQVVAIASNGGKQALESIVAQLSRPD
PALAALTNDHLVALACLGGRPAMDAVKKGLPHAPELIRRVNRRIGERTSHRVAQLVKSELEEKKSELRHKLKYVPHEYIELIEIARNPTQDRILEMKVM
EFFMKVYGYRGEHLGGSRKPDGAIYTVGSPIDYGVIVDTKAYSGGYNLPIGQADEMQRYVKENQTRNKHINPNEWWKVYPSSVTEFKFLFVSGHFKGNY
KAQLTRLNRKTNCNGAVLSVEELLIGGEMIKAGTLTLEEVRRKFNNGEINF

TN50 (Fok-ELDS) (SEQ ID NO:15):
MDYKDHDGDYKDHDIDYKDDDDKMAPKKKRKVGRGSVRSTVAQHHEALVGHGFTHAHIVALSQHPAALGTVAVTYQHIITALPEATHEDIVGVGKQWSG
ARALEALLTDAGELRGPPLQLDTGQLVKIAKRGGVTAMEAVHASRNALTGAPLNLTPDQVVAIASNIGGKQALETVQRLLPVLCQDHGLTPDQVVAIAS
NNGGKQALETVQRLLPVLCQDHGLTPDQVVAIASNIGGKQALETVQRLLPVLCQDHGLTPDQVVAIASNGGKQALETVQRLLPVLCQDHGLTPDQVVA
IASNGGKQALETVQRLLPVLCQDHGLTPDQVVAIASNIGGKQALETVQRLLPVLCQDHGLTPDQVVAIASNIGGKQALETVQRLLPVLCQDHGLT
PDQVVAIASNGGKQALETVQRLLPVLCQDHGLTPDQVVAIASHDGGKQALETVQRLLPVLCQDHGLTPDQVVAIASNIGGKQALETVQRLLPVLCQDH
GLTPDQVVAIASNGGKQALETVQRLLPVLCQDHGLTPDQVVAIASHDGGKQALETVQRLLPVLCQDHGLTPDQVVAIASNGGKQALESIVAQLSRPD
PALAALTNDHLVALACLGGRPAMDAVKKGLPHAPELIRRVNRRIGERTSHRVAQLVKSELEEKKSELRHKLKYVPHEYIELIEIARNPTQDRILEMKVM
EFFMKVYGYRGEHLGGSRKPDGAIYTVGSPIDYGVIVDTKAYSGGYNLPIGQADEMERYVEENQTRDKHLNPNEWWKVYPSSVTEFKLFVSGHFKGNY
KAQLTRLNHITNCNGAVLSVEELLIGGEMIKAGTLTLEEVRRKFNNGEINF

Figure 12

GENETIC CORRECTION OF MUTATED GENES

CROSS REFERENCE TO RELATED APPLICATION

This application is a divisional of U.S. patent application Ser. No. 15/634,425, filed Jun. 27, 2017, which is a divisional of U.S. patent application Ser. No. 14/397,420, filed Oct. 27, 2014, which is a national phase filing under 35 U.S.C. § 371 of International Application No. PCT/US2013/038536, filed Apr. 26, 2013, which claims priority to U.S. Provisional Application No. 61/639,227, filed Apr. 27, 2012, which are incorporated herein by reference in their entirety.

STATEMENT OF GOVERNMENT INTEREST

This invention was made with government support under federal grant number DP2-OD008586 awarded by NIH. The U.S. Government has certain rights to this invention.

SEQUENCE LISTING

This application includes a Sequence Listing which has been submitted electronically in ASCII format and is hereby incorporated by reference in its entirety. The sequence listing text file "028193-9138-US04_Sequence_Listing.txt" was created on Jun. 15, 2023, and is 143,360 bytes in size.

TECHNICAL FIELD

The present disclosure relates to the field of genome engineering and genomic alteration of the mutated gene using transcription activator-like effector nucleases (TALENs).

BACKGROUND

Hereditary genetic diseases have devastating effects on children in the United States. These diseases currently have no cure and can only be managed by attempts to alleviate the symptoms. For decades, the field of gene therapy has promised a cure to these diseases, such as Duchenne muscular dystrophy (DMD), by introducing new genetic material into patient's cells. In contrast to gene addition, genome editing with engineered site-specific endonucleases selectively replace or correct disrupted genes. Technical hurdles regarding the safe and efficient delivery of therapeutic genes to cells and patients have limited these approaches. Scientists have only been able to add new genetic material to cells without any control over where it is inserted into the genome. This strategy has led to a myriad of unforeseen negative consequences that can all be attributed to the inability to correct the existing mutated gene sequences. Current experimental gene therapy strategies for genetic diseases, such as DMD, use repeated administration of transient gene delivery vehicles or rely on permanent integration of foreign genetic material into the genomic DNA. Both of these methods have serious safety concerns. Furthermore, these strategies have been limited by an inability to deliver the large and complex gene sequences.

SUMMARY

The present disclosure is directed to a transcription activator-like effector nuclease (TALEN) protein that may bind to a dystrophin gene. The dystrophin gene may comprise a premature stop codon and the TALEN protein may bind upstream or downstream from the premature stop codon. The TALEN protein may bind to a nucleotide sequence comprising one of SEQ ID NOs: 16-46, 50, 52, 58, and 59, and the complement thereof. The TALEN protein may comprise a nuclease. The nuclease may comprise FokI. The TALEN protein may comprise 15-19 RVD modules. The TALEN protein may comprise an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 15. The TALEN protein may bind to a region in exon 51 of the dystrophin gene. The TALEN protein may bind to a nucleotide sequence comprising one of SEQ ID NOs: 16-24, 26-41, 46, 50, 52, 58, and 59, and the complement thereof. The TALEN protein may comprise a nuclease. The nuclease may comprise FokI. The TALEN protein may comprise 15-19 RVD modules. The TALEN protein may comprise an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13. The TALEN protein may bind to a nucleotide sequence comprising SEQ ID NO: 19, or the complement thereof. The TALEN protein may comprise an amino acid sequence selected from the group consisting of SEQ ID NO: 2 and 4. The TALEN protein may bind to a region in the 5' UTR of the dystrophin gene. The TALEN protein may bind to a nucleotide sequence comprising one of SEQ ID NOs: 25 and 42-45 and the complement thereof. The TALEN protein may comprise a nuclease. The nuclease may comprise FokI. The TALEN protein may comprise 15-19 RVD modules. The TALEN protein may comprise an amino acid sequence selected from the group consisting of SEQ ID NO: 14 and 15. The dystrophin gene may be a human dystrophin gene.

The present disclosure is directed to an isolated polynucleotide comprising a nucleotide sequence encoding said TALEN protein and a vector comprising said isolated polynucleotide. The present disclosure is directed to a cell comprising said isolated polynucleotide or said vector.

The present disclosure is directed to a composition comprising two or more of said TALENs, wherein a first TALEN binds to a first binding region and a second TALEN binds to a second binding region, wherein the first binding region and second binding region are located within a target region and the first binding region and second binding region are not the same. The first binding region and the second binding region may be separated by at least one nucleotide. The first binding region and the second binding region may be separated by 5-25 base pairs.

The present disclosure is directed to a method of treating a subject in need thereof having a mutant dystrophin gene, the method comprising administering to the subject said TALEN protein, said isolated polynucleotide, said vector, said cell or said composition. The subject may be suffering from Duchenne muscular dystrophy.

The present disclosure is directed to a method of correcting a mutant dystrophin gene in a cell, the method comprising administering to a cell containing a mutant dystrophin gene said TALEN protein, said isolated polynucleotide, said vector, or said composition. The correction of the mutant dystrophin gene may comprise homology-directed repair. The method may further comprise administering to the cell a donor DNA. The mutant dystrophin gene may comprise a frameshift mutation which causes a premature stop codon and a truncated gene product. The correction of the mutant dystrophin gene may comprise nuclease mediated non-homologous end joining.

The present disclosure is directed to a method of correcting a mutant gene in a cell, the method comprising administering to a cell containing a mutant gene a first TALEN and a second TALEN, wherein the first TALEN binds to a first binding region and a second TALEN binds to a second binding region, wherein the first binding region and second binding region are located within a target region and the first binding region and second binding region are not the same, wherein the correction of the mutant dystrophin gene may comprise nuclease mediated non-homologous end joining, and wherein the correction restores the mutant gene.

The present disclosure is directed to a method of correcting a mutant dystrophin gene in a cell, the method comprising administering to a cell containing a mutant dystrophin gene a first TALEN and a second TALEN, wherein the first TALEN binds to a first binding region and a second TALEN binds to a second binding region, wherein the first binding region and second binding region are located within a target region and the first binding region and second binding region are not the same. The mutant dystrophin gene may comprise a premature stop codon and the target region is upstream or downstream of the premature stop codon. The correction of the mutant dystrophin gene may comprise nuclease mediated non-homologous end joining. The first binding region and the second binding region may be separated by at least one nucleotide. The first binding region and the second binding region may be separated by 5-25 base pairs. The method may not involve co-administration of exogenous DNA. The correction of the mutant dystrophin gene may comprise homology-directed repair. The method may further comprise administering to the cell a donor DNA.

The present disclosure is directed to a kit comprising said TALEN protein, said isolated polynucleotide, said vector, said cell or said composition.

The present disclosure is directed to a kit for correcting a mutant dystrophin gene, the kit comprising said TALEN protein, said isolated polynucleotide, said vector, said cell or said composition.

BRIEF DESCRIPTION OF THE DRAWINGS

FIG. 2 shows the full amino acid sequences of engineered TALENs targeted to exon 51 of the dystrophin gene. Fok ELD-S/KKR-S refers to the FokI nuclease domain that was fused to the TALE DNA-binding domains. The RVD sequences are underlined.

FIG. 11 shows TALENs targeting the 5' UTR of the mouse and human dystrophin gene for integrating a gene, such as the dystrophin or miniaturized dystrophin cDNA, under the control of the dystrophin promoter. (A) The target site of TN45/50 in the human and mouse dystrophin 5' UTR. (B) The RVD components of TN45/50. (C) Combinations of TALENs were co-transfected into HEK293T cells to screen for highly active TALEN pairs. Gene modification frequency was monitored at day 3 and day 10 to assess stable gene modification. (D) 10 micrograms each plasmid encoding each TN45 and TN50 were electroporated into human skeletal myoblasts from a DMD patients. TALEN-mediated modification of the target locus was determined by the Surveyor assay three days after transfection.

FIG. 12 shows the full amino acid sequences of engineered TALENs targeted to the 5' UTR of the dystrophin gene. Fok ELDS/KKRS refers to the FokI nuclease domain that was fused to the TALE DNA-binding domains.

DETAILED DESCRIPTION

Figure 1:
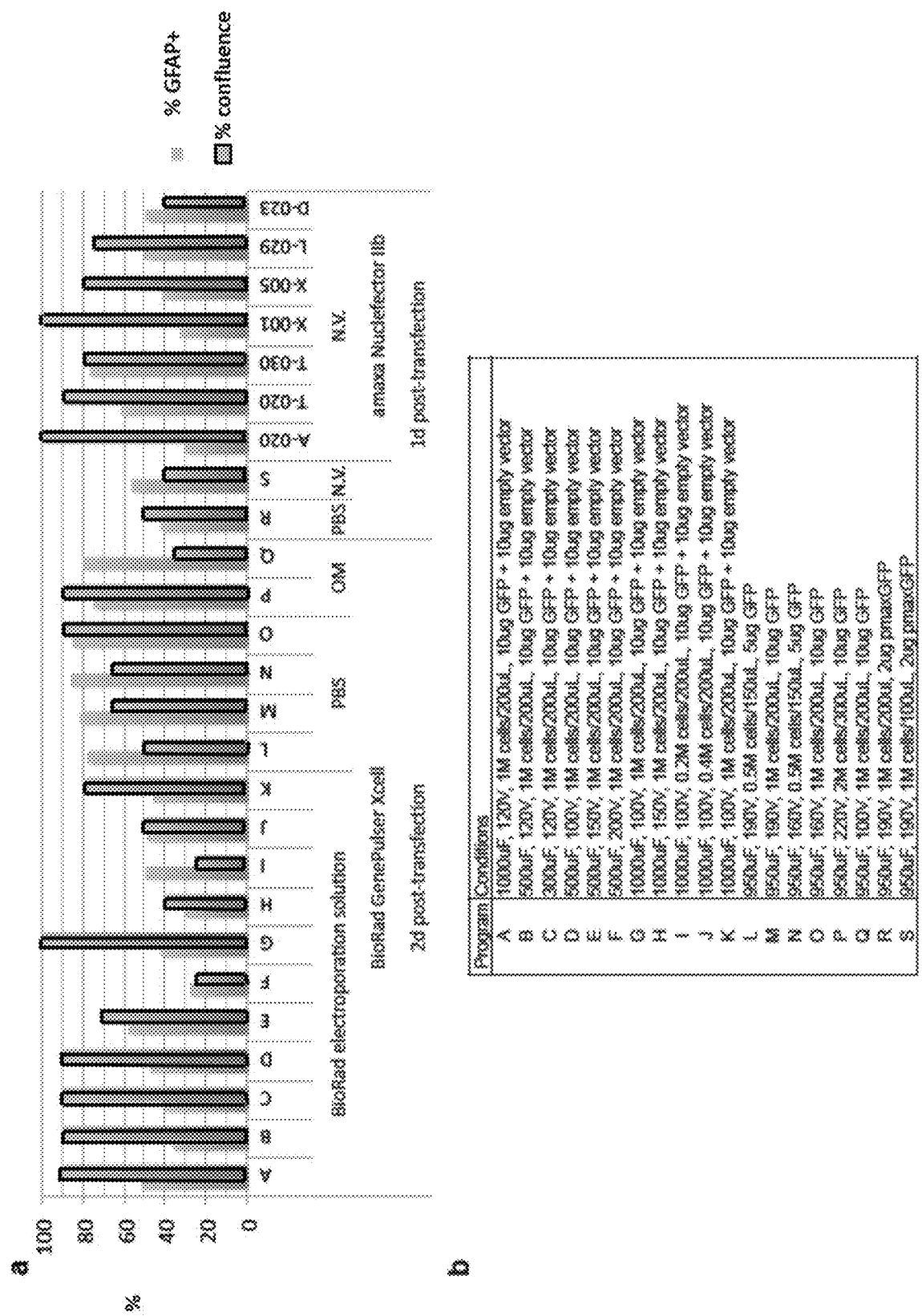
FIG. 1 shows the optimization of electroporation conditions for myoblasts. (a) DMD myoblast cells (cell line 1) were electroporated using BioRad Gene Pulser Xcell or Amaxa Nucleofector IIb devices using the indicated programs. Several different buffers were tested, including BioRad electroporation solution, Sigma phosphate-buffered saline product #D8537 (PBS), Invitrogen OptiMEM 1 (OM), or Amaxa Nucleofector solution V (N.V.). Conditions using the GenePulser device used infinite resistance. For nucleofection, 1 million cells/100 µL nucleofection solution and 2 µg of GFP vector were used according to the manufacturer's specifications. Electroporation using the GenePulser device with program O in PBS solution was selected as the optimal conditions for electroporating myoblasts. (b) Conditions used to optimize BioRad Gene Pulser Xcell electroporation.

As described herein, certain methods and engineered transcription activator-like effector nuclease (TALEN)-related compositions have been discovered to be useful for correcting or reducing the effects of mutations in genes involved in genetic diseases, for example, the dystrophin gene for phenotypic correction of DMD. The present disclosure is directed to genome editing with TALENs with a repair template or donor DNA, which can replace the entire gene or the region containing the mutation and restore the expression of a full-functional or partially-functional protein. The present disclosure is also directed to genome editing with TALENs without a repair template, which can efficiently correct the reading frame and restore the expression of a functional protein involved in a genetic disease. The disclosed TALENs and methods may involve using nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active TALENs with an efficient gene editing method for the treatment of genetic diseases caused by mutations in nonessential coding regions that cause frameshifts or premature stop codons, with no TALEN-mediated off-target changes to the protein-coding regions of the genome.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Binding region" as used herein refers to the region within the target region that is recognized and bound by a TALEN. The TALE DNA-binding domain of the TALEN recognizes and binds to the binding region. For example, the binding region in the dystrophin gene may include a nucleotide sequence found within a target region of SEQ ID NO: 16-25, 44, or 45, or a complement thereof. The binding region may include a nucleotide sequence of SEQ ID NO: 26-43, or a complement thereof.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimize.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Correcting", "genome editing" and "restoring" as used herein refers to changing a mutant gene that encodes a truncated protein or no protein at all, such that a full-length functional or partially full-length functional protein expression is obtained. Correcting or restoring a mutant gene may include replacing the region of the gene that has the mutation or replacing the entire mutant gene with a copy of the gene that does not have the mutation with a repair mechanism such as HDR. Correcting or restoring a mutant gene may also include repairing a frameshift mutation that causes a premature stop codon by generating a double stranded break in the gene that is then repaired using NHEJ. NHEJ may add or delete at least one base pair during repair which may restore the proper reading frame and eliminate the premature stop codon.

"Donor DNA", "donor template" and "repair template" as used interchangeably herein refers to a double-stranded DNA fragment or molecule that includes at least a portion of the gene of interest. The donor DNA may encode a full-functional protein or a partially-functional protein.

"Duchenne Muscular Dystrophy" or "DMD" as used interchangeably herein refers to a recessive, fatal, X-linked disorder that results in muscle degeneration and eventual death. DMD is a common hereditary monogenic disease and occurs in 1 in 3500 males. DMD is the result of inherited or spontaneous mutations that cause nonsense or frame shift mutations in the dystrophin gene. The majority of dystrophin mutations that cause DMD are deletions of exons that disrupt the reading frame and cause premature translation termination in the dystrophin gene. DMD patients typically lose the ability to physically support themselves during childhood, become progressively weaker during the teenage years, and die in their twenties.

"Dystrophin" as used herein refers to a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane that is responsible for regulating muscle cell integrity and function. The dystrophin gene or "DMD gene" as used interchangeably herein is 2.2 mcgabases at locus Xp21. The primary transcription measures about 2,400 kb with the mature mRNA being about 14 kb. 79 exons code for the protein which is over 3500 amino acids.

"Exon 51" as used herein refers to the $51^{st}$ exon of the dystrophin gene. Exon 51 is frequently adjacent to frame-disrupting deletions in DMD patients and has been targeted in clinical trials for oligonucleotide-based exon skipping. A clinical trial for the exon 51 skipping compound eteplirsen recently reported a significant functional benefit across 48 weeks, with an average of 47% dystrophin positive fibers compared to baseline. Mutations in exon 51 are ideally suited for permanent correction by NHEJ-based genome editing.

"Frameshift" or "frameshift mutation" as used interchangeably herein refers to a type of gene mutation wherein the addition or deletion of one or more nucleotides causes a shift in the reading frame of the codons in the mRNA. The shift in reading frame may lead to the alteration in the amino acid sequence at protein translation, such as a missense mutation or a premature stop codon.

"Functional" and "full-functional" as used herein describes protein that has biological activity. A "functional gene" refers to a gene transcribed to mRNA, which is translated to a functional protein.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genetic disease" as used herein refers to a disease, partially or completely, directly or indirectly, caused by one or more abnormalities in the genome, especially a condition that is present from birth. The abnormality may be a mutation, an insertion or a deletion. The abnormality may affect the coding sequence of the gene or its regulatory sequence. The genetic disease may be, but not limited to DMD, cystic fibrosis, Huntington's chorea, familial hypercholesterolemia (LDL receptor defect), hepatoblastoma, Wilson's disease, congenital hepatic porphyria, inherited disorders of hepatic metabolism, Lesch Nyhan syndrome, sickle cell anemia, thalassaemias, xeroderma pigmentosum, Fanconi's anemia retinitis pigmentosa, ataxia telangiectasia, Bloom's syndrome, retinoblastoma, and Tay-Sachs disease.

"Homology-directed repair" or "HDR" as used interchangeably herein refers to a mechanism in cells to repair double strand DNA lesions when a homologous piece of DNA is present in the nucleus, mostly in G2 and S phase of the cell cycle. HDR uses a donor DNA template to guide repair and may be used to create specific sequence changes to the genome, including the targeted addition of whole genes. If a donor template is provided along with the TALENs, then the cellular machinery will repair the break by homologous recombination, which is enhanced several orders of magnitude in the presence of DNA cleavage. When the homologous DNA piece is absent, non-homologous end, oining may take place instead.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Mutant gene" or "mutated gene" as used interchangeably herein refers to a gene that has undergone a detectable mutation. A mutant gene has undergone a change, such as the loss, gain, or exchange of genetic material, which affects the normal transmission and expression of the gene. A "disrupted gene" as used herein refers to a mutant gene that has a mutation that causes a premature stop codon. The disrupted gene product is truncated relative to a full-length undisrupted gene product.

"Non-homologous end joining (NHEJ) pathway" as used herein refers to a pathway that repairs double-strand breaks in DNA by directly ligating the break ends without the need for a homologous template. The template-independent re-ligation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called micro-homologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible.

"Nuclease mediated NHEJ" as used herein refers to NHEJ that is initiated after a nuclease, such as a TALEN, cuts double stranded DNA.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Partially-functional" as used herein describes a protein that is encoded by a mutant gene and has less biological activity than a functional protein but more than a non-functional protein.

"Premature stop codon" or "out-of-frame stop codon" as used interchangeably herein refers to nonsense mutation in a sequence of DNA, which results in a stop codon at location not normally found in the wild-type gene. A premature stop codon may cause a protein to be truncated or shorter compared to the full-length version of the protein.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Repeat variable diresidue" or "RVD" as used interchangeably herein refers to a pair of adjacent amino acid residues within the DNA recognition motif (also known as "RVD module"), which includes 33-35 amino acids, of the TALE DNA-binding domain. The RVD determines the nucleotide specificity of the RVD module. RVD modules may be combined to produce an RVD array. The "RVD array length" as used herein refers to the number of RVD modules that corresponds to the length of the nucleotide sequence within the target region that is recognized by the TALEN, i.e., the binding region.

"Spacers" and "spacer region" as used interchangeably herein refers to the region within the target region that is between, but not a part of, the binding regions for two TALENs.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Target gene" as used herein refers to any nucleotide sequence encoding a known or putative gene product. The target gene may be a mutated gene involved in a genetic disease.

"Target region" as used herein refers to the region of the target gene to which two or more TALENs are designed to bind and cleave. The target region includes the binding regions for the TALENS and the spacer region, which occurs between the binding regions. The two TALENs bind to different binding regions within the target region, after which the target region is cleaved. For example, the target region in the dystrophin gene may include a nucleotide sequence of SEQ ID NO: 16-25, 44-46, 50, 52, 58, or 59, or a complement thereof. The target region in the dystrophin gene may include one or more of SEQ ID NO: 26-43, or a complement thereof. Each of SEQ ID NO: 26-43, or a complement thereof, may represent a binding region.

"Transcription activator-like effector" or "TALE" as used herein refers to a protein structure that recognizes and binds to a particular DNA sequence. The "TALE DNA-binding domain" refers to a DNA-binding domain that includes an array of tandem 33-35 amino acid repeats, also known as RVD modules, each of which specifically recognizes a single base pair of DNA. RVD modules may be arranged in any order to assemble an array that recognizes a defined sequence.

A binding specificity of a TALE DNA-binding domain is determined by the RVD array followed by a single truncated repeat of 20 amino acids. A TALE DNA-binding domain may have 12 to 27 RVD modules, each of which contains an RVD and recognizes a single base pair of DNA. Specific RVDs have been identified that recognize each of the four possible DNA nucleotides (A, T, C, and G). Because the TALE DNA-binding domains are modular, repeats that recognize the four different DNA nucleotides may be linked together to recognize any particular DNA sequence. These targeted DNA-binding domains may then be combined with catalytic domains to create functional enzymes, including artificial transcription factors, methyltransferases, integrases, nucleases, and recombinases.

"Transcription activator-like effector nucleases" or "TALENs" as used interchangeably herein refers to engineered fusion proteins of the catalytic domain of a nuclease, such as endonuclease FokI, and a designed TALE DNA-binding domain that may be targeted to a custom DNA sequence. A "TALEN monomer" refers to an engineered fusion protein with a catalytic nuclease domain and a designed TALE DNA-binding domain. Two TALEN monomers may be designed to target and cleave a target region.

TALENs may be used to introduce site-specific double strand breaks at targeted genomic loci. Site-specific double-strand breaks are created when two independent TALENs bind to nearby DNA sequences, thereby permitting dimerization of FokI and cleavage of the target DNA. TALENs have advanced genome editing due to their high rate of successful and efficient genetic modification. This DNA cleavage may stimulate the natural DNA-repair machinery, leading to one of two possible repair pathways: homology-directed repair (HDR) or the non-homologous end joining (NHEJ) pathway. For example, a TALEN directed towards the dystrophin gene may include an amino acid sequence of any one of SEQ ID NO: 1-15.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. For example, the vector may encode a TALEN protein comprising the amino acid sequence of one of SEQ ID NO: 1-15.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. TALENs

Provided herein are TALENs for use in genome editing and treating genetic diseases. The TALENs may be designed to target any gene involved in a genetic disease. The TALENs may include a nuclease and a TALE DNA-binding domain that binds to the target gene. The target gene may have a mutation such as a frameshift mutation or a nonsense mutation. If the target gene has a mutation that causes a premature stop codon, the TALEN may be designed to recognize and bind a nucleotide sequence upstream or downstream from the premature stop codon.

The TALE DNA-binding domain may have an RVD array length between 1-30 modules, between 1-25 modules, between 1-20 modules, between 1-15 modules, between 5-30 modules, between 5-25 modules, between 5-20 modules, between 5-15 modules, between 7-25 modules, between 7-23 modules, between 7-20 modules, between 10-30 modules, between 10-25 modules, between 10-20 modules, between 10-15 modules, between 15-30 modules, between 15-25 modules, between 15-20 modules, between 15-19 modules, between 16-26 modules, between 16-41 modules, between 20-30 modules, or between 20-25 modules in length. The RVD array length may be 5 modules, 8 modules, 10 modules, 11 modules, 12 modules, 13 modules, 14 modules, 15 modules, 16 modules, 17 modules, 18 modules, 19 modules, 20 modules, 22 modules, 25 modules or 30 modules.

a. Dystrophin

Dystrophin is a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane. The dystrophin gene is 2.2 megabases at locus Xp21. The primary transcription measures about 2,400 kb with the mature mRNA being about 14 kb. 79 exons code for the protein which is over 3500 amino acids. Normal skeleton muscle tissue contains only small amounts of dystrophin but its absence of abnormal expression leads to the development of severe and incurable symptoms. Some mutations in the dystrophin gene lead to the production of defective dystrophin and severe dystrophic phenotype in affected patients. Some mutations in the dystrophin gene lead to partially-functional dystrophin protein and a much milder dystrophic phenotype in affected patients.

DMD is the result of inherited or spontaneous mutations that cause nonsense or frame shift mutations in the dystrophin gene. Naturally occurring mutations and their consequences are relatively well understood for DMD. It is known that in-frame deletions that occur in the exon 45-55 region contained within the rod domain can produce highly functional dystrophin proteins, and many carriers are asymptomatic or display mild symptoms. Furthermore, more than 60% of patients may theoretically be treated by targeting exons in this region of the dystrophin gene. Efforts have been made to restore the disrupted dystrophin reading frame in DMD patients by skipping non-essential exons during mRNA splicing to produce internally deleted but functional dystrophin proteins. The deletion of internal dystrophin exons retain the proper reading frame but cause the less severe Becker muscular dystrophy.

b. TALENs for Dystrophin

TALENs specific for dystrophin gene are disclosed herein. The TALENs may include a nuclease and a TALE DNA-binding domain that binds to the dystrophin gene. The TALENs may bind and recognize a target region. TALEN target regions may be chosen immediately upstream of possible out-of-frame stop codons such that insertions or deletions during the repair process restore the dystrophin reading frame in either disrupted frame.

The TALE domain may bind to a nucleic acid sequence of SEQ ID NOs: 16-46, 50, 52, 58, or 59, or a complement thereof. The TALEN may include an amino acid sequence selected from the group consisting of SEQ ID NO: 1-15, or a complement thereof. The nuclease may be FokI. For example, the disclosed TALENs were engineered to mediate highly efficient gene editing at exon 51 and the 5' UTR of the dystrophin gene. These TALENs restored dystrophin protein expression in cells from DMD patients, including skeletal myoblasts and dermal fibroblasts that were reprogrammed to the myogenic lineage by MyoD, with no TALEN-mediated off-target changes to the protein-coding regions of the genome. The TALENS may have varying RVD array sequences and lengths. Examples of RVD arrays may be found in Table 2. The TALENS may have binding regions separated by varying spacer regions. Examples of spacer regions may be found in Table 3 as indicated as the nucleotide sequence that was not underlined.

(1) Exon 51

Exon 51 is frequently adjacent to frame-disrupting deletions in DMD and occurs in approximately 20% of all DMD patients. This class of DMD mutations is ideally suited for permanent correction by NHEJ-based genome editing and HDR. TALENs described herein have been developed for targeted modification of exon 51 in the human dystrophin gene. These TALENs were transfected into human DMD cells and mediated efficient gene modification and conversion to the correct reading frame. Protein restoration was concomitant with frame restoration and detected in a bulk population of TALEN-treated cells.

The TALE DNA-binding domain of these TA LENs may bind to a nucleic acid sequence of SEQ ID NOs: 16-24, 26-41, 46, 50, 52, 58, or 59, or a complement thereof. The TALEN protein may include an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13, or a complement thereof. The nuclease may be FokI.

(2) 5' UTR

TALENs described herein have been developed for targeted modification of the 5' untranslated region (UTR) of the human dystrophin gene. TALENs engineered to target the 5' UTR of the dystrophin gene allows the integration of a replacement dystrophin gene, such as a full-functional dystrophin gene or a minidystrophin expression cassette, to be under the control of the endogenous promoter and regulatory sequences in the normal chromosomal context. Targeting the gene region upstream of the dystrophin coding sequence thereby allows tissue-specific expression of the dystrophin protein at physiologic expression levels. This approach may be used to treat all of the possible mutations within the dystrophin-encoding sequence.

These TALENs may include a nuclease and a TALE DNA-binding domain that binds to 5' UTR of the human dystrophin gene. The TALE DNA-binding domain may bind to a nucleic acid sequence of SEQ ID NOs: 25 or 42-45, or a complement thereof. The TALEN protein may include an amino acid sequence selected from the group consisting of SEQ ID NO: 14 and SEQ ID NO: 15, or a complement thereof. The nuclease may be FokI.

3. Compositions

The present disclosure also provides compositions of two or more TALENs, as described above. These compositions may be used in genome editing. The composition includes a first TALEN, which binds to a first binding region, and a second TALEN, which binds to a second binding region. The first binding region and second binding region are located within a target region or the target gene. The first binding region and second binding region are not the same; the first TALEN binds to a binding region that is different binding region from where the second TALEN binds. The binding regions are separated by at least one base pair. The spacer region between the binding regions of the target region may be between 1-30 bp, between 1-25 bp, between 1-20 bp, between 1-15 bp, between 5-30 bp, between 5-25 bp, between 5-20 bp, between 5-15 bp, between 7-25 bp, between 7-23 bp, between 7-20 bp, between 10-30 bp, between 10-25 bp, between 10-20 bp, between 10-15 bp, between 14-25 bp, between 14-19 bp, between 15-30 bp, between 15-25 bp, between 15-20 bp, between 20-30 bp, or between 20-25 bp in length. The spacer region may be 5 bp, 10 bp, 11 bp, 12 bp, 13 bp, 14 bp, 15 bp, 16 bp, 17 bp, 18 bp, 19 bp, 20 bp, 21 bp, 22 bp, 23 bp, 24 bp, 25 bp, or 30 bp in length.

The two or more TALEN protein may be selected from TALEN proteins that include an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15, or a complement thereof. The composition may include two TALEN proteins having respectively the amino acid sequence of: SEQ ID NO: 1 and SEQ ID NO: 3; SEQ ID NO: 1 and SEQ ID NO: 4; SEQ ID NO: 1 and SEQ ID NO: 8; SEQ ID NO: 1 and SEQ ID NO: 9; SEQ ID NO: 1 and SEQ ID NO: 11; SEQ ID NO: 1 and SEQ ID NO: 13; SEQ ID NO: 2 and SEQ ID NO: 3; SEQ ID NO: 2 and SEQ ID NO: 4; SEQ ID NO: 2 and SEQ ID NO: 8; SEQ ID NO: 2 and SEQ ID NO: 9; SEQ ID NO: 2 and SEQ ID NO: 11; SEQ ID NO: 2 and SEQ ID NO: 13; SEQ ID NO: 5 and SEQ ID NO: 3; SEQ ID NO: 5 and SEQ ID NO: 4; SEQ ID NO: 5 and SEQ ID NO: 8; SEQ ID NO: 5 and SEQ ID NO: 9; SEQ ID NO: 5 and SEQ ID NO: 11; SEQ ID NO: 5 and SEQ ID NO: 13; SEQ ID NO: 6 and SEQ ID NO: 3; SEQ ID NO: 6 and SEQ ID NO: 4; SEQ ID NO: 6 and SEQ ID NO: 8; SEQ ID NO: 6 and SEQ ID NO: 9; SEQ ID NO: 6 and SEQ ID NO: 11; SEQ ID NO: 6 and SEQ ID NO: 13; SEQ ID NO: 7 and SEQ ID NO: 3; SEQ ID NO: 7 and SEQ ID NO: 4; SEQ ID NO: 7 and SEQ ID NO: 8; SEQ ID NO: 7 and SEQ ID NO: 9; SEQ ID NO: 7 and SEQ ID NO: 11; SEQ ID NO: 7 and SEQ ID NO: 13; SEQ ID NO: 10 and SEQ ID NO: 3; SEQ ID NO: 10 and SEQ ID NO: 4; SEQ ID NO: 10 and SEQ ID NO: 8; SEQ ID NO: 10 and SEQ ID NO: 9; SEQ ID NO: 10 and SEQ ID NO: 11; SEQ ID NO: 10 and SEQ ID NO: 13; SEQ ID NO: 12 and SEQ ID NO: 3; SEQ ID NO: 12 and SEQ ID NO: 4; SEQ ID NO: 12 and SEQ ID NO: 8; SEQ ID NO: 12 and SEQ ID NO: 9; SEQ ID NO: 12 and SEQ ID NO: 11; SEQ ID NO: 12 and SEQ ID NO: 13; or SEQ ID NO: 14 and SEQ ID NO:15.

4. Methods of Correcting a Mutant Gene and Treating a Subject

The present disclosure also provides methods of correcting a mutant gene in a cell and treating a subject suffering from a genetic disease, such as DMD. The method may include administering to a cell or subject a TALEN protein, a polynucleotide or vector encoding said TALEN protein, or composition of TALENs as described above. The method may include administering a first TALEN, which binds to a first binding region, and a second TALEN, which binds to a second binding region. The first binding region and second binding region are located within a target region or the target gene. The first binding region and second binding region are not the same; the first TALEN binds to a binding region that is different binding region from where the second TALEN binds. The binding regions are separated by at least one base pair. The spacer region between the binding regions of the target region may be between 1-30 bp, between 1-25 bp, between 1-20 bp, between 1-15 bp, between 5-30 bp, between 5-25 bp, between 5-20 bp, between 5-15 bp, between 7-25 bp, between 7-23 bp, between 7-20 bp, between 10-30 bp, between 10-25 bp, between 10-20 bp, between 10-15 bp, between 14-25 bp, between 14-19 bp, between 15-30 bp, between 15-25 bp, between 15-20 bp, between 20-30 bp, or between 20-25 bp in length. The spacer region may be 5 bp, 10 bp, 11 bp, 12 bp, 13 bp, 14 bp, 15 bp, 16 bp, 17 bp, 18 bp, 19 bp, 20 bp, 21 bp, 22 bp, 23 bp, 24 bp, 25 bp, or 30 bp in length. The two or more TALEN protein may be selected from the TALEN proteins described above. The method may involve homology-directed repair or non-homologous end joining.

a. Homology-Directed Repair

As described herein, the inventors show restoration of protein expression from an endogenous mutated gene using a method involving homology-directed repair. The method as described above further includes administrating a donor template to the cell. The donor template may include a nucleotide sequence encoding a full-functional protein or a partially-functional protein. For example, the donor template may include a miniaturized dystrophin construct, termed minidystrophin ("minidys") or a full-functional dystrophin construct for restoring a mutant dystrophin gene.

b. Nuclease Mediated Non-Homologous End Joining

As described herein, the inventors show restoration of protein expression from an endogenous mutated gene through template-free NHEJ-mediated DNA repair. In contrast to a transient method targeting the target gene RNA, the correction of the target gene reading frame in the genome by transiently expressed TALENs may lead to permanently restored target gene expression by each modified cell and all of its progeny.

Nuclease mediated NHEJ gene correction may correct the mutated target gene and offers several potential advantages over the HDR pathway. For example, NHEJ does not require a donor template, which may cause nonspecific insertional mutagenesis. In contrast to HDR, NHEJ operates efficiently in all stages of the cell cycle and therefore may be effectively exploited in both cycling and post-mitotic cells, such as muscle fibers. This provides a robust, permanent gene restoration alternative to oligonucleotide-based exon skipping or pharmacologic forced read-through of stop codons and could theoretically require as few as one drug treatment. NHEJ-based gene correction using TALENs, as well as other engineered nucleases including meganucleases and zinc finger nucleases, may be combined with other existing ex vivo and in vivo platforms for cell- and gene-based therapies, in addition to the plasmid electroporation approach described here. For example, delivery of TALENs by mRNA-based gene transfer or as purified cell permeable proteins could enable a DNA-free genome editing approach that would circumvent any possibility of insertional mutagenesis.

c. Duchenne Muscular Dystrophy

The method, as described above, may be used for correcting the dystrophin gene and recovering full-functional or partially-functional protein expression of said mutated dystrophin gene. In some aspects and embodiments the disclosure provides a method for reducing the effects (e.g., clinical symptoms/indications) of DMD in a patient. In some aspects and embodiments the disclosure provides a method for treating DMD in a patient. In some aspects and embodiments the disclosure provides a method for preventing DMD in a patient. In some aspects and embodiments the disclosure provides a method for preventing further progression of DMD in a patient.

5. Constructs and Plasmids

The genetic constructs may comprise a nucleic acid sequence that encodes the TALEN disclosed herein. The genetic construct, such as a plasmid, may comprise a nucleic acid that encodes the TALEN. The genetic construct may be present in the cell as a functioning extrachromosomal molecule. The genetic construct may be a linear minichromosome including centromere, telomeres or plasmids or cosmids.

The genetic construct may also be part of a genome of a recombinant viral vector, including recombinant lentivirus, recombinant adenovirus, and recombinant adenovirus associated virus. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer an initiation codon, a stop codon, or a polyadenylation signal.

The nucleic acid sequences may make up a genetic construct that may be a vector. The vector may be capable of expressing the TALEN in the cell of a mammal. The vector may be recombinant. The vector may comprise heterologous nucleic acid encoding the TALEN. The vector may be a plasmid. The vector may be useful for transfecting cells with nucleic acid encoding the TALEN, which the transformed host cell is cultured and maintained under conditions wherein expression of the TALEN takes place.

Coding sequences may be optimized for stability and high levels of expression. In some instances, codons are selected to reduce secondary structure formation of the RNA such as that formed due to intramolecular bonding.

The vector may comprise heterologous nucleic acid encoding the TALEN and may further comprise an initiation codon, which may be upstream of the TA LEN coding sequence, and a stop codon, which may be downstream of the TALEN coding sequence. The initiation and termination codon may be in frame with the TALEN coding sequence. The vector may also comprise a promoter that is operably linked to the TALEN coding sequence. The promoter operably linked to the TALEN coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US Patent Application Publication No. US20040175727, the contents of which are incorporated herein in its entirety.

The vector may also comprise a polyadenylation signal, which may be downstream of the TALEN. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 vector (Invitrogen, San Diego, Calif.).

The vector may also comprise an enhancer upstream of the TALEN. The enhancer may be necessary for DNA expression. The enhancer may be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector may also comprise a mammalian origin of replication in order to maintain the vector extrachromosomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector may comprise the nucleic acid sequence encoding the TALEN comprising the amino acid sequence of at least one of SEQ ID NOs:1-15

6. Pharmaceutical Compositions

The TALEN may be in a pharmaceutical composition. The pharmaceutical composition may comprise about 1 ng to about 10 mg of DNA of the TALEN or TALEN protein. The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity may include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The TALEN may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LOS), or lipid. The transfection facilitating agent is poly-L-glutamate, and more preferably, the poly-L-glutamate is present in the TALEN at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA vector TALEN may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LOS), or lipid.

7. Methods of Delivery

Provided herein is a method for delivering the pharmaceutical formulations, preferably TALENs, for providing genetic constructs and proteins of the TALENs. The delivery of the TALEN may be the transfection or electroporation of the TALEN as a nucleic acid molecule that is expressed in the cell and delivered to the surface of the cell. The nucleic acid molecules may be electroporated using BioRad Gene Pulser Xcell or Amaxa Nucleofector 11b devices. Several different buffers may be used, including BioRad electroporation solution, Sigma phosphate-buffered saline product #D8537 (PBS), Invitrogen OptiMEM 1 (OM), or Amaxa Nucleofector solution V (N.V.). Transfections may include a transfection reagent, such as Lipofectamine 2000.

Upon delivery of the TALEN to the cell, and thereupon the vector into the cells of the mammal, the transfected cells will express the TALEN. The TALEN may be administered to a mammal to correct the dystrophin gene in a mammal. The mammal may be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

8. Routes of Administration

The TALEN proteins and compositions may be administered to a subject by different routes including orally, parenterally, sublingually, transdermally, rectally, transmucosally, topically, via inhalation, via buccal administration, intraplcurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian may readily determine the dosing regimen and route of administration that is most appropriate for a particular animal. The TALEN proteins and compositions may be administered by traditional syringes, needleless injection devices, "microprojectile bombardment gone guns", or other physical methods such as electroporation ("EP"), "hydrodynamic method", or ultrasound.

The vector encoding a TALEN protein may be delivered to the mammal by several technologies including DNA injection (also referred to as DNA vaccination) with and without in vivo electroporation, liposome mediated, nanoparticle facilitated, recombinant vectors such as recombinant lentivirus, recombinant adenovirus, and recombinant adenovirus associated virus.

The nucleotide encoding a TALEN protein may be introduced into a cell to genetically correct the target gene. For example, a nucleotide encoding a TALEN protein directed towards a mutant dystrophin gene may be introduced into a myoblast cell from a DMD patient. The genetically corrected myoblast cell may be treated with MyoD to induce differentiation into fibroblasts, which may be implanted into subjects, such as the damaged muscles of a subject to verify that the corrected dystrophin protein was functional and/or to treat the subject.

9. Cell Types

Any of these delivery methods and/or routes of administration could be utilized with a myriad of cell types currently under investigation for cell-based therapies, including immortalized myoblast cells, such as wild-type and DMD patient derived lines, for example Δ48-50 DMD, C25C14 and DMD-7796 cell lines, primal DMD dermal fibroblasts, induced pluripotent stem cells, bone marrow-derived progenitors, skeletal muscle progenitors, human skeletal myoblasts from DMD patients, CD133+ cells, mesoangioblasts, and MyoD- or Pax7-transduced cells, or other myogenic progenitor cells. Immortalization of human myogenic cells may be used for clonal derivation of genetically corrected myogenic cells.

Cells may be modified ex vivo to isolate and expand clonal populations of immortalized DMD myoblasts that contain a genetically corrected dystrophin gene and are free of nuclease-introduced mutations in protein coding regions of the genome. Alternatively, transient in vivo delivery of nucleases by non-viral or non-integrating viral gene transfer, or by direct delivery of purified proteins containing cell-penetrating motifs may enable highly specific correction in situ with minimal or no risk of exogenous DNA integration.

10. Kits

Provided herein is a kit, which may be used to correct a mutated gene. The kit comprises at least one component for correcting a mutated gene and instructions for using the TALEN. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an interne site that provides the instructions.

At least one component may include at least one TALEN, as described above, that specifically binds and cleaves the mutated gene when a second TALEN is present nearby. Two or more TALENs, as described above, may be included in the kit to specifically bind and target a particular target region in the mutated gene. The TALEN may be specific for a mutated dystrophin gene, as described above. The kit may include donor DNA, as described above.

11. Examples

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present invention has multiple aspects, illustrated by the following non-limiting examples.

Example 1

Materials and Methods

Cell culture and transfection. HEK293T cells were obtained from the American Tissue Collection Center (ATCC) through the Duke Cell Culture Facility and were maintained in DMEM supplemented with 10% bovine calf serum and 1% penicillin/streptomycin. Immortalized myoblasts (Mamchaoui, K. et al. *Skelet Muscle* 1, 1-11 (2011)) (one from a wild-type donor, and two Δ48-50 DMD patient derived lines) were maintained in skeletal muscle media (PromoCell) supplemented with 20% bovine calf serum (Sigma), 50 µg/ml fetuin, 10 ng/ml human epidermal growth factor (Sigma), 1 ng/ml human basic fibroblast growth factor (Sigma), 10 µg/ml human insulin (Sigma), 1% GlutaMAX (Invitrogen), and 1% penicillin/streptomycin (Invitrogen). Primary DMD dermal fibroblasts were obtained from the Coriell Cell repository (GM05162A, Δ46-50) and maintained in DMEM supplemented with 10% fetal bovine serum, 1 ng/mL human basic fibroblast growth factor, and 1% penicillin/streptomycin. All cell lines were maintained at 37° C. and 5% $CO_2$.

HEK293T cells were transfected with Lipofectamine 2000 (Invitrogen) according to the manufacturer's protocol in 24 well plates. Immortalized myoblasts and primary fibroblasts were transfected by electroporation using the Gene Pulser XCell (BioRad) with PBS as an electroporation buffer using optimized conditions for each line (FIG. 1). Transfection efficiencies were measured by delivering an EGFP expression plasmid and using flow cytometry. These efficiencies were routinely ≥95% for HEK293T and ≥70% for the primary fibroblasts and immortalized myoblasts. For all experiments, the indicated mass of electroporated plasmid corresponds to the amount used for each TALEN monomer.

TALE nuclease assembly and off-target site prediction. TALENs targeted to exon 51 of the human dystrophin gene were designed in silico using the TALE-NT webserver (Cermak, T. et al. *Nucleic Acids Res* 39, e82 (2011)). TALEN target sites were chosen to include half-site targets approximately 15-19 bp in length, preceded by a 5'-T (Miller, J. C. et al. *Nat Biotechnol* 29, 143-148 (2011)). Plasmids encoding these TALENs were assembled using the Golden Gate assembly method (Cermak, T. et al. *Nucleic Acids Res* 39, e82 (2011)) and standard cloning techniques into a modified pcDNA3.1 (Invitrogen) destination vector containing the Δ152/+63 TALEN architecture (Miller, J. C. et al. *Nat Biotechnol* 29, 143-148 (2011)) derived from the pTAL3 expression vector provided in the Golden Gate kit from Addgene. The FokI endonuclease domains were codon optimized and contained the ELD/KKR obligate heterodimer (Doyon, Y. et al. *Nat Methods* 8, 74-79 (2010)) and Sharkey mutations (Guo, J. et al. *J Mol Biol* (2010)) as described previously (Perez-Pinera, P. et al. *Nucleic Acids Res* 40, 3741-3752 (2012)). Complete sequences, including TN⅜ sequences, are provided in FIG. 2. Potential off-target sites for TALEN pairs, including TN⅜, in the human genome were predicted in silico using the Paired Target Finder tool on the TALE-NT 2.0 webserver (Doyle, E. L. et al. *Nucleic Acids Res* 40, W117-122 (2012)). All predicted off-target sites were scanned using the following parameters: recommended score cutoff (3.0), spacers of range 12-23 bp, and upstream base set to "T only". Valid likely potential off-target sites were only considered as those with up to 4 mismatches per TALEN half-site binding sequence (maximum of 8 mismatches per TALEN pair target site). Plasmid DNA encoding the modules that were used to construct the TALEs was obtained from the Addgene non-profit plasmid repository.

Cel-1 quantification of endogenous gene modification. TALEN-induced lesions at the endogenous target site were quantified using the Surveyor nuclease assay (Guschin, D. Y. et al. *Meth Mol Biol* 649, 247-256 (2010)), which can detect mutations characteristic of nuclease-mediated NHEJ. After electroporation, cells were incubated for 3 or 10 days at 37° C. and genomic DNA was extracted using the DNcasy Blood and Tissue kit (QIAGEN). The target locus was amplified by 30 cycles of PCR with the AccuPrime High Fidelity PCR kit (Invitrogen) using primers 5'-GAGTTTGGCTCAAATTGT-TACTCTT-3' (SEQ ID NO: 60) and 5'-GG-GAAATGGTCTAGGAGAGTAAAGT-3' (SEQ ID NO: 61). The resulting PCR products were randomly melted and reannealed in a PCR machine with the program: 95° C. for 240 s, followed by 85° C. for 60 s, 75° C. for 60 s, 65° C. for 60 s, 55° C. for 60 s, 45° C. for 60 s, 35° C. for 60 s, and 25° C. for 60 s with a −0.3° C./s rate between steps. Following reannealing, 8 µL of PCR product was mixed with 1 µL of Surveyor Nuclease S and 1 µL of Enhancer S (Transgenomic) and incubated at 42° C. for 1 hour. After incubation, 6 µL of digestion product was loaded onto a 10% TBE polyacrylamide gel and run at 200V for 30 min. The gels were stained with ethidium bromide and quantified using ImageLab (Bio-Rad) by densitometry as previously described (Guschin, D. Y. et al. *Meth Mol Biol* 649, 247-256 (2010)).

Cytotoxicity assay. To quantitatively assess potential TALEN cytotoxicity, HEK293T cells were transfected with 10 ng of a GFP reporter and 100 ng of each nuclease using Lipofectamine 2000 according to the manufacturer's instructions (Invitrogen). The percentage of GFP positive cells was assessed at 2 and 5 days by flow cytometry. The survival rate was calculated as the decrease in GFP positive cells from days 2 to 5 and normalized to cells transfected with an empty nuclease expression vector as described (Cornu, T. I. et al. *Meth Mol Biol* 649, 237-245 (2010)).

Clone isolation procedure. Immortalized DMD myoblasts were electroporated with 10 µg of each TALEN plasmid (20 µg total). After 7 days, isogenic clones were isolated by clonal dilution in hypoxic conditions (5% $O_2$) to accelerate myoblast growth. Genomic DNA was extracted from clones using the QuickExtract Kit (Epicentre) and the target locus amplified by PCR using the Cel-1 primers and conditions above. The resulting PCR products were either mixed with equal amounts of PCR product from untreated cells and analyzed by the Surveyor assay, as described above, or directly submitted for conventional Sanger sequencing to identify modified clones.

Viral transduction and forced MyoD overexpression in primary fibroblasts. 300,000 fibroblasts were plated transduced in 10 cm plates with a lentiviral vector encoding a full-length human MyoD cDNA under the control of a dox-inducible promoter and a constitutive puromycin resistance cassette. Two days post-transduction, fibroblasts were selected for 6 days in 1 µg/mL puromycin (Sigma) to enrich for transduced cells. Fibroblasts were then plated at a density of 200,000 cells in 10 cm dishes and MyoD expression was induced by adding 3 µg/mL doxycycline (Fisher Scientific) to the media, which was exchanged every two days.

Western blot analysis. To assess dystrophin expression, immortalized myoblasts were differentiated into myofibers by replacing the growth medium with DMEM supplemented with 1% insulin-transferrin-selenium (Invitrogen) and 1% antibiotic/antimycotic (Invitrogen) for 4-7 days. Fibroblasts were transdifferentiated into myoblasts by inducing MyoD overexpression and incubating the cells in DMEM supplemented with 1% insulin-transferrin-selenium (Invitrogen), 1% antibiotic/antimycotic (Invitrogen) and 3 µg/mL doxycycline for 15 days. TALEN expression was assessed at 3 days after transfecting HEK293T cells. Cells were collected and lysed in RIPA buffer (Sigma) supplemented with a protease inhibitor cocktail (Sigma) and the total protein amount was quantified using the bicinchoninic acid assay according to the manufacturer's instructions (Pierce). Samples were then mixed with NuPAGE loading buffer (Invitrogen) and 5% β-mercaptoethanol and heated to 85° C. for 10 minutes. Twenty-five micrograms of protein were separated on 4-12% NuPAGE Bis-Tris gels (Invitrogen) with MES buffer (Invitrogen). Proteins were transferred to nitrocellulose membranes for 1-2 hours in transfer buffer containing 10-20% methanol and 0.01% SDS. The blot was then blocked for 1 hour with 5% milk-TBST at room temperature. Blots were probed with the following primary antibodies: NCL-Dys2 (1:25, Leica), MANDYS8 (1:100, Sigma), GAPDH (1:5000, Cell Signaling), anti-FLAG-HRP (1:2000, Cell Signaling), or anti-myogenin F5D (1:200, Santa Cruz). Dystrophin expression was detected using MANDYS8 in DMD myoblast line 2 and the DMD fibroblast line or NCL-Dys2 in DMD myoblast line 1. TALEN expression was detected using anti-FLAG. Blots were then incubated with mouse or rabbit horseradish peroxidase-conjugated secondary antibodies (Santa Cruz) and visualized using the ChemiDoc chemilumescent system (BioRad) and Western-C ECL substrate (BioRad).

Immunofluorescence. Fibroblasts were plated on cover slips in 24 well plates at a density of 30,000 cells/well and MyoD expression was induced for 15 days as described above. Cells were then fixed in 4% paraformaldehyde and blocked for 1 hour at room temperature with PBS containing 5% BSA, 2% goat serum and 0.2% Triton X-100. Cells were then stained overnight at 4° C. with MF20 (1:200, Developmental Studies Hybridoma Bank) primary antibody and then for 1 hour at room temperature with anti-mouse AlexaFluor 488 (Molecular Probes) secondary antibody. Cover slips were mounted with ProLong Gold antifade (Molecular Probes).

Exome sequencing and analysis. The exomes of four clonally derived DMD myoblast lines carrying known TALEN-mediated deletions in exon 51 of the dystrophin gene, as well as the parent line for these cells, were analyzed. Genomic DNA was isolated using the DNeasy Blood and Tissue Kit (QIAGEN) and 3 µg of DNA were submitted to the Duke Institute for Genome Sciences and Policy's Genome Sequencing & Analysis Core. Illumina-compatible libraries were made and enriched for exonic regions using the SureSelect Human All Exon V4 Kit (Agilent). Five total libraries were prepared from the four treatment samples and one parental line reference sample. The libraries were indexed and sequenced on one lane of Illumina HiSeq2000 (100-bp paired-end sequencing). Bioinformatics analyses were performed by Duke Genome Sequencing & Analysis Core. The analysis pipeline includes the initial QC to remove sequencing adaptors and low quality bases to facilitate mapping. Sequence depth of targeted regions was calculated as >97% at 10× coverage, >91% at 20× coverage, and >82% for 30× coverage (Table 1). Table 1 shows the exome capture statistics. DOWT was the parent DMD myoblast cell line used as the reference sample for analysis. DO32, DO106, DO127, and DO141 were the four clonally derived DMD myoblast lines carrying predetermined on-target NHEJ events at the exon 51 dystrophin locus.

TABLE 1

Exome capture statistics

| | Sample Name | | | | | |
|---|---|---|---|---|---|---|
| | DO106 | DO127 | DO141 | DO32 | DOWT | Agilent-Human All Exon V4 |
| capture efficiency | | | | | | |
| Reads on Target | 79.33 | 79.28 | 79.27 | 75.95 | 79.35 | 75 |
| Reads On-Target +/−100bp | 86.84 | 88.96 | 89.15 | 86.11 | 89.15 | 85 |
| Coverage | | | | | | |
| 1x | 99.87 | 99.88 | 99.88 | 99.87 | 99.88 | 99 |
| 10x | 97.4 | 97.71 | 97.48 | 97.53 | 97.46 | 90 |
| 20x | 91.26 | 92.28 | 91.41 | 91.62 | 91.41 | 80 |
| 30x | 82.66 | 84.45 | 82.8 | 83.27 | 82.94 | |
| 50x | 63.51 | 66.35 | 63.54 | 64.35 | 63.9 | |
| 100x | 28.13 | 31.12 | 27.85 | 28.45 | 28.62 | |

Each sequencing reaction generated >64 million reads with >93% of reads above a quality score of 30 and an overall mean quality score of >36.4. High quality reads were mapped to the human reference genome (hg19) using bwa 0.5.9. An exome capture pipeline developed at the Duke Sequencing Core was used to assess the exome capture efficiency. Picard v1.74 was used for removing PCR duplicates. The GATK (v1.6-13) toolkit was used for variant calling, read realignment around INDELs, quality score recalibration and QC filtering. The filtering step discards the variants with 1) low coverage (coverage (<30×), 2) strand-bias, 3) low SNP quality score (<50) and 4) low allelic frequency (<0.5). Each candidate point mutation or INDEL were reviewed manually by IGV to identify false negative artifacts due to insufficient coverage of the parental line. Identical point mutations and INDELs that occurred in more than two of the four clones were verified as artifacts due to coverage of the reference parent cell line and were discarded. Common point mutations and INDELs were removed by comparing to human dbSNP135. The remaining point mutations and INDELs were annotated using Annovar and classified using a perl script written by the Duke Sequencing Core. The non-exonic point mutations were not considered. All point mutations and INDELs were individually visualized and validated on IGV. The flanking 100 bp of each validated mutation was screened for any potential sequence similarity to the TN⅜ target site using the Paired Target Finder tool on the TALE-NT 2.0 webserver using the parameters: recommended score cutoff (3.0), spacers of range 1-30 bp, and upstream base set to "T only."

Example 2

Results

Figure 3:
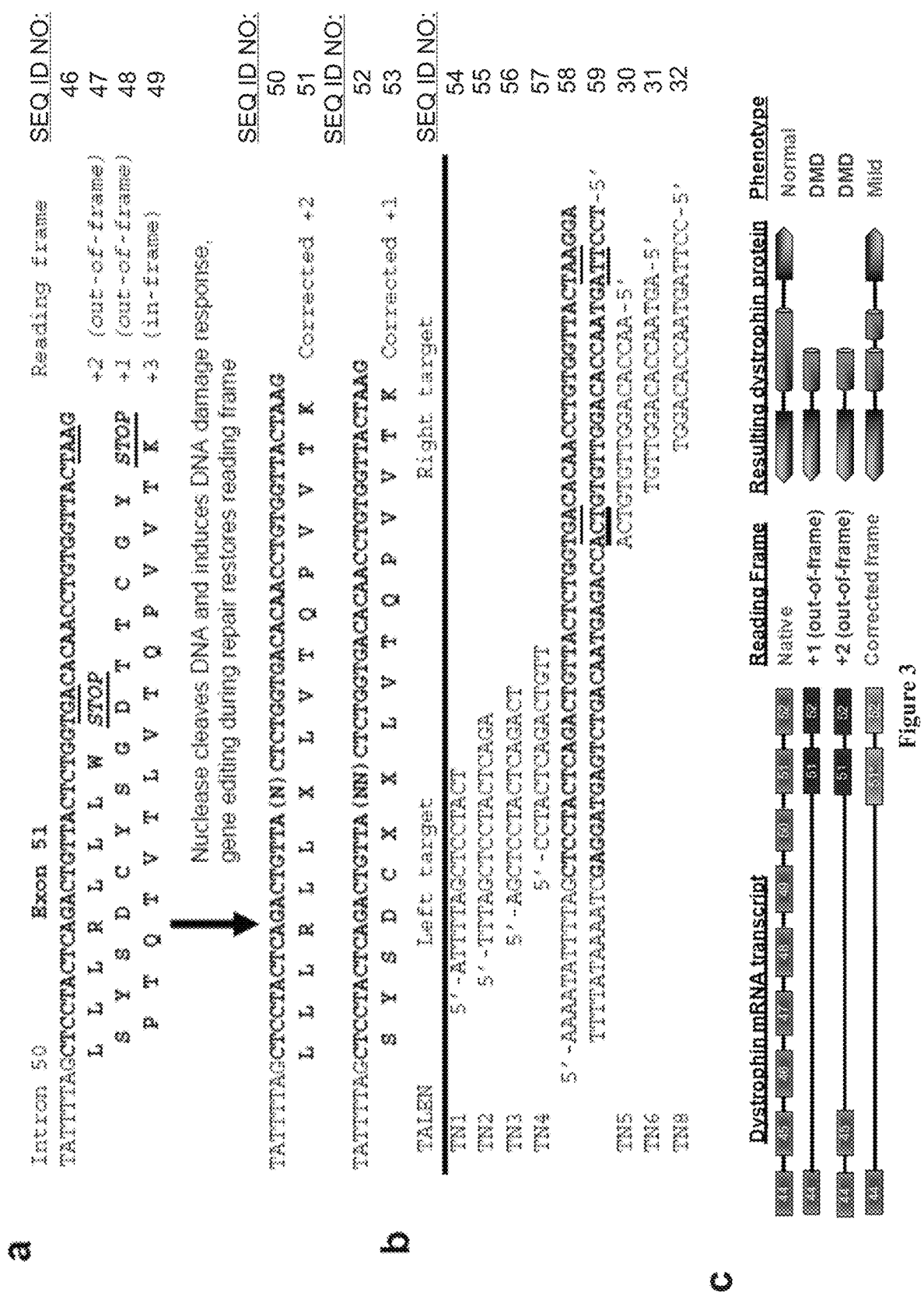
FIG. 3 shows the design of TALENs targeting exon 51 of the human dystrophin gene. (a) The possible reading frames of human dystrophin exon 51 and corresponding amino acid sequences after genome editing. (b) Combinations of TALEN pairs were designed to target immediately upstream of either out-of-frame stop codon (underline) in exon 51 (bold) of the human dystrophin gene. (c) Representative genetic mutations that cause DMD and the resulting dystrophin protein are shown (deletion of exons 45-50 or 46-50). Gene editing from (a) restored the dystrophin reading frame in both types of mutations to create a functional dystrophin protein.

Design and validation of TALENs targeted to the dystrophin gene. To evaluate TALEN-mediated genetic correction by NHEJ, several TALENs were designed to target exon 51 in the dystrophin gene. Plasmids encoding the exemplary TALENs described herein were electroporated into conditionally immortalized myoblasts (muscle cells) isolated from DMD patients. TALEN target sites were chosen immediately upstream of the two possible out-of-frame stop codons (FIG. 3a), such that insertions or deletions could restore the dystrophin reading frame in either disrupted frame. Variable lengths of spacers between TALEN monomers and TALEN RVD array lengths were tested to optimize nuclease activity (FIG. 3b, Table 2), as done previously (Miller, J. C. et al. *Nat Biotechnol* 29, 143-148 (2011)).

TABLE 2

Target sequences of engineered TALENs (TN) and repeat variable diresidues (RVDs) that determine DNA-binding specificity

| | Target sequences | RVD sequence |
|---|---|---|
| TN1 | attttagctcctact (SEQ ID NO: 26) | NI NG NG NG NG NI NN HG NG HD HD NG NI HD NG |
| TN2 | tttagctcctactcaga (SEQ ID NO: 27) | NG NG NG NI NN HD NG HD HD NG NI HD NG HD NI NN NI |
| TN3 | agctcctactcagact (SEQ ID NO: 28) | NI NN HD NG HD HD NG NI HD NG HD NI NN NI HD NG |
| TN4 | cctactcagactgtt (SEQ ID NO: 29) | HD HD NG NI HD NG HD NI NN NI HD NG NN NG NG |
| TN5 | aaccacaggttgtgtca (SEQ ID NO: 30) | NI NI HD HD NI HD NI NN NN NG NG NN NG NN NG HD NI |
| TN6 | agtaaccacaggttgt (SEQ ID NO: 31) | NI NN NG NI NI HD NG NI HD NI NN NN NG NG NN NG |
| TN8 | ccttagtaaccacaggt (SEQ ID NO: 32) | HD HD NG NG NI NN NG NI NI HD HD NI HD NI NN NN NG |
| TN9 | gcaaaaacccaaaatat (SEQ ID NO: 33) | NN HD NI NI NI NI NI HD HD HD NI NI NI NI NG NI NG |
| TN10 | ttgcaaaaacccaaaat (SEQ ID NO: 34) | NG NG NN HD NI NI NI NI NI HD HD HD NI NI NI NI NG |
| TN12 | ccttttttgcaaaaaccc (SEQ ID NO: 35) | HD HD NG NG NG NG NG NN HD NI NI NI NI NI HD HD HD |
| TN13 | caccagagtaacagtct (SEQ ID NO: 36) | HD NI HD HD NI NN NI NN NG NI NI HD NI NN NG HD NG |
| TN17 | gtcaccagagtaacagtct (SEQ ID NO: 37) | NN HD HD NI HD NI NN NI NN NI NI HD NI NN NG HD NG |
| TN26 | ccaaactagaaatgccat (SEQ ID NO: 38) | HD HD NI NI NI HD NG NI NN NI NI NI NG NN HD HD NI NG |
| TN27 | gaaatctgccagagcaggt (SEQ ID NO: 39) | NN NI NI NI NG HD NG NN HD HD NI NN NI NN HD NI NN NG |
| TN28 | ctatagatgagattatct (SEQ ID NO: 40) | HD NG NI NG NI NN NI NG NN NI NN NN NI NN NI NG HD NG |

TABLE 2-continued

Target sequences of engineered TALENs (TN) and repeat variable diresidues (RVDs) that determine DNA-binding specificity

| | Target sequences | RVD sequence |
|---|---|---|
| TN29 | agcaatgcggccatccct (SEQ ID NO: 41) | NI NN HD NI NI NG NN HD NN NN HD HD NI NG HD HD HD NG |

Figure 4:
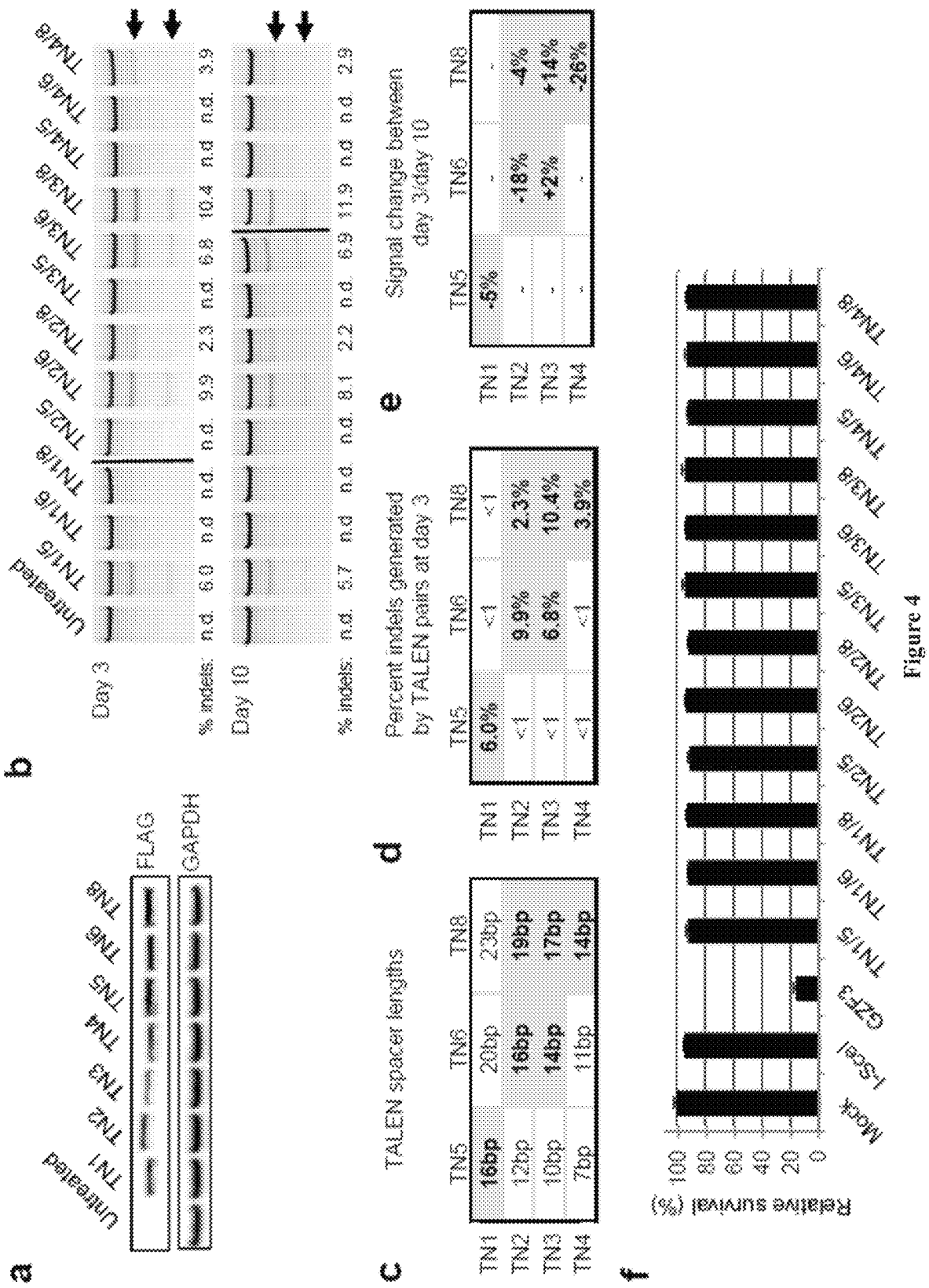
FIG. 4 shows the validation and characterization of TALENs. (a) Each TALEN construct was transfected independently into HEK293T cells to confirm full-length expression. All TALENs were approximately 95-110 kDa. (b) Combinations of TALENs were co-transfected into HEK293T cells to screen for highly active TALEN pairs. Gene modification frequency was monitored at day 3 and day 10 to assess stable gene modification. Arrows denote predicted cleavage band sizes indicative of NHEJ activity. (c) Summary of TALEN spacer lengths. (d) Measured gene modification rates detected by the Surveyor assay from day 3 data in (b). (e) Measured indel signal changes between day 3 and day 10 from the data in (b). (f) Cytotoxicity assay in HEK293T cells for all TALEN combinations. I-SceI is a non-toxic meganuclease and GZF3 is a zinc-finger nuclease known to be cytotoxic to human cells. "n.d." means not detected.
Figure 5:
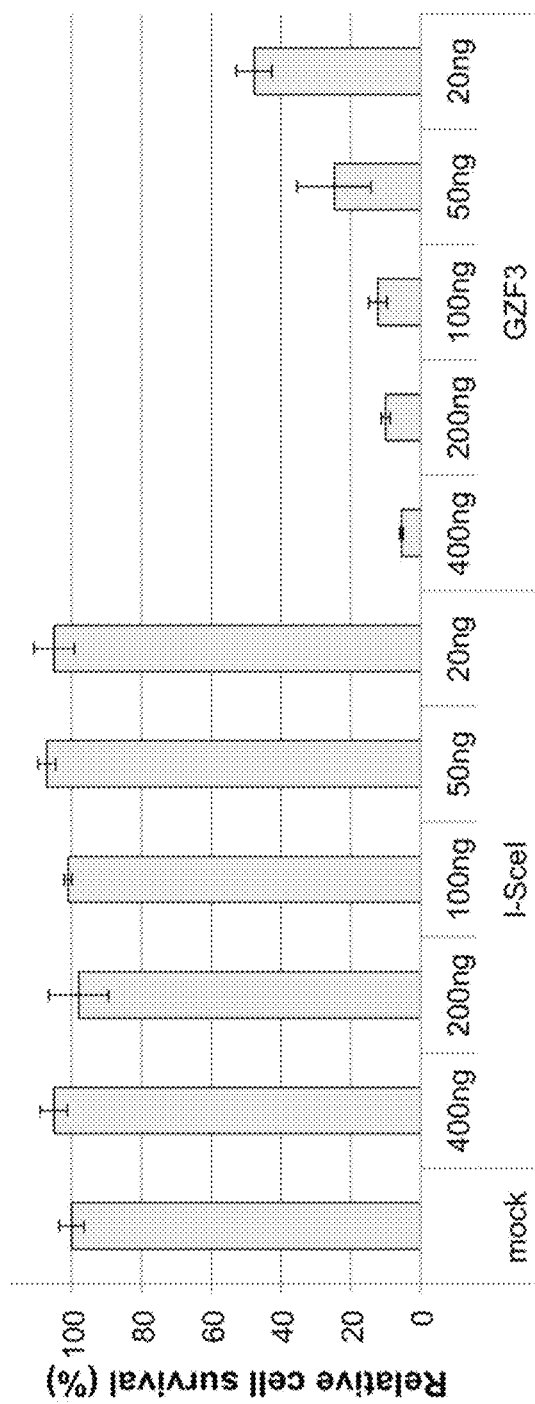
FIG. 5 shows the optimization of cytotoxicity assay using Lipofectamine 2000 in 293T cells. Varying amounts of plasmid encoding the non-toxic endonuclease I-SceI and toxic zinc-finger nuclease GZF3 were transfected into 293T cells and assessed for relative survival rates post-transfection. Based on these data, 100 ng of nuclease expression plasmid was used for the cytotoxicity studies.

Western blots confirmed full-length and robust expression of the TALENs following transfection of TALEN-encoding plasmids into HEK293T cells (FIG. 4a). All combinations of left and right TALENs were then transfected into HEK293T cells and the genomic DNA was assessed for modification by the Surveyor assay, which can detect the frequency of allelic modifications with a dynamic range of ~1-50%. Several TALENs with spacers of 14-19 bp were highly active with gene editing efficiencies exceeding modification of 10% of total alleles (FIGS. 4b-4d). The gene editing frequencies were stable from day 3 to day 10 (FIGS. 4b and 4e), confirming that these TALENs were well tolerated in human cells. Furthermore, the engineered TALENs showed minimal cytotoxicity in human cells similar to the well-characterized non-cytotoxic homing endonuclease I-SceI (FIGS. 4f and 5). TN3/8 was highly active and a well-tolerated TALEN pair and was used for subsequent experiments.

Figure 6:
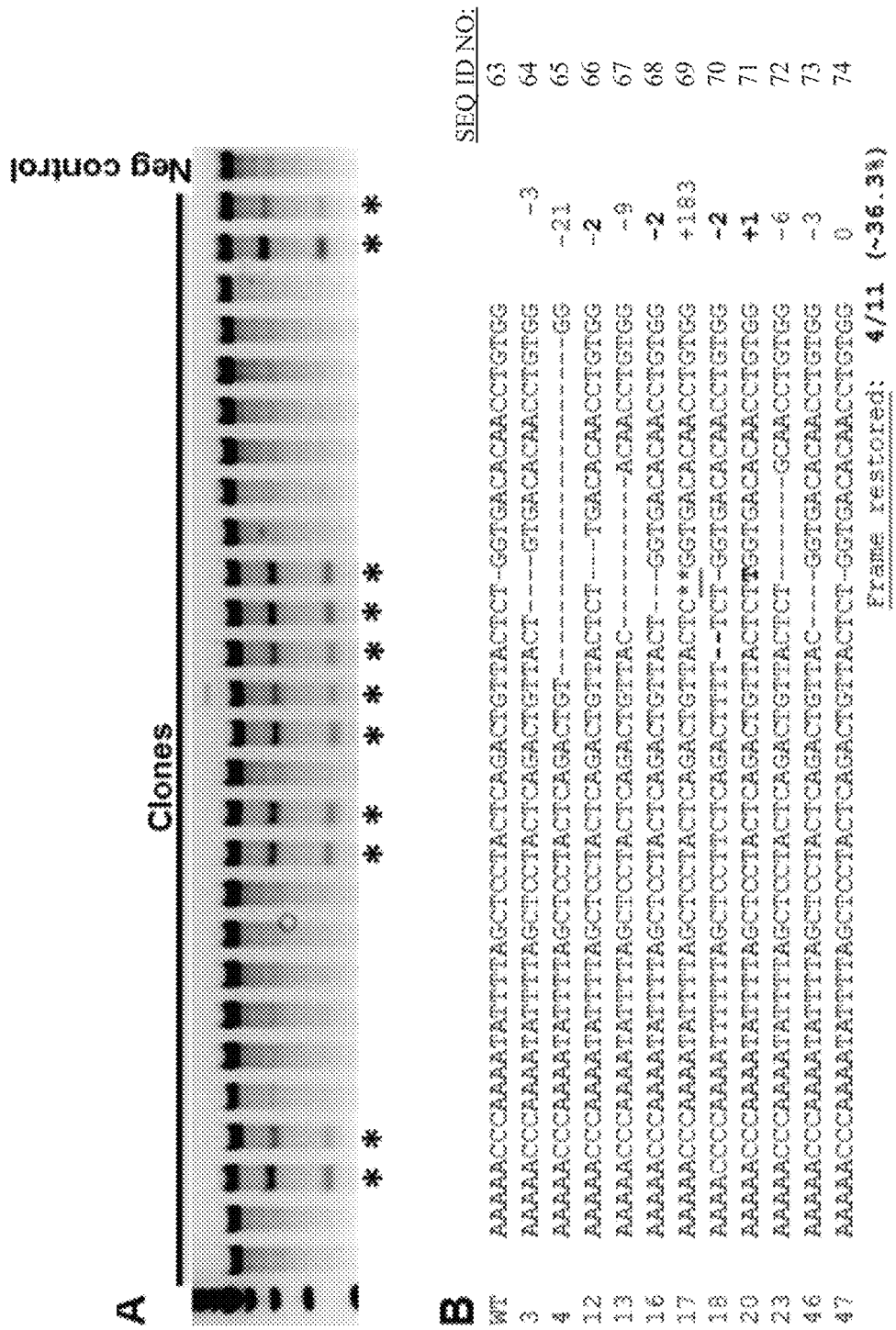
FIG. 6 shows (A) Surveyor assay to detect exon 51 gene modification in clonal cell populations of TALEN-treated DMD myoblasts. Asterisks indicate modified cells. (B) Sequences of modified clonal populations. The size of the insertion/deletion is indicated on the right. The two asterisks represent a 183 nucleotide insertion. Four of eleven modified clones (of 27 total assayed clones) showed indels that lead to reading frame correction
Figure 9:
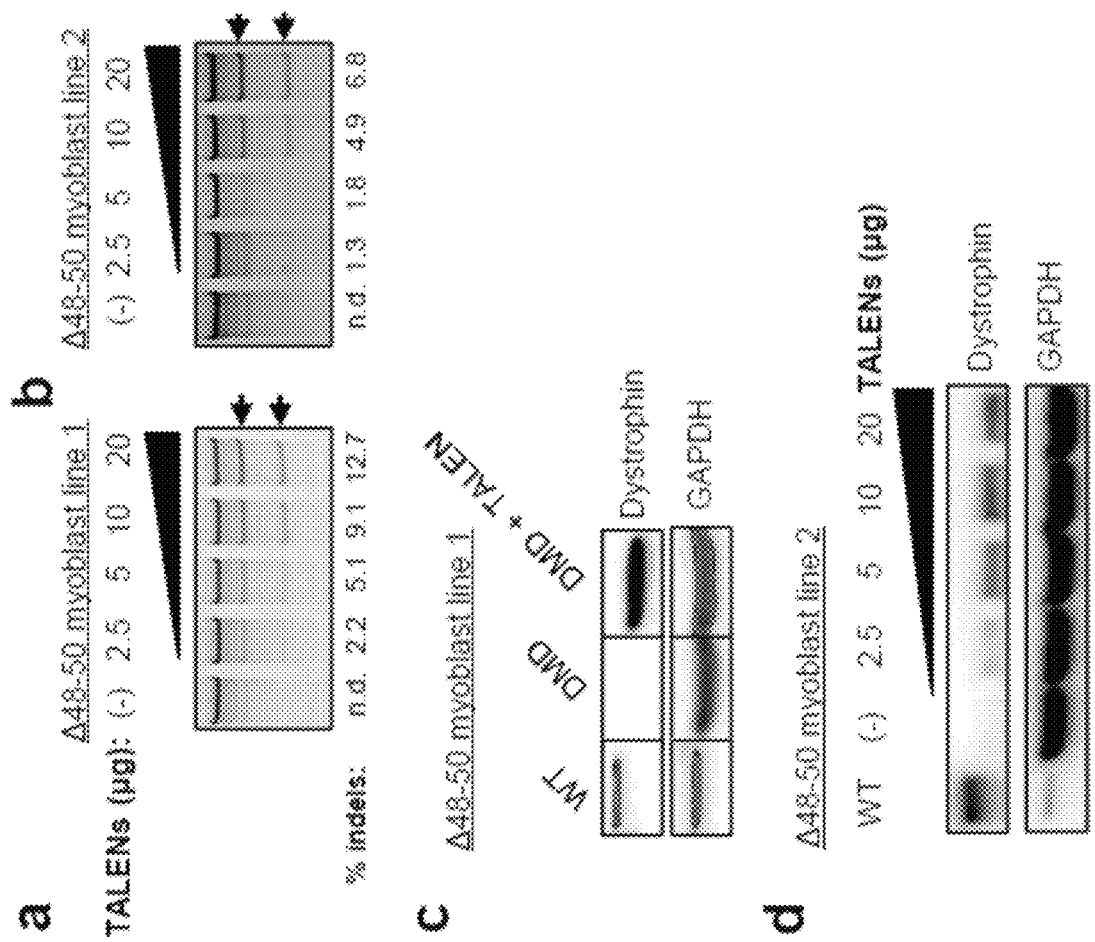
FIG. 9 shows the efficient genetic modification and protein restoration in a bulk population of cells treated with TN3/8. (a,b) Dose-dependent response of NHEJ activity with increasing amounts of TALEN pair TN3/8 measured by the Surveyor assay after transfection of the indicated amount of each TALEN plasmid into two different DMD myoblast lines, each carrying a novel deletion of exons 48-50 (Δ48-50). Arrows denote predicted cleavage band sizes indicative of NHEJ activity. (c) DMD myoblast line 1 was treated with five micrograms of each TALEN plasmid and dystrophin expression was assessed after 7 days of differentiation by western blot using the NCL-Dys2 antibody. (d) DMD myoblast 2 was treated with the indicated amount of each TALEN plasmid and dystrophin expression was assessed after 7 days of differentiation by western blot using the MANDYS8 antibody. Protein from wild-type human myoblasts differentiated in parallel was diluted 1:100 and loaded as a positive control for full-length dystrophin expression (427 kDa) relative to the truncated Δ48-50 product (412 kDa).

TALEN activity in these cells was assessed by the Surveyor assay, which detects DNA cleavage and religation. This analysis showed that several TALEN pairs were active (FIGS. 6 and 9a,b). To verify that the targeted changes to exon 51 mediated by the nucleases were leading to restoration of gene expression, dystrophin expression was determined by Western blot. Myoblasts from DMD patients harboring deletions of exons 45 through 50 were electroporated with TALENs (TN3/TN8) that target exon 51 prior to the premature stop codon. Because no homologous donor was provided, DNA repair by NHEJ to lead to small insertions and deletions (indels) was predicted. Because the size of these indels was random, one-third of the modified cells were predicted to contain indels that restored dystrophin expression. After these cells were moved to differentiation conditions, new dystrophin expression that was not present in untreated cells was detected with both an antibody recognizing the rod domain that was N-terminal of the premature truncation (MANDYS-8, Sigma) and the C-terminus (NCL-Dys2, Leica) (FIGS. 9c and 9d). Dilution of the protein lysates from the differentiated wild-type human myoblasts suggested that the level of correction achieved in the current unoptimized protocol was close to 10% (FIGS. 9c and 9d). The data demonstrated that TALEN delivery to muscle cells from DMD patients resulted in nuclease activity at the target gene (FIGS. 6, 9a, and 9b) and dystrophin protein expression in these cells (FIGS. 9c and 9d) that otherwise was not possible due to DMD mutations.

In order to further characterize the genotype and phenotype of the corrected cells, clonal cell populations were derived from the nuclease-treated human DMD myoblasts. TALEN-treated cells that showed restored dystrophin protein expression (FIGS. 9c and 9d) were clonally diluted. The exon 51 PCR product from genomic DNA of 27 clonal populations was diluted 1:1 with the same PCR product from untreated DMD cells and analyzed by the Surveyor assay, which detects mismatches between DNA sequences (FIG. 6A). Eleven of the 27 clones showed DNA sequences distinct from the untreated cells at the location of TALEN cleavage, suggesting a gene modification rate of 41% (FIG. 6A). This was significantly higher than what was detected in bulk Surveyor assays (~10-15%, FIG. 4b), but was similar to what has been detected with other highly optimized nucleases. The PCR amplicons from these eleven clones were sequenced and 4 of them (36%) showed indels that would be predicted to restore the dystrophin reading frame (FIG. 6B).

These results show correction of dystrophin expression in cells from DMD patients harboring mutations that otherwise would not allow for any dystrophin expression. Although these results show correction by the random generation of indels by NHEJ gene repair in exon 51, these TALENs could be useful for gene correction via other mechanisms, such as exon deletion and gene repair by homologous recombination. Full sequences of all TALENs targeting in and around exon 51 are included in Table 2. Table 2 shows the target sequences and RVDs for TALENs. All target sequences were preceded by a prerequisite 5'T. FIG. 2 shows the amino acid sequences of engineered TALENs targeted to exon 51 of the dystrophin gene. Fok ELD-S/KKR-S refers to the FokI nuclease domain that was fused to the TALE DNA-binding domains and the RVD diresidues are underlined. Table 3 shows the target sequences of the TALEN pairs.

TABLE 3

Target sequences of the TALEN pairs.

| TN2/TN6 | tttagctcctactcagactgttactctggtgacacaa cctgtggttact (SEQ ID NO: 16) |
|---|---|
| TN2/TN8 | tttagctcctactcagactgttactctggtgacacaa cctgtggttactaagg (SEQ ID NO: 17) |
| TN3/6 | agctcctactcagactgttactctggtgacacaaccg tggttact (SEQ ID NO: 8) |
| TN3/TN8 | agctcctactcagactgttactctggtgacacaacct gtggttactaagg (SEQ ID NO: 19) |
| TN9/TN17 | gcaaaaacccaaaatattttagctcctactcagactg ttactctggtgac (SEQ ID NO: 20) |
| TN10/TN17 | ttgcaaaaacccaaaatattttagctcctactcagac tgttactctggtgac (SEQ ID NO: 21) |
| TN12/TN13 | cctttttgcaaaaacccaaaatattttagctcctact cagactgttactctggtg (SEQ ID NO: 22) |
| TN26/TN27 | ccaaactagaaatgccatcttccttgatgttggaggt acctgctctggcagatttc (SEQ ID NO: 23) |
| TN28/TN29 | ctatagatgagattatctgcccatgactggcgcaggg atggccgcattgct (SEQ ID NO: 24) |

Figure 7:
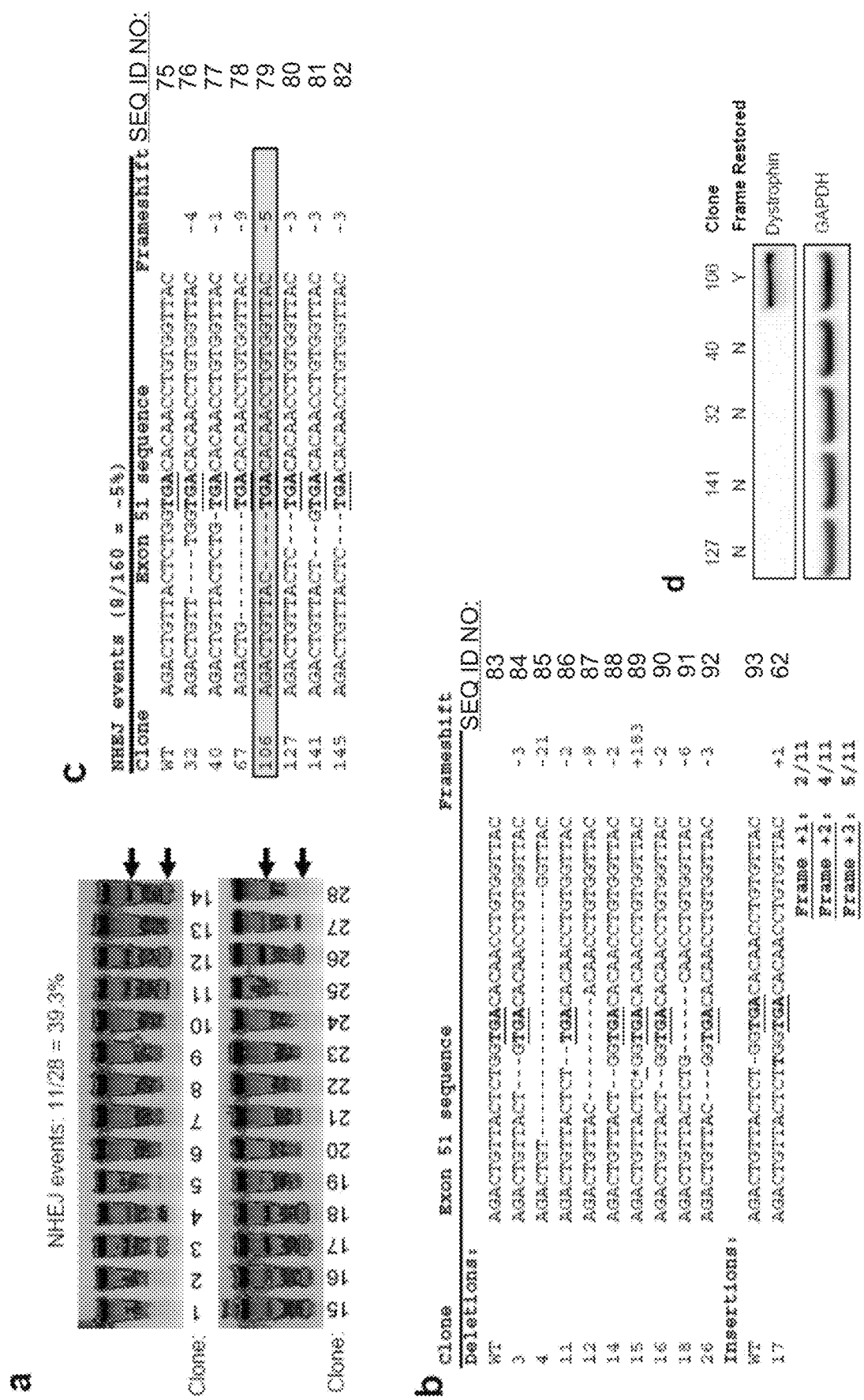
FIG. 7 shows the genetic correction of aberrant dystrophin reading frames by TALEN-mediated genome editing. (a) Isogenic clones were derived from human skeletal myoblasts treated with ten micrograms of each plasmid encoding TN3/8 and screened using the Surveyor assay to detect mutant alleles in reference to the parent (untreated) genomic DNA. Arrows denote predicted cleavage band sizes indicative of NHEJ activity. (b) Sanger sequencing of the TALEN target site in exon 51 in mutant clones identified in (a). The asterisk represents a 183 nucleotide insertion. (c) DMD human myoblast cell line 1 was treated with ten micrograms of each plasmid encoding the TN3/8 TALEN pair and isogenic clones were subsequently derived. Sanger sequencing was used to identify clones with small insertion or deletion mutations at the exon 51 genomic locus characteristic of NHEJ. Clone 106 had a 5 bp deletion that may restore the reading frame (boxed). All other clones had deletions that were not predicted to result in corrective frameshift events. (d) Clonal cell populations with NHEJ events detected at exon 51 were cultured in differentiation conditions for 7 days and analyzed by western blot for dystrophin expression at the predicted molecular weight (412 kDa).

TN3/8 mediates high efficiency conversion to all three reading frames. NHEJ-based gene modification created indels of random length and may cause conversion to any of the three reading frames in an exonic sequence. To validate the overall gene modification rate and possible reading frames generated following TALEN-induced NHEJ, clonal cell populations were derived from human skeletal myoblasts that had been electroporated with TN3/8-encoding plasmids. These clones were assayed for NHEJ events occurring at the dystrophin exon 51 locus using the Surveyor assay to detect sequence differences relative to untreated cells (FIG. 7a). Eleven of 28 (39%) clonal cell populations were modified and subsequent sequencing of the alleles from these clones confirmed indels characteristic of NHEJ (FIG. 7b). Deletions were heavily favored. The random length of these indels verified that conversion to any of the three reading frames was possible. The conversion rate to any one of the three reading frames was observed to be roughly proportional to ⅓ of the total NHEJ events (FIG. 7b). Interestingly, several small deletions were observed that did not alter the original reading frame, demonstrating that this approach could be used to delete aberrant stop-codons (FIG. 7b).

Figure 8:
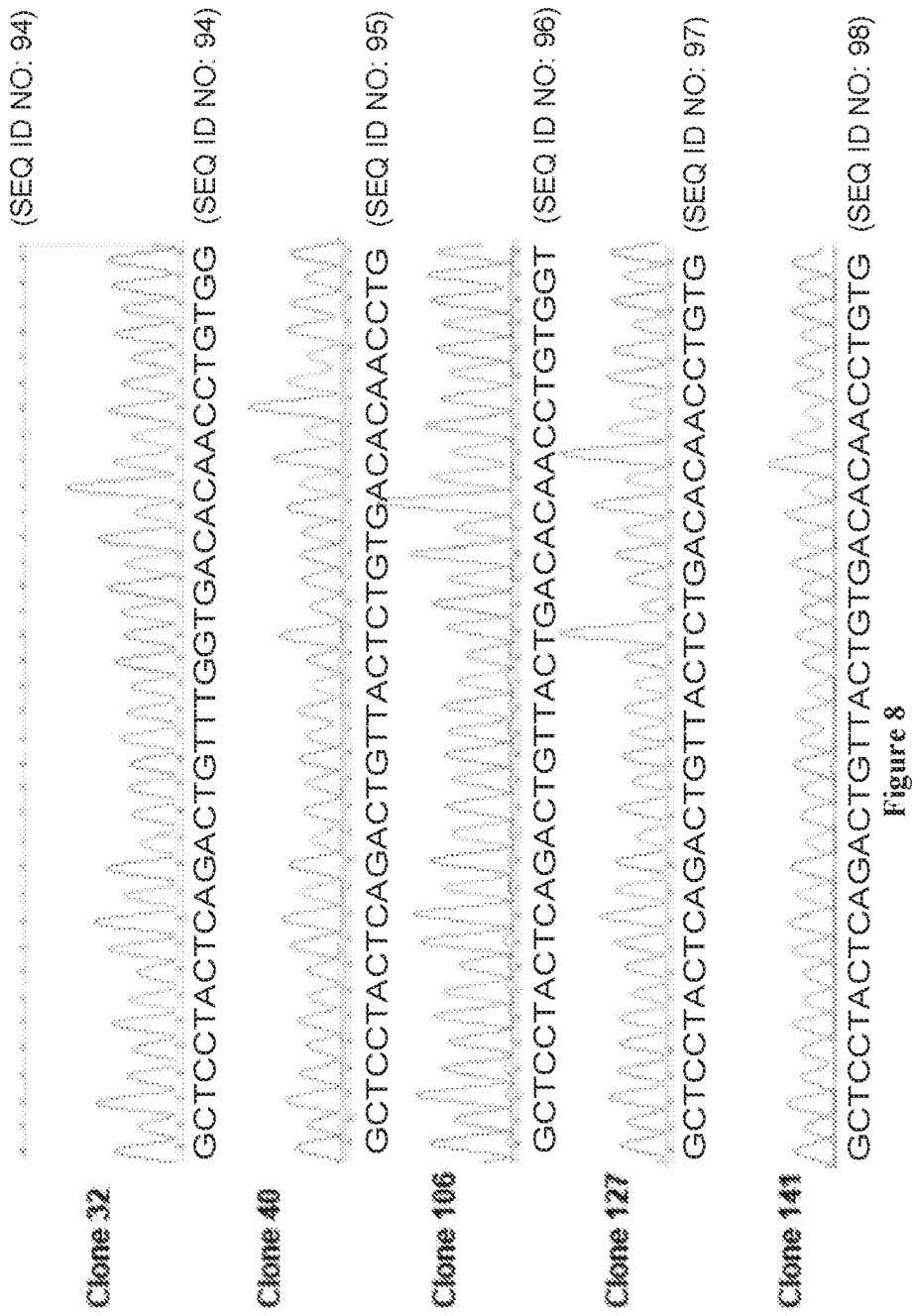
FIG. 8 shows chromatograms of clones from FIG. 7.

Reading frame correction leads to restored protein expression. Whether correction of the dystrophin reading frame by TALEN-mediated NHEJ results in restored dystrophin protein expression was assessed. Immortalized human myoblasts derived from DMD patients with a frame-disrupted dystrophin gene caused by deletion of exons 48-50 (Δ48-50) were electroporated with plasmids encoding TN3/8. Clonal cell populations were isolated and screened by PCR amplification of genomic DNA and Sanger sequencing to identify indels characteristic of NHEJ. Approximately 5% of clones contained modifications in exon 51, including one clone with an NHEJ event that may correct the dystrophin reading frame (FIGS. 7c and 8). Following myogenic differentiation, restored dystrophin protein expression was detected by western blot at its predicted size (~412 kDa) only in the corrected clone, and not in clones with non-corrective NHEJ events (FIG. 7d). These data demonstrate that NHEJ events that restore the dystrophin reading frame also rescue dystrophin protein expression.

TALEN-mediated genetic correction in bulk-treated DMD myoblasts. Efficient in situ frame correction in the absence of selection is a powerful use of NHEJ-based gene correction. Accordingly, the restoration of dystrophin expression in TALEN-treated bulk populations of DMD myoblast lines derived from two different patients containing different deletions of exons 48-50 in the dystrophin gene was investigated. The frequency of gene modification increased with the dose of electroporated TN3/8-encoding plasmids with indels detected in up to 12.7% and 6.8% of alleles, in the two patient lines as measured by the Surveyor assay (FIGS. 9a and 9b). Following 7 days of myogenic differentiation induced by serum removal, restored dystrophin expression was detected in the bulk cell populations at the predicted size (~412 kDa) relative to expression from wild-type cells (427 kDa) (FIGS. 9c and 9d). The increase in dystrophin protein expression with TALEN dose was concomitant with the level NHEJ events detected by the Surveyor assay.

Figure 10:
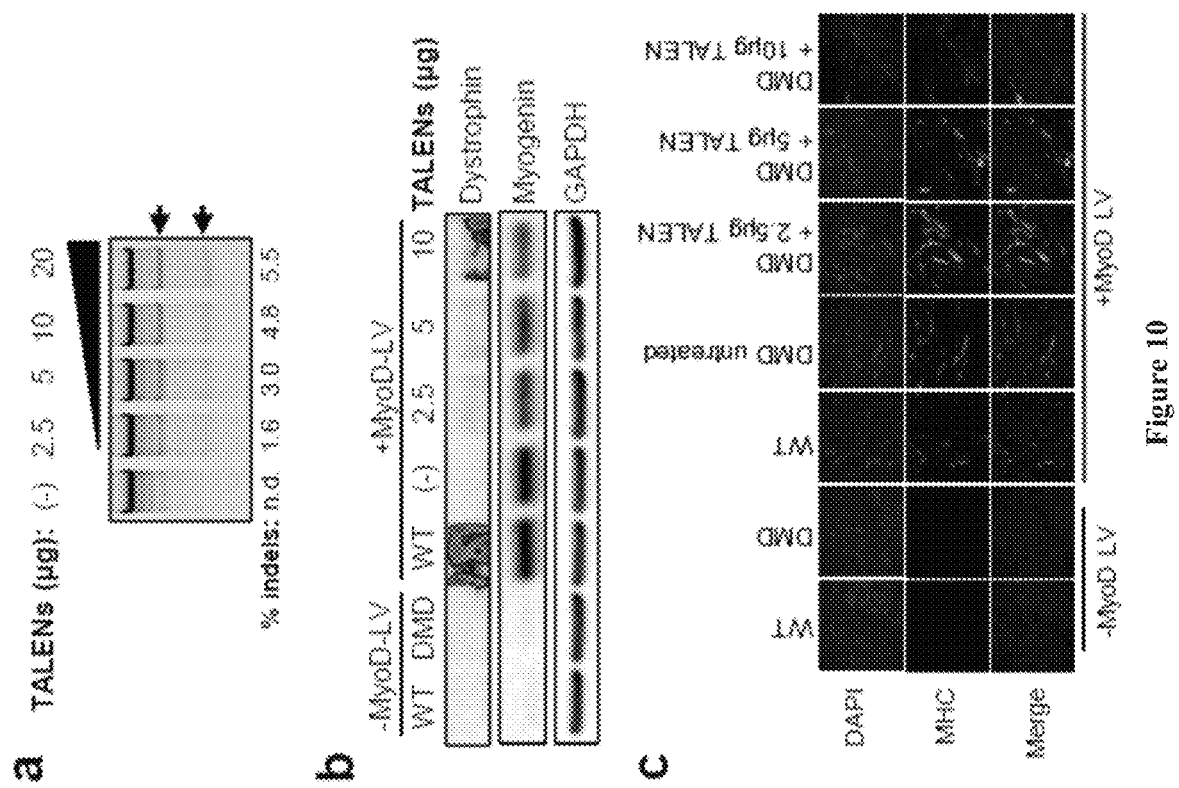
FIG. 10 shows the Dystrophin reading frame restoration in primary dermal fibroblasts. (a) Primary DMD fibroblasts carrying a deletion of exons 46-50 (Δ46-50) were electroporated with increasing doses of the indicated amount of each TALEN plasmid and gene modification rates were quantified with the Surveyor assay. Arrows denote predicted cleavage band sizes indicative of NHEJ activity. (b) Analysis of myogenin and dystrophin expression (MANDYS8) in wild-type and DMD fibroblasts after treatment with TN3/8 and 15 days of forced MyoD expression. Protein from wild-type dermal fibroblasts was included as a positive control for full-length dystrophin expression (427 kDa) relative to the truncated Δ46-50 product (400 kDa). (c) immunofluorescence staining to detect myosin heavy-chain (MHC) after MyoD expression by lentiviral gene transfer.

Gene restoration in primary DMD dermal fibroblasts. The simplicity of this NHEJ-based approach may enable efficient correction in proliferation-limited primary cell lines that may not be amenable to homologous recombination or selection-based gene correction. For example, DMD patient-derived primary dermal fibroblasts carrying a frame-disrupting deletion of exons 46-50 (Δ46-50) were electroporated with plasmids encoding TN3/8, resulting in high frequency gene modification in a dose-dependent manner (FIG. 10a). These treated fibroblasts were then transduced with a lentivirus expressing MyoD under an inducible promoter to stimulate transdifferentiation into the myogenic lineage and dystrophin expression. Expression of myogenin (FIG. 10b) and myosin heavy chain (FIG. 10c) confirmed efficient transdifferentiation of wild type and DMD patient fibroblasts. Rescued dystrophin expression was detected in TALEN-treated MyoD-induced fibroblasts in a dose-dependent manner at the predicted size of approximately 400 kDa (FIG. 10b), similar to the results obtained in skeletal myoblasts (FIGS. 9c and 9d).

Analysis of off-target effects induced by TN3/8. A concern for all genome editing strategies was the potential for off-target gene modification events. TN3/8 did not show significant cytotoxicity and was well tolerated by human cells (FIGS. 4b, 4c, and 4f), suggesting specific gene targeting. Potential off-target sites were assessed in silico using the TALE-NT 2.0 Paired Target Finder Prediction webserver to scan the human genome for sequences containing up to 4 mismatches per TALEN half-site (up to 8 total mismatches per target site) separated by spacers of any length between 12 and 23 bases. This analysis did not produce any potential off-target sites that met these criteria. To further examine unpredicted off-target DNA modifications, the whole exomes of clonally derived DMD myoblasts that were previously confirmed to contain NHEJ events at the on-target exon 51 locus were sequenced (FIG. 7c). Notably, the only insertion or deletion events characteristic of NHEJ were detected at the on-target exon 51 locus of the dystrophin gene in all four clonal lines analyzed, confirming the specificity of these TALENs (Tables 1 and 4). In Table 4, "syn. SNV" refers to synonymous single nucleotide variants and "nonsyn. SNV" refers to nonsynonymous single nucleotide variants.

results in substitutions relative to indels, the detected SNVs were likely to have arisen during clonal expansion as observed in other studies. In summary, there was no apparent off-target activity related to TALEN-mediated, NHEJ-based genetic correction in these clonally derived cells.

As shown above, the TALENs had high specificity as demonstrated by in silico analysis, cytotoxicity assays, and exome sequencing of clonally-derived modified cells.

Example 3

TALENs Targeting the 5' UTR of the Mouse and Human Dystrophin Gene

TALENs were designed to target the promoter region of the Dp427m dystrophin isoform, which has been shown to drive high expression of dystrophin in skeletal and cardiac muscle tissues. A panel of TALEN pairs was designed to optimize spacer length and gene editing activity. These TALENs were designed to target a homologous region in both mouse and human dystrophin promoter sequences to facilitate future animal studies, such as preclinical studies in a small animal model without creating a transgenic animal

TABLE 4

Summary of clonal sequence variants detected by exome sequencing.

| Clone | Mutation Type | Category | AA From | AA To | Gene | Chr | Location | Ref Base | Mutant Base |
|---|---|---|---|---|---|---|---|---|---|
| 32 | Transition | syn. SNV | S | S | ANKS1B | 12 | 99201691 | C | T |
| | Transversion | nonsyn. SNV | F | L | ZNF836 | 19 | 52659835 | G | C |
| | Transition | syn. SNV | P | P | SASH1 | 6 | 148664242 | T | C |
| | Transversion | syn. SNV | L | L | DAXX | 6 | 33287597 | T | G |
| | Transversion | syn. SNV | L | L | CDH7 | 18 | 63525175 | T | A |
| | Deletion | frameshift | — | — | DMD | X | 31792285 | ACCAG | — |
| 106 | Transition | nonsyn. SNV | E | G | ENG | 9 | 130582267 | T | C |
| | Transition | nonsyn. SNV | N | D | CCDC36 | 3 | 49294344 | A | G |
| | Transition | syn. SNV | V | V | TARBP1 | 1 | 234556520 | C | T |
| | Transition | nonsyn. SNV | Q | R | UGT3A1 | 5 | 35988575 | T | C |
| | Transversion | nonsyn. SNV | L | I | SOWAHB | 4 | 77817679 | G | T |
| | Transversion | nonsyn. SNV | Q | P | MEF2A | 15 | 100252738 | A | C |
| | Transversion | nonsyn. SNV | R | L | RFC1 | 4 | 39306505 | C | A |
| | Transition | stopgain SNV | Q | X | ELN | 7 | 73474508 | C | T |
| | Deletion | frameshift | — | — | DMD | X | 31792285 | ACCAG | — |
| 127 | Transition | nonsyn. SNV | A | V | PLEKHH1 | 14 | 68041071 | C | T |
| | Transition | syn. SNV | P | P | RASAL2 | 1 | 178269222 | C | T |
| | Transversion | nonsyn. SNV | S | C | IGDCC4 | 15 | 65676357 | G | C |
| | Transition | syn. SNV | A | A | LMTK3 | 19 | 49001482 | G | A |
| | Transition | stopgain SNV | W | X | PLEKHS1 | 10 | 115526378 | G | A |
| | Transition | nonsyn. SNV | V | I | FAM110C | 2 | 45848 | C | T |
| | Transition | nonsyn. SNV | G | E | TRAK1 | 3 | 42251610 | G | A |
| | Transversion | syn. SNV | S | S | C15orf39 | 15 | 75499997 | A | T |
| | Transition | syn. SNV | L | L | GPBAR1 | 2 | 219127549 | C | T |
| | Deletion | nonframeshift | — | — | DMD | X | 31792284 | CAC | — |
| 141 | Transition | syn. SNV | L | L | MUC16 | 19 | 8999474 | T | C |
| | Transversion | nonsyn. SNV | F | C | RP1 | 8 | 55538286 | T | G |
| | Transversion | nonsyn. SNV | E | A | PPP1R10 | 6 | 30569808 | C | G |
| | Transition | syn. SNV | T | T | CAMKV | 3 | 49896829 | T | C |
| | Transition | syn. SNV | F | F | AK2 | 1 | 33478842 | G | A |
| | Deletion | nonframeshift | — | — | DMD | X | 31792287 | CAG | — |

Consistent with known genomic mutation rates that normally occur during clonal expansion, the exome sequencing revealed several single nucleotide variants (SNVs) in each clone relative to the parental cell line. Using the TALE-NT 2.0 Paired Target Site Prediction webserver, the immediate region around each mutation was scanned for any sequence similarity to the TN3/8 target site to determine if the TALENs could be responsible for the observed SNVs. No target sites with similarity to our TALEN target site with spacers of 1-30 bases were found in the flanking 100 bp of any SNV. Because NHEJ-mediated mutagenesis rarely that carries human sequences. Combinations of TALENs were transfected into human 293T cells to assess activity by the Surveyor assay, as described above (sec FIG. 11C).

One TALEN pair, TN45/50, was identified to have high activity that was stable at 3 and 10 days post-transfection (see FIG. 11A). The RVD components of TN45/50 are shown in FIG. 11B. Full amino acid sequences of engineered TALENs targeted to the 5' UTR of the dystrophin gene are provided, as TN45 (Fok-KKRS) (SEQ ID NO: 14) and TN50 (Fok-ELDS) (SEQ ID NO: 15) (sec FIG. 12). Fok ELDS/KKRS refers to the FokI nuclease domain that was fused to the TALE DNA-binding domains.

10 micrograms of each plasmid encoding each of TN45 and TN50 were electroporated into human skeletal myoblasts from DMD patients. TALEN-mediated modification of the target locus was determined by the Surveyor assay three days after. As shown in FIG. 11D, the TN45/50 TALENs were active at the chromosomal locus in skeletal myoblasts from human DMD patients.

Example 4

Integration of Minidystrophin into 5' UTR of Dystrophin

Figure 13:
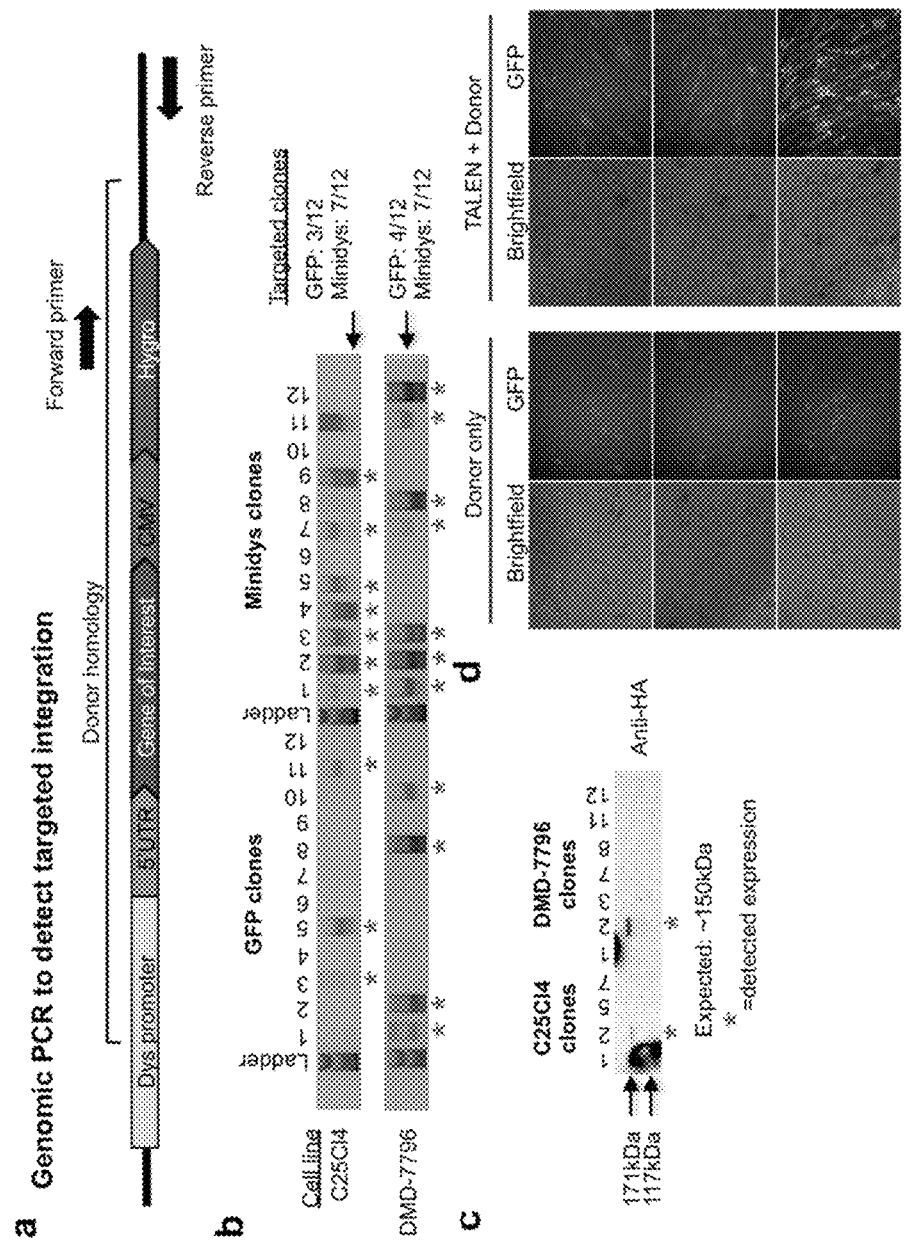
FIG. 13 shows (a) the schematic detailing PCR-based detection of targeted integration events, (b) identification of targeted clones by PCR in which a GFP or minidystrophin gene was inserted into the TALEN target site, asterisks indicate positive targeted events (c) minidystrophin expression in clones positive for targeted integration, (d) GFP expression in differentiation conditions in selected clones from treated DMD patient lines.

Functional replacement of mutated dystrophin genes may be accomplished by expression of a miniaturized dystrophin construct, termed minidystrophin ("minidys") (Wang et al, *Proc Natl Acad Sci USA*. (2000) 97(25):13714-9). The dystrophin 5' UTR was targeted with TALENs (FIG. 13a) to mediate site-specific integration of minidys that would be under control of the endogenous dystrophin promoter. GFP was targeted to the 5' UTR of the dystrophin gene by co-transfecting DMD patient myoblasts with the TN45/50 TALEN pair and a donor construct containing the OFF transgene with a selection marker. Results indicated that integration of a gene encoding OFF into the 5' UTR resulted in robust expression from the endogenous promoter in many targeted clones following myogenic differentiation (FIG. 13b, d). Similarly, DMD patient myoblast clones, C25C14 and DMD-7796 (provided by Vincent Mouly, Université Pierre et Marie Curie, Paris, France), were generated with TALEN-mediated integration of a construct containing the minidystrophin gene and a selection marker at the 5' UTR. As with the GFP construct, minidystrophin expression was detected only in targeted clones by western blot (FIG. 13b, c).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. An isolated polynucleotide comprising a nucleotide sequence encoding an engineered transcription activator-like effector nuclease (TALEN) protein that binds to a dystrophin gene, wherein the TALEN protein binds upstream from a premature stop codon on the dystrophin gene, downstream from a premature stop codon on the dystrophin gene, a region in exon 51 of the dystrophin gene, or a region in the 5' UTR of the dystrophin gene, and wherein the TALEN protein comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 15.

2. The isolated polynucleotide of claim 1, wherein the TALEN protein binds to a nucleotide sequence comprising one of SEQ ID NOs: 16-46, 50, 52, 58, and 59, or a complement thereof.

3. The isolated polynucleotide of claim 1, wherein the TALEN protein comprises a nuclease.

4. The isolated polynucleotide of claim 3, wherein the nuclease comprises FokI.

5. The isolated polynucleotide of claim 1, wherein the TALEN protein comprises 15-19 repeat variable diresidue (RVD) modules.

6. A vector comprising the isolated polynucleotide of claim 1.

7. The vector of claim 6, wherein the TALEN protein binds to a nucleotide sequence comprising one of SEQ ID NOs: 16-46, 50, 52, 58, and 59, or a complement thereof.

8. The vector of claim 6, wherein the TALEN protein comprises a nuclease.

9. The vector of claim 8, wherein the nuclease comprises FokI.

10. The vector of claim 6, wherein the TALEN protein comprises 15-19 repeat variable diresidue (RVD) modules.

11. A cell comprising the isolated polynucleotide of claim 1.

12. The cell of claim 11, wherein the TALEN protein binds to a nucleotide sequence comprising one of SEQ ID NOs: 16-46, 50, 52, 58, and 59, or a complement thereof.

13. The cell of claim 11, wherein the TALEN protein comprises a nuclease.

14. The cell of claim 13, wherein the nuclease comprises FokI.

15. The cell of claim 11, wherein the TALEN protein comprises 15-19 repeat variable diresidue (RVD) modules.

\* \* \* \* \*

SEQUENCE LISTING

```
<160> NUMBER OF SEQ ID NOS: 98

<210> SEQ ID NO 1
<211> LENGTH: 976
<212> TYPE: PRT
<213> ORGANISM: Artificial Sequence
<220> FEATURE:
<223> OTHER INFORMATION: Synthetic

<400> SEQUENCE: 1

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
    130                 135                 140

Asn Ala Leu Thr Gly Ala Pro Leu Asn Leu Thr Pro Asp Gln Val Val
145                 150                 155                 160

Ala Ile Ala Ser Asn Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190
```

```
Val Val Ala Ile Ala Ser Asn Gly Gly Gly Lys Gln Ala Leu Glu Thr
        195                 200                 205

Val Gln Arg Leu Leu Pro Val Leu Cys Gln Asp His Gly Leu Thr Pro
        210                 215                 220

Asp Gln Val Val Ala Ile Ala Ser Asn Gly Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser Asn Ile Gly Gly Lys Gln
                    260                 265                 270

Ala Leu Glu Thr Val Gln Arg Leu Leu Pro Val Leu Cys Gln Asp His
                275                 280                 285

Gly Leu Thr Pro Asp Gln Val Val Ala Ile Ala Ser Asn Asn Gly Gly
            290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser His Asp
                    325                 330                 335

Gly Gly Lys Gln Ala Leu Glu Thr Val Gln Arg Leu Leu Pro Val Leu
                340                 345                 350

Cys Gln Asp His Gly Leu Thr Pro Asp Gln Val Val Ala Ile Ala Ser
                355                 360                 365

Asn Gly Gly Gly Lys Gln Ala Leu Glu Thr Val Gln Arg Leu Leu Pro
            370                 375                 380

Val Leu Cys Gln Asp His Gly Leu Thr Pro Asp Gln Val Val Ala Ile
385                 390                 395                 400

Ala Ser His Asp Gly Gly Lys Gln Ala Leu Glu Thr Val Gln Arg Leu
                    405                 410                 415

Leu Pro Val Leu Cys Gln Asp His Gly Leu Thr Pro Asp Gln Val Val
                420                 425                 430

Ala Ile Ala Ser His Asp Gly Gly Lys Gln Ala Leu Glu Thr Val Gln
            435                 440                 445

Arg Leu Leu Pro Val Leu Cys Gln Asp His Gly Leu Thr Pro Asp Gln
                450                 455                 460

Val Val Ala Ile Ala Ser Asn Gly Gly Gly Lys Gln Ala Leu Glu Thr
465                 470                 475                 480

Val Gln Arg Leu Leu Pro Val Leu Cys Gln Asp His Gly Leu Thr Pro
                    485                 490                 495

Asp Gln Val Val Ala Ile Ala Ser Asn Ile Gly Gly Lys Gln Ala Leu
                500                 505                 510

Glu Thr Val Gln Arg Leu Leu Pro Val Leu Cys Gln Asp His Gly Leu
                515                 520                 525

Thr Pro Asp Gln Val Val Ala Ile Ala Ser His Asp Gly Gly Lys Gln
            530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Gly Gly Gly
                    565                 570                 575

Lys Gln Ala Leu Glu Thr Val Gln Arg Leu Leu Pro Val Leu Cys Gln
                580                 585                 590

Asp His Gly Leu Thr Pro Asp Gln Val Val Ala Ile Ala Ser His Asp
                595                 600                 605
```

```
Gly Gly Lys Gln Ala Leu Glu Thr Val Gln Arg Leu Leu Pro Val Leu
610                 615                 620

Cys Gln Asp His Gly Leu Thr Pro Asp Gln Val Val Ala Ile Ala Ser
625                 630                 635                 640

Asn Ile Gly Gly Lys Gln Ala Leu Glu Thr Val Gln Arg Leu Leu Pro
            645                 650                 655

Val Leu Cys Gln Asp His Gly Leu Thr Pro Asp Gln Val Val Ala Ile
            660                 665                 670

Ala Ser Asn Asn Gly Gly Lys Gln Ala Leu Glu Thr Val Gln Arg Leu
            675                 680                 685

Leu Pro Val Leu Cys Gln Asp His Gly Leu Thr Pro Asp Gln Val Val
690                 695                 700

Ala Ile Ala Ser Asn Ile Gly Gly Lys Gln Ala Leu Glu Ser Ile Val
705                 710                 715                 720

Ala Gln Leu Ser Arg Pro Asp Pro Ala Leu Ala Ala Leu Thr Asn Asp
                725                 730                 735

His Leu Val Ala Leu Ala Cys Leu Gly Gly Arg Pro Ala Met Asp Ala
                740                 745                 750

Val Lys Lys Gly Leu Pro His Ala Pro Glu Leu Ile Arg Arg Val Asn
755                 760                 765

Arg Arg Ile Gly Glu Arg Thr Ser His Arg Val Ala Gln Leu Val Lys
770                 775                 780

Ser Glu Leu Glu Glu Lys Lys Ser Glu Leu Arg His Lys Leu Lys Tyr
785                 790                 795                 800

Val Pro His Glu Tyr Ile Glu Leu Ile Glu Ile Ala Arg Asn Pro Thr
                805                 810                 815

Gln Asp Arg Ile Leu Glu Met Lys Val Met Glu Phe Phe Met Lys Val
                820                 825                 830

Tyr Gly Tyr Arg Gly Glu His Leu Gly Gly Ser Arg Lys Pro Asp Gly
                835                 840                 845

Ala Ile Tyr Thr Val Gly Ser Pro Ile Asp Tyr Gly Val Ile Val Asp
            850                 855                 860

Thr Lys Ala Tyr Ser Gly Gly Tyr Asn Leu Pro Ile Gly Gln Ala Asp
865                 870                 875                 880

Glu Met Glu Arg Tyr Val Glu Glu Asn Gln Thr Arg Asp Lys His Leu
                885                 890                 895

Asn Pro Asn Glu Trp Trp Lys Val Tyr Pro Ser Ser Val Thr Glu Phe
            900                 905                 910

Lys Phe Leu Phe Val Ser Gly His Phe Lys Gly Asn Tyr Lys Ala Gln
            915                 920                 925

Leu Thr Arg Leu Asn His Ile Thr Asn Cys Asn Gly Ala Val Leu Ser
930                 935                 940

Val Glu Glu Leu Leu Ile Gly Gly Glu Met Ile Lys Ala Gly Thr Leu
945                 950                 955                 960

Thr Leu Glu Glu Val Arg Arg Lys Phe Asn Asn Gly Glu Ile Asn Phe
                965                 970                 975

<210> SEQ ID NO 2
<211> LENGTH: 942
<212> TYPE: PRT
<213> ORGANISM: Artificial Sequence
<220> FEATURE:
<223> OTHER INFORMATION: Synthetic

<400> SEQUENCE: 2
```

```
Met Asp Tyr Lys Asp His Asp Gly Asp Tyr Lys Asp His Asp Ile Asp
1               5                   10                  15
Tyr Lys Asp Asp Asp Lys Met Ala Pro Lys Lys Arg Lys Val
            20                  25                  30
Gly Arg Gly Ser Val Arg Ser Thr Val Ala Gln His His Glu Ala Leu
            35                  40                  45
Val Gly His Gly Phe Thr His Ala His Ile Val Ala Leu Ser Gln His
    50                  55                  60
Pro Ala Ala Leu Gly Thr Val Ala Val Thr Tyr Gln His Ile Ile Thr
65                  70                  75                  80
Ala Leu Pro Glu Ala Thr His Glu Asp Ile Val Gly Val Gly Lys Gln
                85                  90                  95
Trp Ser Gly Ala Arg Ala Leu Glu Ala Leu Leu Thr Asp Ala Gly Glu
                100                 105                 110
Leu Arg Gly Pro Pro Leu Gln Leu Asp Thr Gly Gln Leu Val Lys Ile
                115                 120                 125
Ala Lys Arg Gly Gly Val Thr Ala Met Glu Ala Val His Ala Ser Arg
    130                 135                 140
Asn Ala Leu Thr Gly Ala Pro Leu Asn Leu Thr Pro Asp Gln Val Val
145                 150                 155                 160
Ala Ile Ala Ser Asn Ile Gly Gly Lys Gln Ala Leu Glu Thr Val Gln
                165                 170                 175
Arg Leu Leu Pro Val Leu Cys Gln Asp His Gly Leu Thr Pro Asp Gln
                180                 185                 190
Val Val Ala Ile Ala Ser Asn Asn Gly Gly Lys Gln Ala Leu Glu Thr
    195                 200                 205
Val Gln Arg Leu Leu Pro Val Leu Cys Gln Asp His Gly Leu Thr Pro
    210                 215                 220
Asp Gln Val Val Ala Ile Ala Ser His Asp Gly Gly Lys Gln Ala Leu
225                 230                 235                 240
Glu Thr Val Gln Arg Leu Leu Pro Val Leu Cys Gln Asp His Gly Leu
                245                 250                 255
Thr Pro Asp Gln Val Val Ala Ile Ala Ser Asn Gly Gly Gly Lys Gln
                260                 265                 270
Ala Leu Glu Thr Val Gln Arg Leu Leu Pro Val Leu Cys Gln Asp His
                275                 280                 285
Gly Leu Thr Pro Asp Gln Val Val Ala Ile Ala Ser His Asp Gly Gly
    290                 295                 300
Lys Gln Ala Leu Glu Thr Val Gln Arg Leu Leu Pro Val Leu Cys Gln
305                 310                 315                 320
Asp His Gly Leu Thr Pro Asp Gln Val Val Ala Ile Ala Ser His Asp
                325                 330                 335
Gly Gly Lys Gln Ala Leu Glu Thr Val Gln Arg Leu Leu Pro Val Leu
                340                 345                 350
Cys Gln Asp His Gly Leu Thr Pro Asp Gln Val Val Ala Ile Ala Ser
                355                 360                 365
Asn Gly Gly Gly Lys Gln Ala Leu Glu Thr Val Gln Arg Leu Leu Pro
                370                 375                 380
Val Leu Cys Gln Asp His Gly Leu Thr Pro Asp Gln Val Val Ala Ile
385                 390                 395                 400
Ala Ser Asn Ile Gly Gly Lys Gln Ala Leu Glu Thr Val Gln Arg Leu
                405                 410                 415
Leu Pro Val Leu Cys Gln Asp His Gly Leu Thr Pro Asp Gln Val Val
```

```
                420             425             430
Ala Ile Ala Ser His Asp Gly Gly Lys Gln Ala Leu Glu Thr Val Gln
            435             440             445
Arg Leu Leu Pro Val Leu Cys Gln Asp His Gly Leu Thr Pro Asp Gln
            450             455             460
Val Val Ala Ile Ala Ser Asn Gly Gly Gly Lys Gln Ala Leu Glu Thr
465             470             475             480
Val Gln Arg Leu Leu Pro Val Leu Cys Gln Asp His Gly Leu Thr Pro
            485             490             495
Asp Gln Val Val Ala Ile Ala Ser His Asp Gly Gly Lys Gln Ala Leu
            500             505             510
Glu Thr Val Gln Arg Leu Leu Pro Val Leu Cys Gln Asp His Gly Leu
            515             520             525
Thr Pro Asp Gln Val Val Ala Ile Ala Ser Asn Ile Gly Gly Lys Gln
            530             535             540
Ala Leu Glu Thr Val Gln Arg Leu Leu Pro Val Leu Cys Gln Asp His
545             550             555             560
Gly Leu Thr Pro Asp Gln Val Val Ala Ile Ala Ser Asn Gly Gly Gly
            565             570             575
Lys Gln Ala Leu Glu Thr Val Gln Arg Leu Leu Pro Val Leu Cys Gln
            580             585             590
Asp His Gly Leu Thr Pro Asp Gln Val Val Ala Ile Ala Ser Asn Ile
            595             600             605
Gly Gly Lys Gln Ala Leu Glu Thr Val Gln Arg Leu Leu Pro Val Leu
            610             615             620
Cys Gln Asp His Gly Leu Thr Pro Asp Gln Val Val Ala Ile Ala Ser
625             630             635             640
His Asp Gly Gly Lys Gln Ala Leu Glu Thr Val Gln Arg Leu Leu Pro
            645             650             655
Val Leu Cys Gln Asp His Gly Leu Thr Pro Asp Gln Val Val Ala Ile
            660             665             670
Ala Ser Asn Gly Gly Gly Lys Gln Ala Leu Glu Ser Ile Val Ala Gln
            675             680             685
Leu Ser Arg Pro Asp Pro Ala Leu Ala Ala Leu Thr Asn Asp His Leu
            690             695             700
Val Ala Leu Ala Cys Leu Gly Gly Arg Pro Ala Met Asp Ala Val Lys
705             710             715             720
Lys Gly Leu Pro His Ala Pro Glu Leu Ile Arg Arg Val Asn Arg Arg
            725             730             735
Ile Gly Glu Arg Thr Ser His Arg Val Ala Gln Leu Val Lys Ser Glu
            740             745             750
Leu Glu Glu Lys Lys Ser Glu Leu Arg His Lys Leu Lys Tyr Val Pro
            755             760             765
His Glu Tyr Ile Glu Leu Ile Glu Ile Ala Arg Asn Pro Thr Gln Asp
            770             775             780
Arg Ile Leu Glu Met Lys Val Met Glu Phe Phe Met Lys Val Tyr Gly
785             790             795             800
Tyr Arg Gly Glu His Leu Gly Gly Ser Arg Lys Pro Asp Gly Ala Ile
            805             810             815
Tyr Thr Val Gly Ser Pro Ile Asp Tyr Gly Val Ile Val Asp Thr Lys
            820             825             830
Ala Tyr Ser Gly Gly Tyr Asn Leu Pro Ile Gly Gln Ala Asp Glu Met
            835             840             845
```

```
Glu Arg Tyr Val Glu Glu Asn Gln Thr Arg Asp Lys His Leu Asn Pro
            850                 855                 860

Asn Glu Trp Trp Lys Val Tyr Pro Ser Ser Val Thr Glu Phe Lys Phe
865                 870                 875                 880

Leu Phe Val Ser Gly His Phe Lys Gly Asn Tyr Lys Ala Gln Leu Thr
                885                 890                 895

Arg Leu Asn His Ile Thr Asn Cys Asn Gly Ala Val Leu Ser Val Glu
            900                 905                 910

Glu Leu Leu Ile Gly Gly Glu Met Ile Lys Ala Gly Thr Leu Thr Leu
        915                 920                 925

Glu Glu Val Arg Arg Lys Phe Asn Asn Gly Glu Ile Asn Phe
930                 935                 940

<210> SEQ ID NO 3
<211> LENGTH: 942
<212> TYPE: PRT
<213> ORGANISM: Artificial Sequence
<220> FEATURE:
<223> OTHER INFORMATION: Synthetic

<400> SEQUENCE: 3

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Arg Gly Ser Val Arg Ser Thr Val Ala Gln His His Glu Ala Leu
            35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
130                 135                 140

Asn Ala Leu Thr Gly Ala Pro Leu Asn Leu Thr Pro Asp Gln Val Val
145                 150                 155                 160

Ala Ile Ala Ser Asn Ile Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser Asn Asn Gly Gly Lys Gln Ala Leu Glu Thr
        195                 200                 205

Val Gln Arg Leu Leu Pro Val Leu Cys Gln Asp His Gly Leu Thr Pro
210                 215                 220

Asp Gln Val Val Ala Ile Ala Ser Asn Gly Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser Asn Ile Gly Gly Lys Gln
            260                 265                 270
```

```
Ala Leu Glu Thr Val Gln Arg Leu Leu Pro Val Leu Cys Gln Asp His
            275                 280                 285

Gly Leu Thr Pro Asp Gln Val Val Ala Ile Ala Ser Asn Ile Gly Gly
        290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser His Asp
                325                 330                 335

Gly Gly Lys Gln Ala Leu Glu Thr Val Gln Arg Leu Leu Pro Val Leu
            340                 345                 350

Cys Gln Asp His Gly Leu Thr Pro Asp Gln Val Val Ala Ile Ala Ser
            355                 360                 365

His Asp Gly Gly Lys Gln Ala Leu Glu Thr Val Gln Arg Leu Leu Pro
        370                 375                 380

Val Leu Cys Gln Asp His Gly Leu Thr Pro Asp Gln Val Val Ala Ile
385                 390                 395                 400

Ala Ser Asn Ile Gly Gly Lys Gln Ala Leu Glu Thr Val Gln Arg Leu
                405                 410                 415

Leu Pro Val Leu Cys Gln Asp His Gly Leu Thr Pro Asp Gln Val Val
            420                 425                 430

Ala Ile Ala Ser His Asp Gly Gly Lys Gln Ala Leu Glu Thr Val Gln
            435                 440                 445

Arg Leu Leu Pro Val Leu Cys Gln Asp His Gly Leu Thr Pro Asp Gln
        450                 455                 460

Val Val Ala Ile Ala Ser Asn Ile Gly Gly Lys Gln Ala Leu Glu Thr
465                 470                 475                 480

Val Gln Arg Leu Leu Pro Val Leu Cys Gln Asp His Gly Leu Thr Pro
                485                 490                 495

Asp Gln Val Val Ala Ile Ala Ser Asn Asn Gly Gly Lys Gln Ala Leu
            500                 505                 510

Glu Thr Val Gln Arg Leu Leu Pro Val Leu Cys Gln Asp His Gly Leu
            515                 520                 525

Thr Pro Asp Gln Val Val Ala Ile Ala Ser Asn Asn Gly Gly Lys Gln
        530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Gly Gly Gly
                565                 570                 575

Lys Gln Ala Leu Glu Thr Val Gln Arg Leu Leu Pro Val Leu Cys Gln
            580                 585                 590

Asp His Gly Leu Thr Pro Asp Gln Val Val Ala Ile Ala Ser Asn Gly
            595                 600                 605

Gly Gly Lys Gln Ala Leu Glu Thr Val Gln Arg Leu Leu Pro Val Leu
        610                 615                 620

Cys Gln Asp His Gly Leu Thr Pro Asp Gln Val Val Ala Ile Ala Ser
625                 630                 635                 640

Asn Asn Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
            660                 665                 670

Ala Ser Asn Gly Gly Gly Lys Gln Ala Leu Glu Ser Ile Val Ala Gln
            675                 680                 685
```

Leu Ser Arg Pro Asp Pro Ala Leu Ala Ala Leu Thr Asn Asp His Leu
690                 695                 700

Val Ala Leu Ala Cys Leu Gly Gly Arg Pro Ala Met Asp Ala Val Lys
705                 710                 715                 720

Lys Gly Leu Pro His Ala Pro Glu Leu Ile Arg Arg Val Asn Arg Arg
            725                 730                 735

Ile Gly Glu Arg Thr Ser His Arg Val Ala Gln Leu Val Lys Ser Glu
            740                 745                 750

Leu Glu Glu Lys Lys Ser Glu Leu Arg His Lys Leu Lys Tyr Val Pro
            755                 760                 765

His Glu Tyr Ile Glu Leu Ile Glu Ile Ala Arg Asn Pro Thr Gln Asp
770                 775                 780

Arg Ile Leu Glu Met Lys Val Met Glu Phe Phe Met Lys Val Tyr Gly
785                 790                 795                 800

Tyr Arg Gly Glu His Leu Gly Gly Ser Arg Lys Pro Asp Gly Ala Ile
                805                 810                 815

Tyr Thr Val Gly Ser Pro Ile Asp Tyr Gly Val Ile Val Asp Thr Lys
            820                 825                 830

Ala Tyr Ser Gly Gly Tyr Asn Leu Pro Ile Gly Gln Ala Asp Glu Met
            835                 840                 845

Gln Arg Tyr Val Lys Glu Asn Gln Thr Arg Asn Lys His Ile Asn Pro
850                 855                 860

Asn Glu Trp Trp Lys Val Tyr Pro Ser Ser Val Thr Glu Phe Lys Phe
865                 870                 875                 880

Leu Phe Val Ser Gly His Phe Lys Gly Asn Tyr Lys Ala Gln Leu Thr
                885                 890                 895

Arg Leu Asn Arg Lys Thr Asn Cys Asn Gly Ala Val Leu Ser Val Glu
            900                 905                 910

Glu Leu Leu Ile Gly Gly Glu Met Ile Lys Ala Gly Thr Leu Thr Leu
            915                 920                 925

Glu Glu Val Arg Arg Lys Phe Asn Asn Gly Glu Ile Asn Phe
930                 935                 940

<210> SEQ ID NO 4
<211> LENGTH: 976
<212> TYPE: PRT
<213> ORGANISM: Artificial Sequence
<220> FEATURE:
<223> OTHER INFORMATION: Synthetic

<400> SEQUENCE: 4

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Ser Val Arg Ser Thr Val Ala Gln His His Glu Ala Leu
            35                  40                  45

Val Gly His Gly Phe Thr His Ala His Ile Val Ala Leu Ser Gln His
        50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

```
Leu Arg Gly Pro Pro Leu Gln Leu Asp Thr Gly Gln Leu Val Lys Ile
            115                 120                 125
Ala Lys Arg Gly Gly Val Thr Ala Met Glu Ala Val His Ala Ser Arg
130                 135                 140
Asn Ala Leu Thr Gly Ala Pro Leu Asn Leu Thr Pro Asp Gln Val Val
145                 150                 155                 160
Ala Ile Ala Ser His Asp Gly Gly Lys Gln Ala Leu Glu Thr Val Gln
                165                 170                 175
Arg Leu Leu Pro Val Leu Cys Gln Asp His Gly Leu Thr Pro Asp Gln
            180                 185                 190
Val Val Ala Ile Ala Ser His Asp Gly Gly Lys Gln Ala Leu Glu Thr
        195                 200                 205
Val Gln Arg Leu Leu Pro Val Leu Cys Gln Asp His Gly Leu Thr Pro
    210                 215                 220
Asp Gln Val Val Ala Ile Ala Ser Asn Gly Gly Gly Lys Gln Ala Leu
225                 230                 235                 240
Glu Thr Val Gln Arg Leu Leu Pro Val Leu Cys Gln Asp His Gly Leu
                245                 250                 255
Thr Pro Asp Gln Val Val Ala Ile Ala Ser Asn Gly Gly Gly Lys Gln
            260                 265                 270
Ala Leu Glu Thr Val Gln Arg Leu Leu Pro Val Leu Cys Gln Asp His
        275                 280                 285
Gly Leu Thr Pro Asp Gln Val Val Ala Ile Ala Ser Asn Ile Gly Gly
    290                 295                 300
Lys Gln Ala Leu Glu Thr Val Gln Arg Leu Leu Pro Val Leu Cys Gln
305                 310                 315                 320
Asp His Gly Leu Thr Pro Asp Gln Val Val Ala Ile Ala Ser Asn Asn
                325                 330                 335
Gly Gly Lys Gln Ala Leu Glu Thr Val Gln Arg Leu Leu Pro Val Leu
            340                 345                 350
Cys Gln Asp His Gly Leu Thr Pro Asp Gln Val Val Ala Ile Ala Ser
        355                 360                 365
Asn Gly Gly Gly Lys Gln Ala Leu Glu Thr Val Gln Arg Leu Leu Pro
    370                 375                 380
Val Leu Cys Gln Asp His Gly Leu Thr Pro Asp Gln Val Val Ala Ile
385                 390                 395                 400
Ala Ser Asn Ile Gly Gly Lys Gln Ala Leu Glu Thr Val Gln Arg Leu
                405                 410                 415
Leu Pro Val Leu Cys Gln Asp His Gly Leu Thr Pro Asp Gln Val Val
            420                 425                 430
Ala Ile Ala Ser Asn Ile Gly Gly Lys Gln Ala Leu Glu Thr Val Gln
        435                 440                 445
Arg Leu Leu Pro Val Leu Cys Gln Asp His Gly Leu Thr Pro Asp Gln
    450                 455                 460
Val Val Ala Ile Ala Ser His Asp Gly Gly Lys Gln Ala Leu Glu Thr
465                 470                 475                 480
Val Gln Arg Leu Leu Pro Val Leu Cys Gln Asp His Gly Leu Thr Pro
                485                 490                 495
Asp Gln Val Val Ala Ile Ala Ser His Asp Gly Gly Lys Gln Ala Leu
            500                 505                 510
Glu Thr Val Gln Arg Leu Leu Pro Val Leu Cys Gln Asp His Gly Leu
        515                 520                 525
Thr Pro Asp Gln Val Val Ala Ile Ala Ser Asn Ile Gly Gly Lys Gln
```

```
                530             535             540
Ala Leu Glu Thr Val Gln Arg Leu Leu Pro Val Leu Cys Gln Asp His
545                 550             555                 560

Gly Leu Thr Pro Asp Gln Val Val Ala Ile Ala Ser His Asp Gly Gly
                565             570             575

Lys Gln Ala Leu Glu Thr Val Gln Arg Leu Leu Pro Val Leu Cys Gln
            580             585             590

Asp His Gly Leu Thr Pro Asp Gln Val Val Ala Ile Ala Ser Asn Ile
            595             600             605

Gly Gly Lys Gln Ala Leu Glu Thr Val Gln Arg Leu Leu Pro Val Leu
610             615             620

Cys Gln Asp His Gly Leu Thr Pro Asp Gln Val Val Ala Ile Ala Ser
625                 630             635                 640

Asn Asn Gly Gly Lys Gln Ala Leu Glu Thr Val Gln Arg Leu Leu Pro
                645             650             655

Val Leu Cys Gln Asp His Gly Leu Thr Pro Asp Gln Val Val Ala Ile
            660             665             670

Ala Ser Asn Asn Gly Gly Lys Gln Ala Leu Glu Thr Val Gln Arg Leu
            675             680             685

Leu Pro Val Leu Cys Gln Asp His Gly Leu Thr Pro Asp Gln Val Val
690             695             700

Ala Ile Ala Ser Asn Gly Gly Gly Lys Gln Ala Leu Glu Ser Ile Val
705                 710             715                 720

Ala Gln Leu Ser Arg Pro Asp Pro Ala Leu Ala Ala Leu Thr Asn Asp
                725             730             735

His Leu Val Ala Leu Ala Cys Leu Gly Gly Arg Pro Ala Met Asp Ala
            740             745             750

Val Lys Lys Gly Leu Pro His Ala Pro Glu Leu Ile Arg Arg Val Asn
            755             760             765

Arg Arg Ile Gly Glu Arg Thr Ser His Arg Val Ala Gln Leu Val Lys
770             775             780

Ser Glu Leu Glu Glu Lys Lys Ser Glu Leu Arg His Lys Leu Lys Tyr
785                 790             795                 800

Val Pro His Glu Tyr Ile Glu Leu Ile Glu Ile Ala Arg Asn Pro Thr
                805             810             815

Gln Asp Arg Ile Leu Glu Met Lys Val Met Glu Phe Phe Met Lys Val
            820             825             830

Tyr Gly Tyr Arg Gly Glu His Leu Gly Gly Ser Arg Lys Pro Asp Gly
            835             840             845

Ala Ile Tyr Thr Val Gly Ser Pro Ile Asp Tyr Gly Val Ile Val Asp
850             855             860

Thr Lys Ala Tyr Ser Gly Gly Tyr Asn Leu Pro Ile Gly Gln Ala Asp
865                 870             875                 880

Glu Met Gln Arg Tyr Val Lys Glu Asn Gln Thr Arg Asn Lys His Ile
                885             890             895

Asn Pro Asn Glu Trp Trp Lys Val Tyr Pro Ser Ser Val Thr Glu Phe
            900             905             910

Lys Phe Leu Phe Val Ser Gly His Phe Lys Gly Asn Tyr Lys Ala Gln
            915             920             925

Leu Thr Arg Leu Asn Arg Lys Thr Asn Cys Asn Gly Ala Val Leu Ser
930             935             940

Val Glu Glu Leu Leu Ile Gly Gly Glu Met Ile Lys Ala Gly Thr Leu
945                 950             955                 960
```

```
Thr Leu Glu Glu Val Arg Arg Lys Phe Asn Asn Gly Glu Ile Asn Phe
            965                 970                 975

<210> SEQ ID NO 5
<211> LENGTH: 976
<212> TYPE: PRT
<213> ORGANISM: Artificial Sequence
<220> FEATURE:
<223> OTHER INFORMATION: Synthetic

<400> SEQUENCE: 5

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
    130                 135                 140

Asn Ala Leu Thr Gly Ala Pro Leu Asn Leu Thr Pro Asp Gln Val Val
145                 150                 155                 160

Ala Ile Ala Ser Asn Asn Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser His Asp Gly Gly Lys Gln Ala Leu Glu Thr
        195                 200                 205

Val Gln Arg Leu Leu Pro Val Leu Cys Gln Asp His Gly Leu Thr Pro
    210                 215                 220

Asp Gln Val Val Ala Ile Ala Ser Asn Ile Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser Asn Ile Gly Gly Lys Gln
            260                 265                 270

Ala Leu Glu Thr Val Gln Arg Leu Leu Pro Val Leu Cys Gln Asp His
        275                 280                 285

Gly Leu Thr Pro Asp Gln Val Val Ala Ile Ala Ser Asn Ile Gly Gly
    290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser Asn Ile
                325                 330                 335

Gly Gly Lys Gln Ala Leu Glu Thr Val Gln Arg Leu Leu Pro Val Leu
            340                 345                 350
```

```
Cys Gln Asp His Gly Leu Thr Pro Asp Gln Val Val Ala Ile Ala Ser
        355                 360                 365

Asn Ile Gly Gly Lys Gln Ala Leu Glu Thr Val Gln Arg Leu Leu Pro
    370                 375                 380

Val Leu Cys Gln Asp His Gly Leu Thr Pro Asp Gln Val Val Ala Ile
385                 390                 395                 400

Ala Ser His Asp Gly Gly Lys Gln Ala Leu Glu Thr Val Gln Arg Leu
                405                 410                 415

Leu Pro Val Leu Cys Gln Asp His Gly Leu Thr Pro Asp Gln Val Val
            420                 425                 430

Ala Ile Ala Ser His Asp Gly Gly Lys Gln Ala Leu Glu Thr Val Gln
        435                 440                 445

Arg Leu Leu Pro Val Leu Cys Gln Asp His Gly Leu Thr Pro Asp Gln
    450                 455                 460

Val Val Ala Ile Ala Ser His Asp Gly Gly Lys Gln Ala Leu Glu Thr
465                 470                 475                 480

Val Gln Arg Leu Leu Pro Val Leu Cys Gln Asp His Gly Leu Thr Pro
                485                 490                 495

Asp Gln Val Val Ala Ile Ala Ser Asn Ile Gly Gly Lys Gln Ala Leu
            500                 505                 510

Glu Thr Val Gln Arg Leu Leu Pro Val Leu Cys Gln Asp His Gly Leu
        515                 520                 525

Thr Pro Asp Gln Val Val Ala Ile Ala Ser Asn Ile Gly Gly Lys Gln
    530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Ile Gly Gly
                565                 570                 575

Lys Gln Ala Leu Glu Thr Val Gln Arg Leu Leu Pro Val Leu Cys Gln
            580                 585                 590

Asp His Gly Leu Thr Pro Asp Gln Val Val Ala Ile Ala Ser Asn Ile
        595                 600                 605

Gly Gly Lys Gln Ala Leu Glu Thr Val Gln Arg Leu Leu Pro Val Leu
    610                 615                 620

Cys Gln Asp His Gly Leu Thr Pro Asp Gln Val Val Ala Ile Ala Ser
625                 630                 635                 640

Asn Gly Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
            660                 665                 670

Ala Ser Asn Ile Gly Gly Lys Gln Ala Leu Glu Thr Val Gln Arg Leu
        675                 680                 685

Leu Pro Val Leu Cys Gln Asp His Gly Leu Thr Pro Asp Gln Val Val
    690                 695                 700

Ala Ile Ala Ser Asn Gly Gly Gly Lys Gln Ala Leu Glu Ser Ile Val
705                 710                 715                 720

Ala Gln Leu Ser Arg Pro Asp Pro Ala Leu Ala Ala Leu Thr Asn Asp
                725                 730                 735

His Leu Val Ala Leu Ala Cys Leu Gly Gly Arg Pro Ala Met Asp Ala
            740                 745                 750

Val Lys Lys Gly Leu Pro His Ala Pro Glu Leu Ile Arg Arg Val Asn
        755                 760                 765
```

```
Arg Arg Ile Gly Glu Arg Thr Ser His Arg Val Ala Gln Leu Val Lys
        770                 775                 780

Ser Glu Leu Glu Lys Lys Ser Glu Leu Arg His Lys Leu Lys Tyr
785                 790                 795                 800

Val Pro His Glu Tyr Ile Glu Leu Ile Glu Ile Ala Arg Asn Pro Thr
                    805                 810                 815

Gln Asp Arg Ile Leu Glu Met Lys Val Met Glu Phe Phe Met Lys Val
                820                 825                 830

Tyr Gly Tyr Arg Gly Glu His Leu Gly Gly Ser Arg Lys Pro Asp Gly
                835                 840                 845

Ala Ile Tyr Thr Val Gly Ser Pro Ile Asp Tyr Gly Val Ile Val Asp
850                 855                 860

Thr Lys Ala Tyr Ser Gly Gly Tyr Asn Leu Pro Ile Gly Gln Ala Asp
865                 870                 875                 880

Glu Met Glu Arg Tyr Val Glu Glu Asn Gln Thr Arg Asp Lys His Leu
                885                 890                 895

Asn Pro Asn Glu Trp Trp Lys Val Tyr Pro Ser Ser Val Thr Glu Phe
                900                 905                 910

Lys Phe Leu Phe Val Ser Gly His Phe Lys Gly Asn Tyr Lys Ala Gln
                915                 920                 925

Leu Thr Arg Leu Asn His Ile Thr Asn Cys Asn Gly Ala Val Leu Ser
            930                 935                 940

Val Glu Glu Leu Leu Ile Gly Gly Glu Met Ile Lys Ala Gly Thr Leu
945                 950                 955                 960

Thr Leu Glu Glu Val Arg Arg Lys Phe Asn Asn Gly Glu Ile Asn Phe
                965                 970                 975

<210> SEQ ID NO 6
<211> LENGTH: 976
<212> TYPE: PRT
<213> ORGANISM: Artificial Sequence
<220> FEATURE:
<223> OTHER INFORMATION: Synthetic

<400> SEQUENCE: 6

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Arg Gly Ser Val Arg Ser Thr Val Ala Gln His His Glu Ala Leu
            35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
    130                 135                 140

Asn Ala Leu Thr Gly Ala Pro Leu Asn Leu Thr Pro Asp Gln Val Val
145                 150                 155                 160
```

-continued

```
Ala Ile Ala Ser Asn Gly Gly Gly Lys Gln Ala Leu Glu Thr Val Gln
            165                 170                 175
Arg Leu Leu Pro Val Leu Cys Gln Asp His Gly Leu Thr Pro Asp Gln
        180                 185                 190
Val Val Ala Ile Ala Ser Asn Gly Gly Gly Lys Gln Ala Leu Glu Thr
    195                 200                 205
Val Gln Arg Leu Leu Pro Val Leu Cys Gln Asp His Gly Leu Thr Pro
210                 215                 220
Asp Gln Val Val Ala Ile Ala Ser Asn Asn Gly Gly Lys Gln Ala Leu
225                 230                 235                 240
Glu Thr Val Gln Arg Leu Leu Pro Val Leu Cys Gln Asp His Gly Leu
                245                 250                 255
Thr Pro Asp Gln Val Val Ala Ile Ala Ser His Asp Gly Gly Lys Gln
            260                 265                 270
Ala Leu Glu Thr Val Gln Arg Leu Leu Pro Val Leu Cys Gln Asp His
        275                 280                 285
Gly Leu Thr Pro Asp Gln Val Val Ala Ile Ala Ser Asn Ile Gly Gly
    290                 295                 300
Lys Gln Ala Leu Glu Thr Val Gln Arg Leu Leu Pro Val Leu Cys Gln
305                 310                 315                 320
Asp His Gly Leu Thr Pro Asp Gln Val Val Ala Ile Ala Ser Asn Ile
                325                 330                 335
Gly Gly Lys Gln Ala Leu Glu Thr Val Gln Arg Leu Leu Pro Val Leu
            340                 345                 350
Cys Gln Asp His Gly Leu Thr Pro Asp Gln Val Val Ala Ile Ala Ser
        355                 360                 365
Asn Ile Gly Gly Lys Gln Ala Leu Glu Thr Val Gln Arg Leu Leu Pro
    370                 375                 380
Val Leu Cys Gln Asp His Gly Leu Thr Pro Asp Gln Val Val Ala Ile
385                 390                 395                 400
Ala Ser Asn Ile Gly Gly Lys Gln Ala Leu Glu Thr Val Gln Arg Leu
                405                 410                 415
Leu Pro Val Leu Cys Gln Asp His Gly Leu Thr Pro Asp Gln Val Val
            420                 425                 430
Ala Ile Ala Ser Asn Ile Gly Gly Lys Gln Ala Leu Glu Thr Val Gln
        435                 440                 445
Arg Leu Leu Pro Val Leu Cys Gln Asp His Gly Leu Thr Pro Asp Gln
    450                 455                 460
Val Val Ala Ile Ala Ser His Asp Gly Gly Lys Gln Ala Leu Glu Thr
465                 470                 475                 480
Val Gln Arg Leu Leu Pro Val Leu Cys Gln Asp His Gly Leu Thr Pro
                485                 490                 495
Asp Gln Val Val Ala Ile Ala Ser His Asp Gly Gly Lys Gln Ala Leu
            500                 505                 510
Glu Thr Val Gln Arg Leu Leu Pro Val Leu Cys Gln Asp His Gly Leu
        515                 520                 525
Thr Pro Asp Gln Val Val Ala Ile Ala Ser His Asp Gly Gly Lys Gln
    530                 535                 540
Ala Leu Glu Thr Val Gln Arg Leu Leu Pro Val Leu Cys Gln Asp His
545                 550                 555                 560
Gly Leu Thr Pro Asp Gln Val Val Ala Ile Ala Ser Asn Ile Gly Gly
                565                 570                 575
Lys Gln Ala Leu Glu Thr Val Gln Arg Leu Leu Pro Val Leu Cys Gln
```

```
                    580             585                 590
Asp His Gly Leu Thr Pro Asp Gln Val Val Ala Ile Ala Ser Asn Ile
            595                 600             605

Gly Gly Lys Gln Ala Leu Glu Thr Val Gln Arg Leu Leu Pro Val Leu
        610             615                 620

Cys Gln Asp His Gly Leu Thr Pro Asp Gln Val Val Ala Ile Ala Ser
625                 630             635                 640

Asn Ile Gly Gly Lys Gln Ala Leu Glu Thr Val Gln Arg Leu Leu Pro
                645             650                 655

Val Leu Cys Gln Asp His Gly Leu Thr Pro Asp Gln Val Val Ala Ile
        660             665                 670

Ala Ser Asn Ile Gly Gly Lys Gln Ala Leu Glu Thr Val Gln Arg Leu
    675             680             685

Leu Pro Val Leu Cys Gln Asp His Gly Leu Thr Pro Asp Gln Val Val
690                 695             700

Ala Ile Ala Ser Asn Gly Gly Gly Lys Gln Ala Leu Glu Ser Ile Val
705             710             715                 720

Ala Gln Leu Ser Arg Pro Asp Pro Ala Leu Ala Ala Leu Thr Asn Asp
                725             730                 735

His Leu Val Ala Leu Ala Cys Leu Gly Gly Arg Pro Ala Met Asp Ala
            740             745             750

Val Lys Lys Gly Leu Pro His Ala Pro Glu Leu Ile Arg Arg Val Asn
        755             760             765

Arg Arg Ile Gly Glu Arg Thr Ser His Arg Val Ala Gln Leu Val Lys
        770             775             780

Ser Glu Leu Glu Glu Lys Lys Ser Glu Leu Arg His Lys Leu Lys Tyr
785             790             795                 800

Val Pro His Glu Tyr Ile Glu Leu Ile Glu Ile Ala Arg Asn Pro Thr
            805             810                 815

Gln Asp Arg Ile Leu Glu Met Lys Val Met Glu Phe Phe Met Lys Val
            820             825             830

Tyr Gly Tyr Arg Gly Glu His Leu Gly Gly Ser Arg Lys Pro Asp Gly
        835             840             845

Ala Ile Tyr Thr Val Gly Ser Pro Ile Asp Tyr Gly Val Ile Val Asp
850                 855             860

Thr Lys Ala Tyr Ser Gly Gly Tyr Asn Leu Pro Ile Gly Gln Ala Asp
865             870             875                 880

Glu Met Glu Arg Tyr Val Glu Glu Asn Gln Thr Arg Asp Lys His Leu
                885             890             895

Asn Pro Asn Glu Trp Trp Lys Val Tyr Pro Ser Ser Val Thr Glu Phe
            900             905             910

Lys Phe Leu Phe Val Ser Gly His Phe Lys Gly Asn Tyr Lys Ala Gln
            915             920             925

Leu Thr Arg Leu Asn His Ile Thr Asn Cys Asn Gly Ala Val Leu Ser
        930             935             940

Val Glu Glu Leu Leu Ile Gly Gly Glu Met Ile Lys Ala Gly Thr Leu
945             950             955                 960

Thr Leu Glu Glu Val Arg Arg Lys Phe Asn Asn Gly Glu Ile Asn Phe
                965             970             975

<210> SEQ ID NO 7
<211> LENGTH: 976
<212> TYPE: PRT
<213> ORGANISM: Artificial Sequence
```

<220> FEATURE:
<223> OTHER INFORMATION: Synthetic

<400> SEQUENCE: 7

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
            20                  25                  30

Gly Arg Gly Ser Val Arg Ser Thr Val Ala Gln His His Glu Ala Leu
            35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
    130                 135                 140

Asn Ala Leu Thr Gly Ala Pro Leu Asn Leu Thr Pro Asp Gln Val Val
145                 150                 155                 160

Ala Ile Ala Ser His Asp Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser His Asp Gly Gly Lys Gln Ala Leu Glu Thr
        195                 200                 205

Val Gln Arg Leu Leu Pro Val Leu Cys Gln Asp His Gly Leu Thr Pro
    210                 215                 220

Asp Gln Val Val Ala Ile Ala Ser Asn Gly Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser Asn Gly Gly Gly Lys Gln
            260                 265                 270

Ala Leu Glu Thr Val Gln Arg Leu Leu Pro Val Leu Cys Gln Asp His
        275                 280                 285

Gly Leu Thr Pro Asp Gln Val Val Ala Ile Ala Ser Asn Gly Gly Gly
    290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser Asn Gly
                325                 330                 335

Gly Gly Lys Gln Ala Leu Glu Thr Val Gln Arg Leu Leu Pro Val Leu
            340                 345                 350

Cys Gln Asp His Gly Leu Thr Pro Asp Gln Val Val Ala Ile Ala Ser
        355                 360                 365

Asn Gly Gly Gly Lys Gln Ala Leu Glu Thr Val Gln Arg Leu Leu Pro
    370                 375                 380

Val Leu Cys Gln Asp His Gly Leu Thr Pro Asp Gln Val Val Ala Ile
385                 390                 395                 400
```

```
Ala Ser Asn Asn Gly Gly Lys Gln Ala Leu Glu Thr Val Gln Arg Leu
            405                 410                 415

Leu Pro Val Leu Cys Gln Asp His Gly Leu Thr Pro Asp Gln Val Val
        420                 425                 430

Ala Ile Ala Ser His Asp Gly Gly Lys Gln Ala Leu Glu Thr Val Gln
            435                 440                 445

Arg Leu Leu Pro Val Leu Cys Gln Asp His Gly Leu Thr Pro Asp Gln
        450                 455                 460

Val Val Ala Ile Ala Ser Asn Ile Gly Gly Lys Gln Ala Leu Glu Thr
465                 470                 475                 480

Val Gln Arg Leu Leu Pro Val Leu Cys Gln Asp His Gly Leu Thr Pro
            485                 490                 495

Asp Gln Val Val Ala Ile Ala Ser Asn Ile Gly Gly Lys Gln Ala Leu
        500                 505                 510

Glu Thr Val Gln Arg Leu Leu Pro Val Leu Cys Gln Asp His Gly Leu
            515                 520                 525

Thr Pro Asp Gln Val Val Ala Ile Ala Ser Asn Ile Gly Gly Lys Gln
        530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Ile Gly Gly
            565                 570                 575

Lys Gln Ala Leu Glu Thr Val Gln Arg Leu Leu Pro Val Leu Cys Gln
        580                 585                 590

Asp His Gly Leu Thr Pro Asp Gln Val Val Ala Ile Ala Ser Asn Ile
            595                 600                 605

Gly Gly Lys Gln Ala Leu Glu Thr Val Gln Arg Leu Leu Pro Val Leu
610                 615                 620

Cys Gln Asp His Gly Leu Thr Pro Asp Gln Val Val Ala Ile Ala Ser
625                 630                 635                 640

His Asp Gly Gly Lys Gln Ala Leu Glu Thr Val Gln Arg Leu Leu Pro
            645                 650                 655

Val Leu Cys Gln Asp His Gly Leu Thr Pro Asp Gln Val Val Ala Ile
        660                 665                 670

Ala Ser His Asp Gly Gly Lys Gln Ala Leu Glu Thr Val Gln Arg Leu
            675                 680                 685

Leu Pro Val Leu Cys Gln Asp His Gly Leu Thr Pro Asp Gln Val Val
        690                 695                 700

Ala Ile Ala Ser His Asp Gly Gly Lys Gln Ala Leu Glu Ser Ile Val
705                 710                 715                 720

Ala Gln Leu Ser Arg Pro Asp Pro Ala Leu Ala Ala Leu Thr Asn Asp
            725                 730                 735

His Leu Val Ala Leu Ala Cys Leu Gly Gly Arg Pro Ala Met Asp Ala
        740                 745                 750

Val Lys Lys Gly Leu Pro His Ala Pro Glu Leu Ile Arg Arg Val Asn
            755                 760                 765

Arg Arg Ile Gly Glu Arg Thr Ser His Arg Val Ala Gln Leu Val Lys
        770                 775                 780

Ser Glu Leu Glu Glu Lys Lys Ser Glu Leu Arg His Lys Leu Lys Tyr
785                 790                 795                 800

Val Pro His Glu Tyr Ile Glu Leu Ile Glu Ile Ala Arg Asn Pro Thr
            805                 810                 815
```

Gln Asp Arg Ile Leu Glu Met Lys Val Met Glu Phe Phe Met Lys Val
                820                 825                 830

Tyr Gly Tyr Arg Gly Glu His Leu Gly Gly Ser Arg Lys Pro Asp Gly
            835                 840                 845

Ala Ile Tyr Thr Val Gly Ser Pro Ile Asp Tyr Gly Val Ile Val Asp
850                 855                 860

Thr Lys Ala Tyr Ser Gly Gly Tyr Asn Leu Pro Ile Gly Gln Ala Asp
865                 870                 875                 880

Glu Met Glu Arg Tyr Val Glu Gln Asn Gln Thr Arg Asp Lys His Leu
                885                 890                 895

Asn Pro Asn Glu Trp Trp Lys Val Tyr Pro Ser Ser Val Thr Glu Phe
            900                 905                 910

Lys Phe Leu Phe Val Ser Gly His Phe Lys Gly Asn Tyr Lys Ala Gln
        915                 920                 925

Leu Thr Arg Leu Asn His Ile Thr Asn Cys Asn Gly Ala Val Leu Ser
    930                 935                 940

Val Glu Glu Leu Leu Ile Gly Gly Glu Met Ile Lys Ala Gly Thr Leu
945                 950                 955                 960

Thr Leu Glu Glu Val Arg Arg Lys Phe Asn Asn Gly Glu Ile Asn Phe
                965                 970                 975

<210> SEQ ID NO 8
<211> LENGTH: 976
<212> TYPE: PRT
<213> ORGANISM: Artificial Sequence
<220> FEATURE:
<223> OTHER INFORMATION: Synthetic

<400> SEQUENCE: 8

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Arg Gly Ser Val Arg Ser Thr Val Ala Gln His His Glu Ala Leu
            35                  40                  45

Val Gly His Gly Phe Thr His Ala His Ile Val Ala Leu Ser Gln His
        50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
130                 135                 140

Asn Ala Leu Thr Gly Ala Pro Leu Asn Leu Thr Pro Asp Gln Val Val
145                 150                 155                 160

Ala Ile Ala Ser His Asp Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser Asn Ile Gly Gly Lys Gln Ala Leu Glu Thr
        195                 200                 205

```
Val Gln Arg Leu Leu Pro Val Leu Cys Gln Asp His Gly Leu Thr Pro
    210                 215                 220

Asp Gln Val Val Ala Ile Ala Ser His Asp Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser His Asp Gly Gly Lys Gln
            260                 265                 270

Ala Leu Glu Thr Val Gln Arg Leu Leu Pro Val Leu Cys Gln Asp His
        275                 280                 285

Gly Leu Thr Pro Asp Gln Val Val Ala Ile Ala Ser Asn Ile Gly Gly
    290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser Asn Asn
                325                 330                 335

Gly Gly Lys Gln Ala Leu Glu Thr Val Gln Arg Leu Leu Pro Val Leu
            340                 345                 350

Cys Gln Asp His Gly Leu Thr Pro Asp Gln Val Val Ala Ile Ala Ser
        355                 360                 365

Asn Ile Gly Gly Lys Gln Ala Leu Glu Thr Val Gln Arg Leu Leu Pro
    370                 375                 380

Val Leu Cys Gln Asp His Gly Leu Thr Pro Asp Gln Val Val Ala Ile
385                 390                 395                 400

Ala Ser Asn Asn Gly Gly Lys Gln Ala Leu Glu Thr Val Gln Arg Leu
                405                 410                 415

Leu Pro Val Leu Cys Gln Asp His Gly Leu Thr Pro Asp Gln Val Val
            420                 425                 430

Ala Ile Ala Ser Asn Gly Gly Gly Lys Gln Ala Leu Glu Thr Val Gln
        435                 440                 445

Arg Leu Leu Pro Val Leu Cys Gln Asp His Gly Leu Thr Pro Asp Gln
    450                 455                 460

Val Val Ala Ile Ala Ser Asn Ile Gly Gly Lys Gln Ala Leu Glu Thr
465                 470                 475                 480

Val Gln Arg Leu Leu Pro Val Leu Cys Gln Asp His Gly Leu Thr Pro
                485                 490                 495

Asp Gln Val Val Ala Ile Ala Ser Asn Ile Gly Gly Lys Gln Ala Leu
            500                 505                 510

Glu Thr Val Gln Arg Leu Leu Pro Val Leu Cys Gln Asp His Gly Leu
        515                 520                 525

Thr Pro Asp Gln Val Val Ala Ile Ala Ser His Asp Gly Gly Lys Gln
    530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Ile Gly Gly
                565                 570                 575

Lys Gln Ala Leu Glu Thr Val Gln Arg Leu Leu Pro Val Leu Cys Gln
            580                 585                 590

Asp His Gly Leu Thr Pro Asp Gln Val Val Ala Ile Ala Ser Asn Asn
        595                 600                 605

Gly Gly Lys Gln Ala Leu Glu Thr Val Gln Arg Leu Leu Pro Val Leu
    610                 615                 620

Cys Gln Asp His Gly Leu Thr Pro Asp Gln Val Val Ala Ile Ala Ser
```

```
                625                 630                 635                 640
Asn Gly Gly Gly Lys Gln Ala Leu Glu Thr Val Gln Arg Leu Leu Pro
                    645                 650                 655

Val Leu Cys Gln Asp His Gly Leu Thr Pro Asp Gln Val Val Ala Ile
                    660                 665                 670

Ala Ser His Asp Gly Gly Lys Gln Ala Leu Glu Thr Val Gln Arg Leu
                    675                 680                 685

Leu Pro Val Leu Cys Gln Asp His Gly Leu Thr Pro Asp Gln Val Val
                    690                 695                 700

Ala Ile Ala Ser Asn Gly Gly Lys Gln Ala Leu Glu Ser Ile Val
705                 710                 715                 720

Ala Gln Leu Ser Arg Pro Asp Pro Ala Leu Ala Ala Leu Thr Asn Asp
                    725                 730                 735

His Leu Val Ala Leu Ala Cys Leu Gly Gly Arg Pro Ala Met Asp Ala
                    740                 745                 750

Val Lys Lys Gly Leu Pro His Ala Pro Glu Leu Ile Arg Arg Val Asn
                    755                 760                 765

Arg Arg Ile Gly Glu Arg Thr Ser His Arg Val Ala Gln Leu Val Lys
                    770                 775                 780

Ser Glu Leu Glu Glu Lys Lys Ser Glu Leu Arg His Lys Leu Lys Tyr
785                 790                 795                 800

Val Pro His Glu Tyr Ile Glu Leu Ile Glu Ile Ala Arg Asn Pro Thr
                    805                 810                 815

Gln Asp Arg Ile Leu Glu Met Lys Val Met Glu Phe Phe Met Lys Val
                    820                 825                 830

Tyr Gly Tyr Arg Gly Glu His Leu Gly Gly Ser Arg Lys Pro Asp Gly
                    835                 840                 845

Ala Ile Tyr Thr Val Gly Ser Pro Ile Asp Tyr Gly Val Ile Val Asp
                    850                 855                 860

Thr Lys Ala Tyr Ser Gly Gly Tyr Asn Leu Pro Ile Gly Gln Ala Asp
865                 870                 875                 880

Glu Met Gln Arg Tyr Val Lys Glu Asn Gln Thr Arg Asn Lys His Ile
                    885                 890                 895

Asn Pro Asn Glu Trp Trp Lys Val Tyr Pro Ser Ser Val Thr Glu Phe
                    900                 905                 910

Lys Phe Leu Phe Val Ser Gly His Phe Lys Gly Asn Tyr Lys Ala Gln
                    915                 920                 925

Leu Thr Arg Leu Asn Arg Lys Thr Asn Cys Asn Gly Ala Val Leu Ser
                    930                 935                 940

Val Glu Glu Leu Leu Ile Gly Gly Glu Met Ile Lys Ala Gly Thr Leu
945                 950                 955                 960

Thr Leu Glu Glu Val Arg Arg Lys Phe Asn Asn Gly Glu Ile Asn Phe
                    965                 970                 975

<210> SEQ ID NO 9
<211> LENGTH: 1044
<212> TYPE: PRT
<213> ORGANISM: Artificial Sequence
<220> FEATURE:
<223> OTHER INFORMATION: Synthetic

<400> SEQUENCE: 9

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
```

```
                20                  25                  30
Gly Arg Gly Ser Val Arg Ser Thr Val Ala Gln His His Glu Ala Leu
                35                  40                  45
Val Gly His Gly Phe Thr His Ala His Ile Val Ala Leu Ser Gln His
            50                  55                  60
Pro Ala Ala Leu Gly Thr Val Ala Val Thr Tyr Gln His Ile Ile Thr
 65                  70                  75                  80
Ala Leu Pro Glu Ala Thr His Glu Asp Ile Val Gly Val Gly Lys Gln
                85                  90                  95
Trp Ser Gly Ala Arg Ala Leu Glu Ala Leu Leu Thr Asp Ala Gly Glu
                100                 105                 110
Leu Arg Gly Pro Pro Leu Gln Leu Asp Thr Gly Gln Leu Val Lys Ile
                115                 120                 125
Ala Lys Arg Gly Gly Val Thr Ala Met Glu Ala Val His Ala Ser Arg
                130                 135                 140
Asn Ala Leu Thr Gly Ala Pro Leu Asn Leu Thr Pro Asp Gln Val Val
145                 150                 155                 160
Ala Ile Ala Ser Asn Asn Gly Gly Lys Gln Ala Leu Glu Thr Val Gln
                165                 170                 175
Arg Leu Leu Pro Val Leu Cys Gln Asp His Gly Leu Thr Pro Asp Gln
                180                 185                 190
Val Val Ala Ile Ala Ser Asn Gly Gly Gly Lys Gln Ala Leu Glu Thr
                195                 200                 205
Val Gln Arg Leu Leu Pro Val Leu Cys Gln Asp His Gly Leu Thr Pro
                210                 215                 220
Asp Gln Val Val Ala Ile Ala Ser His Asp Gly Gly Lys Gln Ala Leu
225                 230                 235                 240
Glu Thr Val Gln Arg Leu Leu Pro Val Leu Cys Gln Asp His Gly Leu
                245                 250                 255
Thr Pro Asp Gln Val Val Ala Ile Ala Ser Asn Ile Gly Gly Lys Gln
                260                 265                 270
Ala Leu Glu Thr Val Gln Arg Leu Leu Pro Val Leu Cys Gln Asp His
                275                 280                 285
Gly Leu Thr Pro Asp Gln Val Val Ala Ile Ala Ser His Asp Gly Gly
                290                 295                 300
Lys Gln Ala Leu Glu Thr Val Gln Arg Leu Leu Pro Val Leu Cys Gln
305                 310                 315                 320
Asp His Gly Leu Thr Pro Asp Gln Val Val Ala Ile Ala Ser His Asp
                325                 330                 335
Gly Gly Lys Gln Ala Leu Glu Thr Val Gln Arg Leu Leu Pro Val Leu
                340                 345                 350
Cys Gln Asp His Gly Leu Thr Pro Asp Gln Val Val Ala Ile Ala Ser
                355                 360                 365
Asn Ile Gly Gly Lys Gln Ala Leu Glu Thr Val Gln Arg Leu Leu Pro
                370                 375                 380
Val Leu Cys Gln Asp His Gly Leu Thr Pro Asp Gln Val Val Ala Ile
385                 390                 395                 400
Ala Ser Asn Asn Gly Gly Lys Gln Ala Leu Glu Thr Val Gln Arg Leu
                405                 410                 415
Leu Pro Val Leu Cys Gln Asp His Gly Leu Thr Pro Asp Gln Val Val
                420                 425                 430
Ala Ile Ala Ser Asn Ile Gly Gly Lys Gln Ala Leu Glu Thr Val Gln
                435                 440                 445
```

```
Arg Leu Leu Pro Val Leu Cys Gln Asp His Gly Leu Thr Pro Asp Gln
        450                 455                 460

Val Val Ala Ile Ala Ser Asn Asn Gly Gly Lys Gln Ala Leu Glu Thr
465                 470                 475                 480

Val Gln Arg Leu Leu Pro Val Leu Cys Gln Asp His Gly Leu Thr Pro
                485                 490                 495

Asp Gln Val Val Ala Ile Ala Ser Asn Gly Gly Lys Gln Ala Leu
            500                 505                 510

Glu Thr Val Gln Arg Leu Leu Pro Val Leu Cys Gln Asp His Gly Leu
        515                 520                 525

Thr Pro Asp Gln Val Val Ala Ile Ala Ser Asn Ile Gly Gly Lys Gln
    530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Ile Gly Gly
                565                 570                 575

Lys Gln Ala Leu Glu Thr Val Gln Arg Leu Leu Pro Val Leu Cys Gln
            580                 585                 590

Asp His Gly Leu Thr Pro Asp Gln Val Val Ala Ile Ala Ser His Asp
        595                 600                 605

Gly Gly Lys Gln Ala Leu Glu Thr Val Gln Arg Leu Leu Pro Val Leu
    610                 615                 620

Cys Gln Asp His Gly Leu Thr Pro Asp Gln Val Val Ala Ile Ala Ser
625                 630                 635                 640

Asn Ile Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
            660                 665                 670

Ala Ser Asn Asn Gly Gly Lys Gln Ala Leu Glu Thr Val Gln Arg Leu
        675                 680                 685

Leu Pro Val Leu Cys Gln Asp His Gly Leu Thr Pro Asp Gln Val Val
    690                 695                 700

Ala Ile Ala Ser Asn Gly Gly Gly Lys Gln Ala Leu Glu Thr Val Gln
705                 710                 715                 720

Arg Leu Leu Pro Val Leu Cys Gln Asp His Gly Leu Thr Pro Asp Gln
                725                 730                 735

Val Val Ala Ile Ala Ser His Asp Gly Gly Lys Gln Ala Leu Glu Thr
            740                 745                 750

Val Gln Arg Leu Leu Pro Val Leu Cys Gln Asp His Gly Leu Thr Pro
        755                 760                 765

Asp Gln Val Val Ala Ile Ala Ser Asn Gly Gly Gly Lys Gln Ala Leu
    770                 775                 780

Glu Ser Ile Val Ala Gln Leu Ser Arg Pro Asp Pro Ala Leu Ala Ala
785                 790                 795                 800

Leu Thr Asn Asp His Leu Val Ala Leu Ala Cys Leu Gly Gly Arg Pro
                805                 810                 815

Ala Met Asp Ala Val Lys Lys Gly Leu Pro His Ala Pro Glu Leu Ile
            820                 825                 830

Arg Arg Val Asn Arg Arg Ile Gly Glu Arg Thr Ser His Arg Val Ala
        835                 840                 845

Gln Leu Val Lys Ser Glu Leu Glu Glu Lys Lys Ser Glu Leu Arg His
    850                 855                 860
```

```
Lys Leu Lys Tyr Val Pro His Glu Tyr Ile Glu Ile Ala
865                 870                 875                 880

Arg Asn Pro Thr Gln Asp Arg Ile Leu Glu Met Lys Val Met Glu Phe
            885                 890                 895

Phe Met Lys Val Tyr Gly Tyr Arg Gly Glu His Leu Gly Gly Ser Arg
            900                 905                 910

Lys Pro Asp Gly Ala Ile Tyr Thr Val Gly Ser Pro Ile Asp Tyr Gly
            915                 920                 925

Val Ile Val Asp Thr Lys Ala Tyr Ser Gly Gly Tyr Asn Leu Pro Ile
            930                 935                 940

Gly Gln Ala Asp Glu Met Gln Arg Tyr Val Lys Glu Asn Gln Thr Arg
945                 950                 955                 960

Asn Lys His Ile Asn Pro Asn Glu Trp Trp Lys Val Tyr Pro Ser Ser
            965                 970                 975

Val Thr Glu Phe Lys Phe Leu Phe Val Ser Gly His Phe Lys Gly Asn
            980                 985                 990

Tyr Lys Ala Gln Leu Thr Arg Leu Asn Arg Lys Thr Asn Cys Asn Gly
            995                 1000                1005

Ala Val Leu Ser Val Glu Glu Leu Leu Ile Gly Gly Glu Met Ile
        1010                1015                1020

Lys Ala Gly Thr Leu Thr Leu Glu Glu Val Arg Arg Lys Phe Asn
        1025                1030                1035

Asn Gly Glu Ile Asn Phe
        1040

<210> SEQ ID NO 10
<211> LENGTH: 1044
<212> TYPE: PRT
<213> ORGANISM: Artificial Sequence
<220> FEATURE:
<223> OTHER INFORMATION: Synthetic

<400> SEQUENCE: 10

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
130                 135                 140

Asn Ala Leu Thr Gly Ala Pro Leu Asn Leu Thr Pro Asp Gln Val Val
145                 150                 155                 160

Ala Ile Ala Ser His Asp Gly Gly Lys Gln Ala Leu Glu Thr Val Gln
                165                 170                 175
```

```
Arg Leu Leu Pro Val Leu Cys Gln Asp His Gly Leu Thr Pro Asp Gln
            180                 185                 190

Val Val Ala Ile Ala Ser Asn Gly Gly Gly Lys Gln Ala Leu Glu Thr
            195                 200                 205

Val Gln Arg Leu Leu Pro Val Leu Cys Gln Asp His Gly Leu Thr Pro
            210                 215                 220

Asp Gln Val Val Ala Ile Ala Ser Asn Gly Gly Gly Lys Gln Ala Leu
225                 230                 235                 240

Glu Thr Val Gln Arg Leu Leu Pro Val Leu Cys Gln Asp His Gly Leu
            245                 250                 255

Thr Pro Asp Gln Val Val Ala Ile Ala Ser His Asp Gly Gly Lys Gln
            260                 265                 270

Ala Leu Glu Thr Val Gln Arg Leu Leu Pro Val Leu Cys Gln Asp His
            275                 280                 285

Gly Leu Thr Pro Asp Gln Val Val Ala Ile Ala Ser His Asp Gly Gly
            290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser Asn Gly
            325                 330                 335

Gly Gly Lys Gln Ala Leu Glu Thr Val Gln Arg Leu Leu Pro Val Leu
            340                 345                 350

Cys Gln Asp His Gly Leu Thr Pro Asp Gln Val Val Ala Ile Ala Ser
            355                 360                 365

Asn Gly Gly Gly Lys Gln Ala Leu Glu Thr Val Gln Arg Leu Leu Pro
            370                 375                 380

Val Leu Cys Gln Asp His Gly Leu Thr Pro Asp Gln Val Val Ala Ile
385                 390                 395                 400

Ala Ser Asn Asn Gly Gly Lys Gln Ala Leu Glu Thr Val Gln Arg Leu
            405                 410                 415

Leu Pro Val Leu Cys Gln Asp His Gly Leu Thr Pro Asp Gln Val Val
            420                 425                 430

Ala Ile Ala Ser Asn Ile Gly Gly Lys Gln Ala Leu Glu Thr Val Gln
            435                 440                 445

Arg Leu Leu Pro Val Leu Cys Gln Asp His Gly Leu Thr Pro Asp Gln
450                 455                 460

Val Val Ala Ile Ala Ser Asn Gly Gly Gly Lys Gln Ala Leu Glu Thr
465                 470                 475                 480

Val Gln Arg Leu Leu Pro Val Leu Cys Gln Asp His Gly Leu Thr Pro
            485                 490                 495

Asp Gln Val Val Ala Ile Ala Ser Asn Asn Gly Gly Lys Gln Ala Leu
            500                 505                 510

Glu Thr Val Gln Arg Leu Leu Pro Val Leu Cys Gln Asp His Gly Leu
            515                 520                 525

Thr Pro Asp Gln Val Val Ala Ile Ala Ser Asn Gly Gly Gly Lys Gln
            530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Gly Gly Gly
            565                 570                 575

Lys Gln Ala Leu Glu Thr Val Gln Arg Leu Leu Pro Val Leu Cys Gln
            580                 585                 590

Asp His Gly Leu Thr Pro Asp Gln Val Val Ala Ile Ala Ser Asn Asn
```

```
                595                 600                 605
Gly Gly Lys Gln Ala Leu Glu Thr Val Gln Arg Leu Leu Pro Val Leu
        610                 615                 620

Cys Gln Asp His Gly Leu Thr Pro Asp Gln Val Val Ala Ile Ala Ser
625                 630                 635                 640

Asn Asn Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
        660                 665                 670

Ala Ser Asn Ile Gly Gly Lys Gln Ala Leu Glu Thr Val Gln Arg Leu
            675                 680                 685

Leu Pro Val Leu Cys Gln Asp His Gly Leu Thr Pro Asp Gln Val Val
        690                 695                 700

Ala Ile Ala Ser Asn Asn Gly Gly Lys Gln Ala Leu Glu Thr Val Gln
705                 710                 715                 720

Arg Leu Leu Pro Val Leu Cys Gln Asp His Gly Leu Thr Pro Asp Gln
                725                 730                 735

Val Val Ala Ile Ala Ser Asn Asn Gly Gly Lys Gln Ala Leu Glu Thr
        740                 745                 750

Val Gln Arg Leu Leu Pro Val Leu Cys Gln Asp His Gly Leu Thr Pro
            755                 760                 765

Asp Gln Val Val Ala Ile Ala Ser Asn Gly Gly Gly Lys Gln Ala Leu
        770                 775                 780

Glu Ser Ile Val Ala Gln Leu Ser Arg Pro Asp Pro Ala Leu Ala Ala
785                 790                 795                 800

Leu Thr Asn Asp His Leu Val Ala Leu Ala Cys Leu Gly Gly Arg Pro
                805                 810                 815

Ala Met Asp Ala Val Lys Lys Gly Leu Pro His Ala Pro Glu Leu Ile
        820                 825                 830

Arg Arg Val Asn Arg Arg Ile Gly Glu Arg Thr Ser His Arg Val Ala
            835                 840                 845

Gln Leu Val Lys Ser Glu Leu Glu Glu Lys Lys Ser Glu Leu Arg His
        850                 855                 860

Lys Leu Lys Tyr Val Pro His Glu Tyr Ile Glu Leu Ile Glu Ile Ala
865                 870                 875                 880

Arg Asn Pro Thr Gln Asp Arg Ile Leu Glu Met Lys Val Met Glu Phe
                885                 890                 895

Phe Met Lys Val Tyr Gly Tyr Arg Gly Glu His Leu Gly Gly Ser Arg
        900                 905                 910

Lys Pro Asp Gly Ala Ile Tyr Thr Val Gly Ser Pro Ile Asp Tyr Gly
            915                 920                 925

Val Ile Val Asp Thr Lys Ala Tyr Ser Gly Gly Tyr Asn Leu Pro Ile
        930                 935                 940

Gly Gln Ala Asp Glu Met Glu Arg Tyr Val Glu Glu Asn Gln Thr Arg
945                 950                 955                 960

Asp Lys His Leu Asn Pro Asn Glu Trp Trp Lys Val Tyr Pro Ser Ser
                965                 970                 975

Val Thr Glu Phe Lys Phe Leu Phe Val Ser Gly His Phe Lys Gly Asn
        980                 985                 990

Tyr Lys Ala Gln Leu Thr Arg Leu  Asn His Ile Thr Asn  Cys Asn Gly
            995                 1000                 1005

Ala Val  Leu Ser Val Glu Glu  Leu Leu Ile Gly Gly  Glu Met Ile
    1010                 1015                 1020
```

Lys Ala Gly Thr Leu Thr Leu Glu Glu Val Arg Arg Lys Phe Asn
    1025                1030                1035

Asn Gly Glu Ile Asn Phe
    1040

<210> SEQ ID NO 11
<211> LENGTH: 1044
<212> TYPE: PRT
<213> ORGANISM: Artificial Sequence
<220> FEATURE:
<223> OTHER INFORMATION: Synthetic

<400> SEQUENCE: 11

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
    130                 135                 140

Asn Ala Leu Thr Gly Ala Pro Leu Asn Leu Thr Pro Asp Gln Val Val
145                 150                 155                 160

Ala Ile Ala Ser Asn Ile Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser His Asp Gly Gly Lys Gln Ala Leu Glu Thr
        195                 200                 205

Val Gln Arg Leu Leu Pro Val Leu Cys Gln Asp His Gly Leu Thr Pro
    210                 215                 220

Asp Gln Val Val Ala Ile Ala Ser His Asp Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser Asn Gly Gly Lys Gln
            260                 265                 270

Ala Leu Glu Thr Val Gln Arg Leu Leu Pro Val Leu Cys Gln Asp His
        275                 280                 285

Gly Leu Thr Pro Asp Gln Val Val Ala Ile Ala Ser Asn Asn Gly Gly
    290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser His Asp
                325                 330                 335

```
Gly Gly Lys Gln Ala Leu Glu Thr Val Gln Arg Leu Leu Pro Val Leu
            340                 345                 350

Cys Gln Asp His Gly Leu Thr Pro Asp Gln Val Val Ala Ile Ala Ser
        355                 360                 365

Asn Gly Gly Lys Gln Ala Leu Glu Thr Val Gln Arg Leu Leu Pro
    370                 375                 380

Val Leu Cys Gln Asp His Gly Leu Thr Pro Asp Gln Val Val Ala Ile
385                 390                 395                 400

Ala Ser His Asp Gly Lys Gln Ala Leu Glu Thr Val Gln Arg Leu
            405                 410                 415

Leu Pro Val Leu Cys Gln Asp His Gly Leu Thr Pro Asp Gln Val Val
            420                 425                 430

Ala Ile Ala Ser Asn Gly Gly Lys Gln Ala Leu Glu Thr Val Gln
        435                 440                 445

Arg Leu Leu Pro Val Leu Cys Gln Asp His Gly Leu Thr Pro Asp Gln
    450                 455                 460

Val Val Ala Ile Ala Ser Asn Asn Gly Gly Lys Gln Ala Leu Glu Thr
465                 470                 475                 480

Val Gln Arg Leu Leu Pro Val Leu Cys Gln Asp His Gly Leu Thr Pro
            485                 490                 495

Asp Gln Val Val Ala Ile Ala Ser Asn Asn Gly Gly Lys Gln Ala Leu
            500                 505                 510

Glu Thr Val Gln Arg Leu Leu Pro Val Leu Cys Gln Asp His Gly Leu
        515                 520                 525

Thr Pro Asp Gln Val Val Ala Ile Ala Ser His Asp Gly Gly Lys Gln
    530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Ile Gly Gly
            565                 570                 575

Lys Gln Ala Leu Glu Thr Val Gln Arg Leu Leu Pro Val Leu Cys Gln
            580                 585                 590

Asp His Gly Leu Thr Pro Asp Gln Val Val Ala Ile Ala Ser Asn Asn
        595                 600                 605

Gly Gly Lys Gln Ala Leu Glu Thr Val Gln Arg Leu Leu Pro Val Leu
    610                 615                 620

Cys Gln Asp His Gly Leu Thr Pro Asp Gln Val Val Ala Ile Ala Ser
625                 630                 635                 640

Asn Ile Gly Gly Lys Gln Ala Leu Glu Thr Val Gln Arg Leu Leu Pro
            645                 650                 655

Val Leu Cys Gln Asp His Gly Leu Thr Pro Asp Gln Val Val Ala Ile
            660                 665                 670

Ala Ser Asn Gly Gly Gly Lys Gln Ala Leu Glu Thr Val Gln Arg Leu
        675                 680                 685

Leu Pro Val Leu Cys Gln Asp His Gly Leu Thr Pro Asp Gln Val Val
    690                 695                 700

Ala Ile Ala Ser Asn Gly Gly Gly Lys Gln Ala Leu Glu Thr Val Gln
705                 710                 715                 720

Arg Leu Leu Pro Val Leu Cys Gln Asp His Gly Leu Thr Pro Asp Gln
            725                 730                 735

Val Val Ala Ile Ala Ser Asn Gly Gly Gly Lys Gln Ala Leu Glu Thr
            740                 745                 750
```

```
Val Gln Arg Leu Leu Pro Val Leu Cys Gln Asp His Gly Leu Thr Pro
        755                 760                 765

Asp Gln Val Val Ala Ile Ala Ser His Asp Gly Gly Lys Gln Ala Leu
    770                 775                 780

Glu Ser Ile Val Ala Gln Leu Ser Arg Pro Asp Pro Ala Leu Ala Ala
785                 790                 795                 800

Leu Thr Asn Asp His Leu Val Ala Leu Ala Cys Leu Gly Gly Arg Pro
                805                 810                 815

Ala Met Asp Ala Val Lys Lys Gly Leu Pro His Ala Pro Glu Leu Ile
            820                 825                 830

Arg Arg Val Asn Arg Arg Ile Gly Glu Arg Thr Ser His Arg Val Ala
        835                 840                 845

Gln Leu Val Lys Ser Glu Leu Glu Glu Lys Lys Ser Glu Leu Arg His
    850                 855                 860

Lys Leu Lys Tyr Val Pro His Glu Tyr Ile Glu Leu Ile Glu Ile Ala
865                 870                 875                 880

Arg Asn Pro Thr Gln Asp Arg Ile Leu Glu Met Lys Val Met Glu Phe
                885                 890                 895

Phe Met Lys Val Tyr Gly Tyr Arg Gly Glu His Leu Gly Gly Ser Arg
            900                 905                 910

Lys Pro Asp Gly Ala Ile Tyr Thr Val Gly Ser Pro Ile Asp Tyr Gly
        915                 920                 925

Val Ile Val Asp Thr Lys Ala Tyr Ser Gly Gly Tyr Asn Leu Pro Ile
    930                 935                 940

Gly Gln Ala Asp Glu Met Gln Arg Tyr Val Lys Glu Asn Gln Thr Arg
945                 950                 955                 960

Asn Lys His Ile Asn Pro Asn Glu Trp Trp Lys Val Tyr Pro Ser Ser
                965                 970                 975

Val Thr Glu Phe Lys Phe Leu Phe Val Ser Gly His Phe Lys Gly Asn
            980                 985                 990

Tyr Lys Ala Gln Leu Thr Arg Leu Asn Arg Lys Thr Asn Cys Asn Gly
        995                 1000                1005

Ala Val Leu Ser Val Glu Glu Leu Leu Ile Gly Gly Glu Met Ile
    1010                1015                1020

Lys Ala Gly Thr Leu Thr Leu Glu Glu Val Arg Arg Lys Phe Asn
    1025                1030                1035

Asn Gly Glu Ile Asn Phe
    1040

<210> SEQ ID NO 12
<211> LENGTH: 1010
<212> TYPE: PRT
<213> ORGANISM: Artificial Sequence
<220> FEATURE:
<223> OTHER INFORMATION: Synthetic

<400> SEQUENCE: 12

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60
```

```
Pro Ala Ala Leu Gly Thr Val Ala Val Thr Tyr Gln His Ile Ile Thr
 65                  70                  75                  80

Ala Leu Pro Glu Ala Thr His Glu Asp Ile Val Gly Val Gly Lys Gln
                 85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
    130                 135                 140

Asn Ala Leu Thr Gly Ala Pro Leu Asn Leu Thr Pro Asp Gln Val Val
145                 150                 155                 160

Ala Ile Ala Ser His Asp Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser Asn Gly Gly Lys Gln Ala Leu Glu Thr
        195                 200                 205

Val Gln Arg Leu Leu Pro Val Leu Cys Gln Asp His Gly Leu Thr Pro
    210                 215                 220

Asp Gln Val Val Ala Ile Ala Ser Asn Ile Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser Asn Gly Gly Lys Gln
            260                 265                 270

Ala Leu Glu Thr Val Gln Arg Leu Leu Pro Val Leu Cys Gln Asp His
    275                 280                 285

Gly Leu Thr Pro Asp Gln Val Val Ala Ile Ala Ser Asn Ile Gly Gly
    290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser Asn Asn
                325                 330                 335

Gly Gly Lys Gln Ala Leu Glu Thr Val Gln Arg Leu Leu Pro Val Leu
            340                 345                 350

Cys Gln Asp His Gly Leu Thr Pro Asp Gln Val Val Ala Ile Ala Ser
        355                 360                 365

Asn Ile Gly Gly Lys Gln Ala Leu Glu Thr Val Gln Arg Leu Leu Pro
    370                 375                 380

Val Leu Cys Gln Asp His Gly Leu Thr Pro Asp Gln Val Val Ala Ile
385                 390                 395                 400

Ala Ser Asn Gly Gly Gly Lys Gln Ala Leu Glu Thr Val Gln Arg Leu
                405                 410                 415

Leu Pro Val Leu Cys Gln Asp His Gly Leu Thr Pro Asp Gln Val Val
            420                 425                 430

Ala Ile Ala Ser Asn Asn Gly Gly Lys Gln Ala Leu Glu Thr Val Gln
        435                 440                 445

Arg Leu Leu Pro Val Leu Cys Gln Asp His Gly Leu Thr Pro Asp Gln
    450                 455                 460

Val Val Ala Ile Ala Ser Asn Ile Gly Gly Lys Gln Ala Leu Glu Thr
465                 470                 475                 480

Val Gln Arg Leu Leu Pro Val Leu Cys Gln Asp His Gly Leu Thr Pro
```

```
                485                 490                 495
Asp Gln Val Val Ala Ile Ala Ser Asn Asn Gly Gly Lys Gln Ala Leu
                500                 505                 510
Glu Thr Val Gln Arg Leu Leu Pro Val Leu Cys Gln Asp His Gly Leu
                515                 520                 525
Thr Pro Asp Gln Val Val Ala Ile Ala Ser Asn Ile Gly Gly Lys Gln
                530                 535                 540
Ala Leu Glu Thr Val Gln Arg Leu Leu Pro Val Leu Cys Gln Asp His
545                 550                 555                 560
Gly Leu Thr Pro Asp Gln Val Val Ala Ile Ala Ser Asn Gly Gly Gly
                565                 570                 575
Lys Gln Ala Leu Glu Thr Val Gln Arg Leu Leu Pro Val Leu Cys Gln
                580                 585                 590
Asp His Gly Leu Thr Pro Asp Gln Val Val Ala Ile Ala Ser Asn Gly
                595                 600                 605
Gly Gly Lys Gln Ala Leu Glu Thr Val Gln Arg Leu Leu Pro Val Leu
                610                 615                 620
Cys Gln Asp His Gly Leu Thr Pro Asp Gln Val Val Ala Ile Ala Ser
625                 630                 635                 640
Asn Ile Gly Gly Lys Gln Ala Leu Glu Thr Val Gln Arg Leu Leu Pro
                645                 650                 655
Val Leu Cys Gln Asp His Gly Leu Thr Pro Asp Gln Val Val Ala Ile
                660                 665                 670
Ala Ser Asn Gly Gly Gly Lys Gln Ala Leu Glu Thr Val Gln Arg Leu
                675                 680                 685
Leu Pro Val Leu Cys Gln Asp His Gly Leu Thr Pro Asp Gln Val Val
                690                 695                 700
Ala Ile Ala Ser His Asp Gly Gly Lys Gln Ala Leu Glu Thr Val Gln
705                 710                 715                 720
Arg Leu Leu Pro Val Leu Cys Gln Asp His Gly Leu Thr Pro Asp Gln
                725                 730                 735
Val Val Ala Ile Ala Ser Asn Gly Gly Gly Lys Gln Ala Leu Glu Ser
                740                 745                 750
Ile Val Ala Gln Leu Ser Arg Pro Asp Pro Ala Leu Ala Ala Leu Thr
                755                 760                 765
Asn Asp His Leu Val Ala Leu Ala Cys Leu Gly Gly Arg Pro Ala Met
                770                 775                 780
Asp Ala Val Lys Lys Gly Leu Pro His Ala Pro Glu Leu Ile Arg Arg
785                 790                 795                 800
Val Asn Arg Arg Ile Gly Glu Arg Thr Ser His Arg Val Ala Gln Leu
                805                 810                 815
Val Lys Ser Glu Leu Glu Lys Lys Ser Glu Leu Arg His Lys Leu
                820                 825                 830
Lys Tyr Val Pro His Glu Tyr Ile Glu Leu Ile Glu Ile Ala Arg Asn
                835                 840                 845
Pro Thr Gln Asp Arg Ile Leu Glu Met Lys Val Met Glu Phe Phe Met
                850                 855                 860
Lys Val Tyr Gly Tyr Arg Gly Glu His Leu Gly Gly Ser Arg Lys Pro
865                 870                 875                 880
Asp Gly Ala Ile Tyr Thr Val Gly Ser Pro Ile Asp Tyr Gly Val Ile
                885                 890                 895
Val Asp Thr Lys Ala Tyr Ser Gly Gly Tyr Asn Leu Pro Ile Gly Gln
                900                 905                 910
```

```
Ala Asp Glu Met Glu Arg Tyr Val Glu Glu Asn Gln Thr Arg Asp Lys
            915                 920                 925

His Leu Asn Pro Asn Glu Trp Trp Lys Val Tyr Pro Ser Ser Val Thr
        930                 935                 940

Glu Phe Lys Phe Leu Phe Val Ser Gly His Phe Lys Gly Asn Tyr Lys
945                 950                 955                 960

Ala Gln Leu Thr Arg Leu Asn His Ile Thr Asn Cys Asn Gly Ala Val
            965                 970                 975

Leu Ser Val Glu Glu Leu Leu Ile Gly Gly Glu Met Ile Lys Ala Gly
            980                 985                 990

Thr Leu Thr Leu Glu Glu Val Arg  Arg Lys Phe Asn Asn Gly Glu Ile
            995                 1000                1005

Asn Phe
    1010

<210> SEQ ID NO 13
<211> LENGTH: 1010
<212> TYPE: PRT
<213> ORGANISM: Artificial Sequence
<220> FEATURE:
<223> OTHER INFORMATION: Synthetic

<400> SEQUENCE: 13

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
    130                 135                 140

Asn Ala Leu Thr Gly Ala Pro Leu Asn Leu Thr Pro Asp Gln Val Val
145                 150                 155                 160

Ala Ile Ala Ser Asn Ile Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser Asn Asn Gly Gly Lys Gln Ala Leu Glu Thr
        195                 200                 205

Val Gln Arg Leu Leu Pro Val Leu Cys Gln Asp His Gly Leu Thr Pro
    210                 215                 220

Asp Gln Val Val Ala Ile Ala Ser His Asp Gly Gly Lys Gln Ala Leu
225                 230                 235                 240

Glu Thr Val Gln Arg Leu Leu Pro Val Leu Cys Gln Asp His Gly Leu
                245                 250                 255
```

```
Thr Pro Asp Gln Val Val Ala Ile Ala Ser Asn Ile Gly Gly Lys Gln
            260                 265                 270

Ala Leu Glu Thr Val Gln Arg Leu Leu Pro Val Leu Cys Gln Asp His
        275                 280                 285

Gly Leu Thr Pro Asp Gln Val Val Ala Ile Ala Ser Asn Ile Gly Gly
    290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser Asn Gly
                325                 330                 335

Gly Gly Lys Gln Ala Leu Glu Thr Val Gln Arg Leu Leu Pro Val Leu
                340                 345                 350

Cys Gln Asp His Gly Leu Thr Pro Asp Gln Val Val Ala Ile Ala Ser
                355                 360                 365

Asn Asn Gly Gly Lys Gln Ala Leu Glu Thr Val Gln Arg Leu Leu Pro
    370                 375                 380

Val Leu Cys Gln Asp His Gly Leu Thr Pro Asp Gln Val Val Ala Ile
385                 390                 395                 400

Ala Ser His Asp Gly Gly Lys Gln Ala Leu Glu Thr Val Gln Arg Leu
                405                 410                 415

Leu Pro Val Leu Cys Gln Asp His Gly Leu Thr Pro Asp Gln Val Val
                420                 425                 430

Ala Ile Ala Ser Asn Asn Gly Gly Lys Gln Ala Leu Glu Thr Val Gln
        435                 440                 445

Arg Leu Leu Pro Val Leu Cys Gln Asp His Gly Leu Thr Pro Asp Gln
        450                 455                 460

Val Val Ala Ile Ala Ser Asn Asn Gly Gly Lys Gln Ala Leu Glu Thr
465                 470                 475                 480

Val Gln Arg Leu Leu Pro Val Leu Cys Gln Asp His Gly Leu Thr Pro
                485                 490                 495

Asp Gln Val Val Ala Ile Ala Ser His Asp Gly Gly Lys Gln Ala Leu
                500                 505                 510

Glu Thr Val Gln Arg Leu Leu Pro Val Leu Cys Gln Asp His Gly Leu
            515                 520                 525

Thr Pro Asp Gln Val Val Ala Ile Ala Ser His Asp Gly Gly Lys Gln
        530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Ile Gly Gly
                565                 570                 575

Lys Gln Ala Leu Glu Thr Val Gln Arg Leu Leu Pro Val Leu Cys Gln
            580                 585                 590

Asp His Gly Leu Thr Pro Asp Gln Val Val Ala Ile Ala Ser Asn Gly
                595                 600                 605

Gly Gly Lys Gln Ala Leu Glu Thr Val Gln Arg Leu Leu Pro Val Leu
            610                 615                 620

Cys Gln Asp His Gly Leu Thr Pro Asp Gln Val Val Ala Ile Ala Ser
625                 630                 635                 640

His Asp Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
            660                 665                 670
```

```
Ala Ser His Asp Gly Gly Lys Gln Ala Leu Glu Thr Val Gln Arg Leu
            675                 680                 685

Leu Pro Val Leu Cys Gln Asp His Gly Leu Thr Pro Asp Gln Val Val
        690                 695                 700

Ala Ile Ala Ser His Asp Gly Gly Lys Gln Ala Leu Glu Thr Val Gln
705                 710                 715                 720

Arg Leu Leu Pro Val Leu Cys Gln Asp His Gly Leu Thr Pro Asp Gln
                725                 730                 735

Val Val Ala Ile Ala Ser Asn Gly Gly Lys Gln Ala Leu Glu Ser
            740                 745                 750

Ile Val Ala Gln Leu Ser Arg Pro Asp Pro Ala Leu Ala Ala Leu Thr
        755                 760                 765

Asn Asp His Leu Val Ala Leu Ala Cys Leu Gly Gly Arg Pro Ala Met
    770                 775                 780

Asp Ala Val Lys Lys Gly Leu Pro His Ala Pro Glu Leu Ile Arg Arg
785                 790                 795                 800

Val Asn Arg Arg Ile Gly Glu Arg Thr Ser His Arg Val Ala Gln Leu
                805                 810                 815

Val Lys Ser Glu Leu Glu Glu Lys Lys Ser Glu Leu Arg His Lys Leu
            820                 825                 830

Lys Tyr Val Pro His Glu Tyr Ile Glu Leu Ile Glu Ile Ala Arg Asn
        835                 840                 845

Pro Thr Gln Asp Arg Ile Leu Glu Met Lys Val Met Glu Phe Phe Met
    850                 855                 860

Lys Val Tyr Gly Tyr Arg Gly Glu His Leu Gly Gly Ser Arg Lys Pro
865                 870                 875                 880

Asp Gly Ala Ile Tyr Thr Val Gly Ser Pro Ile Asp Tyr Gly Val Ile
                885                 890                 895

Val Asp Thr Lys Ala Tyr Ser Gly Gly Tyr Asn Leu Pro Ile Gly Gln
            900                 905                 910

Ala Asp Glu Met Gln Arg Tyr Val Lys Glu Asn Gln Thr Arg Asn Lys
        915                 920                 925

His Ile Asn Pro Asn Glu Trp Trp Lys Val Tyr Pro Ser Ser Val Thr
    930                 935                 940

Glu Phe Lys Phe Leu Phe Val Ser Gly His Phe Lys Gly Asn Tyr Lys
945                 950                 955                 960

Ala Gln Leu Thr Arg Leu Asn Arg Lys Thr Asn Cys Asn Gly Ala Val
                965                 970                 975

Leu Ser Val Glu Glu Leu Leu Ile Gly Gly Met Ile Lys Ala Gly
            980                 985                 990

Thr Leu Thr Leu Glu Glu Val Arg  Arg Lys Phe Asn Asn Gly Glu Ile
        995                 1000                1005

Asn Phe
    1010

<210> SEQ ID NO 14
<211> LENGTH: 942
<212> TYPE: PRT
<213> ORGANISM: Artificial Sequence
<220> FEATURE:
<223> OTHER INFORMATION: Synthetic

<400> SEQUENCE: 14

Met Asp Tyr Lys Asp His Asp Gly Asp Tyr Lys Asp His Asp Ile Asp
1               5                   10                  15
```

```
Tyr Lys Asp Asp Asp Lys Met Ala Pro Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
            85                  90                  95

Trp Ser Gly Ala Arg Ala Leu Glu Ala Leu Leu Thr Asp Ala Gly Glu
        100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
        130                 135                 140

Asn Ala Leu Thr Gly Ala Pro Leu Asn Leu Thr Pro Asp Gln Val Val
145                 150                 155                 160

Ala Ile Ala Ser Asn Ile Gly Gly Lys Gln Ala Leu Glu Thr Val Gln
            165                 170                 175

Arg Leu Leu Pro Val Leu Cys Gln Asp His Gly Leu Thr Pro Asp Gln
        180                 185                 190

Val Val Ala Ile Ala Ser Asn Ile Gly Gly Lys Gln Ala Leu Glu Thr
        195                 200                 205

Val Gln Arg Leu Leu Pro Val Leu Cys Gln Asp His Gly Leu Thr Pro
        210                 215                 220

Asp Gln Val Val Ala Ile Ala Ser His Asp Gly Gly Lys Gln Ala Leu
225                 230                 235                 240

Glu Thr Val Gln Arg Leu Leu Pro Val Leu Cys Gln Asp His Gly Leu
            245                 250                 255

Thr Pro Asp Gln Val Val Ala Ile Ala Ser Asn Gly Gly Lys Gln
        260                 265                 270

Ala Leu Glu Thr Val Gln Arg Leu Leu Pro Val Leu Cys Gln Asp His
        275                 280                 285

Gly Leu Thr Pro Asp Gln Val Val Ala Ile Ala Ser Asn Asn Gly Gly
        290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser Asn Ile
            325                 330                 335

Gly Gly Lys Gln Ala Leu Glu Thr Val Gln Arg Leu Leu Pro Val Leu
        340                 345                 350

Cys Gln Asp His Gly Leu Thr Pro Asp Gln Val Val Ala Ile Ala Ser
        355                 360                 365

Asn Gly Gly Gly Lys Gln Ala Leu Glu Thr Val Gln Arg Leu Leu Pro
        370                 375                 380

Val Leu Cys Gln Asp His Gly Leu Thr Pro Asp Gln Val Val Ala Ile
385                 390                 395                 400

Ala Ser Asn Asn Gly Gly Lys Gln Ala Leu Glu Thr Val Gln Arg Leu
            405                 410                 415

Leu Pro Val Leu Cys Gln Asp His Gly Leu Thr Pro Asp Gln Val Val
        420                 425                 430

Ala Ile Ala Ser His Asp Gly Gly Lys Gln Ala Leu Glu Thr Val Gln
```

```
            435                 440                 445
Arg Leu Leu Pro Val Leu Cys Gln Asp His Gly Leu Thr Pro Asp Gln
450                 455                 460

Val Val Ala Ile Ala Ser His Asp Gly Gly Lys Gln Ala Leu Glu Thr
465                 470                 475                 480

Val Gln Arg Leu Leu Pro Val Leu Cys Gln Asp His Gly Leu Thr Pro
                485                 490                 495

Asp Gln Val Val Ala Ile Ala Ser Asn Ile Gly Gly Lys Gln Ala Leu
                500                 505                 510

Glu Thr Val Gln Arg Leu Leu Pro Val Leu Cys Gln Asp His Gly Leu
                515                 520                 525

Thr Pro Asp Gln Val Val Ala Ile Ala Ser Asn Asn Gly Gly Lys Gln
                530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Asn Gly Gly
                565                 570                 575

Lys Gln Ala Leu Glu Thr Val Gln Arg Leu Leu Pro Val Leu Cys Gln
                580                 585                 590

Asp His Gly Leu Thr Pro Asp Gln Val Val Ala Ile Ala Ser Asn Ile
                595                 600                 605

Gly Gly Lys Gln Ala Leu Glu Thr Val Gln Arg Leu Leu Pro Val Leu
610                 615                 620

Cys Gln Asp His Gly Leu Thr Pro Asp Gln Val Val Ala Ile Ala Ser
625                 630                 635                 640

Asn Gly Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
                660                 665                 670

Ala Ser Asn Gly Gly Gly Lys Gln Ala Leu Glu Ser Ile Val Ala Gln
                675                 680                 685

Leu Ser Arg Pro Asp Pro Ala Leu Ala Ala Leu Thr Asn Asp His Leu
                690                 695                 700

Val Ala Leu Ala Cys Leu Gly Gly Arg Pro Ala Met Asp Ala Val Lys
705                 710                 715                 720

Lys Gly Leu Pro His Ala Pro Glu Leu Ile Arg Arg Val Asn Arg Arg
                725                 730                 735

Ile Gly Glu Arg Thr Ser His Arg Val Ala Gln Leu Val Lys Ser Glu
                740                 745                 750

Leu Glu Glu Lys Lys Ser Glu Leu Arg His Lys Leu Lys Tyr Val Pro
                755                 760                 765

His Glu Tyr Ile Glu Leu Ile Glu Ile Ala Arg Asn Pro Thr Gln Asp
                770                 775                 780

Arg Ile Leu Glu Met Lys Val Met Glu Phe Phe Met Lys Val Tyr Gly
785                 790                 795                 800

Tyr Arg Gly Glu His Leu Gly Gly Ser Arg Lys Pro Asp Gly Ala Ile
                805                 810                 815

Tyr Thr Val Gly Ser Pro Ile Asp Tyr Gly Val Ile Val Asp Thr Lys
                820                 825                 830

Ala Tyr Ser Gly Gly Tyr Asn Leu Pro Ile Gly Gln Ala Asp Glu Met
                835                 840                 845

Gln Arg Tyr Val Lys Glu Asn Gln Thr Arg Asn Lys His Ile Asn Pro
850                 855                 860
```

```
Asn Glu Trp Trp Lys Val Tyr Pro Ser Ser Val Thr Glu Phe Lys Phe
865                 870                 875                 880

Leu Phe Val Ser Gly His Phe Lys Gly Asn Tyr Lys Ala Gln Leu Thr
            885                 890                 895

Arg Leu Asn Arg Lys Thr Asn Cys Asn Gly Ala Val Leu Ser Val Glu
        900                 905                 910

Glu Leu Leu Ile Gly Gly Glu Met Ile Lys Ala Gly Thr Leu Thr Leu
    915                 920                 925

Glu Glu Val Arg Arg Lys Phe Asn Asn Gly Glu Ile Asn Phe
930                 935                 940
```

<210> SEQ ID NO 15
<211> LENGTH: 942
<212> TYPE: PRT
<213> ORGANISM: Artificial Sequence
<220> FEATURE:
<223> OTHER INFORMATION: Synthetic

<400> SEQUENCE: 15

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
            20                  25                  30

Gly Arg Gly Ser Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Thr Tyr Gln His Ile Ile Thr
65                  70                  75                  80

Ala Leu Pro Glu Ala Thr His Glu Asp Ile Val Gly Val Gly Lys Gln
                85                  90                  95

Trp Ser Gly Ala Arg Ala Leu Glu Ala Leu Leu Thr Asp Ala Gly Glu
            100                 105                 110

Leu Arg Gly Pro Pro Leu Gln Leu Asp Thr Gly Gln Leu Val Lys Ile
        115                 120                 125

Ala Lys Arg Gly Gly Val Thr Ala Met Glu Ala Val His Ala Ser Arg
    130                 135                 140

Asn Ala Leu Thr Gly Ala Pro Leu Asn Leu Thr Pro Asp Gln Val Val
145                 150                 155                 160

Ala Ile Ala Ser Asn Asn Gly Gly Lys Gln Ala Leu Glu Thr Val Gln
                165                 170                 175

Arg Leu Leu Pro Val Leu Cys Gln Asp His Gly Leu Thr Pro Asp Gln
            180                 185                 190

Val Val Ala Ile Ala Ser Asn Asn Gly Gly Lys Gln Ala Leu Glu Thr
        195                 200                 205

Val Gln Arg Leu Leu Pro Val Leu Cys Gln Asp His Gly Leu Thr Pro
    210                 215                 220

Asp Gln Val Val Ala Ile Ala Ser Asn Ile Gly Gly Lys Gln Ala Leu
225                 230                 235                 240

Glu Thr Val Gln Arg Leu Leu Pro Val Leu Cys Gln Asp His Gly Leu
                245                 250                 255

Thr Pro Asp Gln Val Val Ala Ile Ala Ser Asn Ile Gly Gly Lys Gln
            260                 265                 270

Ala Leu Glu Thr Val Gln Arg Leu Leu Pro Val Leu Cys Gln Asp His
        275                 280                 285
```

```
Gly Leu Thr Pro Asp Gln Val Ala Ile Ala Ser Asn Gly Gly
    290                 295                 300

Lys Gln Ala Leu Glu Thr Val Gln Arg Leu Leu Pro Val Leu Cys Gln
305                 310                 315                 320

Asp His Gly Leu Thr Pro Asp Gln Val Val Ala Ile Ala Ser Asn Gly
                325                 330                 335

Gly Gly Lys Gln Ala Leu Glu Thr Val Gln Arg Leu Leu Pro Val Leu
            340                 345                 350

Cys Gln Asp His Gly Leu Thr Pro Asp Gln Val Val Ala Ile Ala Ser
                355                 360                 365

Asn Gly Gly Gly Lys Gln Ala Leu Glu Thr Val Gln Arg Leu Leu Pro
    370                 375                 380

Val Leu Cys Gln Asp His Gly Leu Thr Pro Asp Gln Val Val Ala Ile
385                 390                 395                 400

Ala Ser Asn Asn Gly Gly Lys Gln Ala Leu Glu Thr Val Gln Arg Leu
                405                 410                 415

Leu Pro Val Leu Cys Gln Asp His Gly Leu Thr Pro Asp Gln Val Val
                420                 425                 430

Ala Ile Ala Ser Asn Ile Gly Gly Lys Gln Ala Leu Glu Thr Val Gln
                435                 440                 445

Arg Leu Leu Pro Val Leu Cys Gln Asp His Gly Leu Thr Pro Asp Gln
450                 455                 460

Val Val Ala Ile Ala Ser Asn Ile Gly Gly Lys Gln Ala Leu Glu Thr
465                 470                 475                 480

Val Gln Arg Leu Leu Pro Val Leu Cys Gln Asp His Gly Leu Thr Pro
                485                 490                 495

Asp Gln Val Val Ala Ile Ala Ser Asn Ile Gly Gly Lys Gln Ala Leu
                500                 505                 510

Glu Thr Val Gln Arg Leu Leu Pro Val Leu Cys Gln Asp His Gly Leu
            515                 520                 525

Thr Pro Asp Gln Val Val Ala Ile Ala Ser Asn Gly Gly Gly Lys Gln
                530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser Asn Ile Gly Gly
                565                 570                 575

Lys Gln Ala Leu Glu Thr Val Gln Arg Leu Leu Pro Val Leu Cys Gln
                580                 585                 590

Asp His Gly Leu Thr Pro Asp Gln Val Val Ala Ile Ala Ser Asn Gly
            595                 600                 605

Gly Gly Lys Gln Ala Leu Glu Thr Val Gln Arg Leu Leu Pro Val Leu
    610                 615                 620

Cys Gln Asp His Gly Leu Thr Pro Asp Gln Val Val Ala Ile Ala Ser
625                 630                 635                 640

His Asp Gly Gly Lys Gln Ala Leu Glu Thr Val Gln Arg Leu Leu Pro
                645                 650                 655

Val Leu Cys Gln Asp His Gly Leu Thr Pro Asp Gln Val Val Ala Ile
                660                 665                 670

Ala Ser His Asp Gly Gly Lys Gln Ala Leu Glu Ser Ile Val Ala Gln
            675                 680                 685

Leu Ser Arg Pro Asp Pro Ala Leu Ala Ala Leu Thr Asn Asp His Leu
    690                 695                 700
```

```
Val Ala Leu Ala Cys Leu Gly Gly Arg Pro Ala Met Asp Ala Val Lys
705                 710                 715                 720

Lys Gly Leu Pro His Ala Pro Glu Leu Ile Arg Arg Val Asn Arg Arg
            725                 730                 735

Ile Gly Glu Arg Thr Ser His Arg Val Ala Gln Leu Val Lys Ser Glu
        740                 745                 750

Leu Glu Glu Lys Lys Ser Glu Leu Arg His Lys Leu Lys Tyr Val Pro
            755                 760                 765

His Glu Tyr Ile Glu Leu Ile Glu Ile Ala Arg Asn Pro Thr Gln Asp
    770                 775                 780

Arg Ile Leu Glu Met Lys Val Met Glu Phe Phe Met Lys Val Tyr Gly
785                 790                 795                 800

Tyr Arg Gly Glu His Leu Gly Gly Ser Arg Lys Pro Asp Gly Ala Ile
                805                 810                 815

Tyr Thr Val Gly Ser Pro Ile Asp Tyr Gly Val Ile Val Asp Thr Lys
            820                 825                 830

Ala Tyr Ser Gly Gly Tyr Asn Leu Pro Ile Gly Gln Ala Asp Glu Met
        835                 840                 845

Glu Arg Tyr Val Glu Glu Asn Gln Thr Arg Asp Lys His Leu Asn Pro
850                 855                 860

Asn Glu Trp Trp Lys Val Tyr Pro Ser Ser Val Thr Glu Phe Lys Phe
865                 870                 875                 880

Leu Phe Val Ser Gly His Phe Lys Gly Asn Tyr Lys Ala Gln Leu Thr
                885                 890                 895

Arg Leu Asn His Ile Thr Asn Cys Asn Gly Ala Val Leu Ser Val Glu
            900                 905                 910

Glu Leu Leu Ile Gly Gly Glu Met Ile Lys Ala Gly Thr Leu Thr Leu
        915                 920                 925

Glu Glu Val Arg Arg Lys Phe Asn Asn Gly Glu Ile Asn Phe
    930                 935                 940

<210> SEQ ID NO 16
<211> LENGTH: 49
<212> TYPE: DNA
<213> ORGANISM: Homo sapiens

<400> SEQUENCE: 16
tttagctcct actcagactg ttactctggt gacacaacct gtggttact              49

<210> SEQ ID NO 17
<211> LENGTH: 53
<212> TYPE: DNA
<213> ORGANISM: Homo sapiens

<400> SEQUENCE: 17
tttagctcct actcagactg ttactctggt gacacaacct gtggttacta agg          53

<210> SEQ ID NO 18
<211> LENGTH: 46
<212> TYPE: DNA
<213> ORGANISM: Homo sapiens

<400> SEQUENCE: 18
agctcctact cagactgtta ctctggtgac acaacctgtg gttact                 46

<210> SEQ ID NO 19
<211> LENGTH: 50
<212> TYPE: DNA
```

<213> ORGANISM: Homo sapiens

<400> SEQUENCE: 19
agctcctact cagactgtta ctctggtgac acaacctgtg gttactaagg         50

<210> SEQ ID NO 20
<211> LENGTH: 50
<212> TYPE: DNA
<213> ORGANISM: Homo sapiens

<400> SEQUENCE: 20
gcaaaaaccc aaaatatttt agctcctact cagactgtta ctctggtgac         50

<210> SEQ ID NO 21
<211> LENGTH: 52
<212> TYPE: DNA
<213> ORGANISM: Homo sapiens

<400> SEQUENCE: 21
ttgcaaaaac ccaaaatatt ttagctccta ctcagactgt tactctggtg ac      52

<210> SEQ ID NO 22
<211> LENGTH: 55
<212> TYPE: DNA
<213> ORGANISM: Homo sapiens

<400> SEQUENCE: 22 ccttttgca aaaacccaaa atattttagc tcctactcag actgttactc tggtg     55

<210> SEQ ID NO 23
<211> LENGTH: 56
<212> TYPE: DNA
<213> ORGANISM: Homo sapiens

<400> SEQUENCE: 23
ccaaactaga aatgccatct tccttgatgt tggaggtacc tgctctggca gatttc   56

<210> SEQ ID NO 24
<211> LENGTH: 51
<212> TYPE: DNA
<213> ORGANISM: Homo sapiens

<400> SEQUENCE: 24
ctatagatga gattatctgc ccatgactgg cgcagggatg gccgcattgc t        51

<210> SEQ ID NO 25
<211> LENGTH: 48
<212> TYPE: DNA
<213> ORGANISM: Homo sapiens

<400> SEQUENCE: 25
tggaatttga aatatccggg ggcctctaca gaatcctggc atcagtta            48

<210> SEQ ID NO 26
<211> LENGTH: 15
<212> TYPE: DNA
<213> ORGANISM: Homo sapiens

<400> SEQUENCE: 26
attttagctc ctact                                               15

<210> SEQ ID NO 27
<211> LENGTH: 17

```
<212> TYPE: DNA
<213> ORGANISM: Homo sapiens

<400> SEQUENCE: 27
tttagctcct actcaga                                                  17

<210> SEQ ID NO 28
<211> LENGTH: 16
<212> TYPE: DNA
<213> ORGANISM: Homo sapiens

<400> SEQUENCE: 28
agctcctact cagact                                                   16

<210> SEQ ID NO 29
<211> LENGTH: 15
<212> TYPE: DNA
<213> ORGANISM: Homo sapiens

<400> SEQUENCE: 29
cctactcaga ctgtt                                                    15

<210> SEQ ID NO 30
<211> LENGTH: 17
<212> TYPE: DNA
<213> ORGANISM: Homo sapiens

<400> SEQUENCE: 30
aaccacaggt tgtgtca                                                  17

<210> SEQ ID NO 31
<211> LENGTH: 16
<212> TYPE: DNA
<213> ORGANISM: Homo sapiens

<400> SEQUENCE: 31
agtaaccaca ggttgt                                                   16

<210> SEQ ID NO 32
<211> LENGTH: 17
<212> TYPE: DNA
<213> ORGANISM: Homo sapiens

<400> SEQUENCE: 32
ccttagtaac cacaggt                                                  17

<210> SEQ ID NO 33
<211> LENGTH: 17
<212> TYPE: DNA
<213> ORGANISM: Homo sapiens

<400> SEQUENCE: 33 gcaaaaccc aaaatat                                                   17

<210> SEQ ID NO 34
<211> LENGTH: 17
<212> TYPE: DNA
<213> ORGANISM: Homo sapiens

<400> SEQUENCE: 34
ttgcaaaaac ccaaaat                                                  17

<210> SEQ ID NO 35
```

-continued

```
<211> LENGTH: 17
<212> TYPE: DNA
<213> ORGANISM: Homo sapiens

<400> SEQUENCE: 35
cctttttgca aaaccc                                                     17

<210> SEQ ID NO 36
<211> LENGTH: 17
<212> TYPE: DNA
<213> ORGANISM: Homo sapiens

<400> SEQUENCE: 36
caccagagta acagtct                                                    17

<210> SEQ ID NO 37
<211> LENGTH: 19
<212> TYPE: DNA
<213> ORGANISM: Homo sapiens

<400> SEQUENCE: 37
gtcaccagag taacagtct                                                  19

<210> SEQ ID NO 38
<211> LENGTH: 18
<212> TYPE: DNA
<213> ORGANISM: Homo sapiens

<400> SEQUENCE: 38
ccaaactaga aatgccat                                                   18

<210> SEQ ID NO 39
<211> LENGTH: 19
<212> TYPE: DNA
<213> ORGANISM: Homo sapiens

<400> SEQUENCE: 39
gaaatctgcc agagcaggt                                                  19

<210> SEQ ID NO 40
<211> LENGTH: 18
<212> TYPE: DNA
<213> ORGANISM: Homo sapiens

<400> SEQUENCE: 40
ctatagatga gattatct                                                   18

<210> SEQ ID NO 41
<211> LENGTH: 18
<212> TYPE: DNA
<213> ORGANISM: Homo sapiens

<400> SEQUENCE: 41
agcaatgcgg ccatccct                                                   18

<210> SEQ ID NO 42
<211> LENGTH: 17
<212> TYPE: DNA
<213> ORGANISM: Homo sapiens

<400> SEQUENCE: 42
taactgatgc caggatt                                                    17
```

-continued

```
<210> SEQ ID NO 43
<211> LENGTH: 17
<212> TYPE: DNA
<213> ORGANISM: Homo sapiens

<400> SEQUENCE: 43
tggaatttga aatatcc                                                      17

<210> SEQ ID NO 44
<211> LENGTH: 48
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(31)
<223> OTHER INFORMATION: n is a, c, g, or t

<400> SEQUENCE: 44
tggaatttga aatatccnnn nnnnnnnnnn naatcctggc atcagtta                    48

<210> SEQ ID NO 45
<211> LENGTH: 48
<212> TYPE: DNA
<213> ORGANISM: Mus musculus

<400> SEQUENCE: 45
tggaatttga aatatccaga ggcctctaca gaatcctggc atcagtta                    48

<210> SEQ ID NO 46
<211> LENGTH: 55
<212> TYPE: DNA
<213> ORGANISM: Homo sapiens

<400> SEQUENCE: 46
tattttagct cctactcaga ctgttactct ggtgacacaa cctgtggtta ctaag           55

<210> SEQ ID NO 47
<211> LENGTH: 8
<212> TYPE: PRT
<213> ORGANISM: Homo sapiens

<400> SEQUENCE: 47

Leu Leu Leu Arg Leu Leu Leu Trp
1               5

<210> SEQ ID NO 48
<211> LENGTH: 14
<212> TYPE: PRT
<213> ORGANISM: Homo sapiens

<400> SEQUENCE: 48

Ser Tyr Ser Asp Cys Tyr Ser Gly Asp Thr Thr Cys Gly Tyr
1               5                   10

<210> SEQ ID NO 49
<211> LENGTH: 15
<212> TYPE: PRT
<213> ORGANISM: Homo sapiens

<400> SEQUENCE: 49

Pro Thr Gln Thr Val Thr Leu Val Thr Gln Pro Val Val Thr Lys
1               5                   10                  15
```

<210> SEQ ID NO 50
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (27)..(27)
<223> OTHER INFORMATION: n is a, c, g, or t

<400> SEQUENCE: 50
tattttagct cctactcaga ctgttanctc tggtgacaca acctgtggtt actaag            56

<210> SEQ ID NO 51
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 51

Leu Leu Leu Arg Leu Leu Xaa Leu Val Thr Gln Pro Val Val Thr Lys
1               5                   10                  15

<210> SEQ ID NO 52
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (27)..(28)
<223> OTHER INFORMATION: n is a, c, g, or t

<400> SEQUENCE: 52
tattttagct cctactcaga ctgttannct ctggtgacac aacctgtggt tactaag           57

<210> SEQ ID NO 53
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: Xaa can be any naturally occurring amino acid

<400> SEQUENCE: 53

Ser Tyr Ser Asp Cys Xaa Xaa Leu Val Thr Gln Pro Val Val Thr Lys
1               5                   10                  15

<210> SEQ ID NO 54
<211> LENGTH: 15
<212> TYPE: DNA
<213> ORGANISM: Homo sapiens

<400> SEQUENCE: 54
attttagctc ctact            15

<210> SEQ ID NO 55
<211> LENGTH: 17
<212> TYPE: DNA

```
<213> ORGANISM: Homo sapiens

<400> SEQUENCE: 55
tttagctcct actcaga                                              17

<210> SEQ ID NO 56
<211> LENGTH: 16
<212> TYPE: DNA
<213> ORGANISM: Homo sapiens

<400> SEQUENCE: 56
agctcctact cagact                                               16

<210> SEQ ID NO 57
<211> LENGTH: 15
<212> TYPE: DNA
<213> ORGANISM: Homo sapiens

<400> SEQUENCE: 57
cctactcaga ctgtt                                                15

<210> SEQ ID NO 58
<211> LENGTH: 61
<212> TYPE: DNA
<213> ORGANISM: Homo sapiens

<400> SEQUENCE: 58
aaaatatttt agctcctact cagactgtta ctctggtgac acaacctgtg gttactaagg  60
a                                                                61

<210> SEQ ID NO 59
<211> LENGTH: 61
<212> TYPE: DNA
<213> ORGANISM: Homo sapiens

<400> SEQUENCE: 59
tccttagtaa ccacaggttg tgtcaccaga gtaacagtct gagtaggagc taaaatattt  60
t                                                                61

<210> SEQ ID NO 60
<211> LENGTH: 25
<212> TYPE: DNA
<213> ORGANISM: Artificial Sequence
<220> FEATURE:
<223> OTHER INFORMATION: Synthetic

<400> SEQUENCE: 60
gagtttggct caaattgtta ctctt                                     25

<210> SEQ ID NO 61
<211> LENGTH: 25
<212> TYPE: DNA
<213> ORGANISM: Artificial Sequence
<220> FEATURE:
<223> OTHER INFORMATION: Synthetic

<400> SEQUENCE: 61
gggaaatggt ctaggagagt aaagt                                     25

<210> SEQ ID NO 62
<211> LENGTH: 34
<212> TYPE: DNA
<213> ORGANISM: Artificial Sequence
```

```
<220> FEATURE:
<223> OTHER INFORMATION: Synthetic

<400> SEQUENCE: 62
agactgttac tcttggtgac acaacctgtg ttac                           34

<210> SEQ ID NO 63
<211> LENGTH: 59
<212> TYPE: DNA
<213> ORGANISM: Homo sapiens

<400> SEQUENCE: 63
aaaaacccaa aatattttag ctcctactca gactgttact ctggtgacac aacctgtgg  59

<210> SEQ ID NO 64
<211> LENGTH: 56
<212> TYPE: DNA
<213> ORGANISM: Artificial Sequence
<220> FEATURE:
<223> OTHER INFORMATION: Synthetic

<400> SEQUENCE: 64
aaaaacccaa aatattttag ctcctactca gactgttact gtgacacaac ctgtgg    56

<210> SEQ ID NO 65
<211> LENGTH: 38
<212> TYPE: DNA
<213> ORGANISM: Artificial Sequence
<220> FEATURE:
<223> OTHER INFORMATION: Synthetic

<400> SEQUENCE: 65
aaaaacccaa aatattttag ctcctactca gactgtgg                       38

<210> SEQ ID NO 66
<211> LENGTH: 57
<212> TYPE: DNA
<213> ORGANISM: Artificial Sequence
<220> FEATURE:
<223> OTHER INFORMATION: Synthetic

<400> SEQUENCE: 66
aaaaacccaa aatattttag ctcctactca gactgttact cttgacacaa cctgtgg   57

<210> SEQ ID NO 67
<211> LENGTH: 49
<212> TYPE: DNA
<213> ORGANISM: Artificial Sequence
<220> FEATURE:
<223> OTHER INFORMATION: Synthetic

<400> SEQUENCE: 67
aaaacccaaa atattttagc tcctactcag actgttacac aacctgtgg            49

<210> SEQ ID NO 68
<211> LENGTH: 57
<212> TYPE: DNA
<213> ORGANISM: Artificial Sequence
<220> FEATURE:
<223> OTHER INFORMATION: Synthetic

<400> SEQUENCE: 68
aaaaacccaa aatattttag ctcctactca gactgttact ggtgacacaa cctgtgg   57

<210> SEQ ID NO 69
```

<211> LENGTH: 241
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (42)..(224)
<223> OTHER INFORMATION: n is a, c, g, or t

<400> SEQUENCE: 69
aaaaacccaa aatattttag ctcctactca gactgttact cnnnnnnnnn nnnnnnnnnn    60
nnnnnnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnnnnnn nnnnnnnnnn nnnnnnnnnn nnnnggtgac acaacctgtg   240
g                                                                  241

<210> SEQ ID NO 70
<211> LENGTH: 57
<212> TYPE: DNA
<213> ORGANISM: Artificial Sequence
<220> FEATURE:
<223> OTHER INFORMATION: Synthetic

<400> SEQUENCE: 70
aaaaccccaa aattttttag ctccttctca gactttttct ggtgacacaa cctgtgg    57

<210> SEQ ID NO 71
<211> LENGTH: 60
<212> TYPE: DNA
<213> ORGANISM: Artificial Sequence
<220> FEATURE:
<223> OTHER INFORMATION: Synthetic

<400> SEQUENCE: 71
aaaaacccaa aatattttag ctcctactca gactgttact cttggtgaca caacctgtgg    60

<210> SEQ ID NO 72
<211> LENGTH: 53
<212> TYPE: DNA
<213> ORGANISM: Artificial Sequence
<220> FEATURE:
<223> OTHER INFORMATION: Synthetic

<400> SEQUENCE: 72
aaaaacccaa aatattttag ctcctactca gactgttact ctgcaacctg tgg    53

<210> SEQ ID NO 73
<211> LENGTH: 56
<212> TYPE: DNA
<213> ORGANISM: Artificial Sequence
<220> FEATURE:
<223> OTHER INFORMATION: Synthetic

<400> SEQUENCE: 73
aaaaacccaa aatattttag ctcctactca gactgttacg gtgacacaac ctgtgg    56

<210> SEQ ID NO 74
<211> LENGTH: 59
<212> TYPE: DNA
<213> ORGANISM: Artificial Sequence
<220> FEATURE:
<223> OTHER INFORMATION: Synthetic

<400> SEQUENCE: 74

| aaaaacccaa aatattttag ctcctactca gactgttact ctggtgacac aacctgtgg | 59 |

<210> SEQ ID NO 75
<211> LENGTH: 34
<212> TYPE: DNA
<213> ORGANISM: Homo sapiens

<400> SEQUENCE: 75

| agactgttac tctggtgaca caacctgtgg ttac | 34 |

<210> SEQ ID NO 76
<211> LENGTH: 30
<212> TYPE: DNA
<213> ORGANISM: Artificial Sequence
<220> FEATURE:
<223> OTHER INFORMATION: Synthetic

<400> SEQUENCE: 76

| agactgtttg gtgacacaac ctgtggttac | 30 |

<210> SEQ ID NO 77
<211> LENGTH: 33
<212> TYPE: DNA
<213> ORGANISM: Artificial Sequence
<220> FEATURE:
<223> OTHER INFORMATION: Synthetic

<400> SEQUENCE: 77

| agactgttac tctgtgacac aacctgtggt tac | 33 |

<210> SEQ ID NO 78
<211> LENGTH: 25
<212> TYPE: DNA
<213> ORGANISM: Artificial Sequence
<220> FEATURE:
<223> OTHER INFORMATION: Synthetic

<400> SEQUENCE: 78

| agactgtgac acaacctgtg gttac | 25 |

<210> SEQ ID NO 79
<211> LENGTH: 29
<212> TYPE: DNA
<213> ORGANISM: Artificial Sequence
<220> FEATURE:
<223> OTHER INFORMATION: Synthetic

<400> SEQUENCE: 79

| agactgttac tgacacaacc tgtggttac | 29 |

<210> SEQ ID NO 80
<211> LENGTH: 31
<212> TYPE: DNA
<213> ORGANISM: Artificial Sequence
<220> FEATURE:
<223> OTHER INFORMATION: Synthetic

<400> SEQUENCE: 80

| agactgttac tctgacacaa cctgtggtta c | 31 |

<210> SEQ ID NO 81
<211> LENGTH: 31
<212> TYPE: DNA
<213> ORGANISM: Artificial Sequence
<220> FEATURE:

<223> OTHER INFORMATION: Synthetic

<400> SEQUENCE: 81
agactgttac tgtgacacaa cctgtggtta c          31

<210> SEQ ID NO 82
<211> LENGTH: 31
<212> TYPE: DNA
<213> ORGANISM: Artificial Sequence
<220> FEATURE:
<223> OTHER INFORMATION: Synthetic

<400> SEQUENCE: 82
agactgttac tctgacacaa cctgtggtta c          31

<210> SEQ ID NO 83
<211> LENGTH: 34
<212> TYPE: DNA
<213> ORGANISM: Homo sapiens

<400> SEQUENCE: 83
agactgttac tctggtgaca caacctgtgg ttac          34

<210> SEQ ID NO 84
<211> LENGTH: 31
<212> TYPE: DNA
<213> ORGANISM: Artificial Sequence
<220> FEATURE:
<223> OTHER INFORMATION: Synthetic

<400> SEQUENCE: 84
agactgttac tgtgacacaa cctgtggtta c          31

<210> SEQ ID NO 85
<211> LENGTH: 13
<212> TYPE: DNA
<213> ORGANISM: Artificial Sequence
<220> FEATURE:
<223> OTHER INFORMATION: Synthetic

<400> SEQUENCE: 85
agactgtggt tac          13

<210> SEQ ID NO 86
<211> LENGTH: 32
<212> TYPE: DNA
<213> ORGANISM: Artificial Sequence
<220> FEATURE:
<223> OTHER INFORMATION: Synthetic

<400> SEQUENCE: 86
agactgttac tcttgacaca acctgtggtt ac          32

<210> SEQ ID NO 87
<211> LENGTH: 25
<212> TYPE: DNA
<213> ORGANISM: Artificial Sequence
<220> FEATURE:
<223> OTHER INFORMATION: Synthetic

<400> SEQUENCE: 87
agactgttac acaacctgtg gttac          25

<210> SEQ ID NO 88
<211> LENGTH: 32

```
<212> TYPE: DNA
<213> ORGANISM: Artificial Sequence
<220> FEATURE:
<223> OTHER INFORMATION: Synthetic

<400> SEQUENCE: 88
agactgttac tggtgacaca acctgtggtt ac                              32

<210> SEQ ID NO 89
<211> LENGTH: 216
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(195)
<223> OTHER INFORMATION: n is a, c, g, or t

<400> SEQUENCE: 89
agactgttac tcnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnnnnnnnn nnnnnnnnnn nnnnnnnnnn nnnnnnnnnn nnnnnnnnnn nnnnnnnnnn   180
nnnnnnnnnn nnnnnggtga cacaacctgt ggttac                             216

<210> SEQ ID NO 90
<211> LENGTH: 32
<212> TYPE: DNA
<213> ORGANISM: Artificial Sequence
<220> FEATURE:
<223> OTHER INFORMATION: Synthetic

<400> SEQUENCE: 90
agactgttac tggtgacaca acctgtggtt ac                              32

<210> SEQ ID NO 91
<211> LENGTH: 28
<212> TYPE: DNA
<213> ORGANISM: Artificial Sequence
<220> FEATURE:
<223> OTHER INFORMATION: Synthetic

<400> SEQUENCE: 91
agactgttac tctgcaacct gtggttac                                   28

<210> SEQ ID NO 92
<211> LENGTH: 31
<212> TYPE: DNA
<213> ORGANISM: Artificial Sequence
<220> FEATURE:
<223> OTHER INFORMATION: Synthetic

<400> SEQUENCE: 92
agactgttac ggtgacacaa cctgtggtta c                               31

<210> SEQ ID NO 93
<211> LENGTH: 33
<212> TYPE: DNA
<213> ORGANISM: Homo sapiens

<400> SEQUENCE: 93
agactgttac tctggtgaca caacctgtgt tac                             33

<210> SEQ ID NO 94
```

```
<211> LENGTH: 36
<212> TYPE: DNA
<213> ORGANISM: Artificial Sequence
<220> FEATURE:
<223> OTHER INFORMATION: Synthetic

<400> SEQUENCE: 94
gctcctactc agactgtttg gtgacacaac ctgtgg                                 36

<210> SEQ ID NO 95
<211> LENGTH: 36
<212> TYPE: DNA
<213> ORGANISM: Artificial Sequence
<220> FEATURE:
<223> OTHER INFORMATION: Synthetic

<400> SEQUENCE: 95
gctcctactc agactgttac tctgtgacac aacctg                                 36

<210> SEQ ID NO 96
<211> LENGTH: 36
<212> TYPE: DNA
<213> ORGANISM: Artificial Sequence
<220> FEATURE:
<223> OTHER INFORMATION: Synthetic

<400> SEQUENCE: 96
gctcctactc agactgttac tgacacaacc tgtggt                                 36

<210> SEQ ID NO 97
<211> LENGTH: 36
<212> TYPE: DNA
<213> ORGANISM: Artificial Sequence
<220> FEATURE:
<223> OTHER INFORMATION: Synthetic

<400> SEQUENCE: 97
gctcctactc agactgttac tctgacacaa cctgtg                                 36

<210> SEQ ID NO 98
<211> LENGTH: 36
<212> TYPE: DNA
<213> ORGANISM: Artificial Sequence
<220> FEATURE:
<223> OTHER INFORMATION: Synthetic

<400> SEQUENCE: 98
gctcctactc agactgttac tgtgacacaa cctgtg                                 36
```